US010793556B2

(12) United States Patent
Kuehnert et al.

(10) Patent No.: US 10,793,556 B2
(45) Date of Patent: *Oct. 6, 2020

(54) 8-AMINO-2-OXO-1,3-DIAZA-SPIRO-[4.5]-DECANE DERIVATIVES

(71) Applicant: Grünenthal GmbH, Aachen (DE)

(72) Inventors: Sven Kuehnert, Dueren (DE); Rene Michael Koenigs, Erkelenz (DE); Achim Kless, Aachen (DE); Anita Wegert, Aldenhoven (DE); Paul Ratcliffe, Aachen (DE); Ruth Jostock, Stolberg (DE); Thomas Koch, Stolberg (DE); Klaus Linz, Rheinbach (DE); Wolfgang Schroeder, Aachen (DE)

(73) Assignee: GRUENENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/450,259

(22) Filed: Jun. 24, 2019

(65) Prior Publication Data

US 2019/0375738 A1 Dec. 12, 2019

Related U.S. Application Data

(63) Continuation of application No. 16/207,916, filed on Dec. 3, 2018, now abandoned, which is a continuation of application No. 15/984,995, filed on May 21, 2018, now abandoned, which is a continuation of application No. 15/405,627, filed on Jan. 13, 2017, now abandoned.

(30) Foreign Application Priority Data

Jan. 13, 2016 (EP) .................... 16151015

(51) Int. Cl.
| C07D 409/06 | (2006.01) |
| C07D 235/02 | (2006.01) |
| C07D 401/04 | (2006.01) |
| C07D 401/06 | (2006.01) |
| C07D 401/14 | (2006.01) |
| C07D 403/06 | (2006.01) |
| C07D 405/04 | (2006.01) |
| C07D 405/06 | (2006.01) |
| C07D 409/04 | (2006.01) |

(52) U.S. Cl.
CPC ......... *C07D 409/06* (2013.01); *C07D 235/02* (2013.01); *C07D 401/04* (2013.01); *C07D 401/06* (2013.01); *C07D 401/14* (2013.01); *C07D 403/06* (2013.01); *C07D 405/04* (2013.01); *C07D 405/06* (2013.01); *C07D 409/04* (2013.01)

(58) Field of Classification Search
None
See application file for complete search history.

(56) References Cited

U.S. PATENT DOCUMENTS

| 5,698,567 A | 12/1997 | Guillonneau et al. |
| 7,282,515 B2 | 10/2007 | Meese et al. |
| 2004/0067930 A1 | 4/2004 | Bhatti et al. |
| 2004/0192916 A1 | 9/2004 | Buschmann et al. |
| 2006/0004034 A1 | 1/2006 | Hinze et al. |
| 2007/0254904 A1 | 11/2007 | Janssens et al. |
| 2008/0103183 A1 | 5/2008 | Ackermann et al. |
| 2008/0249122 A1 | 10/2008 | Bignan et al. |
| 2008/0287478 A1 | 11/2008 | Hansen et al. |
| 2009/0247530 A1 | 10/2009 | Nolte et al. |
| 2009/0253727 A1 | 10/2009 | Goehring et al. |
| 2010/0331353 A1 | 12/2010 | Schrimpf et al. |
| 2012/0029006 A1 | 5/2012 | Linz et al. |
| 2017/0197919 A1 | 7/2017 | Kuenert et al. |
| 2017/0197947 A1 | 7/2017 | Kuehnert et al. |
| 2017/0197949 A1 | 7/2017 | Kuehnert et al. |
| 2017/0197970 A1 | 7/2017 | Kuehnert et al. |
| 2017/0197971 A1 | 7/2017 | Kuehnert et al. |
| 2018/0201616 A1 | 7/2018 | Kuehnert et al. |
| 2018/0282341 A1 | 10/2018 | Kuehnert et al. |
| 2019/0016735 A1 | 1/2019 | Smith, II et al. |
| 2019/0016768 A1 | 1/2019 | Chien et al. |
| 2019/0100497 A1 | 4/2019 | Kuehnert et al. |
| 2019/0100515 A1 | 4/2019 | Kuehnert et al. |
| 2019/0106429 A1 | 4/2019 | Kuehnert et al. |
| 2019/0106430 A1 | 4/2019 | Kuehnert et al. |
| 2020/0002319 A1 | 1/2020 | Kuehnert et al. |

FOREIGN PATENT DOCUMENTS

| CL | 2003-02246 | 5/2004 |
| CL | 2009-00734 | 5/2009 |
| CL | 2013-00266 | 5/2013 |
| CL | 2018-01899 | 11/2013 |
| CL | 2018-01868 | 8/2018 |

(Continued)

OTHER PUBLICATIONS

Schroeder et al., "Functional plasticity of the N/OFQ-NOP receptor system determines analgesic properties of NOP receptor agonists", British Journal of Pharmacology, Apr. 15, 2014, pp. 3777-3800.
Witkin et al., "The biology of Nociceptin/Orphanin FQ (N/OFQ) related to obesity, stress, anxiety, mood, and drug dependence", Pharmacology & Therapeutics 141, 2014, pp. 283-299, Elsevier.
Jenck et al., "Orphanin FQ acts as an anxiolytic to attenuate behavioral responses to stress", The National Academy of Sciences, Dec. 1997, pp. 14854-14858, vol. 94.
Mabrouk et al., "Stimulation of δ Opioid Receptor and Blockade of Nociceptin/Orphanin FQ Receptor Synergistically Attenuate Parkinsonism", The Journal of Neuroscience, Sep. 24, 2014, vol. 34, No. 19, pp. 12953-12962.
Pradhan et al., "The delta opioid receptor: an evolving target for the treatment of brain disorders", Trends in Pharmacological Sciences, CE Press, Oct. 2011, pp. 581-590, vol. 32, No. 10.
Gupta et al., "A Systematic Review of the Peripheral Analgesic Effects of Intraarticular Morphine", International Anesthesia Research Society, 2001, pp. 761-770, vol. 93.

(Continued)

*Primary Examiner* — Po-Chih Chen
(74) *Attorney, Agent, or Firm* — Norris McLaughlin, P.A.

(57) ABSTRACT

The invention relates to 8-amino-2-oxo-1,3-diaza-spiro-[4.5]-decane derivatives, their preparation and their use in medicine, particularly in the treatment of pain.

30 Claims, No Drawings

(56) References Cited

FOREIGN PATENT DOCUMENTS

| CL | 2018-01909 | | 10/2018 |
|---|---|---|---|
| CL | 2018-01910 | | 10/2018 |
| CL | 2018-01911 | | 10/2018 |
| CL | 2018-01912 | | 10/2018 |
| CL | 2018-01913 | | 10/2018 |
| EP | 1401841 | B1 | 8/2005 |
| EP | 1888596 | B1 | 11/2006 |
| EP | 1893620 | B1 | 11/2006 |
| EP | 2078718 | A1 | 7/2009 |
| EP | 2411381 | | 9/2010 |
| EP | 2598503 | B1 | 2/2012 |
| EP | 2010531 | B1 | 11/2017 |
| WO | 2004/043967 | A1 | 5/2004 |
| WO | WO 2006/122769 | A2 | 11/2006 |
| WO | WO 2006/122770 | A1 | 11/2006 |
| WO | WO 2007/000325 | A2 | 1/2007 |
| WO | WO 2007/124903 | A1 | 11/2007 |
| WO | WO 2008/046758 | A2 | 4/2008 |
| WO | 2009/118168 | A1 | 10/2009 |
| WO | WO 2010/108651 | A1 | 9/2010 |
| WO | 2012/013343 | A1 | 2/2012 |
| WO | 2015/192039 | A1 | 12/2015 |

OTHER PUBLICATIONS

Kalso et al., "No pain, no gain: clinical excellence and scientific rigour—lessons learned from IA morphine", International Association for the Study of Pain, 2002, pp. 269-275, vol. 98, Elsevier Science B.V.

Stein et al., "Attacking pain at its source: new perspectives on opioids", Nature Medicine, Aug. 2003, pp. 1003-1008, vol. 9, No. 8, Nature Publishing Group.

Zoellner et al., "Topical Fentanyl in a Randomized, Double-blind Study in Patients With Corneal Damage", Clin J Pain, Oct. 2008, pp. 690-696, vol. 24, No. 8, Lippincott Williams & Wilkins.

Bignan et al., "Recent advances towards the discovery of ORL-1 receptor agonists and antagonists", 2005, pp. 357-388, vol. 15, No. 4, Ashley Publications.

Chu et al., "Synthesis and DNA binding studies of bis-intercalators with a novel spiro-cyclic linker", Tetrahedron, 206, 62, 5536-5548.

U.S. Appl. No. 15/405,485, filed Jan. 13, 2017.
U.S. Appl. No. 15/405,896, filed Jan. 13, 2017.
U.S. Appl. No. 15/405,919, filed Jan. 13, 2017.
U.S. Appl. No. 15/405,482, filed Jan. 13, 2017.
U.S. Appl. No. 15/923,948, filed Mar. 16, 2018.

Almutairy, B. et. al., "Development and Characterization of a Floating Drug Delivery System prepared via Hot-Melt Extrusion Technology Coupled with Pressurized $CO_2$ for a Thermo-Labile API," University of Mississippi, 2016, AAPS, Nov. 2016.

8-AMINO-2-OXO-1,3-DIAZA-SPIRO-[4.5]-DECANE DERIVATIVES

This application is a continuation of U.S. Nonprovisional patent application Ser. No. 16/207,916, filed Dec. 3, 2018, pending, which is a continuation of U.S. Nonprovisional patent application Ser. No. 15/984,995, filed May 21, 2018, now abandoned, which is a continuation of U.S. Nonprovisional patent application Ser. No. 15/405,627, filed Jan. 13, 2017, now abandoned, which claims foreign priority benefit under 35 U.S.C. § 119 of European Patent Application No. 16 151 015.1, filed Jan. 13, 2016, the disclosures of which are incorporated herein by reference.

The invention relates to 8-amino-2-oxo-1,3-diaza-spino-[4.5]-decane derivatives, their preparation and use in medicine, particularly in various neurological disorders, including but not limited to pain, neurodegenerative disorders, neuroinflammatory disorders, neuropsychiatric disorders, substance abuse/dependence.

Opioid receptors are a group of Gi/o protein-coupled receptors which are widely distributed in the human body. The opioid receptors are currently subdivided into four major classes, i.e. the three classical opioid receptors mu-opioid (MOP) receptor, kappa-opioid (KOP) receptor, and delta-opioid (DOP) receptor as well as the opioid receptor-like (ORL-1) receptor, which was more recently discovered based on its high homology with said classical opioid receptors. After identification of the endogenous ligand of the ORL-1 receptor, known as nociceptin/orphanin FQ, a highly basic 17 amino acid peptide isolated from tissue extracts in 1995, the ORL-1 receptor was renamed "nociceptin opioid peptide receptor" and abbreviated as "NOP-receptor".

The classical opioid receptors (MOP, KOP and DOP) as well as the NOP receptor are widely distributed/expressed in the human body, including in the brain, the spinal cord, on peripheral sensory neurons and the intestinal tract, wherein the distribution pattern differs between the different receptor classes.

Nociceptin acts at the molecular and cellular level in very much the same way as opioids. However, its pharmacological effects sometimes differ from, and even oppose those of opioids. NOP-receptor activation translates into a complex pharmacology of pain modulation, which, depending on route of administration, pain model and species involved, leads to either pronociceptive or antinociceptive activity. Furthermore, the NOP receptor system is upregulated under conditions of chronic pain. Systemic administration of selective NOP receptor agonists was found to exert a potent and efficacious analgesia in non-human primate models of acute and inflammatory pain in the absence of side effects. The activation of NOP receptors has been demonstrated to be devoid of reinforcing effects but to inhibit opioid-mediated reward in rodents and non-human primates (Review: Schroeder et al, Br J Pharmacol 2014; 171 (16): 3777-3800, and references therein).

Besides the involvement of the NOP receptor in nociception, results from preclinical experiments suggest that NOP receptor agonists might be useful inter alia in the treatment of neuropsychiatric disorders (Witkin et al, Pharmacology & Therapeutics, 141 (2014) 283-299; Jenck et al., Proc. Natl. Acad. Sci. USA 94, 1997, 14854-14858). Remarkably, the DOP receptor is also implicated to modulate not only pain but also neuropsychiatric disorders (Mabrouk et al, 2014; Pradhan et al., 2011).

Strong opioids acting at the MOP receptor site are widely used to treat moderate to severe acute and chronic pain. However, the therapeutic window of strong opioids is limited by severe side effects such as nausea and vomiting, constipation, dizziness, somnolence, respiratory depression, physical dependence and abuse. Furthermore, it is known that MOP receptor agonists show only reduced effectiveness under conditions of chronic and neuropathic pain.

It is known that some of the above mentioned side-effects of strong opioids are mediated by activation of classic opioid-receptors within the central nervous system. Furthermore, peripheral opioid receptors, when activated, can inhibit transmission of nociceptive signals shown in both, clinical and animal studies (Gupta et al., 2001; Kalso et al., 2002; Stein et al., 2003; Zollner et al., 2008).

Thus, to avoid CNS-mediated adverse effects after systemic administration, one approach has been to provide peripherally restricted opioid receptor ligands that do not easily cross the blood-brain barrier and therefore distribute poorly to the central nervous system (see for instance WO 2015/192039). Such peripherally acting compounds might combine effective analgesia with limited side-effects.

Another approach has been to provide compounds which interact with both the NOP receptor and the MOP receptor. Such compounds have for instance been described in WO 2004/043967, WO 2012/013343 and WO 2009/118168.

A further approach has been to provide multi-opioid receptor analgesics that modulate more than one of the opioid receptor subtypes to provide additive or synergistic analgesia and/or reduced side effects like abuse liability or tolerance.

On the one hand, it would be desirable to provide analgesics that selectively act on the NOP receptor system but less pronounced on the classic opioid receptor system, especially MOP receptor system, whereas it would be desirable to distinguish between central nervous activity and peripheral nervous activity. On the other hand, it would be desirable to provide analgesics that act on the NOP receptor system and also to a balanced degree on the MOP receptor system, whereas it would be desirable to distinguish between central nervous activity and peripheral nervous activity.

There is a need for medicaments which are effective in the treatment of pain and which have advantages compared to the compounds of the prior art. Where possible, such medicaments should contain such a small dose of active ingredient that satisfactory pain therapy can be ensured without the occurrence of intolerable treatment-emergent adverse events.

It is an object of the invention to provide pharmacologically active compounds, preferably analgesics that have advantages compared to the prior art.

This object has been achieved by the subject-matter of the patent claims.

A first aspect of the invention relates to 8-amino-2-oxo-1,3-diaza-spiro-[4.5]-decane derivatives according to general formula (I)

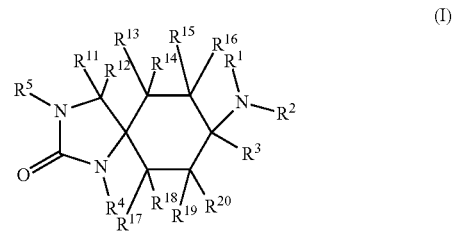

wherein

R¹ and R² independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —OH, —$OCH_3$, —CN and —$CO_2CH_3$;

a 3-12-membered cycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered cycloalkyl moiety is optionally connected through —$C_1$-$C_6$-alkylene-, linear or branched, saturated or unsaturated, unsubstituted; or a 3-12-membered heterocycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered heterocycloalkyl moiety is optionally connected through —$C_1$-$C_6$-alkylene-, linear or branched, saturated or unsaturated, unsubstituted; or R¹ and R² together with the nitrogen atom to which they are attached form a ring and mean —$(CH_2)_{3-6}$—; —$(CH_2)_2$—O—$(CH_2)_2$—; or —$(CH_2)_2$—$NR^A$—$(CH_2)_2$—, wherein $R^A$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

preferably with the proviso that R¹ and R² do not simultaneously mean —H;

R³ means —$C_1$-$C_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

R⁴ means

—H;

—$C_1$-$C_6$-alkyl, linear or branched, saturated or unsaturated, unsubstituted, mono- or polysubstituted; wherein said —$C_1$-$C_6$-alkyl is optionally connected through —C(=O)—, —C(=O)O—, or —$S(=O)_2$—;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally optionally connected through —C(=O)—, —C(=O)O—, —C(=O)O—$CH_2$—, or —$S(=O)_2$—;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—$CH_2$—, or —$S(=O)_2$—;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—$CH_2$—, or —$S(=O)_2$—; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—$CH_2$—, or —$S(=O)_2$—;

R⁵ means

—H;

—$C_1$-$C_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or a moiety according to general formula (X);

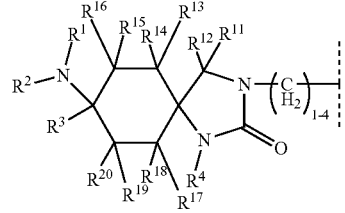

$R^{12}$, $R^{13}$, $R^{14}$, $R^{15}$, $R^{16}$, $R^{17}$, $R^{18}$, $R^{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;

wherein "mono- or polysubstituted" means that one or more hydrogen atoms are replaced by a substituent independently of one another selected from the group consisting of —F, —Cl, —Br, —I, —CN, —$R^{21}$, —C(=O)$R^{21}$, —C(=O)O$R^{21}$, —C(=O)N$R^{21}R^{22}$, —O—$(CH_2CH_2$—$O)_{1-30}$—H, —O—(CH$_2$CH$_2$—O)$_{1-30}$—CH$_3$, =O, —OR$^{21}$, —OC(=O)R$^{21}$, —OC(=O)OR$^{21}$, —OC(=O)NR$^{21}$R$^{22}$, —NO$_2$, —NR$^{21}$R$^{22}$, —NR$^{21}$—(CH$_2$)$_{1-6}$—C(=O)R$^{22}$, —NR$^{21}$—(CH$_2$)$_{1-6}$—C(=O)OR$^{22}$, —NR$^{23}$—(CH$_2$)$_{1-6}$—C(=O)NR$^{21}$R$^{22}$, —NR$^{21}$C(=O)R$^{22}$, —NR$^{21}$C(=O)—OR$^{22}$, —NR$^{23}$C(=O)NR$^{21}$R$^{22}$, —NR$^{21}$S(=O)$_2$R$^{22}$, —SR$^{21}$, —S(=O)R$^{21}$, —S(=O)$_2$R$^{21}$, —S(=O)$_2$OR$^{21}$, and —S(=O)$_2$NR$^{21}$R$^{22}$;
wherein
R$^{21}$, R$^{22}$ and R$^{23}$ independently of one another mean
—H; —C$_1$-C$_6$-alkyl, linear or branched, saturated or unsaturated, unsubstituted or substituted with one, two, three or four substituents independently of one another selected from the group consisting of —F, —Cl, —Br, —I, —CN, —OH, —NH$_2$, and —O—C$_1$-C$_6$-alkyl;
a 3-12-membered cycloalkyl moiety, saturated or unsaturated, unsubstituted; wherein said 3-12-membered cycloalkyl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;
a 3-12-membered heterocycloalkyl moiety, saturated or unsaturated, unsubstituted; wherein said 3-12-membered heterocycloalkyl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;
a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;
a 5-14-membered heteroaryl moiety, unsubstituted, mono- or polysubstituted; wherein said 5-14-membered heteroaryl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;
or R$^{21}$ and R$^{22}$ within —C(=O)NR$^{21}$R$^{22}$, —OC(=O)NR$^{21}$R$^{22}$, —NR$^{21}$R$^{22}$, —NR$^{23}$—(CH$_2$)$_{1-6}$—C(=O)NR$^{21}$R$^{22}$, —NR$^{23}$C(=O)NR$^{21}$R$^{22}$, or —S(=O)$_2$NR$^{21}$R$^{22}$ together with the nitrogen atom to which they are attached form a ring and mean —(CH$_2$)$_{3-6}$—; —(CH$_2$)$_2$—O—(CH$_2$)$_2$—; or —(CH$_2$)$_2$—NR$^B$—(CH$_2$)$_2$—, wherein R$^B$ means —H or —C$_1$-C$_6$-alkyl, linear or branched, saturated or unsaturated, unsubstituted or substituted with one, two, three or four substituents independently of one another selected from the group consisting of —F, —Cl, —Br and —I;
or a physiologically acceptable salt thereof.

Preferably, aryl includes but is not limited to phenyl and naphthyl. Preferably, heteroaryl includes but is not limited to -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl. Preferably, cycloalkyl includes but is not limited to -cyclopropyl, -cyclobutyl, -cyclopentyl and -cyclohexyl. Preferably, heterocycloalkyl includes but is not limited to -aziridinyl, -azetidinyl, -pyrrolidinyl, -piperidinyl, -piperazinyl, -morpholinyl, sulfamorpholinyl, -oxiridinyl, -oxetanyl, -tetrahydropyranyl, and -pyranyl.

When a moiety is connected through an asymmetric group such as —C(=O)O— or —C(=O)O—CH$_2$—, said asymmetric group may be arranged in either direction. For example, when R$^4$ is connected to the core structure through —C(=O)O—, the arrangement may be either R$^4$—C(=O)O-core or core-C(=O)O—R$^4$.

In preferred embodiments of the compound according to the invention, R$^{11}$, R$^{12}$, R$^{13}$, R$^{14}$, R$^{15}$, R$^{16}$, R$^{17}$, R$^{18}$, R$^{19}$, and R$^{20}$ independently of one another mean —H, —F, —OH, or —C$_1$-C$_6$-alkyl; preferably —H.

In a preferred embodiment of the compound according to the invention, R$^1$ means —H; and R$^2$ means —C$_1$-C$_6$-alkyl, linear or branched, saturated or unsaturated, unsubstituted, mono- or polysubstituted. Preferably, R$^1$ means —H and R$^2$ means —CH$_3$.

In another preferred embodiment of the compound according to the invention, R$^1$ means —CH$_3$; and R$^2$ means —C$_1$-C$_6$-alkyl, linear or branched, saturated or unsaturated, unsubstituted, mono- or polysubstituted. Preferably, R$^1$ means —CH$_3$ and R$^2$ means —CH$_3$.

In still another preferred embodiment of the compound according to the invention, R$^1$ and R$^2$ together with the nitrogen atom to which they are attached form a ring and mean —(CH$_2$)$_{3-6}$—. Preferably, R$^1$ and R$^2$ together with the nitrogen atom to which they are attached form a ring and mean —(CH$_2$)$_3$—.

In yet another preferred embodiment,
R$^1$ means —H or —CH$_3$; and
R$^2$ means a 3-12-membered cycloalkyl moiety, saturated or unsaturated, unsubstituted; wherein said 3-12-membered cycloalkyl moiety is connected through —CH$_2$—, unsubstituted; preferably —CH$_2$-cycloalkyl, —CH$_2$-cyclobutyl or —CH$_2$-cyclopentyl; or R$^2$ means a 3-12-membered heterocycloalkyl moiety, saturated or unsaturated, unsubstituted; wherein said 3-12-membered heterocycloalkyl moiety is connected through —CH$_2$—, unsubstituted; preferably —CH$_2$-oxetanyl or —CH$_2$-tetrahydrofuranyl.

In a preferred embodiment of the compound according to the invention, R$^3$ means —C$_1$-C$_6$-alkyl, linear or branched, saturated or unsaturated, unsubstituted, mono- or polysubstituted. Preferably, R$^3$ means —C$_1$-C$_6$-alkyl, linear or branched, saturated or unsaturated, unsubstituted or monosubstituted with —OCH$_3$.

In another preferred embodiment of the compound according to the invention, R$^3$ means a 6-14-membered aryl moiety, unsubstituted, mono- or polysubstituted, optionally connected through —C$_1$-C$_6$-alkylene-, linear or branched, saturated or unsaturated, unsubstituted. In a preferred embodiment, R$^3$ means -phenyl unsubstituted, mono- or polysubstituted. More preferably, R$^3$ means -phenyl unsubstituted, mono- or disubstituted with —F, —Cl, —CH$_3$, —CF$_3$, —OH, —OCH$_3$, —OCF$_3$ or —OCH$_2$OCH$_3$, preferably —F. In another preferred embodiment, R$^3$ means -benzyl unsubstituted, mono- or polysubstituted. More preferably, R$^3$ means -benzyl unsubstituted, mono- or disubstituted with —F, —Cl, —CH$_3$, —CF$_3$, —OH, —OCH$_3$, —OCF$_3$ or —OCH$_2$OCH$_3$, preferably —F.

In still another preferred embodiment of the compound according to the invention, R$^3$ means a 5-14-membered heteroaryl moiety, unsubstituted, mono- or polysubstituted. Preferably, R$^3$ means -thienyl or -pyridinyl, in each case unsubstituted, mono- or polysubstituted. More preferably, $R^3$ means -thienyl, -pyridinyl, -imidazolyl or benzimidazolyl, in each case unsubstituted or monosubstituted with —F, —Cl or —CH$_3$.

In a preferred embodiment of the compound according to the invention, $R^4$ means —H.

In another preferred embodiment of the compound according to the invention, $R^4$ means —C$_1$-C$_6$-alkyl, linear or branched, saturated or unsaturated, unsubstituted, mono- or polysubstituted. Preferably, $R^4$ means —C$_1$-C$_6$-alkyl, linear or branched, saturated or unsaturated, unsubstituted or monosubstituted with a substituent selected from the group consisting of —F, —Cl, —Br, —I, —CN, —CF$_3$, —OH, —O—C$_1$-C$_4$-alkyl, —OCF$_3$, —O—(CH$_2$CH$_2$—O)$_{1-30}$—H, —O—(CH$_2$CH$_2$—O)$_{1-30}$—CH$_3$, —OC(=O)C$_1$-C$_4$-alkyl, —C(=O)C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)NHC$_1$-C$_4$-alkylene-CN, —C(=O)NHC$_1$-C$_4$-alkylene-O—C$_1$-C$_4$-alkyl, —C(=O)N(C$_1$-C$_4$-alkyl)$_2$; —S(=O)C$_1$-C$_4$-alkyl, and —S(=O)$_2$C$_1$-C$_4$-alkyl; or with —C(=O)NR$^{21}$R$^{22}$ wherein R$^{21}$ and R$^{22}$ together with the nitrogen atom to which they are attached form a ring and mean —(CH$_2$)$_{3-6}$—, —(CH$_2$)$_2$—O—(CH$_2$)$_2$—, or —(CH$_2$)$_2$—NR$^B$—(CH$_2$)$_2$—, wherein R$^B$ means —H or —C$_1$-C$_6$-alkyl; or with —C(=O)NH-3-12-membered cycloalkyl, saturated or unsaturated, unsubstituted or monosubstituted with —F, —Cl, —Br, —I, —CN, or —OH; or with —C(=O)NH-3-12-membered heterocycloalkyl, saturated or unsaturated, unsubstituted or monosubstituted with —F, —Cl, —Br, —I, —CN, or —OH. More preferably, $R^4$ means —C$_1$-C$_6$-alkyl, linear or branched, saturated or unsaturated, unsubstituted or monosubstituted with —O—C$_1$-C$_4$-alkyl or —C(=O)N(C$_1$-C$_4$-alkyl)$_2$.

In still another preferred embodiment of the compound according to the invention, $R^4$ means a 3-12-membered cycloalkyl moiety, saturated or unsaturated, unsubstituted, mono- or polysubstituted; wherein the 3-12-membered cycloalkyl moiety is connected through —C$_1$-C$_6$-alkylene-, linear or branched, saturated or unsaturated, unsubstituted, mono- or polysubstituted. Preferably, $R^4$ means a 3-12-membered cycloalkyl moiety, saturated or unsaturated, unsubstituted, mono- or polysubstituted; wherein said 3-12-membered cycloalkyl moiety is connected through —CH$_2$— or —CH$_2$CH$_2$—. More preferably, $R^4$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said 3-12-membered cycloalkyl moiety is connected through —CH$_2$— or —CH$_2$CH$_2$—.

In a preferred embodiment of the compound according to the invention, $R^4$ means a 3-12-membered heterocycloalkyl moiety, saturated or unsaturated, unsubstituted, mono- or polysubstituted; wherein said 3-12-membered heterocycloalkyl moiety is connected through —C$_1$-C$_6$-alkylene-, linear or branched, saturated or unsaturated, unsubstituted, mono- or polysubstituted. Preferably, $R^4$ means a 3-12-membered heterocycloalkyl moiety, saturated or unsaturated, unsubstituted, mono- or polysubstituted; wherein said 3-12-membered heterocycloalkyl moiety is connected through —CH$_2$— or —CH$_2$CH$_2$—. More preferably, $R^4$ means -oxetanyl, -tetrahydrofuranyl or -tetrahydropyranyl, in each case unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said -oxetanyl, -tetrahydrofuranyl or -tetrahydropyranyl is connected through —CH$_2$— or —CH$_2$CH$_2$—.

In yet another preferred embodiment of the compound according to the invention, $R^4$ means a 6-14-membered aryl moiety, unsubstituted, mono- or polysubstituted; wherein said 6-14-membered aryl moiety is connected through —C$_1$-C$_6$-alkylene-, linear or branched, saturated or unsaturated, unsubstituted, mono- or polysubstituted. Preferably, $R^4$ means -phenyl, unsubstituted, mono- or polysubstituted; wherein said -phenyl is connected through —CH$_2$— or —CH$_2$CH$_2$—. More preferably, $R^4$ means -phenyl, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said -phenyl is connected through —CH$_2$— or —CH$_2$CH$_2$—.

In a further preferred embodiment of the compound according to the invention, $R^4$ means a 5-14-membered heteroaryl moiety, unsubstituted, mono- or polysubstituted; wherein said 5-14-membered heteroaryl moiety is connected through —C$_1$-C$_6$-alkylene-, linear or branched, saturated or unsaturated, unsubstituted, mono- or polysubstituted. Preferably, $R^4$ means a 5-14-membered heteroaryl moiety, unsubstituted, mono- or polysubstituted; wherein said -phenyl is connected through —CH$_2$— or —CH$_2$CH$_2$—. More preferably, $R^4$ means -pyridinyl, -pyrimidinyl, -pyrazinyl, or -pyrazolinyl, in each case unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said -pyridinyl, -pyrimidinyl, -pyrazinyl, or -pyrazolinyl is connected through —CH$_2$— or —CH$_2$CH$_2$—.

In a preferred embodiment of the compound according to the invention, $R^5$ means —H.

In another preferred embodiment of the compound according to the invention, $R^5$ means —C$_1$-C$_6$-alkyl, linear or branched, saturated or unsaturated, unsubstituted or substituted with one, two, three or four substituents independently of one another selected from the group consisting of —F, —Cl, —Br, —I, —CN, —OH, —O—C$_1$-C$_4$-alkyl, —O—(CH$_2$CH$_2$—O)$_{1-30}$—H, —O—(CH$_2$CH$_2$—O)$_{1-30}$—CH$_3$, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl. Preferably, $R^5$ means —C$_1$-C$_6$-alkyl, linear or branched, saturated or unsaturated, unsubstituted or monosubstituted with —F, —Cl, —Br, —I, —CN, —OH, —O—C$_1$-C$_4$-alkyl, —O—(CH$_2$CH$_2$—O)$_{1-30}$—H, —O—(CH$_2$CH$_2$—O)$_{1-30}$—CH$_3$, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl or —S(=O)$_2$C$_1$-C$_4$-alkyl. More preferably, (i) $R^5$ means —C$_1$-C$_6$-alkyl, linear or branched, saturated or unsaturated, unsubstituted or monosubstituted with —F, —Cl, —Br, —I, —CN, —OH, —O—C$_1$-C$_4$-alkyl, —O—(CH$_2$CH$_2$—O)$_{1-30}$—H, —O—(CH$_2$CH$_2$—O)$_{1-30}$—CH$_3$, —S(=O)C$_1$-C$_4$-alkyl or —S(=O)$_2$C$_1$-C$_4$-alkyl; or (ii) $R^5$ means —$C_3$-$C_6$-alkyl, linear or branched, saturated or unsaturated, monosubstituted with —C(=O)NH$_2$, —C(=O)NHC$_1$-C$_4$-alkyl, or —C(=O)N(C$_1$-C$_4$-alkyl)$_2$.

In another preferred embodiment of the compound according to the invention, $R^5$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C$_1$-C$_4$-alkyl-OH, —O—(CH$_2$CH$_2$—O)$_{1-30}$—H, —O—(CH$_2$CH$_2$—O)$_{1-30}$—CH$_3$, —C(=O)OH, —C(=O)C$_1$-C$_4$-alkyl, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —NH$_2$, —NHC$_1$-C$_4$-alkyl, N(C$_1$-C$_4$-alkyl)$_2$, —NHC(=O)—C$_1$-C$_4$-alkyl, —N(C$_1$-C$_4$-alkyl)C(=O)C$_1$-C$_4$-alkyl, —S(=O)C$_1$-C$_4$-alkyl and —S(=O)$_2$C$_1$-C$_4$-alkyl; wherein said 3-12-membered cycloalkyl moiety is optionally connected through —C$_1$-C$_6$-alkylene-, linear or branched, saturated or unsaturated, unsubstituted.

In a preferred embodiment of the compound according to the invention, $R^5$ means a 3-12-membered heterocycloalkyl moiety, saturated or unsaturated, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C$_1$-C$_4$-alkyl-OH, —O—(CH$_2$CH$_2$—O)$_{1-30}$—H, —O—(CH$_2$CH$_2$—O)$_{1-30}$—CH$_3$, —C(=O)OH, —C(=O)C$_1$-C$_4$-alkyl, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —NH$_2$, —NHC$_1$-C$_4$-alkyl, N(C$_1$-C$_4$-alkyl)$_2$, —NHC(=O)—C$_1$-C$_4$-alkyl, —N(C$_1$-C$_4$-alkyl)C(=O)C$_1$-C$_4$-alkyl, —S(=O)C$_1$-C$_4$-alkyl and —S(=O)$_2$C$_1$-C$_4$-alkyl; wherein said 3-12-membered heterocycloalkyl moiety is optionally connected through —C$_1$-C$_6$-alkylene-, linear or branched, saturated or unsaturated, unsubstituted. Preferably, $R^5$ means -oxetanyl, -tetrahydrofuranyl, -tetrahydropyranyl, -piperidinyl, -piperazinyl, -morpholinyl or -thiomorpholinyl, in each case unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said -oxetanyl, -tetrahydrofuranyl, -tetrahydropyranyl, -piperidinyl, -piperazinyl, -morpholinyl or -thiomorpholinyl is connected through —CH$_2$— or —CH$_2$CH$_2$—.

In a preferred embodiment of the compound according to the invention, $R^5$ means
—H;
—C$_1$-C$_6$-alkyl, linear or branched, saturated or unsaturated, unsubstituted or substituted with one, two, three or four substituents independently of one another selected from the group consisting of —F, —Cl, —Br, —I, —CN, =O, —OH, —O—C$_1$-C$_4$-alkyl, —O—(CH$_2$CH$_2$—O)$_{1-30}$—H, —O—(CH$_2$CH$_2$—O)$_{1-30}$—CH$_3$, —C(=O)OH, —C(=O)C$_1$-C$_4$-alkyl, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl, —S(=O)$_2$C$_1$-C$_4$-alkyl, —NH$_2$, —NH—C$_1$-C$_4$-alkyl, —N(C$_1$-C$_4$-alkyl)$_2$, —NHC(=O)—C$_1$-C$_4$-alkyl, —NH—S(=O)$_2$C$_1$-C$_4$-alkyl; or
3-12-membered cycloalkyl, saturated or unsaturated, unsubstituted or substituted with one, two, three or four substituents independently of one another selected from the group consisting of —F, —Cl, —Br, —I, —CN, =O, —OH, —C$_1$-C$_4$-alkyl, —C$_1$-C$_4$-alkyl-OH, —NH$_2$, —NH—C$_1$-C$_4$-alkyl, —N(C$_1$-C$_4$-alkyl)$_2$, —NHC(=O)—C$_1$-C$_4$-alkyl, —NHS(=O)$_2$—C$_1$-C$_4$-alkyl, —O—C$_1$-C$_4$-alkyl, —O—(CH$_2$CH$_2$—O)$_{1-30}$—H, —O—(CH$_2$CH$_2$—O)$_{1-30}$—CH$_3$, —C(=O)OH, —C(=O)OC$_1$-C$_4$-alkyl, —C(=O)C$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl, —S(=O)$_2$C$_1$-C$_4$-alkyl, -phenyl, —C(=O)-phenyl, —C(=O)-pyridyl, -thiazolyl, —N-methyldiazolyl, -pyridyl, -pyrimidinyl, and -pyridazinyl; wherein said 3-12-membered cycloalkyl moiety is optionally connected through —C$_1$-C$_6$-alkylene-, linear or branched, saturated or unsaturated, unsubstituted; or
3-12-membered heterocycloalkyl, saturated or unsaturated, unsubstituted or substituted with one, two, three or four substituents independently of one another selected from the group consisting of —F, —Cl, —Br, —I, —CN, =O, —OH, —C$_1$-C$_4$-alkyl, —C$_1$-C$_4$-alkyl-OH, —NH$_2$, —NH—C$_1$-C$_4$-alkyl, —N(C$_1$-C$_4$-alkyl)$_2$, —NHC(=O)—C$_1$-C$_4$-alkyl, —NHS(=O)$_2$—C$_1$-C$_4$-alkyl, —O—C$_1$-C$_4$-alkyl, —O—(CH$_2$CH$_2$—O)$_{1-30}$—H, —O—(CH$_2$CH$_2$—O)$_{1-30}$—CH$_3$, —C(=O)OH, —C(=O)OC$_1$-C$_4$-alkyl, —C(=O)C$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl, —S(=O)$_2$C$_1$-C$_4$-alkyl, -phenyl, —C(=O)-phenyl, —C(=O)-pyridyl, -thiazolyl, —N-methyldiazolyl, -pyridyl, -pyrimidinyl, and -pyridazinyl; wherein said 3-12-membered heterocycloalkyl moiety is optionally connected through —C$_1$-C$_6$-alkylene-, linear or branched, saturated or unsaturated, unsubstituted.

In preferred embodiments, the compound according to the invention has a structure according to any of general formulas (II-A) to (VIII-C):

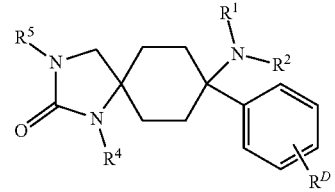
(II-A)

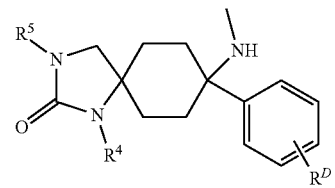
(II-B)

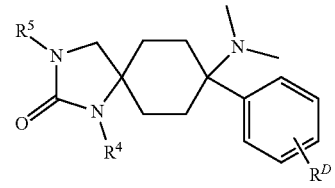
(II-C)

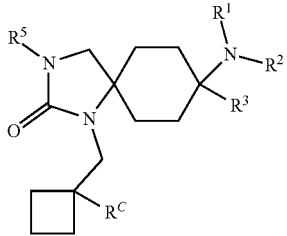
(III-A)

-continued
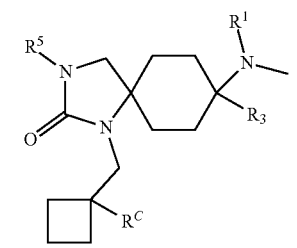
(III-B)
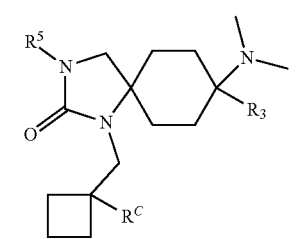
(III-C)
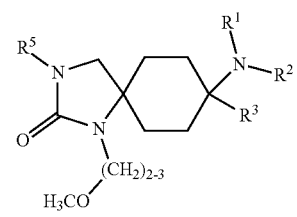
(IV-A)
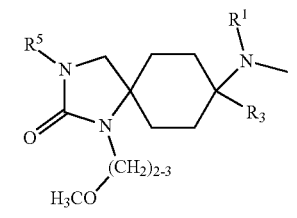
(IV-B)
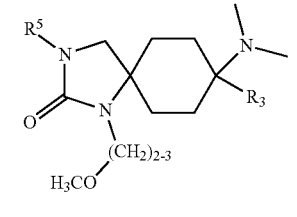
(IV-C)
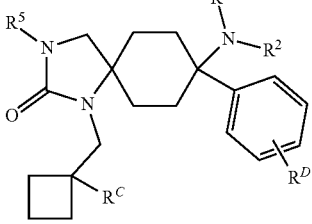
(V-A)
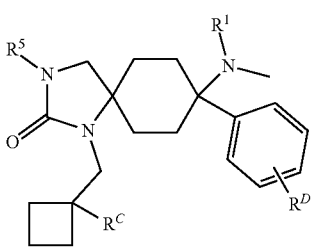
(V-B)
-continued
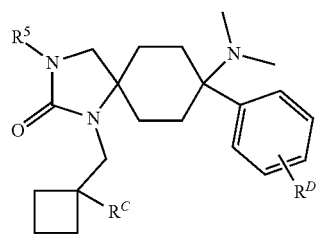
(V-C)
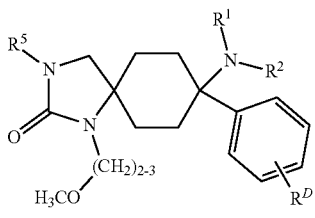
(VI-A)
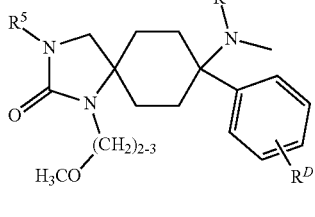
(VI-B)
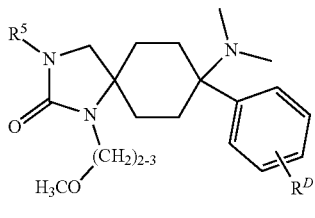
(VI-C)
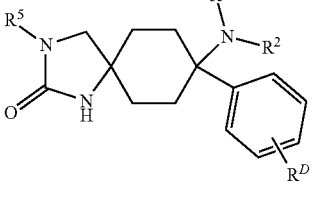
(VII-A)
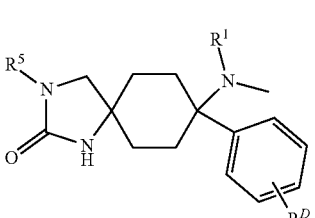
(VII-B)
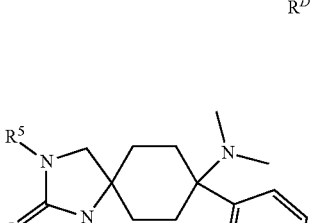
(VII-C)

-continued (VIII-A)

(VIII-B)

(VIII-C)

wherein in each case
R¹, R², R³, R⁴, and R⁵ are defined as above,
$R^C$ means —H, —OH, —F, —CN or —$C_1$-$C_4$-alkyl; preferably —H or —OH;
$R^D$ means —H or —F;
or a physiologically acceptable salt thereof.

Preferably, in the compounds according to general formula (I) or any of the compounds according to general formulas (II-A) to (VIII-C), R⁵ is selected from the group consisting of:

-continued

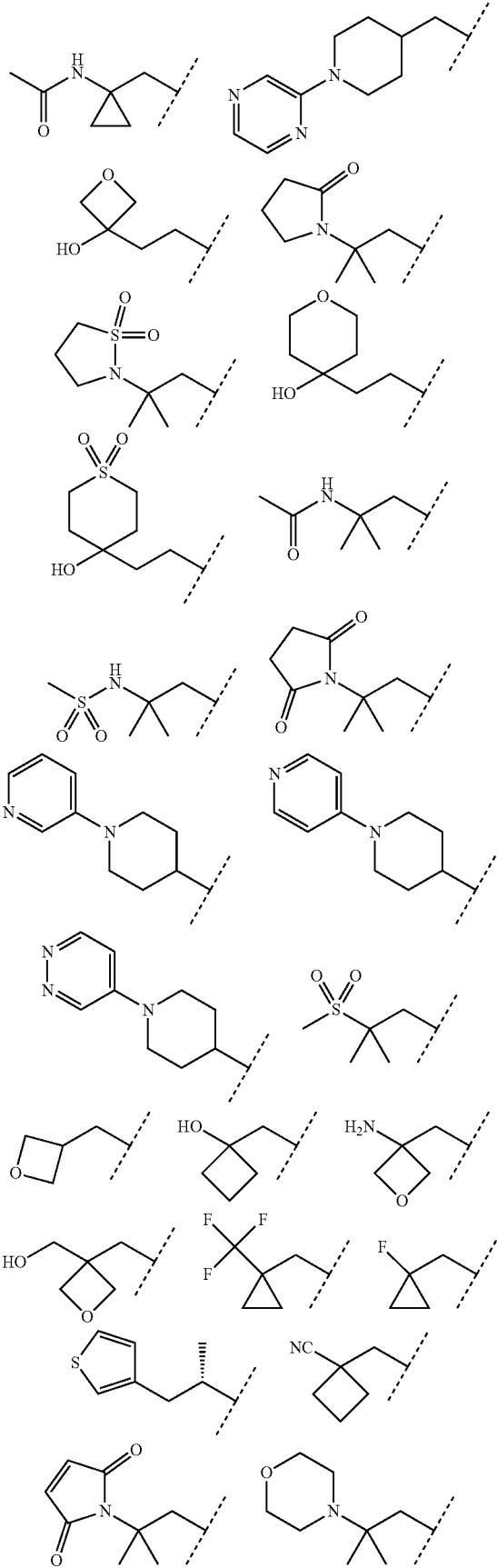
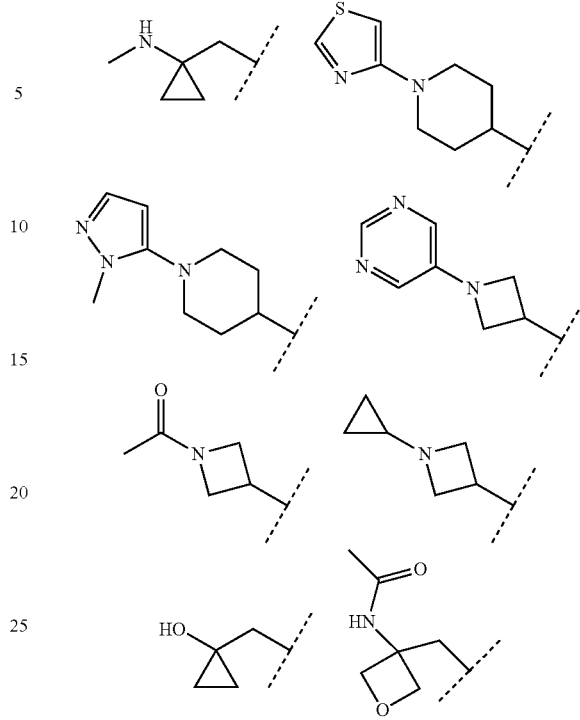

In a particularly preferred embodiment of the compound according to the invention $R^1$ means —H or —$CH_3$;

$R^2$ means —$C_1$-$C_6$-alkyl, linear or branched, saturated, unsubstituted;

$R^3$ means -phenyl, -thienyl or -pyridinyl, in each case unsubstituted or substituted with one, two, three or four substituents independently of one another selected from the group consisting of —F, —Cl, —CN, —$CH_3$, —$CH_2CH_3$, —$CH_2F$, —$CHF_2$, —$CF_3$, —$OCF_3$, —OH, —$OCH_3$, —C(=O)$NH_2$, C(=O)$NHCH_3$, —C(=O)N($CH_3$)$_2$, —$NH_2$, —$NHCH_3$, —N($CH_3$)$_2$, —NHC(=O)$CH_3$, —$CH_2OH$, $SOCH_3$ and $SO_2CH_3$; or $R^4$ means

—H;

—$C_1$-$C_6$-alkyl, linear or branched, saturated, unsubstituted or substituted with one, two, three or four substituents independently of one another selected from the group consisting of —F, —Cl, —Br, —I, —CN, —OH, =O, —S(=O)$_2$—$C_1$-$C_4$-alkyl and —O—$C_1$-$C_4$-alkyl;

3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$C_1$-$C_6$-alkylene;

3-12-membered heterocycloalkyl, saturated or unsaturated, unsubstituted or substituted with one, two, three or four substituents independently of one another selected from the group consisting of —F, —Cl, —Br, —I, —CN, —OH, and —O—$C_1$-$C_4$-alkyl; wherein said 3-12-membered heterocycloalkyl is optionally connected through —$C_1$-$C_6$-alkylene-, unsubstituted or substituted with =O;

6-14-membered aryl, unsubstituted or substituted with one, two, three or four substituents independently of one another selected from the group consisting of —F, —Cl, —Br, —I, —CN, —OH, and —O—$C_1$-$C_4$-alkyl; wherein said 6-14-membered aryl is optionally connected through —$C_1$-$C_6$-alkylene- or —S(=O)$_2$—;

$R^5$ means
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —CN, =O, —OH, —O—$C_1$-$C_4$-alkyl, —O—(CH$_2$CH$_2$—O)$_{1-30}$—H, —O—(CH$_2$CH$_2$—O)$_{1-30}$—CH$_3$, —C(=O)OH, —C(=O)$C_1$-$C_4$-alkyl, —C(=O)O$C_1$-$C_4$-alkyl, —C(=O)NH$_2$, —C(=O)NH$C_1$-$C_4$-alkyl, —C(=O)N($C_1$-$C_4$-alkyl)$_2$, —S(=O)$C_1$-$C_4$-alkyl, —S(=O)$_2$$C_1$-$C_4$-alkyl, —NH$_2$, —NH—$C_1$-$C_4$-alkyl, —N($C_1$-$C_4$-alkyl)$_2$, —NHC(=O)—$C_1$-$C_4$-alkyl, —NH—S(=O)$_2$$C_1$-$C_4$-alkyl; or
3-12-membered heterocycloalkyl, saturated or unsaturated, unsubstituted or substituted with one, two, three or four substituents independently of one another selected from the group consisting of —F, —Cl, —Br, —I, —CN, =O, —OH, —$C_1$-$C_4$-alkyl, —NH$_2$, —NH—$C_1$-$C_4$-alkyl, —N($C_1$-$C_4$-alkyl)$_2$, —NHC(=O)—$C_1$-$C_4$-alkyl, —NHS(=O)$_2$—$C_1$-$C_4$-alkyl, —O—$C_1$-$C_4$-alkyl, —O—(CH$_2$CH$_2$—O)$_{1-30}$—H, —O—(CH$_2$CH$_2$—O)$_{1-30}$—CH$_3$, —C(=O)OH, —C(=O)O$C_1$-$C_4$-alkyl, —C(=O)$C_1$-$C_4$-alkyl, —C(=O)NH$_2$, —C(=O)NH$C_1$-$C_4$-alkyl, —C(=O)N($C_1$-$C_4$-alkyl)$_2$, —S(=O)$C_1$-$C_4$-alkyl, —S(=O)$_2$$C_1$-$C_4$-alkyl, -phenyl, —C(=O)-phenyl, —C(=O)-pyridyl, -pyridyl, -pyrimidinyl, and -pyridazinyl;
wherein said 3-12-membered heterocycloalkyl moiety is optionally connected through —$C_1$-$C_6$-alkylene-, linear or branched, saturated or unsaturated, unsubstituted; and
$R^{11}$, $R^{12}$, $R^{13}$, $R^{14}$, $R^{15}$, $R^{16}$, $R^{17}$, $R^{18}$, $R^{19}$, and $R^{20}$ mean —H.

In a particularly preferred embodiment of the compound according to the invention
$R^1$ means —H or —CH$_3$; and/or
$R^2$ means —$C_1$-$C_6$-alkyl, linear or branched, saturated, unsubstituted; preferably $R^2$ means —CH$_3$ or —CH$_2$CH$_3$; more preferably, $R^1$ and $R^2$ both mean —CH$_3$; and/or
$R^3$ means -phenyl, -thienyl or -pyridinyl, in each case unsubstituted or substituted with one, two, three or four substituents independently of one another selected from the group consisting of —F, —Cl, —CN, —CH$_3$, —CH$_2$CH$_3$, —CH$_2$F, —CHF$_2$, —CF$_3$, —OCF$_3$, —OH, —OCH$_3$, —C(=O)NH$_2$, C(=O)NHCH$_3$, —C(=O)N(CH$_3$)$_2$, —NH$_2$, —NHCH$_3$, —N(CH$_3$)$_2$, —NHC(=O)CH$_3$, —CH$_2$OH, SOCH$_3$ and SO$_2$CH$_3$; preferably, $R^3$ means -phenyl, -thienyl or -pyridinyl, in each case unsubstituted or substituted with —F; more preferably, $R^3$ means phenyl, unsubstituted; and/or
$R^4$ means
—H;
—$C_1$-$C_6$-alkyl, linear or branched, saturated, unsubstituted or substituted with one, two, three or four substituents independently of one another selected from the group consisting of —F, —Cl, —Br, —I, —CN, —OH, and —O—$C_1$-$C_4$-alkyl; or 3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$C_1$-$C_6$-alkylene; preferably, $R^4$ means 3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —CH$_2$— or —CH$_2$CH$_2$—; more preferably, $R^4$ means -cyclobutyl, unsubstituted or monosubstituted with —OH, wherein said -cyclobutyl is connected through —CH$_2$—;

$R^5$ means
—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —O—$C_1$-$C_4$-alkyl, —O—(CH$_2$CH$_2$—O)$_{1-30}$—H, —O—(CH$_2$CH$_2$—O)$_{1-30}$—CH$_3$, —C(=O)OH, —C(=O)O$C_1$-$C_4$-alkyl, —C(=O)NH$_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl; preferably, $R^5$ means —$C_1$-$C_6$-alkyl, linear or branched, saturated or unsaturated, unsubstituted or monosubstituted with —F, —Cl, —Br, —I, —CN, —OH, —O—$C_1$-$C_4$-alkyl, —O—(CH$_2$CH$_2$—O)$_{1-30}$—H, —O—(CH$_2$CH$_2$—O)$_{1-30}$—CH$_3$, —C(=O)NH$_2$, —C(=O)NH$C_1$-$C_4$-alkyl, —C(=O)N($C_1$-$C_4$-alkyl)$_2$, —S(=O)$C_1$-$C_4$-alkyl or —S(=O)$_2$$C_1$-$C_4$-alkyl; or
3-12-membered heterocycloalkyl, saturated or unsaturated, unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —O—(CH$_2$CH$_2$—O)$_{1-30}$—H, —O—(CH$_2$CH$_2$—O)$_{1-30}$—CH$_3$, —C(=O)OH, —C(=O)O$C_1$-$C_4$-alkyl, —C(=O)NH$_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl; wherein said 3-12-membered heterocycloalkyl moiety is optionally connected through —$C_1$-$C_6$-alkylene-, linear or branched, saturated or unsaturated, unsubstituted; preferably, $R^5$ means -oxetanyl, -tetrahydrofuranyl, -tetrahydropyranyl, -piperidinyl, -piperazinyl, -morpholinyl or -thiomorpholinyl, in each case unsubstituted or substituted with one, two, three or four substituents independently of one another selected from the group consisting of —F, —Cl, —Br, —I, —CN, —OH, —$C_1$-$C_4$-alkyl, —O—$C_1$-$C_4$-alkyl, —C(=O)OH, —C(=O)O$C_1$-$C_4$-alkyl, —C(=O)NH$_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl; wherein said -oxetanyl, -tetrahydrofuranyl, -tetrahydropyranyl, -piperidinyl, -piperazinyl, -morpholinyl or -thiomorpholinyl is connected through —CH$_2$— or —CH$_2$CH$_2$—; and
$R^{11}$, $R^{12}$, $R^{13}$, $R^{14}$, $R^{15}$, $R^{16}$, $R^{17}$, $R^{18}$, $R^{19}$, and $R^{20}$ mean —H.

Preferred compounds according to the invention are selected from the group consisting of:

| | |
|---|---|
| SC_4001 | CIS-4-[1-(Cyclobutyl-methyl)-8-dimethylamino-2-oxo-8-phenyl-1,3-diazaspiro[4.5]decan-3-yl]-butyramide |
| SC_4002 | CIS-1-(Cyclobutyl-methyl)-8-dimethylamino-3-[2-[2-[2-[2-(2-methoxy-ethoxy)-ethoxy]-ethoxy]-ethoxy]-ethyl]-8-phenyl-1,3-diazaspiro[4.5]decan-2-one |
| SC_4003 | CIS-1-(Cyclobutyl-methyl)-8-dimethylamino-3-[2-[2-(2-methoxy-ethoxy)-ethoxy]-ethyl]-8-phenyl-1,3-diazaspiro[4.5]decan-2-one |

-continued

| | |
|---|---|
| SC_4004 | CIS-1-(Cyclobutyl-methyl)-8-dimethylamino-3-[2-[2-[2-[2-[2-(2-methoxy-ethoxy)-ethoxy]-ethoxy]-ethoxy]-ethoxy]-ethyl]-8-phenyl-1,3-diazaspiro[4.5]decan-2-one |
| SC_4005 | CIS-1-(Cyclobutyl-methyl)-8-dimethylamino-3-[2-[2-[2-[2-(2-methoxy-ethoxy)-ethoxy]-ethoxy]-ethoxy]-ethyl]-8-phenyl-1,3-diazaspiro[4.5]decan-2-one |
| SC_4006 | CIS-1-(Cyclobutyl-methyl)-8-dimethylamino-3-[2-(2-methoxy-ethoxy)-ethyl]-8-phenyl-1,3-diazaspiro[4.5]decan-2-one |
| SC_4007 | CIS-1-(Cyclobutyl-methyl)-8-dimethylamino-3-(2-methoxy-ethyl)-8-phenyl-1,3-diazaspiro[4.5]decan-2-one |
| SC_4008 | CIS-1-(Cyclobutyl-methyl)-8-dimethylamino-3-[2-[2-[2-(2-methoxy-ethoxy)-ethoxy]-ethoxy]-ethyl]-8-phenyl-1,3-diazaspiro[4.5]decan-2-one |
| SC_4009 | CIS-1-(Cyclobutyl-methyl)-8-dimethylamino-3-(2-methylsulfonyl-ethyl)-8-phenyl-1,3-diazaspiro[4.5]decan-2-one |
| SC_4010 | CIS-1-(Cyclobutyl-methyl)-8-methylamino-3-(2-methylsulfonyl-ethyl)-8-phenyl-1,3-diazaspiro[4.5]decan-2-one |
| SC_4011 | CIS-8-Dimethylamino-1-[(1-hydroxy-cyclobutyl)-methyl]-3-(2-methylsulfonyl-ethyl)-8-phenyl-1,3-diazaspiro[4.5]decan-2-one |
| SC_4012 | CIS-4-[1-(Cyclobutyl-methyl)-8-dimethylamino-2-oxo-8-phenyl-1,3-diazaspiro[4.5]decan-3-yl]-butyronitrile |
| SC_4013 | CIS-4-[1-(Cyclobutyl-methyl)-8-dimethylamino-2-oxo-8-phenyl-1,3-diazaspiro[4.5]decan-3-yl]-N-methyl-butyramide |
| SC_4014 | CIS-3-[1-(Cyclobutyl-methyl)-8-dimethylamino-2-oxo-8-phenyl-1,3-diazaspiro[4.5]decan-3-yl]-2,2-dimethyl-propionitrile |
| SC_4017 | CIS-1-(Cyclobutyl-methyl)-8-dimethylamino-3-[2-[2-[2-[2-[2-[2-(2-methoxy-ethoxy)-ethoxy]-ethoxy]-ethoxy]-ethoxy]-ethoxy]-ethyl]-8-phenyl-1,3-diazaspiro[4.5]decan-2-one |
| SC_4018 | CIS-1-(Cyclobutyl-methyl)-8-dimethylamino-3-methyl-8-phenyl-1,3-diazaspiro[4.5]decan-2-one |
| SC_4021 | CIS-1-[(1-Hydroxy-cyclobutyl)-methyl]-8-methylamino-3-(2-methylsulfonyl-ethyl)-8-phenyl-1,3-diazaspiro[4.5]decan-2-one |
| SC_4022 | CIS-3-[1-[(1-Hydroxy-cyclobutyl)-methyl]-8-methylamino-2-oxo-8-phenyl-1,3-diazaspiro[4.5]decan-3-yl]-propionitrile |
| SC_4024 | CIS-2-[1-[(1-Hydroxy-cyclobutyl)-methyl]-8-methylamino-2-oxo-8-phenyl-1,3-diazaspiro[4.5]decan-3-yl]-acetonitrile |
| SC_4025 | CIS-8-Dimethylamino-1-[(1-hydroxy-cyclobutyl)-methyl]-8-phenyl-3-(tetrahydro-pyran-4-yl-methyl)-1,3-diazaspiro[4.5]decan-2-one |
| SC_4026 | CIS-8-Dimethylamino-1-[(1-hydroxy-cyclobutyl)-methyl]-3-(2-morpholin-4-yl-ethyl)-8-phenyl-1,3-diazaspiro[4.5]decan-2-one |
| SC_4027 | CIS-3-(3-Chloro-propyl)-1-(cyclobutyl-methyl)-8-dimethylamino-8-phenyl-1,3-diazaspiro[4.5]decan-2-one |
| SC_4028 | CIS-4-[1-(Cyclobutyl-methyl)-8-dimethylamino-2-oxo-8-phenyl-1,3-diazaspiro[4.5]decan-3-yl]-butyric acid methyl ester |
| SC_4029 | CIS-3-[8-Dimethylamino-1-[(1-hydroxy-cyclobutyl)-methyl]-2-oxo-8-phenyl-1,3-diazaspiro[4.5]decan-3-yl]-propionitrile |
| SC_4030 | CIS-2-[8-Dimethylamino-1-[(1-hydroxy-cyclobutyl)-methyl]-2-oxo-8-phenyl-1,3-diazaspiro[4.5]decan-3-yl]-acetonitrile |
| SC_4031 | CIS-3-Acetyl-8-dimethylamino-8-phenyl-1,3-diazaspiro[4.5]decan-2-one |
| SC_4032 | CIS-8-Dimethylamino-3-(2-methylsulfonyl-ethyl)-8-phenyl-1,3-diazaspiro[4.5]decan-2-one |
| SC_4033 | CIS-1-Acetyl-8-dimethylamino-8-phenyl-1,3-diazaspiro[4.5]decan-2-one |
| SC_4034 | CIS-1-(Cyclopropyl-methyl)-8-dimethylamino-3-(2-methylsulfonyl-ethyl)-8-phenyl-1,3-diazaspiro[4.5]decan-2-one |
| SC_4035 | CIS-8-Dimethylamino-3-(2-methylsulfonyl-ethyl)-1-(oxetan-3-yl-methyl)-8-phenyl-1,3-diazaspiro[4.5]decan-2-one |
| SC_4036 | CIS-8-Dimethylamino-1-(3-methoxy-propyl)-3-(2-methylsulfonyl-ethyl)-8-phenyl-1,3-diazaspiro[4.5]decan-2-one |
| SC_4037 | CIS-8-Dimethylamino-8-phenyl-1-(p-tolylsulfonyl)-1,3-diazaspiro[4.5]decan-2-one |
| SC_4038 | CIS-8-Dimethylamino-3-[(1,1-dioxo-thian-4-yl)-methyl]-1-[(1-hydroxy-cyclobutyl)-methyl]-8-phenyl-1,3-diazaspiro[4.5]decan-2-one |
| SC_4039 | CIS-1-(Cyclobutyl-methyl)-8-dimethylamino-3-[(4-hydroxy-tetrahydro-pyran-4-yl)-methyl]-8-phenyl-1,3-diazaspiro[4.5]decan-2-one |
| SC_4040 | CIS-1-(Cyclopropyl-methyl)-8-dimethylamino-8-phenyl-3-tetrahydro-pyran-4-yl-1,3-diazaspiro[4.5]decan-2-one |
| SC_4041 | CIS-1-(Cyclobutyl-methyl)-8-dimethylamino-3-[(4-hydroxy-1,1-dioxo-thian-4-yl)-methyl]-8-phenyl-1,3-diazaspiro[4.5]decan-2-one |
| SC_4042 | CIS-8-Dimethylamino-1-[(1-hydroxy-cyclobutyl)-methyl]-8-phenyl-3-tetrahydro-pyran-4-yl-1,3-diazaspiro[4.5]decan-2-one |
| SC_4043 | CIS-1-[[8-Dimethylamino-3-(2-methylsulfonyl-ethyl)-2-oxo-8-phenyl-1,3-diazaspiro[4.5]decan-1-yl]-methyl]-cyclobutane-1-carbonitrile |
| SC_4044 | CIS-8-Dimethylamino-1-[(1-hydroxy-cyclobutyl)-methyl]-3-[(4-hydroxy-tetrahydro-pyran-4-yl)-methyl]-8-phenyl-1,3-diazaspiro[4.5]decan-2-one |
| SC_4045 | CIS-8-Dimethylamino-1-[(1-hydroxy-cyclobutyl)-methyl]-3-[(4-hydroxy-1,1-dioxo-thian-4-yl)-methyl]-8-phenyl-1,3-diazaspiro[4.5]decan-2-one |
| SC_4046 | CIS-1-(Cyclopropyl-methyl)-8-dimethylamino-3-(1,1-dioxo-thian-4-yl)-8-phenyl-1,3-diazaspiro[4.5]decan-2-one |
| SC_4047 | CIS-8-Dimethylamino-3-(1,1-dioxo-thian-4-yl)-1-[(1-hydroxy-cyclobutyl)-methyl]-8-phenyl-1,3-diazaspiro[4.5]decan-2-one |
| SC_4048 | CIS-3-(1-Acetyl-piperidin-4-yl)-1-(cyclopropyl-methyl)-8-dimethylamino-8-phenyl-1,3-diazaspiro[4.5]decan-2-one |

-continued

| | |
|---|---|
| SC_4049 | CIS-3-(1-Benzoyl-piperidin-4-yl)-1-(cyclopropyl-methyl)-8-dimethylamino-8-phenyl-1,3-diazaspiro[4.5]decan-2-one |
| SC_4050 | CIS-1-(Cyclopropyl-methyl)-8-dimethylamino-8-phenyl-3-[1-(pyridine-4-carbonyl)-piperidin-4-yl]-1,3-diazaspiro[4.5]decan-2-one |
| SC_4051 | CIS-1-(Cyclopropyl-methyl)-8-dimethylamino-3-[(4-hydroxy-tetrahydro-pyran-4-yl)-methyl]-8-phenyl-1,3-diazaspiro[4.5]decan-2-one |
| SC_4052 | CIS-1-(Cyclobutyl-methyl)-8-dimethylamino-3-[2-(4-hydroxy-tetrahydro-pyran-4-yl)-ethyl]-8-phenyl-1,3-diazaspiro[4.5]decan-2-one |
| SC_4053 | CIS-3-[(1-Acetyl-piperidin-4-yl)-methyl]-1-(cyclopropyl-methyl)-8-dimethylamino-8-phenyl-1,3-diazaspiro[4.5]decan-2-one |
| SC_4054 | CIS-1-(Cyclopropyl-methyl)-8-dimethylamino-8-phenyl-3-piperidin-4-yl-1,3-diazaspiro[4.5]decan-2-one |
| SC_4055 | CIS-1-(Cyclopropyl-methyl)-8-dimethylamino-3-(2-hydroxy-2-methyl-propyl)-8-phenyl-1,3-diazaspiro[4.5]decan-2-one |
| SC_4056 | CIS-1-(Cyclopropyl-methyl)-8-dimethylamino-8-phenyl-3-(1-pyrimidin-5-yl-pipendin-4-yl)-1,3-diazaspiro[4.5]decan-2-one |
| SC_4057 | CIS-1-(Cyclopropyl-methyl)-8-dimethylamino-8-phenyl-3-(1-phenyl-piperidin-4-yl)-1,3-diazaspiro[4.5]decan-2-one |
| SC_4058 | CIS-1-(Cyclopropyl-methyl)-8-dimethylamino-8-phenyl-3-(piperidin-4-yl-methyl)-1,3-diazaspiro[4.5]decan-2-one |
| SC_4059 | CIS-3-(1-Benzoyl-piperidin-4-yl)-8-dimethylamino-8-phenyl-1,3-diazaspiro[4.5]decan-2-one |
| SC_4060 | CIS-8-Dimethylamino-8-phenyl-3-[1-(pyridine-4-carbonyl)-piperidin-4-yl]-1,3-diazaspiro[4.5]decan-2-one |
| SC_4061 | CIS-3-(1-Acetyl-piperidin-4-yl)-8-dimethylamino-8-phenyl-1,3-diazaspiro[4.5]decan-2-one |
| SC_4062 | CIS-1-(Cyclopropyl-methyl)-8-dimethylamino-3-[(4-hydroxy-1,1-dioxo-thian-4-yl)-methyl]-8-phenyl-1,3-diazaspiro[4.5]decan-2-one |
| SC_4063 | CIS-8-Dimethylamino-1-[(1-hydroxy-cyclobutyl)-methyl]-3-(2-hydroxy-2-methyl-propyl)-8-phenyl-1,3-diazaspiro[4.5]decan-2-one |
| SC_4064 | CIS-3-[(1-Amino-cyclopropyl)-methyl]-1-(cyclopropyl-methyl)-8-dimethylamino-8-phenyl-1,3-diazaspiro[4.5]decan-2-one |
| SC_4066 | CIS-8-Dimethylamino-1,3-bis(2-methylsulfonyl-ethyl)-8-phenyl-1,3-diazaspiro[4.5]decan-2-one |
| SC_4067 | CIS-N-[1-[[1-(Cyclopropyl-methyl)-8-dimethylamino-2-oxo-8-phenyl-1,3-diazaspiro[4.5]decan-3-yl]-methyl]-cyclopropyl]-acetamide |
| SC_4068 | CIS-1-(Cyclopropyl-methyl)-8-dimethylamino-8-phenyl-3-[(1-pyrimidin-5-yl-pipendm-4-yl)-methyl]-1,3-diazaspiro[4.5]decan-2-one |
| SC_4069 | CIS-8-Dimethylamino-8-phenyl-3-[(1-pyrimidin-5-yl-piperidin-4-yl)-methyl]-1,3-diazaspiro[4.5]decan-2-one |
| SC_4070 | CIS-8-Dimethylamino-8-phenyl-3-(1-pyrimidin-5-yl-piperidin-4-yl)-1,3-diazaspiro[4.5]decan-2-one |
| SC_4071 | CIS-1-(Cyclobutyl-methyl)-8-dimethylamino-3-[2-(3-hydroxy-oxetan-3-yl)-ethyl]-8-phenyl-1,3-diazaspiro[4.5]decan-2-one |
| SC_4072 | CIS-1-(Cyclopropyl-methyl)-8-dimethylamino-3-[2-methyl-2-(2-oxo-pyrrolidin-1-yl)-propyl]-8-phenyl-1,3-diazaspiro[4.5]decan-2-one |
| SC_4073 | CIS-1-(Cyclopropyl-methyl)-8-dimethylamino-3-[2-(1,1-dioxo-[1,2]thiazolidin-2-yl)-2-methyl-propyl]-8-phenyl-1,3-diazaspiro[4.5]decan-2-one |
| SC_4074 | CIS-8-Dimethylamino-1-[(1-hydroxy-cyclobutyl)-methyl]-3-[2-(4-hydroxy-tetrahydro-pyran-4-yl)-ethyl]-8-phenyl-1,3-diazaspiro[4.5]decan-2-one |
| SC_4075 | CIS-1-(Cyclobutyl-methyl)-8-dimethylamino-3-[2-(4-hydroxy-1,1-dioxo-thian-4-yl)-ethyl]-8-phenyl-1,3-diazaspiro[4.5]decan-2-one |
| SC_4076 | CIS-3-[(1-Acetyl-piperidin-4-yl)-methyl]-8-dimethylamino-8-phenyl-1,3-diazaspiro[4.5]decan-2-one |
| SC_4077 | CIS-8-Dimethylamino-3-(2-methylsulfonyl-ethyl)-1-(2-oxo-2-pyrrolidin-1-yl-ethyl)-8-phenyl-1,3-diazaspiro[4.5]decan-2-one |
| SC_4078 | TRANS-8-Dimethylamino-3-(2-methylsulfonyl-ethyl)-8-phenyl-1,3-diazaspiro[4.5]decan-2-one |
| SC_4079 | CIS-8-Dimethylamino-1-[(1-hydroxy-cyclobutyl)-methyl]-3-[2-(4-hydroxy-1,1-dioxo-thian-4-yl)-ethyl]-8-phenyl-1,3-diazaspiro[4.5]decan-2-one |
| SC_4080 | CIS-8-Dimethylamino-8-phenyl-3-(1-phenyl-piperidin-4-yl)-1,3-diazaspiro[4.5]decan-2-one |
| SC_4081 | CIS-N-[2-[1-(Cyclopropyl-methyl)-8-dimethylamino-2-oxo-8-phenyl-1,3-diazaspiro[4.5]decan-3-yl]-1,1-dimethyl-ethyl]-acetamide |
| SC_4082 | CIS-N-[2-[1-(Cyclopropyl-methyl)-8-dimethylamino-2-oxo-8-phenyl-1,3-diazaspiro[4.5]decan-3-yl]-1,1-dimethyl-ethyl]-methanesulfonic acid amide |
| SC_4083 | CIS-8-Dimethylamino-1-[(1-hydroxy-cyclobutyl)-methyl]-3-[2-(3-hydroxy-oxetan-3-yl)-ethyl]-8-phenyl-1,3-diazaspiro[4.5]decan-2-one |
| SC_4084 | CIS-1-[2-[1-(Cyclopropyl-methyl)-8-dimethylamino-2-oxo-8-phenyl-1,3-diazaspiro[4.5]decan-3-yl]-1,1-dimethyl-ethyl]-pyrrolidine-2,5-dione |
| SC_4085 | CIS-N-[2-[8-Dimethylamino-1-[(1-hydroxy-cyclobutyl)-methyl]-2-oxo-8-phenyl-1,3-diazaspiro[4.5]decan-3-yl]-1,1-dimethyl-ethyl]-acetamide |
| SC_4086 | CIS-N-[2-[8-Dimethylamino-1-[(1-hydroxy-cyclobutyl)-methyl]-2-oxo-8-phenyl-1,3-diazaspiro[4.5]decan-3-yl]-1,1-dimethyl-ethyl]-methanesulfonic acid amide |
| SC_4087 | CIS-1-(Cyclopropyl-methyl)-8-dimethylamino-8-phenyl-3-(1-pyridin-3-yl-pipendin-4-yl)-1,3-diazaspiro[4.5]decan-2-one |
| SC_4088 | CIS-1-(Cyclopropyl-methyl)-8-dimethylamino-8-(3-fluorophenyl)-3-(2-methylsulfonyl-ethyl)-1,3-diazaspiro[4.5]decan-2-one |

| | |
|---|---|
| SC_4089 | CIS-1-(Cyclopropyl-methyl)-8-dimethylamino-8-phenyl-3-(1-pyridin-4-yl-pipendin-4-yl)-1,3-diazaspiro[4.5]decan-2-one |
| SC_4090 | CIS-8-Dimethylamino-1-[(1-hydroxy-cyclobutyl)-methyl]-3-[2-methyl-2-(2-oxo-pyrrolidin-1-yl)-propyl]-8-phenyl-1,3-diazaspiro[4.5]decan-2-one |
| SC_4091 | CIS-1-(Cyclobutyl-methyl)-8-dimethylamino-3-(2-methyl-2-methylsulfonyl-propyl)-8-phenyl-1,3-diazaspiro[4.5]decan-2-one |
| SC_4092 | TRANS-1-(Cyclobutyl-methyl)-8-dimethylamino-3-(2-methyl-2-methylsulfonyl-propyl)-8-phenyl-1,3-diazaspiro[4.5]decan-2-one |
| SC_4093 | CIS-8-Dimethylamino-3-[2-(1,1-dioxo-[1,2]thiazolidin-2-yl)-2-methyl-propyl]-1-[(1-hydroxy-cyclobutyl)-methyl]-8-phenyl-1,3-diazaspiro[4.5]decan-2-one |
| SC_4094 | CIS-1-(Cyclopropyl-methyl)-8-dimethylamino-8-(3-fluorophenyl)-3-[(4-hydroxy-tetrahydro-pyran-4-yl)-methyl]-1,3-diazaspiro[4.5]decan-2-one |
| SC_4095 | CIS-8-Dimethylamino-1-[(1-hydroxy-cyclobutyl)-methyl]-8-phenyl-3-(1-pyrimidin-5-yl-piperidin-4-yl)-1,3-diazaspiro[4.5]decan-2-one |
| SC_4096 | CIS-1-(Cyclopropyl-methyl)-8-dimethylamino-8-phenyl-3-(1-pyridazin-4-yl-pipendrin-4-yl)-1,3-diazaspiro[4.5]decan-2-one |
| SC_4097 | CIS-2-[8-Dimethylamino-3-(2-methylsulfonyl-ethyl)-2-oxo-8-phenyl-1,3-diazaspiro[4.5]decan-1-yl]-N,N-dimethyl-acetamide |
| SC_4098 | TRANS-8-Dimethylamino-1-[(1-hydroxy-cyclobutyl)-methyl]-3-(2-methylsulfonyl-ethyl)-8-phenyl-1,3-diazaspiro[4.5]decan-2-one |
| SC_4099 | CIS-1-(Cyclopropyl-methyl)-8-dimethylamino-8-(3-fluorophenyl)-3-(1-pyrimidin-5-yl-piperidin-4-yl)-1,3-diazaspiro[4.5]decan-2-one |
| SC_4100 | CIS-1-(cyclopropylmethyl)-8-(3-fluorophenyl)-8-(methylamino)-3-(2-(methylsulfonyl)ethyl)-1,3-diazaspiro[4.5]decan-2-one |
| SC_4101 | CIS-1-(cyclopropylmethyl)-8-(dimethylamino)-3-((1-hydroxycyclobutyl)methyl)-8-phenyl-1,3-diazaspiro[4.5]decan-2-one |
| SC_4102 | CIS-8-(dimethylamino)-8-(3-fluorophenyl)-3-((4-hydroxy-1,1-dioxidotetrahydro-2H-thiopyran-4-yl)methyl)-1-((1-hydroxycyclobutyl)methyl)-1,3-diazaspiro[4.5]decan-2-one |
| SC_4103 | CIS-8-(dimethylamino)-8-(3-fluorophenyl)-1-((1-hydroxycyclobutyl)methyl)-3-((4-hydroxytetrahydro-2H-pyran-4-yl)methyl)-1,3-diazaspiro[4.5]decan-2-one |
| SC_4104 | CIS-1-(cyclopropylmethyl)-8-(dimethylamino)-8-(3-fluorophenyl)-3-((4-hydroxy-1,1-dioxidotetrahydro-2H-thiopyran-4-yl)methyl)-1,3-diazaspiro[4.5]decan-2-one |
| SC_4105 | CIS-1-(cyclopropylmethyl)-8-(dimethylamino)-3-(oxetan-3-ylmethyl)-8-phenyl-1,3-diazaspiro[4.5]decan-2-one |
| SC_4106 | CIS-8-(dimethylamino)-8-phenyl-3-((S)-1-(thiophen-3-yl)propan-2-yl)-1,3-diazaspiro[4.5]decan-2-one |
| SC_4107 | CIS-8-(dimethylamino)-8-phenyl-1,3-bis((1-(trifluoromethyl)cyclopropyl)methyl)-1,3-diazaspiro[4.5]decan-2-one |
| SC_4108 | CIS-8-(dimethylamino)-1,3-bis((1-fluorocyclopropyl)methyl)-8-phenyl-1,3-diazaspiro[4.5]decan-2-one |
| SC_4109 | CIS-1-(cyclopropylmethyl)-8-(dimethylamino)-3-((3-(hydroxymethyl)oxetan-3-yl)methyl)-8-phenyl-1,3-diazaspiro[4.5]decan-2-one |
| SC_4110 | CIS-3-((3-aminooxetan-3-yl)methyl)-1-(cyclopropylmethyl)-8-(dimethylamino)-8-phenyl-1,3-diazaspiro[4.5]decan-2-one |
| SC_4111 | CIS-1-((1-(cyclopropylmethyl)-8-(dimethylamino)-2-oxo-8-phenyl-1,3-diazaspiro[4.5]decan-3-yl)methyl)cyclobutanecarbonitrile |
| SC_4112 | CIS-3-(8-(dimethylamino)-1-((1-fluorocyclopropyl)methyl)-2-oxo-8-phenyl-1,3-diazaspiro[4.5]decan-3-yl)-2,2-dimethylpropanenitrile |
| SC_5061 | CIS-3-[8-(Ethyl-methyl-amino)-2-oxo-8-phenyl-1,3-diazaspiro[4.5]decan-3-yl]-2,2-dimethyl-propionitrile |
| SC_5062 | CIS-3-(8-Dimethylamino-2-oxo-8-phenyl-1,3-diazaspiro[4.5]decan-3-yl)-2,2-dimethyl-propionitrile |
| SC_5063 | CIS-2,2-Dimethyl-3-(8-methylamino-2-oxo-8-phenyl-1,3-diazaspiro[4.5]decan-3-yl)-propionitrile |
| SC_5065 | CIS-3-[8-(Ethyl-methyl-amino)-1-methyl-2-oxo-8-phenyl-1,3-diazaspiro[4.5]decan-3-yl]-2,2-dimethyl-propionitrile |
| SC_5068 | CIS-3-(8-Ethylamino-2-oxo-8-phenyl-1,3-diazaspiro[4.5]decan-3-yl)-2,2-dimethyl-propionitrile |
| SC_5075 | CIS-3-[1-(Cyclopropyl-methyl)-8-dimethylamino-2-oxo-8-phenyl-1,3-diazaspiro[4.5]decan-3-yl]-2,2-dimethyl-propionitrile |
| SC_5080 | TRANS-3-[1-(Cyclopropyl-methyl)-8-dimethylamino-2-oxo-8-phenyl-1,3-diazaspiro[4.5]decan-3-yl]-2,2-dimethyl-propionitrile | and the physiologically acceptable salts thereof.

According to the invention, unless expressly stated otherwise, "—$C_1$-$C_4$-alkyl", "—$C_1$-$C_6$-alkyl" and any other alkyl residues can be linear or branched, saturated or unsaturated. Linear saturated alkyl includes methyl, ethyl, n-propyl, n-butyl, n-pentyl and n-hexyl. Examples of branched saturated alkyl include but are not limited to iso-propyl, sec-butyl, and tert-butyl. Examples of linear unsaturated alkyl include but are not limited to vinyl, propenyl, allyl, and propargyl.

According to the invention, unless expressly stated otherwise, "—$C_1$-$C_4$-alkyl", "—$C_1$-$C_6$-alkyl" and any other alkyl residues can be unsubstituted, mono- or polysubstituted. Examples of substituted alkyl include but are not limited to —$CH_2CH_2OH$, —$CH_2CH_2OCH_3$, —$CH_2CH_2CH_2OCH_3$, —$CH_2CH_2S(=O)_2CH_3$, —$CH_2C(=O)NH_2$, —$C(CH_3)_2C(=O)NH_2$, —$CH_2C(CH_3)_2C(=O)NH_2$, and —$CH_2CH_2C(=O)N(CH_3)_2$.

According to the invention, unless expressly stated otherwise, "—$C_1$-$C_6$-alkylene-", "—$C_1$-$C_4$-alkylene" and any other alkylene residue can be unsubstituted, mono- or polysubstituted. Examples of saturated alkylene include but are not limited to —$CH_2$—, —$CH(CH_3)$—, —$C(CH_3)_2$—, —$CH_2CH_2$—, —$CH(CH_3)CH_2$—, —$CH_2CH(CH_3)$—, —CH(CH$_3$)—CH(CH$_3$)—, —C(CH$_3$)$_2$CH$_2$—, —CH$_2$C(CH$_3$)$_2$—, —CH(CH$_3$)C(CH$_3$)$_2$—, —C(CH$_3$)$_2$CH(CH$_3$)—, C(CH$_3$)$_2$C(CH$_3$)$_2$—, —CH$_2$CH$_2$CH$_2$—, and —C(CH$_3$)$_2$CH$_2$CH$_2$—. Examples of unsaturated alkylene include but are not limited to —CH═CH—, —C≡C—, —C(CH$_3$)═CH—, —CH═C(CH$_3$)—, —C(CH$_3$)═C(CH$_3$)—, —CH$_2$CH═CH—, —CH═CHCH$_2$—, —CH═CH—CH═CH—, and —CH═CH—C≡C—.

According to the invention, unless expressly stated otherwise, "—C$_1$-C$_6$-alkylene-", "—C$_1$-C$_4$-alkylene" and any other alkylene residue can be unsubstituted, mono- or polysubstituted. Examples of substituted —C$_1$-C$_6$-alkylene- include but are not limited to —CHF—, —CF$_2$—, —CHOH— and —C(═O)—.

According to the invention, moieties may be connected through —C$_1$-C$_6$-alkylene-, i.e. the moieties may not be directly bound to the core structure of compound according to general formula (I), but may be connected to the core structure of compound according to general formula (I) or its periphery through a —C$_1$-C$_6$-alkylene- linker.

According to the invention, "3-12-membered cycloalkyl moiety" means a non-aromatic, monocyclic, bicyclic or tricyclic moiety comprising 3 to 12 ring carbon atoms but no heteroatoms in the ring. Examples of preferred saturated 3-12-membered cycloalkyl moieties according to the invention include but are not limited to cyclopropane, cyclobutane, cyclopentane, cyclohexane, cycloheptane, cyclooctane, hydrindane, and decaline. Examples of preferred unsaturated 3-12-membered cycloalkyl moiety moieties according to the invention include but are not limited to cyclopropene, cyclobutene, cyclopentene, cyclopentadiene, cyclohexene, 1,3-cyclohexadiene, and 1,4-cyclohexadiene. The 3-12-membered cycloalkyl moiety, which is bonded to the compound according to the invention, in its periphery may optionally be condensed with a 3-12-membered heterocycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered cycloalkyl moiety. Examples of 3-12-membered cycloalkyl moieties condensed with 3-12-membered heterocycloalkyl moieties include but are not limited to octahydro-1H-indol, decahydroquinoline, decahydroisoquinoline, octahydro-2H-benzo[b][1,4]oxazin, and decahydroquinoxalin, which in each case are connected through the 3-12-membered cycloalkyl moiety. Examples of 3-12-membered cycloalkyl moieties condensed with 6-14-membered aryl moieties include but are not limited to 2,3-dihydro-1H-indene and tetraline, which in each case are connected through the 3-12-membered cycloalkyl moiety. Examples of 3-12-membered cycloalkyl moieties condensed with 5-14-membered heteroaryl moieties include but are not limited to 5,6,7,8-tetrahydroquinoline and 5,6,7,8-tetrahydroquinazoline, which in each case are connected through the 3-12-membered cycloalkyl moiety.

According to the invention, the 3-12-membered cycloalkyl moiety may optionally be connected through —C$_1$-C$_6$-alkylene-, i.e. the 3-12-membered cycloalkyl moiety may not be directly bound to the compound according to general formula (I) but may be connected thereto through a —C$_1$-C$_6$-alkylene- linker. Examples include but are not limited to —CH$_2$-cyclopropyl, —CH$_2$-cyclobutyl, —CH$_2$-cyclopentyl, —CH$_2$-cyclohexyl, —CH$_2$CH$_2$-cyclopropyl, —CH$_2$CH$_2$-cyclobutyl, —CH$_2$CH$_2$-cyclopentyl, and —CH$_2$CH$_2$-cyclohexyl.

According to the invention, unless expressly stated otherwise, the 3-12-membered cycloalkyl moiety can be unsubstituted, mono- or polysubstituted. Examples of substituted 3-12-membered cycloalkyl moieties include but are not limited to —CH$_2$—1-hydroxy-cyclobutyl.

According to the invention, "3-12-membered heterocycloalkyl moiety" means a non-aromatic, monocyclic, bicyclic or tricyclic moiety comprising 3 to 12 ring atoms, wherein each cycle comprises independently of one another 1, 2, 3, 4 or more heteroatoms independently of one another selected from the group consisting of nitrogen, oxygen and sulfur, whereas sulfur may be oxidized (S(═O) or (S(═O)$_2$), whereas the remaining ring atoms are carbon atoms, and whereas bicyclic or tricyclic systems may share common heteroatom(s). Examples of preferred saturated 3-12-membered heterocycloalkyl moieties according to the invention include but are not limited to aziridin, azetidine, pyrrolidine, imidazolidine, pyrazolidine, piperidine, piperazine, triazolidine, tetrazolidine, oxiran, oxetane, tetrahydrofurane, tetrahydropyrane, thiirane, thietane, tetrahydrothiophene, diazepane, oxazolidine, isoxazolidine, thiazolidine, isothiazolidine, thiadiazolidine, morpholine, thiomorpholine. Examples of preferred unsaturated 3-12-membered heterocycloalkyl moiety moieties according to the invention include but are not limited to oxazoline, pyrazoline, imidazoline, isoxazoline, thiazoline, isothiazoline, and dihydropyran. The 3-12-membered heterocycloalkyl moiety, which is bonded to the compound according to the invention, in its periphery may optionally be condensed with a 3-12-membered cycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered heterocycloalkyl moieties. Examples of 3-12-membered heterocycloalkyl moieties condensed with 3-12-membered cycloalkyl moieties include but are not limited to octahydro-1H-indol, decahydroquinoline, decahydroisoquinoline, octahydro-2H-benzo[b][1,4]oxazin, and decahydroquinoxalin, which in each case are connected through the 3-12-membered heterocycloalkyl moiety. An examples of a 3-12-membered heterocycloalkyl moiety condensed with a 6-14-membered aryl moiety includes but is not limited to 1,2,3,4-tetrahydroquinoline, which is connected through the 3-12-membered heterocycloalkyl moiety. An example of a 3-12-membered heterocycloalkyl moiety condensed with a 5-14-membered heteroaryl moieties includes but is not limited to 5,6,7,8-tetrahydro-[1,2,4]triazolo[1,5-a]pyrazine, which is connected through the 3-12-membered heterocycloalkyl moiety.

According to the invention, the 3-12-membered heterocycloalkyl moiety may optionally be connected through —C$_1$-C$_6$-alkylene-, i.e. the 3-12-membered heterocycloalkyl moiety may not be directly bound to the compound according to general formula (I) but may be connected thereto through a —C$_1$-C$_6$-alkylene- linker. Said linker may be connected to a carbon ring atom or to a hetero ring atom of the 3-12-membered heterocycloalkyl moiety. Examples include but are not limited to —CH$_2$-oxetane, —CH$_2$-pyrrolidine, —CH$_2$-piperidine, —CH$_2$-morpholine, —CH$_2$CH$_2$-oxetane, —CH$_2$CH$_2$-pyrrolidine, —CH$_2$CH$_2$-piperidine, and —CH$_2$CH$_2$-morpholine.

According to the invention, unless expressly stated otherwise, the 3-12-membered heterocycloalkyl moiety can be unsubstituted, mono- or polysubstituted. Examples of substituted 3-12-membered heterocycloalkyl moieties include but are not limited to 2-carboxamido-N-pyrrolidinyl-, 3,4-dihydroxy-N-pyrrolidinyl, 3-hydroxy-N-pyrimidinyl, 3,4-dihydroxy-N-pyrimidinyl, 3-oxo-N-piperazinyl, -tetrahydro-2H-thiopyranyl dioxide and thiomorpholinyl dioxide.

According to the invention, "6-14-membered aryl moiety" means an aromatic, monocyclic, bicyclic or tricyclic moiety comprising 6 to 14 ring carbon atoms but no heteroatoms in the ring. Examples of preferred 6-14-membered aryl moieties according to the invention include but are not limited to benzene, naphthalene, anthracen, and phenanthren. The 6-14-membered aryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 5-14-membered heteroaryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 6-14-membered aryl moieties condensed with 3-12-membered cycloalkyl moieties include but are not limited to 2,3-dihydro-1H-indene and tetraline, which in each case are connected through the 6-14-membered aryl moiety. An example of a 6-14-membered aryl moiety condensed with a 3-12-membered heterocycloalkyl moiety includes but is not limited to 1,2,3,4-tetrahydroquinoline, which is connected through the 6-14-membered aryl moiety. Examples of 6-14-membered aryl moieties condensed with 5-14-membered heteroaryl moieties include but are not limited to quinoline, isoquinoline, phenazine and phenoxacine, which in each case are connected through the 6-14-membered aryl moiety.

According to the invention, the 6-14-membered aryl moiety may optionally be connected through $-C_1$-$C_6$-alkylene-, i.e. the 6-14-membered aryl moiety may not be directly bound to the compound according to general formula (I) but may be connected thereto through a $-C_1$-$C_6$-alkylene- linker. Said linker may be connected to a carbon ring atom or to a hetero ring atom of the 6-14-membered aryl moiety. Examples include but are not limited to $-CH_2-C_6H_5$, $-CH_2CH_2-C_6H_5$ and $-CH=CH-C_6H_5$.

According to the invention, unless expressly stated otherwise, the 6-14-membered aryl moiety can be unsubstituted, mono- or polysubstituted. Examples of substituted 6-14-membered aryl moieties include but are not limited to 2-fluorophenyl, 3-fluorophenyl, 2-methoxyphenyl and 3-methoxyphenyl.

According to the invention, "5-14-membered heteroaryl moiety" means an aromatic, monocyclic, bicyclic or tricyclic moiety comprising 6 to 14 ring atoms, wherein each cycle comprises independently of one another 1, 2, 3, 4 or more heteroatoms independently of one another selected from the group consisting of nitrogen, oxygen and sulfur, whereas the remaining ring atoms are carbon atoms, and whereas bicyclic or tricyclic systems may share common heteroatom(s). Examples of preferred 5-14-membered heteroaryl moieties according to the invention include but are not limited to pyrrole, pyrazole, imidazole, triazole, tetrazole, furane, thiophene, oxazole, isoxazole, thiazole, isothiazole, pyridine, pyridazine, pyrimidine, pyrazine, indolicine, 9H-chinolicine, 1,8-naphthyridine, purine, imidazo[1,2-a]pyrazine, and pteridine. The 5-14-membered heteroaryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 6-14-membered aryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 5-14-membered heteroaryl moieties condensed with 3-12-membered cycloalkyl moieties include but are not limited to 5,6,7,8-tetrahydroquinoline and 5,6,7,8-tetrahydroquinazoline, which in each case are connected through the 5-14-membered heteroaryl moiety. An examples of a 5-14-membered heteroaryl moiety condensed with a 3-12-membered heterocycloalkyl moiety includes but is not limited to 5,6,7,8-tetrahydro-[1,2,4]triazolo[1,5-a]pyrazine, which is connected through the 5-14-membered heteroaryl moiety. Examples of 5-14-membered heteroaryl moieties condensed with 6-14-membered aryl moieties include but are not limited to quinoline, isoquinoline, phenazine and phenoxacine, which in each case are connected through the 5-14-membered heteroaryl moiety.

According to the invention, the 5-14-membered heteroaryl moiety may optionally be connected through $-C_1$-$C_6$-alkylene-, i.e. the 5-14-membered heteroaryl moiety may not be directly bound to the compound according to general formula (I) but may be connected thereto through a $-C_1$-$C_6$-alkylene- linker. Said linker may be connected to a carbon ring atom or to a hetero ring atom of the 5-14-membered heteroaryl moiety. Examples include but are not limited to $-CH_2$-oxazole, $-CH_2$-isoxazole, $-CH_2$-imidazole, $-CH_2$-pyridine, $-CH_2$-pyrimidine, $-CH_2$-pyridazine, $-CH_2CH_2$-oxazole, $-CH_2CH_2$-isoxazole, $-CH_2CH_2$-imidazole, $-CH_2CH_2$-pyridine, $-CH_2CH_2$-pyrimidine, and $-CH_2CH_2$-pyridazine.

According to the invention, unless expressly stated otherwise, the 5-14-membered heteroaryl moiety can be unsubstituted, mono- or polysubstituted. Examples of 5-14-membered heteroaryl moieties include but are not limited to 2-methoxy-4-pyridinyl, 2-methoxy-5-pyridinyl, 3-methoxy-4-pyridinyl, 3-methoxy-6-pyridinyl, 4-methoxy-2-pyridinyl, 2-methylsulfonyl-5-pyridinyl, 3-methylsulfonyl-6-pyridinyl, 3-methoxy-6-pyridazinyl, 2-nitrilo-5-pyrimidinyl, 4-hydroxy-2-pyrimidinyl, 4-methoxy-pyrimidinyl, and 2-methoxy-6-pyrazinyl.

Preferably, the compounds according to the invention have a structure according to general formula (I')

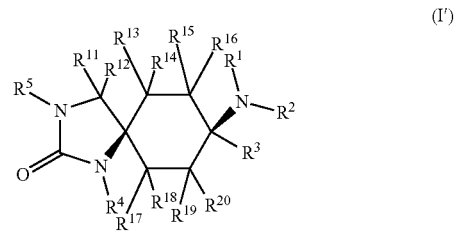

wherein $R^1$ to $R^5$, $R^{10}$ to $R^{20}$ are defined as above, or a physiologically acceptable salt thereof.

In one preferred embodiment, the excess of the cis-isomer so designated is at least 50% de, more preferably at least 75% de, yet more preferably at least 90% de, most preferably at least 95% de and in particular at least 99% de.

Preferably, the compounds according to the invention have a structure according to general formula (IX)

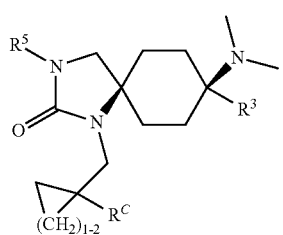

(IX)

wherein
$R^C$ means —H or —OH;
$R^3$ means -phenyl or -3-fluorophenyl;
$R^5$ means
$C_1$-$C_6$-alkyl, linear or branched, saturated, unsubstituted or monosubstituted with —OH, —CN, —NH$_2$, —NHC(=O)$C_1$-$C_4$-alkyl, —NHS(=O)$_2$—$C_1$-$C_4$-alkyl, or —S(=O)$_2$—$C_1$-$C_4$-alkyl; or
3-6-membered heterocycloalkyl, saturated, unsubstituted or substituted with —OH; wherein said 3-6-membered heterocycloalkyl is optionally connected through —CH$_2$— or —(CH$_2$)$_2$—;
or a physiologically acceptable salt thereof.

Preferably, the 3-6-membered heterocycloalkyl is selected from the group consisting of oxetanyl, tetrahydrofuranyl and tetrahydropyranyl.

In a preferred embodiment, the compounds according to the invention are in the form of the free bases.

In another preferred embodiment, the compounds according to the invention are in the form of the physiologically acceptable salts.

For the purposes of the description, a "salt" is to be understood as being any form of the compound in which it assumes an ionic form or is charged and is coupled with a counter-ion (a cation or anion) or is in solution. The term is also to be understood as meaning complexes of the compound with other molecules and ions, in particular complexes which are associated via ionic interactions. Preferred salts are physiologically acceptable, in particular physiologically acceptable salts with anions or acids or also a salt formed with a physiologically acceptable acid.

Physiologically acceptable salts with anions or acids are salts of the particular compound in question with inorganic or organic acids which are physiologically acceptable, in particular when used in humans and/or mammals. Examples of physiologically acceptable salts of particular acids include but are not limited to salts of hydrochloric acid, sulfuric acid, and acetic acid.

The invention also includes isotopic isomers of a compound according to the invention, wherein at least one atom of the compound is replaced by an isotope of the respective atom which is different from the naturally predominantly occurring isotope, as well as any mixtures of isotopic isomers of such a compound. Preferred isotopes are $^2$H (deuterium), $^3$H (tritium), $^{13}$C and $^{14}$C.

Certain compounds according to the invention are useful for modulating a pharmacodynamic response from one or more opioid receptors (mu, delta, kappa, NOP/ORL-1) either centrally or peripherally, or both. The pharmacodynamic response may be attributed to the compound either stimulating (agonizing) or inhibiting (antagonizing) the one or more receptors. Certain compounds according to the invention may antagonize one opioid receptor, while also agonizing one or more other receptors. Compounds according to the invention having agonist activity may be either full agonists or partial agonists.

As used herein, compounds that bind to receptors and mimic the regulatory effects of endogenous ligands are defined as "agonists". Compounds that bind to a receptor but produce no regulatory effect, but rather block the binding of ligands to the receptor, are defined as "antagonists".

In certain embodiments, the compounds according to the invention are agonists at the mu opioid (MOP) and/or kappa opioid (KOP) and/or delta opioid (DOP) and/or nociceptin opioid (NOP/ORL-1) receptors.

The compounds according to the invention potently bind to the MOP and/or KOP and/or DOP and/or NOP receptors.

The compounds according to the invention can be modulators at the MOP and/or KOP and/or DOP and/or NOP receptors, and therefore the compounds according to the invention can be used/administered to treat, ameliorate, or prevent pain.

In some embodiments, the compounds according to the invention are agonists of one or more opioid receptors. In some embodiments, the compounds according to the invention are agonists of the MOP and/or KOP and/or DOP and/or NOP receptors.

In some embodiments, the compounds according to the invention are antagonists of one or more opioid receptors. In some embodiments, the compounds according to the invention are antagonists of the MOP and/or KOP and/or DOP and/or NOP receptors.

In some embodiments, the compounds according to the invention have both, (i) agonist activity at the NOP receptor; and (ii) agonist activity at one or more of the MOP, KOP, and DOP receptors.

In some embodiments, the compounds according to the invention have both, (i) agonist activity at the NOP receptor; and (ii) antagonist activity at one or more of the MOP, KOP, and DOP receptors.

In some embodiments, the compounds according to the invention have both, (i) antagonist activity at the NOP receptor; and (ii) agonist activity at one or more of the MOP, KOP, and DOP receptors.

In some embodiments, the compounds according to the invention have both, (i) antagonist activity at the NOP receptor; and (ii) antagonist activity at one or more of the MOP, KOP, and DOP receptors.

In some embodiments, preferably with respect to receptors of the peripheral nervous system, the compounds according to the invention have selective agonist activity at the NOP receptor. In some embodiments, preferably with respect to receptors of the peripheral nervous system, the compounds according to the invention
  have agonist activity at the NOP receptor, but no significant activity at the MOP receptor;
  have agonist activity at the NOP receptor, but no significant activity at the KOP receptor;
  have agonist activity at the NOP receptor, but no significant activity at the DOP receptor;
  have agonist activity at the NOP receptor, but no significant activity at the MOP receptor as well as no significant activity at the KOP receptor;
  have agonist activity at the NOP receptor, but no significant activity at the MOP receptor as well as no significant activity at the DOP receptor; or have agonist activity at the NOP receptor, but no significant activity at the MOP receptor as well as no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the MOP receptor. In some embodiments, preferably with respect to receptors of the peripheral nervous system, the compounds according to the invention have agonist activity at the NOP receptor as well as agonist activity at the MOP receptor;
have agonist activity at the NOP receptor as well as agonist activity at the MOP receptor as well as agonist activity at the KOP receptor;
have agonist activity at the NOP receptor as well as agonist activity at the MOP receptor as well as agonist activity at the DOP receptor;
can be regarded as opioid pan agonists, i.e. have agonist activity at the NOP receptor as well as agonist activity at the MOP receptor as well as agonist activity at the KOP receptor as well as agonist activity at the DOP receptor;
have agonist activity at the NOP receptor as well as agonist activity at the MOP receptor, but no significant activity at the KOP receptor;
have agonist activity at the NOP receptor as well as agonist activity at the MOP receptor, but no significant activity at the DOP receptor; or
have agonist activity at the NOP receptor as well as agonist activity at the MOP receptor, but no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the KOP receptor. In some embodiments, preferably with respect to receptors of the peripheral nervous system, the compounds according to the invention have agonist activity at the NOP receptor as well as agonist activity at the KOP receptor;
have agonist activity at the NOP receptor as well as agonist activity at the KOP receptor as well as agonist activity at the MOP receptor;
have agonist activity at the NOP receptor as well as agonist activity at the KOP receptor as well as agonist activity at the DOP receptor;
have agonist activity at the NOP receptor as well as agonist activity at the KOP receptor, but no significant activity at the MOP receptor;
have agonist activity at the NOP receptor as well as agonist activity at the KOP receptor, but no significant activity at the DOP receptor; or
have agonist activity at the NOP receptor as well as agonist activity at the KOP receptor, but no significant activity at the MOP receptor as well as no significant activity at the DOP receptor.

In some embodiments, preferably with respect to receptors of the peripheral nervous system, the compounds according to the invention have balanced agonist activity at the NOP receptor as well as at the DOP receptor. In some embodiments, preferably with respect to receptors of the peripheral nervous system, the compounds according to the invention have agonist activity at the NOP receptor as well as agonist activity at the DOP receptor;
have agonist activity at the NOP receptor as well as agonist activity at the DOP receptor, but no significant activity at the MOP receptor;
have agonist activity at the NOP receptor as well as agonist activity at the DOP receptor, but no significant activity at the KOP receptor; or
have agonist activity at the NOP receptor as well as agonist activity at the DOP receptor, but no significant activity at the MOP receptor as well as no significant activity at the KOP receptor.

In some embodiments, preferably with respect to receptors of the peripheral nervous system, the compounds according to the invention have selective agonist activity at the KOP receptor. In some embodiments, preferably with respect to receptors of the peripheral nervous system, the compounds according to the invention have agonist activity at the KOP receptor, but no significant activity at the MOP receptor;
have agonist activity at the KOP receptor, but no significant activity at the NOP receptor;
have agonist activity at the KOP receptor, but no significant activity at the DOP receptor;
have agonist activity at the KOP receptor, but no significant activity at the MOP receptor as well as no significant activity at the NOP receptor;
have agonist activity at the KOP receptor, but no significant activity at the MOP receptor as well as no significant activity at the DOP receptor; or
have agonist activity at the KOP receptor, but no significant activity at the MOP receptor as well as no significant activity at the NOP receptor as well as no significant activity at the DOP receptor.

In some embodiments, preferably with respect to receptors of the peripheral nervous system, the compounds according to the invention have agonist activity at the MOP receptor, agonist activity at the KOP receptor, and antagonist activity at the DOP receptor. In some embodiments, preferably with respect to receptors of the peripheral nervous system, the compounds according to the invention have agonist activity at the MOP receptor as well as agonist activity at the KOP receptor as well as antagonist activity at the DOP receptor;
have agonist activity at the MOP receptor as well as agonist activity at the KOP receptor as well as antagonist activity at the DOP receptor as well as agonist activity at the NOP receptor;
have agonist activity at the MOP receptor as well as agonist activity at the KOP receptor as well as antagonist activity at the DOP receptor as well as antagonist activity at the NOP receptor; or
have agonist activity at the MOP receptor as well as agonist activity at the KOP receptor as well as antagonist activity at the DOP receptor, no significant activity at the NOP receptor.

In some embodiments, preferably with respect to receptors of the central nervous system, the compounds according to the invention have selective agonist activity at the NOP receptor. In some embodiments, preferably with respect to receptors of the central nervous system, the compounds according to the invention have agonist activity at the NOP receptor, but no significant activity at the MOP receptor;
have agonist activity at the NOP receptor, but no significant activity at the KOP receptor;

have agonist activity at the NOP receptor, but no significant activity at the DOP receptor;

have agonist activity at the NOP receptor, but no significant activity at the MOP receptor as well as no significant activity at the KOP receptor;

have agonist activity at the NOP receptor, but no significant activity at the MOP receptor as well as no significant activity at the DOP receptor; or have agonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have selective antagonist activity at the NOP receptor. In some embodiments, preferably with respect to receptors of the central nervous system, the compounds according to the invention have antagonist activity at the NOP receptor, but no significant activity at the MOP receptor;

have antagonist activity at the NOP receptor, but no significant activity at the KOP receptor;

have antagonist activity at the NOP receptor, but no significant activity at the DOP receptor;

have antagonist activity at the NOP receptor, but no significant activity at the MOP receptor as well as no significant activity at the KOP receptor;

have antagonist activity at the NOP receptor, but no significant activity at the MOP receptor as well as no significant activity at the DOP receptor; or have antagonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have antagonist activity at the NOP receptor as well as agonist activity at the DOP receptor. In some embodiments, preferably with respect to receptors of the central nervous system, the compounds according to the invention have antagonist activity at the NOP receptor as well as agonist activity at the DOP receptor;

have antagonist activity at the NOP receptor as well as agonist activity at the DOP receptor, but no significant activity at the MOP receptor;

have antagonist activity at the NOP receptor as well as agonist activity at the DOP receptor, but no significant activity at the KOP receptor; or have antagonist activity at the NOP receptor as well as agonist activity at the DOP receptor, but no significant activity at the MOP receptor as well as no significant activity at the KOP receptor.

For the purpose of the specification, "no significant activity" means that the activity (agonist/antagonist) of the given compound at this receptor is lower by a factor of 1000 or more compared to its activity (agonist/antagonist) at one or more of the other opioid receptors.

A further aspect of the invention relates to the compounds according to the invention as medicaments.

A further aspect of the invention relates to the compounds according to the invention for use in the treatment of pain. A further aspect of the invention relates to a method of treating pain comprising the administration of a pain alleviating amount of a compound according to the invention to a subject in need thereof, preferably to a human. The pain is preferably acute or chronic. The pain is preferably nociceptive or neuropathic.

A further aspect of the invention relates to the compounds according to the invention for use in the treatment of neurodegenerative disorders, neuroinflammatory disorders, neuropsychiatric disorders, and substance abuse/dependence. A further aspect of the invention relates to a method of treating any one of the aforementioned disorders, diseases or conditions comprising the administration of a therapeutically effective amount of a compound according to the invention to a subject in need thereof, preferably to a human.

Another aspect of the invention relates to a pharmaceutical composition which contains a physiologically acceptable carrier and at least one compound according to the invention.

Preferably, the composition according to the invention is solid, liquid or pasty; and/or contains the compound according to the invention in an amount of from 0.001 to 99 wt. %, preferably from 1.0 to 70 wt. %, based on the total weight of the composition.

The pharmaceutical composition according to the invention can optionally contain suitable additives and/or auxiliary substances and/or optionally further active ingredients.

Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical composition according to the invention contains the compound according to the invention in an amount of preferably from 0.001 to 99 wt. %, more preferably from 0.1 to 90 wt. %, yet more preferably from 0.5 to 80 wt. %, most preferably from 1.0 to 70 wt. % and in particular from 2.5 to 60 wt. %, based on the total weight of the pharmaceutical composition.

The pharmaceutical composition according to the invention is preferably for systemic, topical or local administration, preferably for oral administration.

Another aspect of the invention relates to a pharmaceutical dosage form which contains the pharmaceutical composition according to the invention.

In one preferred embodiment, the pharmaceutical dosage form according to the invention is produced for administration twice daily, for administration once daily or for administration less frequently than once daily. Administration is preferably systemic, in particular oral.

The pharmaceutical dosage form according to the invention can be administered, for example, as a liquid dosage form in the form of injection solutions, drops or juices, or as a semi-solid dosage form in the form of granules, tablets, pellets, patches, capsules, plasters/spray-on plasters or aerosols. The choice of auxiliary substances etc. and the amounts thereof to be used depend on whether the form of administration is to be administered orally, perorally, parenterally, intravenously, intraperitoneally, intradermally, intramuscularly, intranasally, buccally, rectally or locally, for example to the skin, the mucosa or into the eyes.

Pharmaceutical dosage forms in the form of tablets, dragees, capsules, granules, drops, juices and syrups are suitable for oral administration, and solutions, suspensions, readily reconstitutable dry preparations and also sprays are suitable for parenteral, topical and inhalatory administration. Compounds according to the invention in a depot, in dissolved form or in a plaster, optionally with the addition of agents promoting penetration through the skin, are suitable percutaneous administration preparations.

The amount of the compounds according to the invention to be administered to the patient varies in dependence on the weight of the patient, on the type of administration, on the indication and on the severity of the disease. Usually, from 0.00005 mg/kg to 50 mg/kg, preferably from 0.001 mg/kg to 10 mg/kg, of at least one compound according to the invention is administered.

Another aspect of the invention relates to a process for the preparation of the compounds according to the invention. Suitable processes for the synthesis of the compounds according to the invention are known in principle to the person skilled in the art.

Preferred synthesis routes are described below:

The compounds according to the invention can be obtained via different synthesis routes. Depending on the synthesis route, different intermediates are prepared and subsequently further reacted.

In a preferred embodiment, the synthesis of the compounds according to the invention proceeds via a synthesis route which comprises the preparation of an intermediate according to general formula (IIIa):

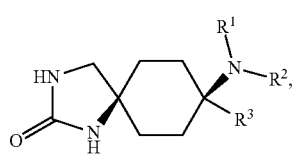

(IIIa)

wherein $R^1$, $R^2$ and $R^3$ are defined as above.

In another preferred embodiment, the synthesis of the compounds according to the invention proceeds via a synthesis route which comprises the preparation of an intermediate according to general formula (IIIb):

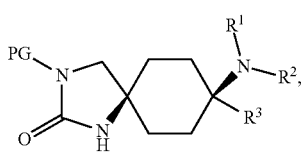

(IIIb)

wherein $R^1$, $R^2$ and $R^3$ are defined as above and PG is a protecting group.

Preferably the protecting group is -p-methoxybenzyl. Therefore, in another preferred embodiment, the synthesis of the compounds according to the invention proceeds via a synthesis route which comprises the preparation of an intermediate according to general formula (IIIc):

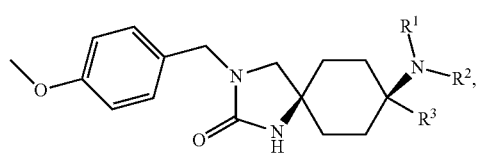

(IIIc)

wherein $R^1$, $R^2$ and R are defined as above.

As already indicated, in general formula (IIIc), the -p-methoxybenzyl moiety represents a protecting group which can be cleaved in the course of the synthesis route.

In yet another preferred embodiment, the synthesis of the compounds according to the invention proceeds via a synthesis route which comprises the preparation of

- an intermediate according to general formula (IIIa) and according to general formula (IIIb); or
- an intermediate according to general formula (IIIa) and according to general formula (IIIc); or
- an intermediate according to general formula (IIIb) and according to general formula (IIIc); or
- an intermediate according to general formula (IIIa), according to general formula (IIIb) and according to general formula (IIIc).

The following examples further illustrate the invention but are not to be construed as limiting its scope.

EXAMPLES

"RT" means room temperature (23±7° C.), "M" are indications of concentration in mol/l, "aq." means aqueous, "sat." means saturated, "sol." means solution, "conc." means concentrated.

Further Abbreviations brine saturated aqueous sodium chloride solution
CC column chromatography
cHex cyclohexane
DCM dichloromethane
DIPEA N,N-diisopropylethylamine
DMF N,N-dimethylformamide
Et Ethyl
ether diethyl ether
EE ethyl acetate
EtOAc ethyl acetate
EtOH ethanol
h hour(s)
$H_2O$ water
HATU O-(7-aza-benzotriazol-1-yl)-N,N,N',N'-tetramethyl-uroniumhexafluorophosphate
LDA Lithium-di-isoproyl-amid
Me Methyl
m/z mass-to-charge ratio
MeOH methanol
MeCN acetonitrile
min minutes
MS mass spectrometry
NBS N-bromo-succinimide
$NEt_3$ triethylamine
PE Petrol Ether (60-80° C.)
RM reaction mixture
RT room temperature
T3P 2,4,6-Tripropyl-1,3,5,2,4,6-trioxatriphosphorinane-2,4,6-trioxide
tBME tert-.butyl methyl ether
THF tetrahydrofuran
v/v volume to volume
w/w weight to weight The yields of the compounds prepared were not optimised. All temperatures are uncorrected.

All starting materials, which are not explicitly described, were either commercially available (the details of suppliers such as for example Acros, Aldrich, Bachem, Butt park, Enamine, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, repspectively, for example) or can be prepared using the conventional methods known to the person skilled in the art.

The mixing ratios of solvents or eluents for chromatography are specified in v/v.

All the intermediate products and exemplary compounds were analytically characterised by mass spectrometry (MS, m/z for [M+H]+). In addition $^1$H-NMR and $^{13}$C spectroscopy was carried out for all the exemplary compounds and selected intermediate products.

Remark Regarding Stereochemistry

CIS refers to the relative configuration of compounds described herein, in which both nitrogen atoms are drawn on the same face of the cyclohexane ring as described in the following exemplary structure. Two depictions are possible:

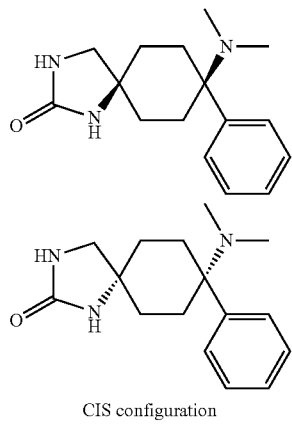

CIS configuration

TRANS refers to compounds, in which both nitrogen atoms are on opposite faces of the cyclohexane ring as described in the following exemplary structure. Two depictions are possible:

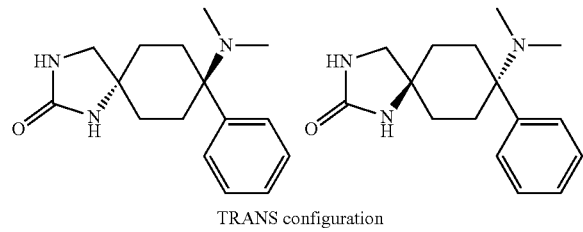

TRANS configuration

Synthesis of Intermediates

Synthesis of INT-799: CIS-8-Dimethylamino-1-[(1-hydroxy-cyclobutyl)-methyl]-8-phenyl-1,3-diazaspiro[4.5]decan-2-one

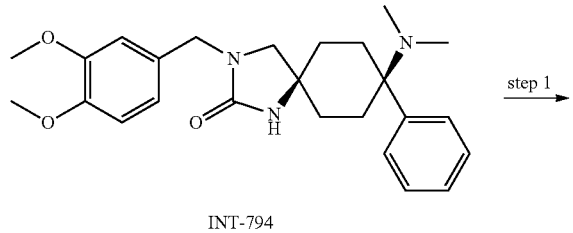

INT-794

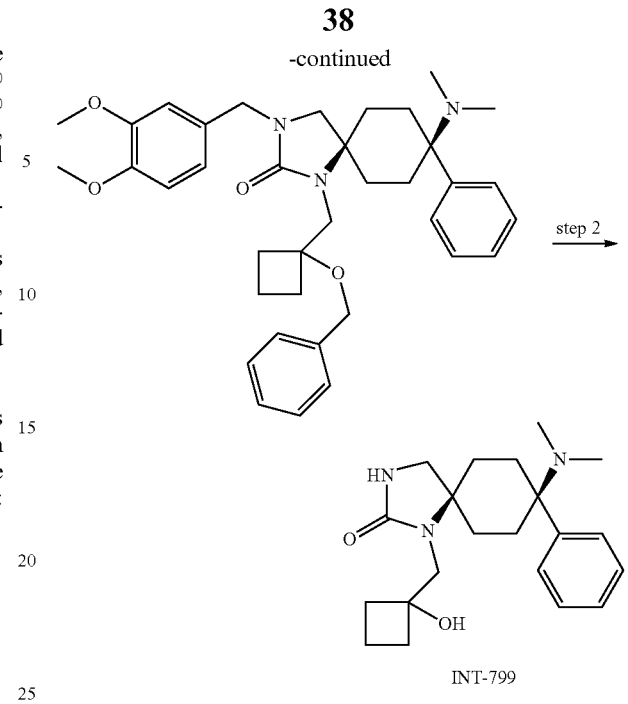

INT-799

Step 1: CIS-1-((1-(benzyloxy)cyclobutyl)methyl)-3-(3,4-dimethoxybenzyl)-8-(dimethylamino)-8-phenyl-1,3-diazaspiro[4.5]decan-2-one NaOH (1.42 g, 35.5 mmol) was added to a solution of CIS-3-(3,4-dimethoxybenzyl)-8-(dimethylamino)-8-phenyl-1,3-diazaspiro[4.5]decan-2-one (INT-794) (3 g, 7.09 mmol) in DMSO (90 mL) under argon atmosphere and the reaction mixture was stirred at 80° C. for 30 min. ((1-(Bromomethyl)cyclobutoxy)methyl)benzene (5.4 g, 21.3 mmol) was added and stirring was continued for 2 days at 80° C. The reaction completion was monitored by TLC. The reaction mixture was diluted with water (500 mL) and extracted with diethyl ether (4×300 mL). The combined organic extracts were dried over anhydrous Na$_2$SO$_4$ and concentrated under reduced pressure. The residue was purified by column chromatography (230-400 mesh silica gel; 65-70% EtOAc in petroleum ether as eluent) to afford 2.5 g (59%) of CIS-1-((1-(benzyloxy)cyclobutyl)methyl)-3-(3,4-dimethoxybenzyl)-8-(dimethylamino)-8-phenyl-1,3-diazaspiro[4.5]decan-2-one (TLC system: 10% MeOH in DCM; Rf: 0.8).

Step 2: CIS-8-Dimethylamino-1-[(1-hydroxy-cyclobutyl)-methyl]-8-phenyl-1,3-diazaspiro[4.5]decan-2-one TFA (12 mL) was added to CIS-1-((1-(benzyloxy)cyclobutyl)methyl)-3-(3,4-dimethoxybenzyl)-8-(dimethylamino)-8-phenyl-1,3-diazaspiro[4.5]decan-2-one (2.5 g, 4.18 mmol) at 0° C. and the resulting mixture was stirred at 70° C. for 6 h. The reaction completion was monitored by LCMS. The reaction mixture was concentrated under reduced pressure. To the residue sat. aq. NaHCO$_3$ was added (until pH 10) and the organic product was extracted with DCM (3×150 mL). The combined organic extracts were dried over anhydrous Na$_2$SO$_4$ and concentrated under reduced pressure. The residue was purified by column chromatography (230-400 mesh silica gel; 5% MeOH in DCM as eluent) to afford 500 mg (33%) of CIS-8-dimethylamino-1-[(1-hydroxy-cyclobutyl)-methyl]-8-phenyl-1,3-diazaspiro[4.5]decan-2-one (INT-799) (TLC system: 10% MeOH in DCM; Rf: 0.5). [M+H]⁺ 358.2

Synthesis of INT-951: CIS-1-[(8-Dimethylamino-2-oxo-8-phenyl-1,3-diazaspiro[4.5]decan-1-yl)-methyl]-cyclobutane-1-carbonitrile

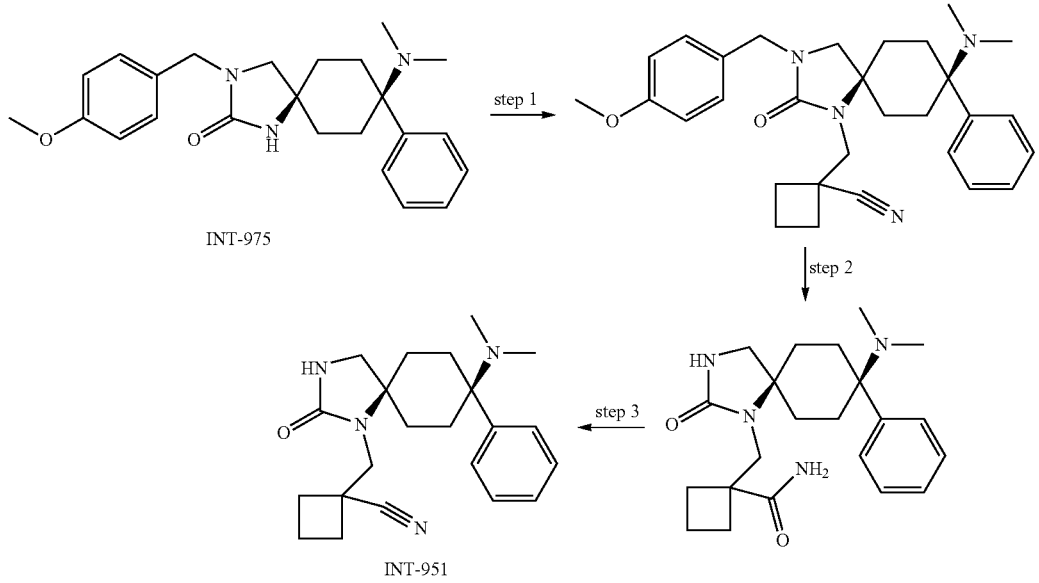

Step 1: 1-((CIS-8-(dimethylamino)-3-(4-methoxy-benzyl)-2-oxo-8-phenyl-1,3-diazaspiro[4.5]decan-1-yl)methyl)cyclobutanecarbonitrile NaH (50% in mineral oil) (2.44 g, 50.89 mmol) was added to a solution of CIS-8-dimethylamino-3-[(4-methoxyphenyl)-methyl]-8-phenyl-1,3-diazaspiro[4.5]decan-2-one (INT-975) (5 g, 12.72 mmol) in DMF (100 mL) at 0° C. portionwise over 10 min. 1-(Bromomethyl)cyclobutanecarbonitrile (4.4 g, 25.44 mmol) was added dropwise over 10 minutes at 0° C. The reaction mixture was allowed to stir at RT for 3 h, then quenched with water and the organic product was extracted with ethyl acetate (3×200 mL). The combined organic extracts were dried over anhydrous Na₂SO₄ and concentrated under reduced pressure to afford 5 g (crude) of 1-((CIS-8-(dimethylamino)-3-(4-methoxybenzyl)-2-oxo-8-phenyl-1,3-diazaspiro[4.5]decan-1-yl)methyl) cyclobutane-carbonitrile as gummy brown liquid. The material was used for the next step without further purification.

Step 2: 1-((CIS-8-(dimethylamino)-2-oxo-8-phenyl-1,3-diazaspiro[4.5]decan-1-yl)methyl)cyclobutanecarboxamide TFA (100 mL) was added to 1-((CIS-8-(dimethylamino)-3-(4-methoxybenzyl)-2-oxo-8-phenyl-1,3-diazaspiro[4.5]decan-1-yl)methyl)cyclobutanecarbonitrile (5 g, 10.28 mmol) at 0° C. and the reaction mixture at mixture was stirred at RT for 2 days. The reaction mixture was concentrated in vacuo. To the residue sat. aq. NaHCO₃ was added (until pH 10) and the organic product was extracted with dichloromethane (3×150 mL). The combined organic extracts were dried over anhydrous Na₂SO₄ and concentrated under reduced pressure to afford 3.5 g (crude) of 1-((CIS-8-(dimethylamino)-2-oxo-8-phenyl-1,3-diazaspiro[4.5]decan-1-yl)methyl)cyclobutanecarboxamide. The material was used for the next step without further purification.

Step 3: 1-((cis-8-(dimethylamino)-2-oxo-8-phenyl-1,3-diazaspiro[4.5]decan-1-yl)methyl)cyclobutane carbonitrile Thionyl chloride (35 mL) was added to 1-((cis-8-(dimethylamino)-2-oxo-8-phenyl-1,3-diazaspiro[4.5]decan-1-yl) methyl)cyclobutanecarboxamide (3.5 g, 9.11 mmol) at RT and the resulting mixture was stirred at reflux for 2 h. The reaction mixture was concentrated in vacuo. To the residue sat. aq. NaHCO₃ was added (until pH 10) and the organic product was extracted with dichloromethane (3×150 mL). The combined organic layer was dried over anhydrous Na₂SO₄ and concentrated in vacuo. The residue was purified by column chromatography to afford 1.3 g (34% after three steps) of CIS-1-[(8-dimethylamino-2-oxo-8-phenyl-1,3-diazaspiro[4.5]decan-1-yl)-methyl]-cyclobutane-1-carbonitrile (INT-951). [M+H]⁺ 367.2.

Synthesis of INT-952: CIS-1-(Cyclobutyl-methyl)-8-dimethylamino-8-phenyl-3-[(4-methoxyphenyl)-methyl]-1,3-diazaspiro[4.5]decan-2-one

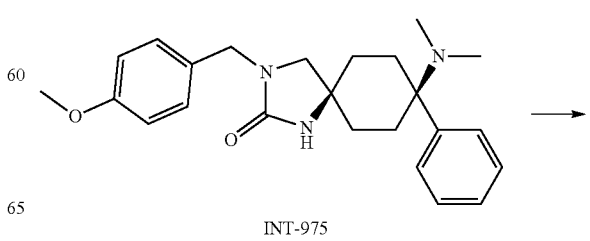

INT-975

-continued

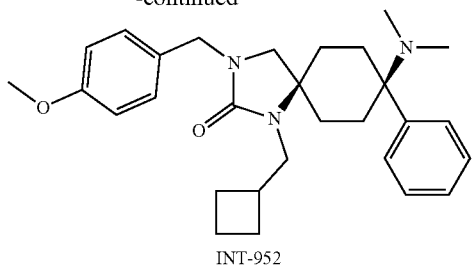

INT-952

To a solution of CIS-8-dimethylamino-3-[(4-methoxyphenyl)-methyl]-8-phenyl-1,3-diazaspiro[4.5]decan-2-one (INT-975) (10 g, 25 mmol) in THF (500 mL) was added KOtBu (7.1 g, 63 mmol) at 50° C. The reaction mixture was heated up to reflux, cyclobutylmethylbromide (11.3 g, 76 mmol) was added in one portion, and stirring was continued at reflux for 12 h. KOtBu (7.1 g) and cyclobutylmethylbromide (11.3 g) were added again. The reaction mixture was allowed to stir another 2 h at reflux, then cooled to RT, diluted with water (150 mL) and the layers partitioned. The aqueous layer was extracted with EtOAc (3×300 mL). The combined organic layers were dried over Na$_2$SO$_4$ and then concentrated in vacuo. The residue was filtered through a plug of silica gel using a DCM/MeOH (19/1 v/v) mixture. The filtrate was concentrated in vacuo and the resulting solid was recrystallized from hot ethanol to yield 7.8 g of CIS-1-(cyclobutyl-methyl)-8-dimethylamino-8-phenyl-3-[(4-methoxyphenyl)-methyl]-1,3-diazaspiro[4.5]decan-2-one (INT-952). [M+H]$^+$ 461.3.

Synthesis of INT-953: CIS-1-(Cyclobutyl-methyl)-8-(methyl-(2-methyl-propyl)-amino)-8-phenyl-1,3-diazaspiro[4.5]decan-2-one continued for 50 h. TLC analysis showed complete consumption of the starting material. The reaction mixture was quenched with sat. aq. NH$_4$Cl (50 ml) and extracted with EtOAc (3×200 ml). The combined organic phase was dried over Na$_2$SO$_4$ and concentrated under reduced pressure. The resulting residue was purified column chromatography (neutral aluminum oxide, EtOAc-petroleum ether (2:8)) to give 1-cyclobutylmethyl-3-(4-methoxy-benzyl)-9,12-dioxa-1,3-diaza-dispiro[4.2.4.2]tetradecan-2-one (2.4 g, 50%, white solid). TLC system: EtOAc-pet ether (6:4); R$_f$=0.48.

Step 2: 1-Cyclobutylmethyl-3-(4-methoxy-benzyl)-1,3-diaza-spiro[4.5]decane-2,8-dione To a stirred solution of 1-cyclobutylmethyl-3-(4-methoxy-benzyl)-9,12-dioxa-1,3-diaza-dispiro[4.2.4.2]tetradecan-2-one (1 g, 2.5 mmol) in MeOH (7 ml) was added 10% aq. HCl (8 ml) at 0° C. The reaction mixture was warmed up to RT and stirred for 16 h. TLC analysis showed complete consumption of the starting material. The reaction mixture was quenched with sat. aq. NaHCO$_3$ (30 ml) and extracted with EtOAc (3×50 ml). The combined organic phase was dried over Na$_2$SO$_4$ and concentrated under reduced pressure. The resulting residue was purified by column chromatography (silica gel, 230-400 mesh, EtOAc-pet ether (1:3)→(3:7)) to give 1-cyclobutylmethyl-3-(4-methoxy-benzyl)-1,3-diaza-spiro[4.5]decane-2,8-dione (650 mg, 73%, colorless viscous oil). TLC system: EtOAc-pet ether (6:4); R$_f$=0.40.

Step 3: 1-(cyclobutylmethyl)-8-(isobutyl(methyl)amino)-3-(4-methoxybenzyl)-2-oxo-1,3-diazaspiro[4.5]decane-8-carbonitrile To a stirred solution of N-isobutyl-N-methylamine (1.34 ml, 11.23 mmol) and MeOH/H$_2$O (8 ml, 1:1, v/v) was added 4N aq. HCl (1.5 ml) and the reaction mixture was stirred for 10 min at 0° C. (ice bath). A solution of 1-cyclobutylmethyl-3-(4-methoxy-benzyl)-1,3-diaza-spiro[4.5]decane-2,8-dione (1 g, 2.80 mmol) in MeOH (7 ml) and KCN (548 mg, 8.42 mmol) were added and the reaction mixture was stirred at 45° C. for 20 h. TLC analysis showed complete consumption of the starting material. The reaction mixture was diluted with water (30 ml), extracted with EtOAc (3×30 ml), the combined organic phase was dried over Na$_2$SO$_4$ and concentrated under reduced pressure to give 1-(cyclobutyl-

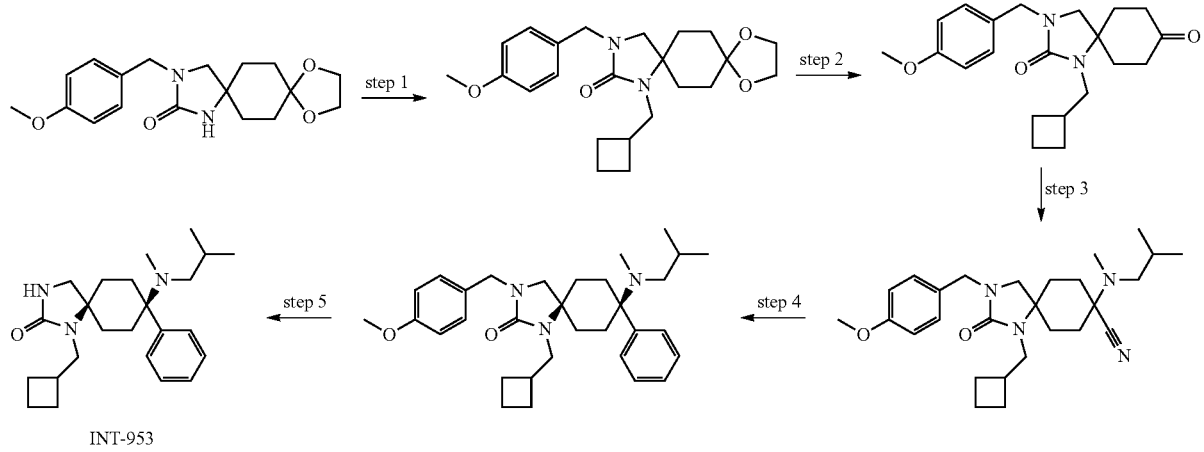

INT-953

Step 1: 1-Cyclobutylmethyl-3-(4-methoxy-benzyl)-9,12-dioxa-1,3-diaza-dispiro[4.2.4.2]tetradecan-2-one To a stirred solution of 3-(4-methoxy-benzyl)-9,12-dioxa-1,3-diaza-dispiro[4.2.4.2]tetradecan-2-one (4 g, 12.04 mmol) in anhydrous DMF (60 ml) was added NaH (1.38 g, 60% dispersion in oil, 36.14 mmol) at RT. The reaction mixture was stirred for 10 min, bromomethylcyclobutane (3 ml, 26.5 mmol) was added dropwise and stirring was methyl)-8-(isobutyl(methyl)amino)-3-(4-methoxybenzyl)-2-oxo-1,3-diazaspiro[4.5]decane-8-carbonitrile (1.3 g, viscous yellow oil). TLC system: EtOAc-pet ether (1:1); R=0.45. The product was used for the next step without additional purification.

Step 4: CIS-1-(cyclobutylmethyl)-8-(isobutyl(methyl)amino)-3-(4-methoxybenzyl)-8-phenyl-1,3-diazaspiro[4.5]decan-2-one A round bottom flask containing 1-(cyclobutylmethyl)-8-(isobutyl(methyl)amino)-3-(4-methoxybenzyl)-2-oxo-1,3-diazaspiro[4.5]decane-8-carbonitrile (1.3 g, 2.81 mmol) was cooled in an ice bath (~0° C.) and a solution of phenylmagnesium bromide (26 ml, ~2M in THF) was added slowly at 0° C.–5° C. The ice bath was removed and the reaction mixture was stirred for 30 min, then diluted with sat. aq. NH₄Cl (25 ml) and extracted with EtOAc (4×30 ml). The combined organic phase was dried over Na₂SO₄ and concentrated under reduced pressure to give pale yellow viscous oil. This residue was purified by column chromatography (silica gel, 230-400 mesh, eluent: EtOAc-pet ether (15:85)→(2:4)) to give CIS-1-(cyclobutylmethyl)-8-(isobutyl(methyl)amino)-3-(4-methoxybenzyl)-8-phenyl-1,3-diazaspiro[4.5]decan-2-one (135 mg, 10%, white solid). TLC system: EtOAc-pet ether (1:1); $R_f$=0.6

Step 5: CIS-1-(Cyclobutyl-methyl)-8-(methyl-(2-methyl-propyl)-amino)-8-phenyl-1,3-diazaspiro[4.5]decan-2-one A round bottom flask containing CIS-1-(cyclobutylmethyl)-8-(isobutyl(methyl)amino)-3-(4-methoxybenzyl)-8-phenyl-1,3-diazaspiro[4.5]decan-2-one (130 mg, 0.25 mmol) was cooled in an ice bath and a mixture of TFA/CH₂Cl₂ (2.6 ml, 1:1, v/v) was added slowly at 0° C.–5° C. The reaction mixture was warmed to RT and stirred for 20 h, then quenched with methanolic NH₃ (10 ml, ~10% in MeOH) and concentrated under reduced pressure to give pale yellow viscous oil. This residue was purified twice by column chromatography (silica gel, 230-400 mesh, eluent: MeOH—CHCl₃ (1:99)→(2:98)) to give CIS-1-(cyclobutyl-methyl)-8-(methyl-(2-methyl-propyl)-amino)-8-phenyl-1,3-diazaspiro[4.5]decan-2-one (INT-953) (65 mg, 66%, white solid). TLC system: MeOH—CHCl₃ (5:95); $R_f$=0.25; [M+H]⁺ 384.3

Synthesis of INT-958:
4-Oxo-1-pyridin-2-yl-cyclohexane-1-carbonitrile

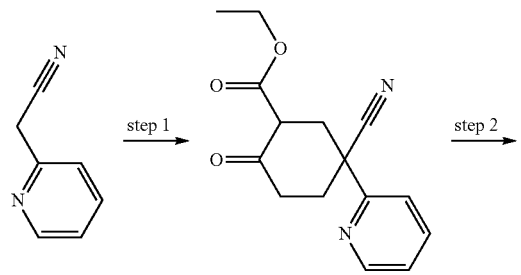

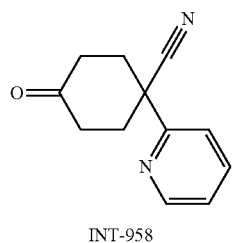

INT-958

Step 1: Ethyl 5-cyano-2-oxo-5-(pyridin-2-yl)cyclohexanecarboxylate

KOtBu (57.0 g, 508.4 mmol) was added to the solution of 2-(pyridin-2-yl)acetonitrile (50.0 g, 423.7 mmol) and ethyl acrylate (89.0 g, 889.8 mmol) in THF (500 mL) at 0° C. and stirred for 16 h at RT. The reaction mixture was quenched with sat. aq. NH₄Cl and extracted with EtOAc (2×500 mL). The combined organic layer was washed with brine, dried over Na₂SO₄ and concentrated under reduced pressure to afford 68.0 g (60%; crude) of ethyl 5-cyano-2-oxo-5-(pyridin-2-yl)cyclohexanecarboxylate as a brown liquid (TLC system: 50% ethyl acetate in petroleum ether; Rf: 0.65).

Step 2:
4-Oxo-1-pyridin-2-yl-cyclohexane-1-carbonitrile

A solution of ethyl 5-cyano-2-oxo-5-(pyridin-2-yl)cyclohexanecarboxylate (68.0 g, 250.0 mmol) was added to a mixture of conc. aq. HCl and glacial acetic acid (170 mL/510 mL) at 0° C. The reaction mixture was heated to 100° C. for 16 h. All volatiles were evaporated under reduced pressure. The residue was diluted with sat. aq. NaHCO₃ and extracted with ethyl acetate (3×300 mL). The combined organic layer was washed with brine, dried over Na₂SO₄ and concentrated under reduced pressure to afford 44.0 g (88%) of 4-oxo-1-pyridin-2-yl-cyclohexane-1-carbonitrile INT-958 as a brown solid (TLC system: 50% ethyl acetate in pet ether; Rf: 0.45). [M+H]⁺ 201.1

Synthesis of INT-961:
4-Dimethylamino-4-pyridin-2-yl-cyclohexan-1-one

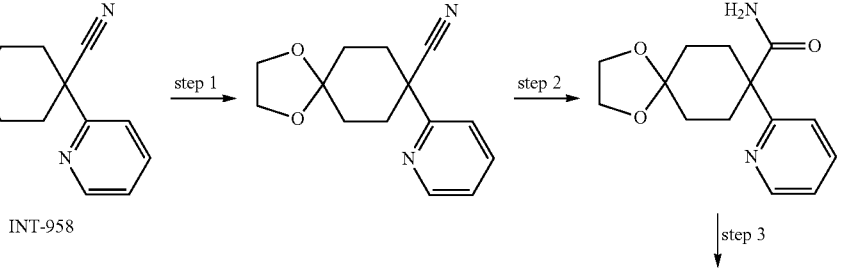

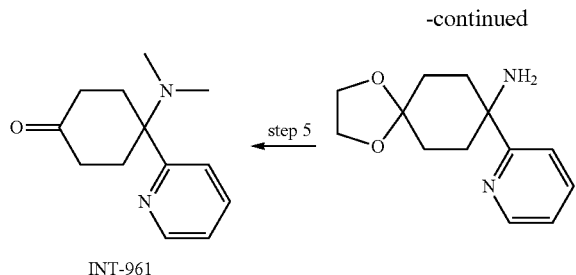
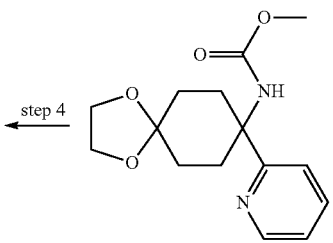

Step 1: 8-(pyridin-2-yl)-1,4-dioxaspiro[4.5]decane-8-carbonitrile

A solution of 4-oxo-1-pyridin-2-yl-cyclohexane-1-carbonitrile (INT-958) (44.0 g, 220.0 mmol), ethylene glycol (27.0 g, 440.0 mmol) and PTSA (4.2 g, 22.0 mmol) in toluene (450 mL) was heated to 120° C. for 16 h using Dean Stark apparatus. All volatiles were evaporated under reduced pressure. The residue was diluted with sat. aq. NaHCO$_3$ and extracted with ethyl acetate (3×300 mL). The combined organic layer was washed with brine, dried over Na$_2$SO$_4$ and concentrated under reduced pressure to afford 45.0 g (85%) of 8-(pyridin-2-yl)-1,4-dioxaspiro[4.5]decane-8-carbonitrile as a light brown solid (TLC system: 50% ethyl acetate in petroleum ether; Rf: 0.55).

Step 2: 8-(pyridin-2-yl)-1,4-dioxaspiro[4.5]decane-8-carboxamide

Potassium carbonate (50.0 g, 368.84 mmol) and 30% aq. H$_2$O$_2$ (210.0 mL, 1844.2 mmol) were added to the solution of 8-(pyridin-2-yl)-1,4-dioxaspiro[4.5]decane-8-carbonitrile (45.0 g, 184.42 mmol) in DMSO (450 mL) at 0° C. and the resulting mixture was stirred at RT for 14 h. The reaction mixture was diluted with water (1.5 L) and stirred for 1 h. The precipitated solid was separated by filtration, washed with water, petroleum ether and dried under reduced pressure to get 32.0 g (66%) of 8-(pyridin-2-yl)-1,4-dioxaspiro[4.5]decane-8-carboxamide as a white solid. (TLC system: 10% MeOH in DCM R$_f$: 0.35).

Step 3: methyl 8-(pyridin-2-yl)-1,4-dioxaspiro[4.5]decan-8-ylcarbamate

A mixture of 8-(pyridin-2-yl)-1,4-dioxaspiro[4.5]decane-8-carboxamide (25.0 g, 95.41 mmol), sodium hypochlorite (5 wt % aq. solution, 700 mL, 477.09 mmol) and KF—Al$_2$O$_3$ (125.0 g) in methanol (500 mL) was heated to 80° C. for 16 h. The reaction mixture was filtered through celite and the solid residue was washed with methanol. The combined filtrate was concentrated under reduced pressure. The residue was diluted with water and extracted with ethyl acetate (3×500 mL). The combined organic layer was washed with brine, dried over Na$_2$SO$_4$ and concentrated under reduced pressure to afford 18.0 g (66%) of methyl 8-(pyridin-2-yl)-1,4-dioxaspiro[4.5]decan-8-ylcarbamate as a light brown solid. (TLC system: 5% MeOH in DCM Rf: 0.52.)

Step 4: 8-(pyridin-2-yl)-1,4-dioxaspiro[4.5]decan-8-amine

A suspension of methyl 8-(pyridin-2-yl)-1,4-dioxaspiro[4.5]decan-8-ylcarbamate (18.0 g, 61.64 mmol) in 10 wt % aq. NaOH (200 mL) was heated to 100° C. for 24 h. The reaction mixture was filtered through celite pad, the solid residue was washed with water and the combined filtrate was extracted with EtOAc (4×200 mL). The combined organic layer washed with brine, dried over Na$_2$SO$_4$ and concentrated under reduced pressure to afford 12.5 g (88%) of 8-(pyridin-2-yl)-1,4-dioxaspiro[4.5]decan-8-amine as a light brown semi-solid. (TLC system: 5% MeOH in DCM R$_f$: 0.22.).

Step 5: 4-Dimethylamino-4-pyridin-2-yl-cyclohexan-1-one

Sodium cyanoborohydride (13.7 g, 0.213 mol) was added portionwise to a solution of 8-(pyridin-2-yl)-1,4-dioxaspiro[4.5]decan-8-amine (12.5 g, 53.418 mmol) and 35 wt % aq. formaldehyde (45 mL, 0.534 mol) in acetonitrile (130 mL) at 0° C. The reaction mixture was warmed up to room temperature and stirred for 16 h. The reaction mixture was quenched with sat. aq. NH$_4$Cl and concentrated under reduced pressure. The residue was dissolved in water and extracted with EtOAc (3×200 mL). The combined organic layer was washed with brine, dried over Na$_2$SO$_4$ and concentrated under reduced pressure to afford 10.5 g (72%) of 4-dimethylamino-4-pyridin-2-yl-cyclohexan-1-one (INT-961) as a light brown solid. (TLC system: 5% MeOH in DCM Rf: 0.32.). [M+H]$^+$ 219.1

Synthesis of INT-965:
4-Dimethylamino-4-phenyl-cyclohexan-1-one

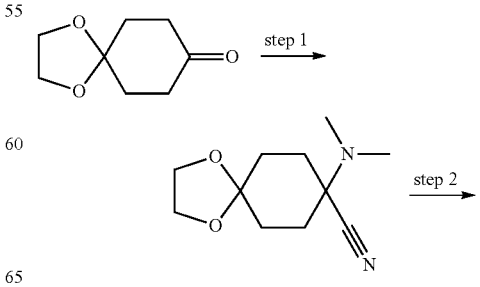

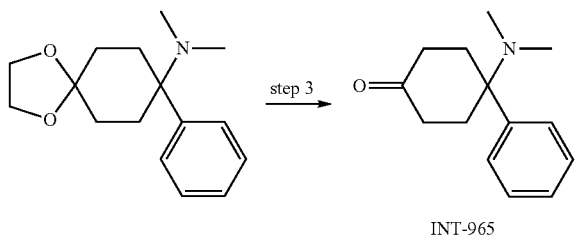

Step 1: 8-(Dimethylamino)-1,4-dioxaspiro 4.5]decane-8-carbonitrile

Dimethylamine hydrochloride (52 g, 0.645 mol) was added to the solution of 1,4-dioxaspiro-[4.5]-decan-8-one (35 g, 0.224 mmol) in MeOH (35 mL) at RT under argon atmosphere. The solution was stirred for 10 min and 40 wt % aq. dimethylamine (280 mL, 2.5 mol) and KCN (32 g, 0.492 mol) were sequentially added. The reaction mixture was stirred for 48 h at RT, then diluted with water (100 mL) and extracted with EtOAc (2×200 mL). The combined organic layer was dried over anhydrous Na$_2$SO$_4$ and concentrated under reduced pressure to afford 44 g of 8-(dimethylamino)-1,4-dioxaspiro-[4.5]-decane-8-carbonitrile (93%) as a white solid.

Step 2: N,N-dimethyl-8-phenyl-1,4-dioxaspiro[4.5]decan-8-amine 8-(Dimethylamino)-1,4-dioxaspiro[4.5]decane-8-carbonitrile (35 g, 0.167 mol) in THF (350 mL) was added to the solution of 3M phenylmagnesium bromide in diethyl ether (556 mL, 1.67 mol) dropwise at −10° C. under argon atmosphere. The reaction mixture was stirred for 4 h at −10° C. to 0° C. and then at RT for 18 h. The reaction completion was monitored by TLC. The reaction mixture was cooled to 0° C., diluted with sat. aq. NH$_4$Cl (1 L) and extracted with EtOAc (2×600 mL). The combined organic layer was dried over anhydrous Na$_2$SO$_4$ and concentrated under reduced pressure to afford 60 g of, N N-dimethyl-8-phenyl-1,4-dioxaspiro-[4.5]-decane-8-amine as a liquid.

Step 3: 4-(dimethylamino)-4-phenylcyclohexanone

A solution of N,N-dimethyl-8-phenyl-1,4-dioxaspiro[4.5]decan-8-amine (32 g, 0.123 mol) in 6N aq. HCl (320 mL) was stirred at 0° C. for 2 h and then at RT for 18 h. The reaction completion was monitored by TLC. The reaction mixture was extracted with DCM (2×150 mL). The aqueous layer was basified to pH 10 with solid NaOH and extracted with ethyl acetate (2×200 mL). The combined organic layer was dried over anhydrous Na$_2$SO$_4$ and concentrated under reduced pressure. The solid residue was washed with hexane and dried in vacuo to afford 7 g of 4-dimethylamino-4-phenyl-cyclohexan-1-one (INT-965) (25% over 2 steps) as a brown solid. [M+H]$^+$ 218.1

Synthesis of INT-966: 3-[(4-Methoxyphenyl)-methyl]-1,3-diazaspiro[4.5]decane-2,8-dione

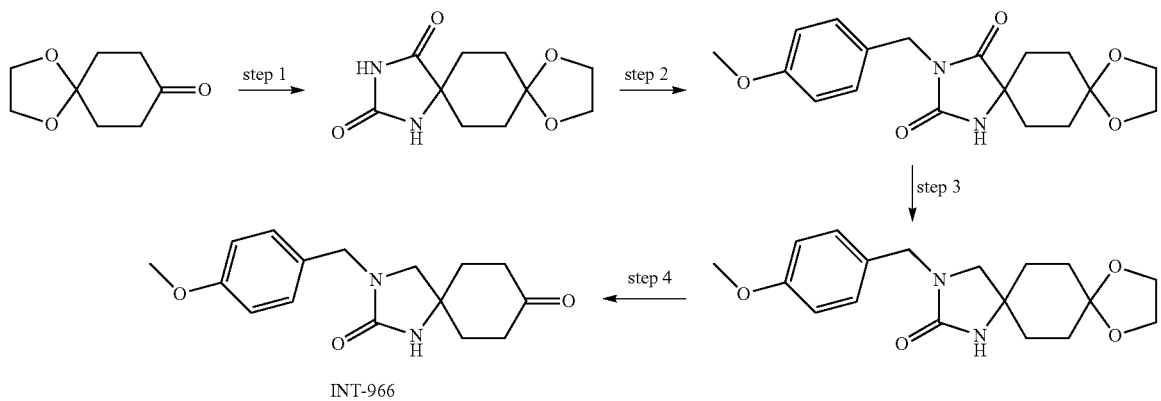

Step 1: 9,12-Dioxa-2,4-diazadispiro[4.2.4^{8}0.2^{5}]tetradecane-1,3-dione

KCN (93.8 g, 1441.6 mmol) and (NH$_4$)$_2$CO$_3$ (271.8 g, 1729.9 mmol) were added to the solution of 1,4-dioxaspiro[4.5]decan-8-one (150 g, 961 mmol) in MeOH:H$_2$O (1:1 v/v) (1.92 L) at RT under argon atmosphere. The reaction mixture was stirred at 60° C. for 16 h. The reaction completion was monitored by TLC. The reaction mixture was cooled to 0° C., the precipitated solid was filtered off and dried in vacuo to afford 120 g (55%) of 9,12-dioxa-2,4-diazadispiro[4.2.4^{8}0.2^{5}]tetradecane-1,3-dione. The filtrate was extracted with DCM (2×1.5 L). The combined organic layer was dried over anhydrous Na$_2$SO$_4$ and concentrated under reduced pressure to afford additional 30 g (14%) of 9,12-dioxa-2,4-diazadispiro[4.2.4^{8}0.2^{5}]tetradecane-1,3-dione (TLC system: 10% Methanol in DCM; Rf: 0.4).

Step 2: 2-[(4-Methoxyphenyl)-methyl]-9,12-dioxa-2,4-diazadispiro[4.2.4^{8}0.2^{5}]tetradecane-1,3-dione Cs$_2$CO$_3$ (258.7 g, 796.1 mmol) was added to the solution of 73a (150 g, 663.4 mmol) in MeCN (1.5 L) under argon atmosphere and the reaction mixture was stirred for 30 min. A solution of p-methoxybenzyl bromide (96 mL, 663.4 mmol) was added. The reaction mixture was stirred at RT for 48 h. The reaction completion was monitored by TLC. The reaction mixture was quenched with sat. aq. NH₄Cl (1.0 L) and the organic product was extracted with EtOAc (2×1.5 L). The combined organic layer was dried over anhydrous Na₂SO₄ and concentrated under reduced pressure. The residue was washed with diethyl ether and pentane and dried under reduced pressure to afford 151 g (65%) of 2-[(4-Methoxyphenyl)-methyl]-9,12-dioxa-2,4-diazadispiro[4.2.4^{8}0.2^{5}]tetradecane-1,3-dione as an off white solid (TLC system: 10% MeOH in DCM; Rf: 0.6).

Step 3: 2-[(4-Methoxyphenyl)-methyl]-9,12-dioxa-2,4-diazadispiro[4.2.4^{8}0.2^{5}]tetradecan-3-one AlCl₃ (144.3 g, 1082.6 mmol) was added to a solution of LiAlH₄ (2M in THF) (433 mL, 866.10 mmol) in THF (4.5 L) at 0° C. under argon atmosphere and the resulting mixture was stirred at RT for 1 h. 2-[(4-Methoxyphenyl)-methyl]-9,12-dioxa-2,4-diazadispiro[4.2.4^{8}0.2^{5}]tetradecane-1,3-dione (150 g, 433.05 mmol) was added at 0° C. The reaction mixture was stirred at RT for 16 h. The reaction completion was monitored by TLC. The reaction mixture was cooled to 0° C., quenched with sat. aq. NaHCO₃ (500 mL) and filtered through celite pad. The filtrate was extracted with EtOAc (2×2.0 L). The combined organic layer was dried over anhydrous Na₂SO₄ and concentrated in vacuo to afford 120 g (84%) of 2-[(4-methoxyphenyl)-methyl]-9,12-dioxa-2,4-diazadispiro[4.2.4^{8}0.2^{5}]tetradecan-3-one as an off-white solid. (TLC system: 10% MeOH in DCM, Rf: 0.5).

Step 4: 3-[(4-Methoxyphenyl)-methyl]-1,3-diazaspiro[4.5]decane-2,8-dione

A solution of 2-[(4-methoxyphenyl)-methyl]-9,12-dioxa-2,4-diazadispiro[4.2.4^{8}0.2^{5}]tetradecan-3-one (120 g, 361.03 mmol) in 6N aq. HCl (2.4 L) was stirred at 0° C. for 2 h and then at RT for 18 h. The reaction completion was monitored by TLC. The reaction mixture was extracted with DCM (2×2.0 L). The aqueous layer was basified to pH 10 with 50% aq. NaOH and then extracted with DCM (2×2.0 L). Combined organic extracts were dried over anhydrous Na₂SO₄ and concentrated under reduced pressure. The solid residue was washed with hexane and dried in vacuo to afford 90 g of 3-[(4-Methoxyphenyl)-methyl]-1,3-diazaspiro[4.5]decane-2,8-dione (INT-966) as an off-white solid (TLC system: 10% MeOH in DCM; Rf: 0.4) [M+H]⁺ 289.11.

Synthesis of INT-971: CIS-1-(Cyclobutyl-methyl)-8-dimethylamino-8-(3-hydroxyphenyl)-3-[(4-methoxyphenyl)-methyl]-1,3-diazaspiro[4.5]decan-2-one

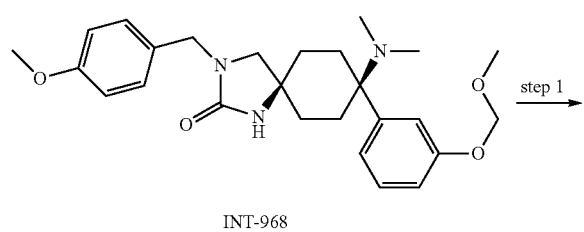

INT-968

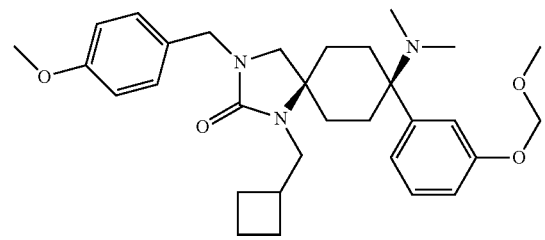

step 2

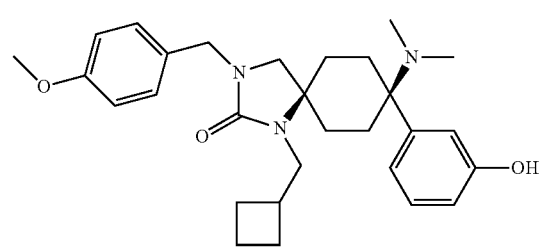

INT-971

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-Dimethylamino-8-[3-(methoxymethyloxy)-phenyl]-3-[(4-methoxyphenyl)-methyl]-1,3-diazaspiro[4.5]decan-2-one (INT-968) was converted into CIS-1-(cyclobutylmethyl)-8-(dimethylamino)-3-(4-methoxybenzyl)-8-(3-(methoxymethoxy)phenyl)-1,3-diazaspiro[4.5]decan-2-one.

Step 2: CIS-1-(Cyclobutyl-methyl)-8-dimethylamino-8-(3-hydroxyphenyl)-3-[(4-methoxyphenyl)-methyl]-1,3-diazaspiro[4.5]decan-2-one TFA (0.2 mL) was added to the solution of CIS-1-(cyclobutylmethyl)-8-(dimethylamino)-3-(4-methoxybenzyl)-8-(3-methoxyphenyl)-1,3-diazaspiro[4.5]decan-2-one (300 mg, 0.57 mmol) in DCM (1.5 mL) at 0° C. The reaction mixture was stirred at 0° C. for 3 h. The reaction completion was monitored by TLC. The reaction mixture was quenched with sat. aq. NaHCO₃ and the organic product was extracted with DCM (3×10 mL). The combined organic extracts were dried over anhydrous Na₂SO₄ and concentrated under reduced pressure. Purification of the residue by preparative TLC (3% MeOH in DCM as mobile phase) yielded 50 mg (18%) of CIS-1-(Cyclobutyl-methyl)-8-dimethylamino-8-(3-hydroxyphenyl)-3-[(4-methoxyphenyl)-methyl]-1,3-diazaspiro[4.5]decan-2-one (INT-971) as an off white solid. (TLC system: 10% MeOH in DCM; Rf: 0.20) [M+H]⁺ 478.3

Synthesis of INT-974: CIS-8-Dimethylamino-8-(3-fluorophenyl)-3-[(4-methoxyphenyl)-methyl]-1,3-diazaspiro[4.5]decan-2-one

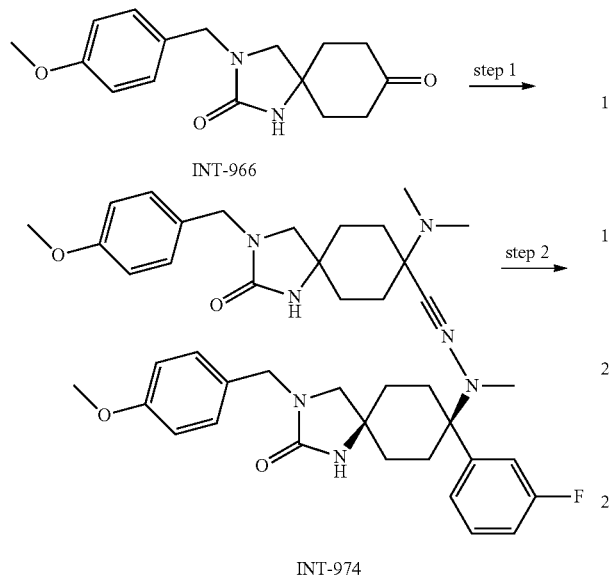

product by flash column chromatography on silica gel (230-400 mesh) (2 times) (0-20% methanol in DCM) eluent and subsequently by washing with pentane yielded 5.6 g (11%) of CIS-8-dimethylamino-8-(3-fluorophenyl)-3-[(4-methoxyphenyl)-methyl]-1,3-diazaspiro[4.5]decan-2-one (INT-974) as an off-white solid. (TLC system: 5% MeOH in DCM in presence of ammonia; Rf: 0.1). [M+H]$^+$ 412.2

Synthesis of INT-975: CIS-8-Dimethylamino-3-[(4-methoxyphenyl)-methyl]-8-phenyl-1,3-diazaspiro[4.5]decan-2-one

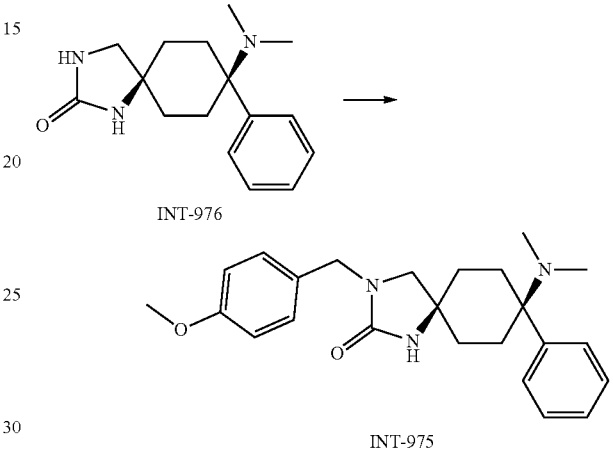

Step 1: 8-(dimethylamino)-3-(4-methoxybenzyl)-2-oxo-1,3-diazaspiro[4.5]decane-8-carbonitrile Dimethylamine hydrochloride (76.4 g, 936.4 mmol) was added to a solution of 3-[(4-methoxyphenyl)-methyl]-1,3-diazaspiro[4.5]decane-2,8-dione (INT-966) (90 g, 312.13 mmol) in MeOH (180 mL) at RT under argon atmosphere. The solution was stirred for 15 min and 40 wt % aq. dimethylamine (780 mL) and KCN (48.76 g, 749.11 mmol) were sequentially added. The reaction mixture was stirred for 48 h and the completion of the reaction was monitored by NMR. The reaction mixture was diluted with water (1.0 L) and the organic product was extracted with ethyl acetate (2×2.0 L). The combined organic layer was dried over anhydrous Na$_2$SO$_4$ and concentrated under reduced pressure to afford 90 g (85%) of 8-(dimethylamino)-3-(4-methoxybenzyl)-2-oxo-1,3-diazaspiro[4.5]decane-8-carbonitrile as an off white solid (TLC system: TLC system: 10% MeOH in DCM; Rf: 0.35, 0.30).

Step 2: CIS-8-Dimethylamino-8-(3-fluorophenyl)-3-[(4-methoxyphenyl)-methyl]-1,3-diazaspiro[4.5]decan-2-one 3-Fluorophenylmagnesium bromide (1M in THF) (220 mL, 219.17 mmol) was added dropwise to a solution of 8-(dimethylamino)-3-(4-methoxybenzyl)-2-oxo-1,3-diazaspiro[4.5]decane-8-carbonitrile (15 g, 43.83 mmol) in THF (300 mL) at 0° C. under argon atmosphere. The reaction mixture was stirred for 16 h at RT. The reaction completion was monitored by TLC. The reaction mixture was cooled to 0° C., quenched with sat. aq. NH$_4$Cl (200 mL) and the organic product was extracted with EtOAc (2×200 mL). The combined organic layer was dried over anhydrous Na$_2$SO$_4$ and concentrated under reduced pressure. The reaction was carried out in 4 batches (15 g×2 and 5 g×2) and the batches were combined for purification. Purification of the crude KOtBu (1M in THF) (29.30 mL, 29.30 mmol) was added to the solution of CIS-8-Dimethylamino-8-phenyl-1,3-diazaspiro[4.5]decan-2-one INT-976 (8.0 g, 29.30 mmol) in THF (160 mL) under argon atmosphere and the reaction mixture was stirred for 30 min. 4-Methoxybenzyl bromide (4.23 mL, 29.30 mmol) was added and stirring was continued at RT for 4 h. The reaction completion was monitored by TLC. The reaction mixture was diluted with sat. aq. NH$_4$Cl (150 mL) and the organic product was extracted with EtOAc (2×150 mL). The combined organic layer was dried over anhydrous Na$_2$SO$_4$ and concentrated in vacuo. The reaction was carried out in 2 batches (8 g×2) and the batches were combined for purification. Purification of the crude product by flash column chromatography on silica gel (0-10% methanol in DCM) and subsequently by washing with pentane yielded 11 g (47%) of CIS-8-Dimethylamino-3-[(4-methoxyphenyl)-methyl]-8-phenyl-1,3-diazaspiro[4.5]decan-2-one (INT-975) as a white solid. [M+H]$^+$ 394.2

Synthesis of INT-976: CIS-8-Dimethylamino-8-phenyl-1,3-diazaspiro[4.5]decan-2-one

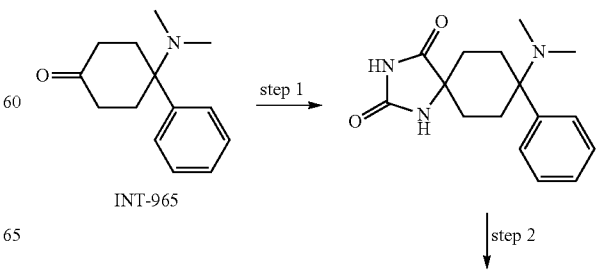

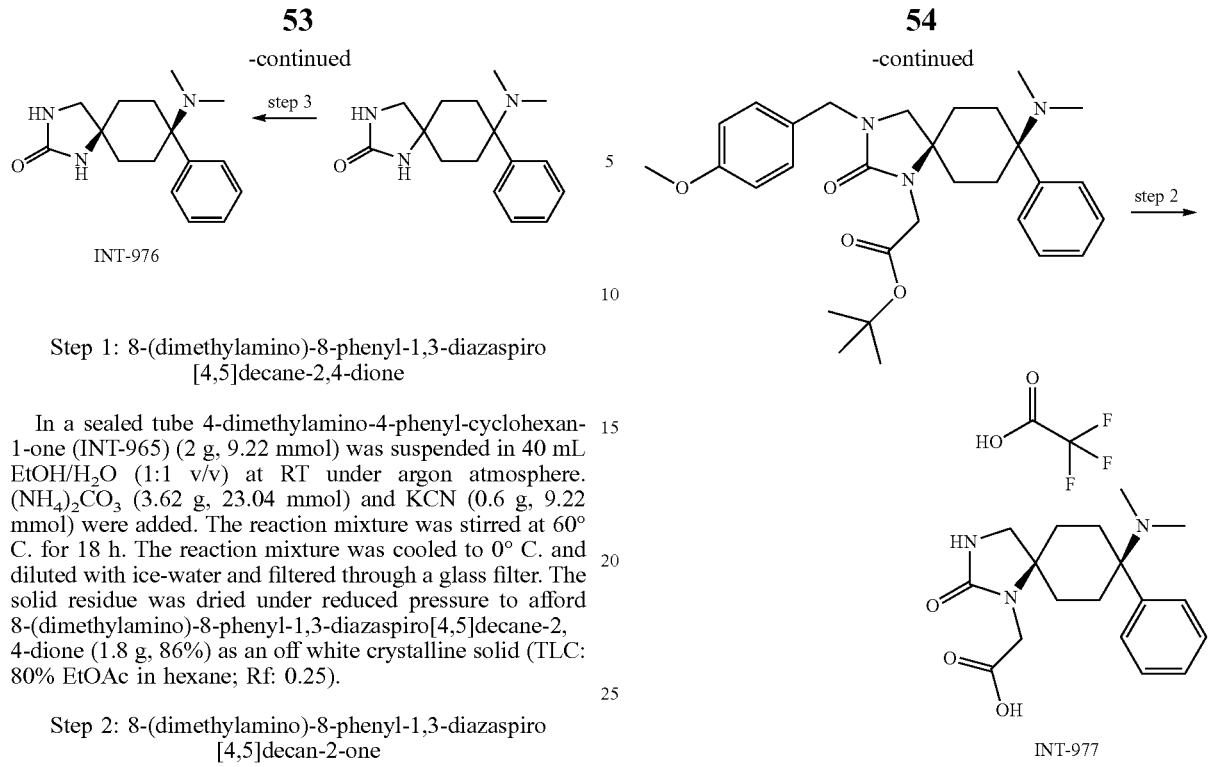

Step 1: 8-(dimethylamino)-8-phenyl-1,3-diazaspiro[4,5]decane-2,4-dione

In a sealed tube 4-dimethylamino-4-phenyl-cyclohexan-1-one (INT-965) (2 g, 9.22 mmol) was suspended in 40 mL EtOH/H$_2$O (1:1 v/v) at RT under argon atmosphere. (NH$_4$)$_2$CO$_3$ (3.62 g, 23.04 mmol) and KCN (0.6 g, 9.22 mmol) were added. The reaction mixture was stirred at 60° C. for 18 h. The reaction mixture was cooled to 0° C. and diluted with ice-water and filtered through a glass filter. The solid residue was dried under reduced pressure to afford 8-(dimethylamino)-8-phenyl-1,3-diazaspiro[4,5]decane-2,4-dione (1.8 g, 86%) as an off white crystalline solid (TLC: 80% EtOAc in hexane; Rf: 0.25).

Step 2: 8-(dimethylamino)-8-phenyl-1,3-diazaspiro[4,5]decan-2-one

LiAlH$_4$ (2M in THF) (70 mL, 139.4 mmol) was added to the solution of 8-(dimethylamino)-8-phenyl-1,3-diazaspiro[4,5]decane-2,4-dione (10 g, 34.8 mmol) in THF/Et$_2$O (2:1 v/v) (400 mL) at 0° C. under argon atmosphere. The reaction mixture was stirred for 4 h at 60° C. The reaction completion was monitored by TLC. The reaction mixture was cooled to 0° C., quenched with saturated Na$_2$SO$_4$ solution (100 mL) and filtered through Celite pad. The filtrate was dried over anhydrous Na$_2$SO$_4$ and concentrated in vacuo to afford 5.7 g (59%) of 8-(dimethylamino)-8-phenyl-1,3-diazaspiro[4,5]decan-2-one as an off white solid. (TLC system: 10% MeOH in DCM, Rf: 0.3).

Step 3: CIS-8-Dimethylamino-8-phenyl-1,3-diazaspiro[4.5]decan-2-one

A mixture of CIS- and TRANS-8-(dimethylamino)-8-phenyl-1,3-diazaspiro[4,5]decan-2-one (8 g, 29.30 mmol) was purified by preparative chiral SFC (column: Chiralcel AS-H, 60% CO$_2$, 40% (0.5% DEA in MeOH)) to get 5 g of CIS-8-Dimethylamino-8-phenyl-1,3-diazaspiro[4.5]decan-2-one (INT-976) as a white solid. [M+H]$^+$ 274.2.

Synthesis of INT-977: CIS-2-(8-Dimethylamino-2-oxo-8-phenyl-1,3-diazaspiro[4.5]decan-1-yl)-acetic acid; 2,2,2-trifluoro-acetic acid salt

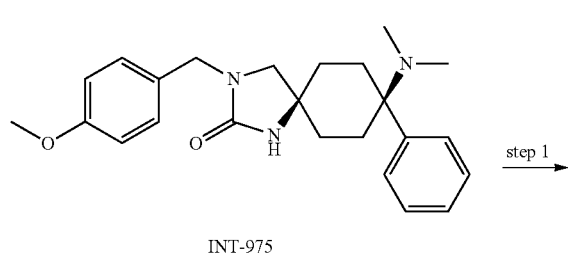

INT-975

Step 1: CIS-2-[8-Dimethylamino-3-[(4-methoxyphenyl)-methyl]-2-oxo-8-phenyl-1,3-diazaspiro[4.5]decan-1-yl]-acetic acid tert-butyl ester A solution of CIS-8-Dimethylamino-3-[(4-methoxyphenyl)-methyl]-8-phenyl-1,3-diazaspiro[4.5]decan-2-one (INT-975) (5.0 g, 12.7 mmol) in THF (18 mL) was cooled to 0° C. and treated with LDA solution (2M in THF/heptane/ether, 25.4 mL, 50.8 mmol). The resulting mixture was was allowed to warm up to RT over 30 min. The solution was then cooled to 0° C. again and tert-butyl-bromoacetate (5.63 mL, 38.1 mmol) was added. The reaction mixture was stirred at RT for 16 h, quenched with water and extracted with DCM (3×). The combined organic layers were dried over Na$_2$SO$_4$, filtered and concentrated under reduced pressure. Purification of the residue by column chromatography on silica gel provided CIS-2-[8-dimethylamino-3-[(4-methoxyphenyl)-methyl]-2-oxo-8-phenyl-1,3-diazaspiro[4.5]decan-1-yl]-acetic acid tert-butyl ester (4.4 g).

Step 2: cis-2-(8-Dimethylamino-2-oxo-8-phenyl-1,3-diazaspiro[4.5]decan-1-yl)-acetic acid trifluoroacetic acid salt CIS-2-[8-Dimethylamino-3-[(4-methoxyphenyl)-methyl]-2-oxo-8-phenyl-1,3-diazaspiro[4.5]decan-1-yl]-acetic acid tert-butyl ester (200 mg, 0.4 mmol) was dissolved in TFA (5 mL) and heated to reflux overnight. After cooling to RT all volatiles are removed in vacuo. The residue was taken up in THF (1 mL) and added dropwise to diethyl ether (20 mL). The resulting precipitate was filtered off and dried under reduced pressure to give CIS-2-(8-dimethylamino-2-oxo-8-phenyl-1,3-diazaspiro[4.5]decan-1-yl)-acetic acid; 2,2,2-trifluoro-acetic acid salt (INT-977) (119 mg) as a white solid. [M+H]$^+$ 332.2

Synthesis of INT-978: CIS-2-(8-Dimethylamino-2-oxo-8-phenyl-1,3-diazaspiro[4.5]decan-1-yl)-N,N-dimethyl-acetamide

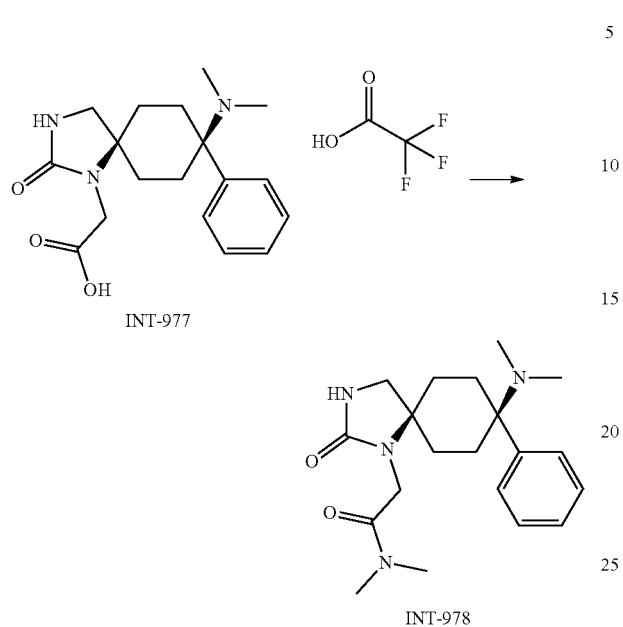

INT-977

INT-978

CIS-2-(8-Dimethylamino-2-oxo-8-phenyl-1,3-diazaspiro[4.5]decan-1-yl)-acetic acid (INT-977) trifluoroacetic acid salt (119 mg, 0.35 mmol) was dissolved in DCM (5 mL). Triethylamine (0.21 mL, 1.6 mmol), dimethylamine (0.54 mL, 1.1 mmol) and T3P (0.63 mL, 1.1 mmol) were sequentially added. The reaction mixture was stirred at RT overnight, then diluted with 1 M aq. Na$_2$CO$_3$ (5 mL). The aqueous layer was extracted with DCM (3×5 mL), the combined organic layers were dried over Na$_2$SO$_4$ and concentrated under reduced pressure. The residue was purified by flash chromatography on silica gel to yield CIS-2-(8-dimethylamino-2-oxo-8-phenyl-1,3-diazaspiro[4.5]decan-1-yl)-N,N-dimethyl-acetamide (INT-978) (39 mg) as a white solid. [M+H]$^+$ 359.2

Synthesis of INT-982: CIS-8-Dimethylamino-1-[(1-methyl-cyclobutyl)-methyl]-8-phenyl-1,3-diazaspiro[4.5]decan-2-one

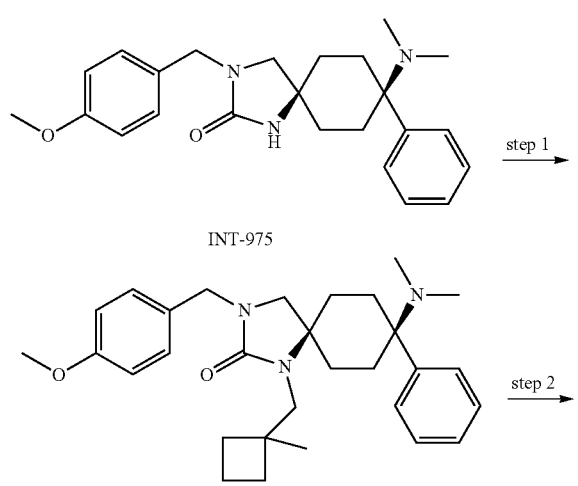

INT-975

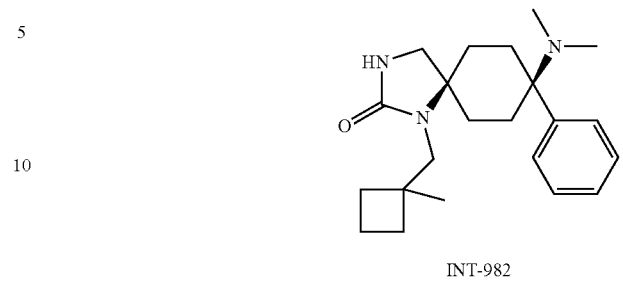

INT-982

Step 1: CIS-8-(dimethylamino)-3-(4-methoxybenzyl)-1-((1-methylcyclobutyl)methyl)-8-phenyl-1,3-diazaspiro[4.5]decan-2-one A solution of NaOH (2.85 g, 71.2 mmol) in DMSO (25 mL) was stirred at RT for 10 min. CIS-8-Dimethylamino-3-[(4-methoxyphenyl)-methyl]-8-phenyl-1,3-diazaspiro[4.5]decan-2-one (INT-975) (7.00 g, 17.8 mmol) was added and stirring was continued for 15 min. 1-(Bromo-methyl)-1-methyl-cyclobutane (8.7 g, 53.4 mmol) was added at 0° C. The reaction mixture was heated to 60° C. for 16 h. After cooling down to RT, water (100 mL) was added and the mixture was extracted with DCM (3×150 mL). The combined organic layers were washed with water (70 mL), brine (100 mL), dried over Na$_2$SO$_4$ and concentrated under reduced pressure. Purification of the residue by column chromatography on silica gel provided CIS-8-(dimethylamino)-3-(4-methoxybenzyl)-1-((1-methylcyclobutyl)methyl)-8-phenyl-1,3-diazaspiro[4.5]decan-2-one (6.5 g) as a light yellow solid.

Step 2: CIS-8-Dimethylamino-1-[(1-methyl-cyclobutyl)-methyl]-8-phenyl-1,3-diazaspiro[4.5]decan-2-one To the solution of CIS-8-Dimethylamino-1-[(1-methyl-cyclobutyl)-methyl]-8-phenyl-1,3-diazaspiro[4.5]decan-2-one (6.66 g, 14.0 mmol) in DCM (65 mL) was added TFA (65 mL) and the resulting mixture was stirred at RT for 16 h. The reaction mixture was concentrated under reduced pressure. The residue was taken up in DCM (100 mL) and water (60 mL) and basified with 2M aq. NaOH to pH 10. The organic layer was separated and washed with brine (40 mL), dried over MgSO$_4$, filtered and concentrated under reduced pressure. Crystallization of the residue from EtOAc provided CIS-8-Dimethylamino-1-[(1-methyl-cyclobutyl)-methyl]-8-phenyl-1,3-diazaspiro[4.5]decan-2-one (INT-982) (3.41 g) as an off-white solid. [M+H]$^+$ 356.3

Synthesis of INT-984: CIS-1-(Cyclobutyl-methyl)-8-(ethyl-methyl-amino)-8-phenyl-1,3-diazaspiro[4.5]decan-2-one

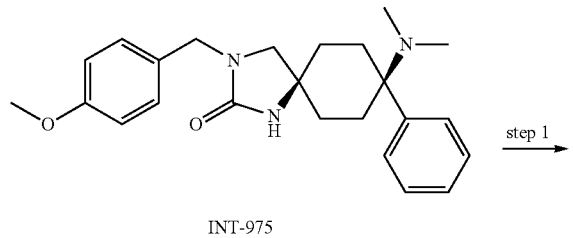

INT-975

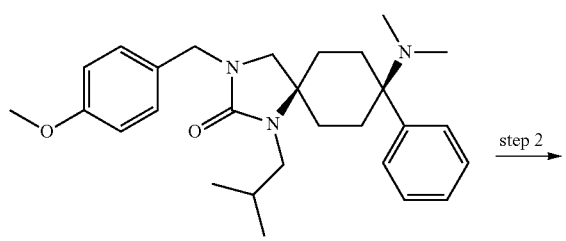

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-Dimethylamino-3-[(4-methoxyphenyl)-methyl]-8-phenyl-1,3-diazaspiro[4.5]decan-2-one (INT-975) was converted into CIS-8-(dimethylamino)-1-isobutyl-3-(4-methoxybenzyl)-8-phenyl-1,3-diazaspiro[4.5]decan-2-one.

Step 2: CIS-1-(Cyclobutyl-methyl)-8-(ethyl-methyl-amino)-8-phenyl-1,3-diazaspiro[4.5]decan-2-one In analogy to the method described for INT-982 step 2 CIS-8-(dimethylamino)-1-isobutyl-3-(4-methoxybenzyl)-8-phenyl-1,3-diazaspiro[4.5]decan-2-one was converted into CIS-1-(Cyclobutyl-methyl)-8-(ethyl-methyl-amino)-8-phenyl-1,3-diazaspiro[4.5]decan-2-one (INT-984).

Synthesis of INT-986: CIS-1-(Cyclobutyl-methyl)-8-(ethyl-methyl-amino)-8-phenyl-1,3-diazaspiro[4.5]decan-2-one

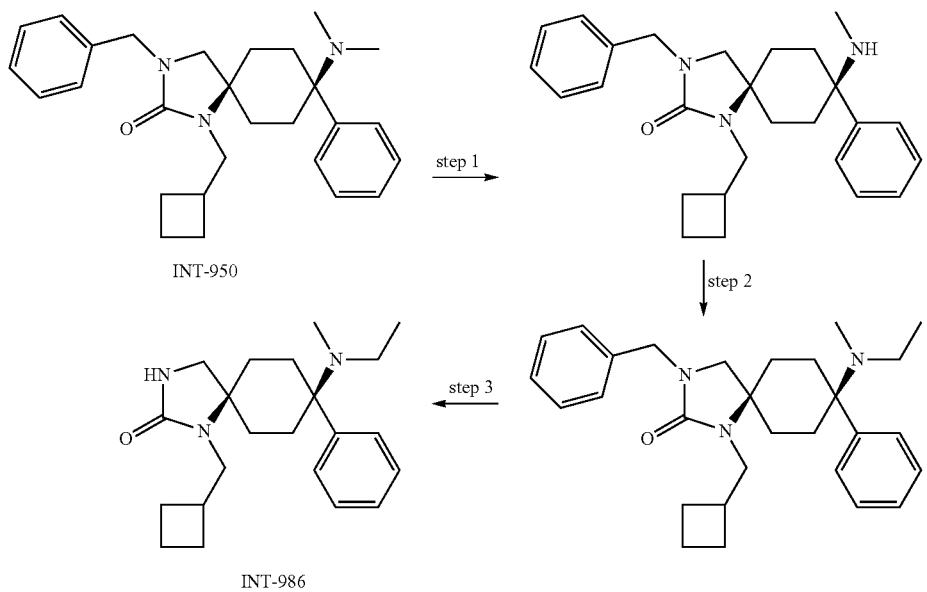

INT-950

INT-986

-continued

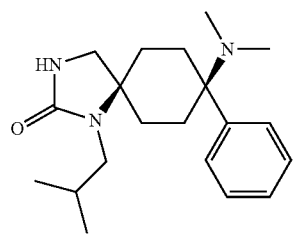

INT-984

Step 1: CIS-3-benzyl-1-(cyclobutylmethyl)-8-(methylamino)-8-phenyl-1,3-diazaspiro[4.5]decan-2-one N-Iodosuccinimide (3.11 g, 13.92 mmol) was added to the solution of CIS-1-(Cyclobutyl-methyl)-8-dimethylamino-8-phenyl-3-[phenyl-methyl]-1,3-diazaspiro[4.5]decan-2-one (INT-950) (4 g, 9.28 mmol) in a mixture of acetonitrile and THF (1:1 v/v, 80 mL) and the resulting mixture was stirred at RT for 16 h. The reaction mixture was basified with 2N aq. NaOH to pH~10 and the organic product was extracted with DCM (3×10 mL). The combined organic extracts were dried over anhydrous $Na_2SO_4$ and concentrated in vacuo. The residue was stirred vigorously with a mixture of 10 wt % aq. citric acid (5 mL) and DCM (10 mL) at RT for 10 min.

The reaction mixture was basified with 5N aq. NaOH to pH~10 and extracted with DCM (3×10 mL). The combined organic layer was dried over anhydrous Na₂SO₄ and concentrated in vacuo to give 3.5 g (crude) of CIS-3-benzyl-1-(cyclobutylmethyl)-8-(methylamino)-8-phenyl-1,3-diazaspiro[4.5]decan-2-one as semi solid (TLC system: 10% MeOH in DCM; $R_f$: 0.60.).

Step 2: CIS-3-benzyl-1-(cyclobutylmethyl)-8-(ethyl (methyl)amino)-8-phenyl-1,3-diazaspiro[4.5]decan-2-one Sodium cyanoborohydride (1.56 g, 25.17 mmol, 3 equiv.) was added to the solution of CIS-3-benzyl-1-(cyclobutylmethyl)-8-(methylamino)-8-phenyl-1,3-diazaspiro[4.5]decan-2-one (3.5 g, 8.39 mmol), acetaldehyde (738 mg, 16.78 mmol, 2 equiv.) and acetic acid (0.5 mL) in methanol (20 mL). The reaction mixture was stirred at RT for 3 h, then quenched with sat. aq. NaHCO₃ and the organic product was extracted with DCM (3×50 mL). The combined organic extracts were dried over anhydrous Na₂SO₄ and concentrated in vacuo. Purification of the residue by flash column chromatography on silica gel (230-400 mesh) (20-25% ethyl acetate in petroleum ether) yielded 2.3 g (62%) of CIS-3-benzyl-1-(cyclobutylmethyl)-8-(ethyl(methyl)amino)-8-phenyl-1,3-diazaspiro[4.5]decan-2-one as a solid. (TLC system: 50% EtOAc in Pet. Ether; $R_f$: 0.65).

Step 3: CIS-1-(Cyclobutyl-methyl)-8-(ethyl-methyl-amino)-8-phenyl-1,3-diazaspiro[4.5]decan-2-one (INT-986)

Sodium metal (1.18 g, 51.68 mmol, 10 equiv.) was added to liquid ammonia (~25 mL) at −78° C. The resulting mixture was stirred for 10 min at −78° C. A solution of CIS-3-benzyl-1-(cyclobutylmethyl)-8-(ethyl(methyl) amino)-8-phenyl-1,3-diazaspiro[4.5]decan-2-one (2.3 g, 5.16 mmol) in THF (25 mL) was added at −78° C. The reaction mixture was stirred for 15 min, then quenched with sat. aq. NH₄Cl, warmed to RT and stirred for 1 h. The organic product was extracted with DCM (3×50 mL). The combined organic layer was washed with water, brine and concentrated under reduced pressure to afford 1.30 g (72%) of CIS-1-(cyclobutylmethyl)-8-(ethyl(methyl)amino)-8-phenyl-1,3-diazaspiro[4.5]decan-2-one (INT-986) as an off-white solid. (TLC system: 10% MeOH in DCM $R_f$: 0.15.). [M+H]+ 356.3

Synthesis of INT-987: CIS-1-(Cyclobutyl-methyl)-8-dimethylamino-8-phenyl-1,3-diazaspiro[4.5]decan-2-one

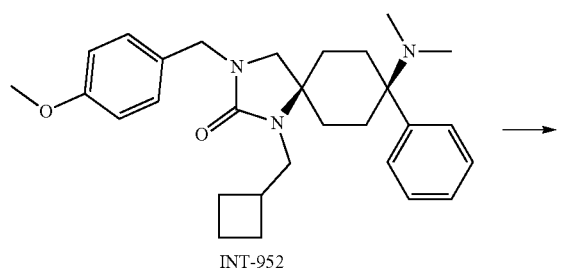

INT-952

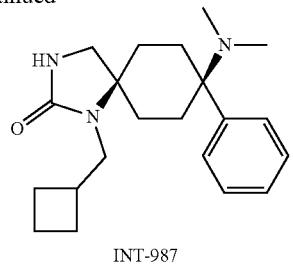

INT-987

In analogy to the method as described for INT-982 step 2 CIS-1-(Cyclobutyl-methyl)-8-dimethylamino-8-phenyl-3-[(4-methoxyphenyl)-methyl]-1,3-diazaspiro[4.5]decan-2-one (INT-952) was converted into CIS-1-(Cyclobutyl-methyl)-8-dimethylamino-8-phenyl-1,3-diazaspiro[4.5] decan-2-one (INT-987).

Synthesis of INT-988: CIS-8-(dimethylamino)-1-(2-(1-methoxycyclobutyl)ethyl)-8-phenyl-1,3-diazaspiro[4.5]decan-2-one

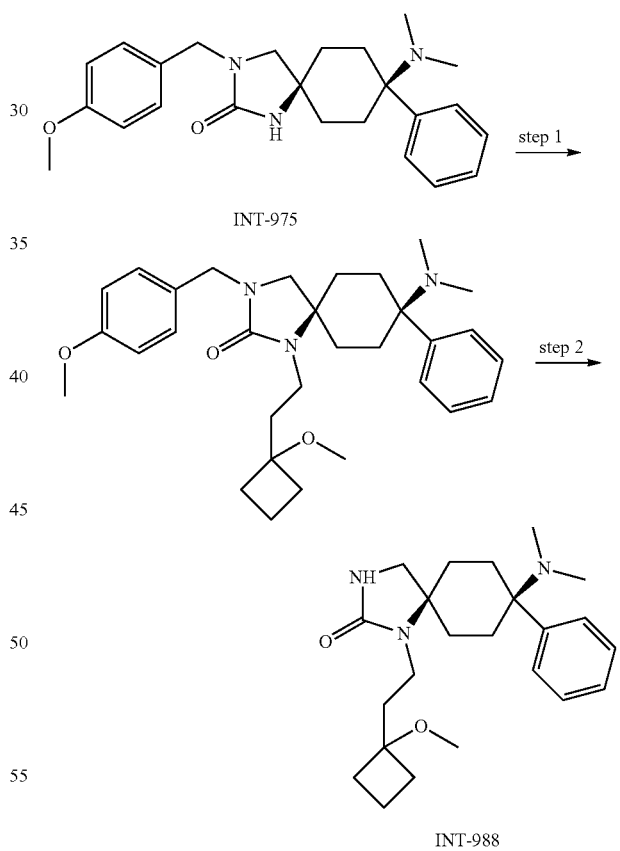

Step 1: CIS-8-(dimethylamino)-1-[2-(1-methoxycyclobutyl)ethyl]-3-[(4-methoxyphenyl)methyl]-8-phenyl-1,3-diazaspiro[4.5]decan-2-one Sodium hydroxide (78.06 mg, 4.0 equiv.) was suspended in DMSO (3.5 mL), stirred for 10 minutes, 8-(dimethylamino)-3-[(4-methoxyphenyl)methyl]-8-phenyl-1,3-diazaspiro[4.5]decan-2-one (INT-975) (192.0 mg, 1.0 equiv.) was added, the reaction mixture was stirred for 5 min followed by addition of 2-(1-methoxycyclobutyl)ethyl 4-methylbenzenesulfonate (416.2 mg, 3.0 equiv.) in DMSO (1.5 mL). The resulting mixture was stirred overnight at 50° C. The reaction mixture was quenched with water and extracted with DCM (3×20 mL). The combined organic phases were washed with brine, dried over $Na_2SO_4$ and concentrated under reduced pressure. The residue (283 mg yellow oil) was purified by column chromatography on silica gel (eluent DCM/EtOH 98/2 to 96/4) to give 8-(dimethylamino)-1-[2-(1-methoxycyclobutyl)ethyl]-3-[(4-methoxyphenyl)methyl]-8-phenyl-1,3-diazaspiro[4.5]decan-2-one 163 mg (66%).

Step 2: CIS-8-(dimethylamino)-1-(2-(1-methoxycyclobutyl)ethyl)-8-phenyl-1,3-diazaspiro[4.5]decan-2-one (INT-988)

In analogy to the method described for INT-982 step 2 CIS-8-(dimethylamino)-1-[2-(1-methoxycyclobutyl)ethyl]-3-[(4-methoxyphenyl)methyl]-8-phenyl-1,3-diazaspiro[4.5]decan-2-one was converted into CIS-8-(dimethylamino)-1-(2-(1-methoxycyclobutyl)ethyl)-8-phenyl-1,3-diazaspiro[4.5]decan-2-one (INT-988). Mass: m/z 386.3 $(M+H)^+$.

Synthesis of INT-1008: CIS-8-ethylamino-8-phenyl-1,3-diaza-spiro[4.5]decan-2-one Step 1 and step 2: ethyl-(8-phenyl-1,4-dioxa-spiro[4.5]dec-8-yl)-amine hydrochloride (INT-1004)

A mixture of 1,4-dioxa-spiro[4.5]decan-8-one (25.0 g, 160.25 mmol, 1.0 eq.) and 2M solution of $EtNH_2$ in THF (200 ml, 2.5 eq. 400.64 mmol) in EtOH (30 ml) was stirred at RT for 48 h. The reaction mixture was concentrated under argon atmosphere and the residue was diluted with ether (60 ml), and a freshly prepared PhLi solution was added [prepared by addition of 2.5M n-BuLi in THF (70.5 ml, 1.1 eq. 176.27 mmol) to a solution of bromobenzene (27.675 g, 1.1 eq. 176.275 mmol) in ether (100 ml) at ~30° C. and stirred at RT for 1 h). The reaction mixture was stirred at RT for 1.5 h, quenched with saturated $NH_4Cl$ solution (100 ml) at 0° C. and extracted with ethyl acetate (2×750 ml). The combined organic layer was washed with water (3×350 ml), brine (300 ml), dried over $Na_2SO_4$ and concentrated under reduced pressure. The resulting residue was dissolved in ethyl methyl ketone (100 ml) and trimethylsilyl chloride (37.5 ml) was added at 0° C. The resulting mixture was stirred at RT for 16 h. The precipitated solid was filtered off and washed with acetone followed by THF to get ethyl-(8-phenyl-1,4-dioxa-spiro[4.5]dec-8-yl)-amine hydrochloride as an off white solid. This reaction was done in 2 batches of 25 g scale and the yield is given for 2 combined batches. Yield: 18% (17.1 g, 57.575 mmol). LCMS: m/z 262.2 (M+H)+.

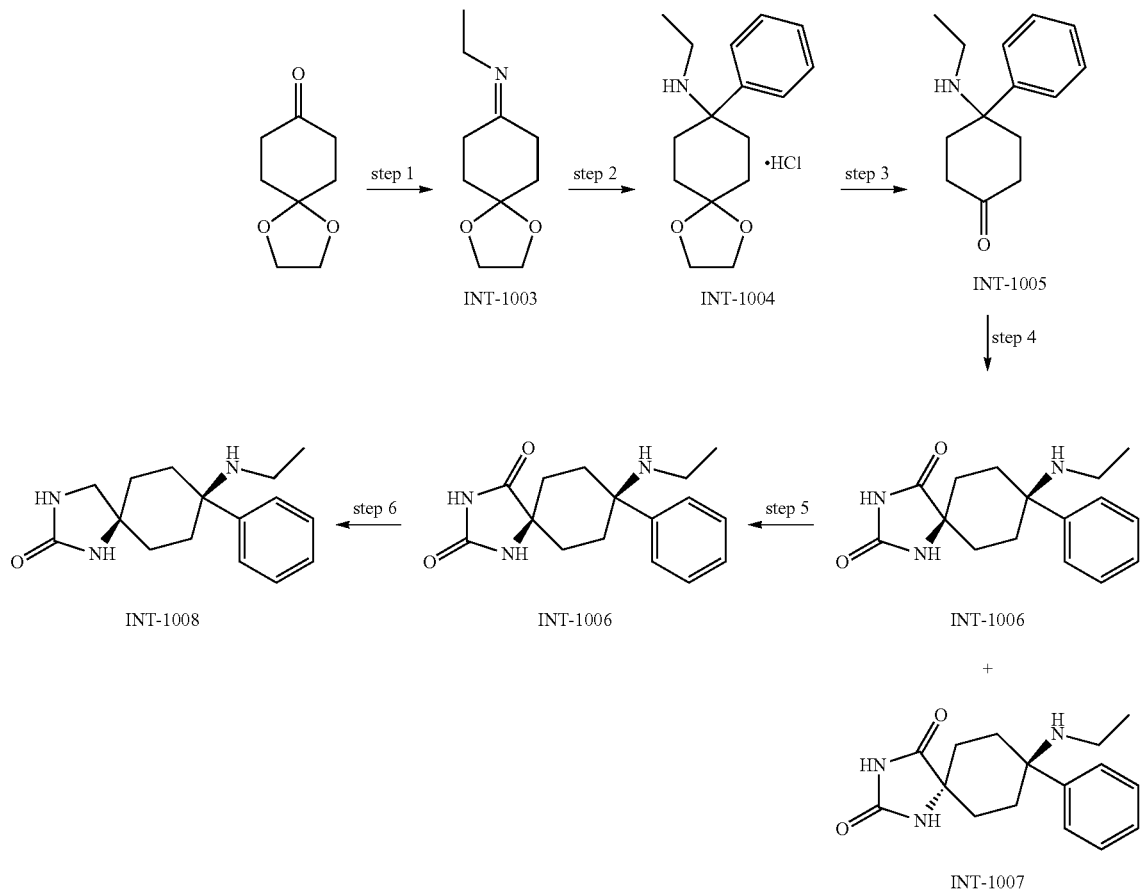

Step 3: 4-ethylamino-4-phenyl-cyclohexanone (INT-1005)

To a solution of ethyl-(8-phenyl-1,4-dioxa-spiro[4.5]dec-8-yl)-amine hydrochloride (10.1 g, 34.0 mmol, 1 eq.) in water (37.5 ml) was added conc. aq. HCl (62.5 ml) at 0° C. and the resulting mixture was stirred at RT for 16 h. The reaction mixture was basified with aq. NaOH (pH ~14) at 0° C. and extracted with DCM (2×750 ml). Organic layer was washed with water (400 ml), brine (400 ml), dried over Na$_2$SO$_4$ and concentrated under reduced pressure to yield 4-ethylamino-4-phenyl-cyclohexanone which was used in the next step without further purification. This reaction was carried out in another batch of 15.1 g scale and the yield is given for 2 combined batches. Yield: 92% (17.0 g, 78.34 mmol).

Step 4: cis and trans mixture of 8-ethylamino-8-phenyl-1,3-diaza-spiro[4.5]decane-2,4-dione (INT-1006 and INT-1007)

To a solution of 4-ethylamino-4-phenyl-cyclohexanone (17 g, 78.341 mmol, 1.0 eq.) in EtOH (250 ml) and water (200 ml) was added (NH$_4$)$_2$CO$_3$ (18.8 g, 195.85 mmol, 2.5 eq.) and the reaction mixture was stirred at RT for 15 min. KCN (5.09 g, 78.341 mmol, 1.0 eq.) was added and stirring was continued at 60° C. for 18 h. The reaction mixture was cooled down to RT. The precipitated solid was filtered off, washed with water (250 ml), EtOH (300 ml), hexane (200 ml) and dried under reduced pressure to yield cis and trans mixture of 8-ethylamino-8-phenyl-1,3-diaza-spiro[4.5]decane-2,4-dione (13.0 g, 45.29 mmol, 58%) as a white solid. Yield: 58% (13 g, 45.296 mmol). LC-MS: m/z [M+1]$^+$=288.2.

Step 5: CIS-8-ethylamino-8-phenyl-1,3-diaza-spiro[4.5]decane-2,4-dione (INT-1006)

To a solution of cis and trans mixture of 8-ethylamino-8-phenyl-1,3-diaza-spiro[4.5]decane-2,4-dione (12 g) in MeOH-DCM (1:1, 960 ml) was added a solution of L-tartaric acid in MeOH (25 ml) and the resulting mixture stirred at RT for 2 h and then kept in refrigerator for 16 h. The precipitated solid was filtered off and washed with MeOH-DCM (1:5, 50 ml) to get tartrate salt of 8-ethylamino-8-phenyl-1,3-diaza-spiro[4.5]decane-2,4-dione (7.5 g) as a white solid. To this solid sat. aq. NaHCO$_3$ was added (pH~8) and the resulting mixture was extracted with 25% MeOH-DCM (2×800 ml). Combined organic layer was washed with water (300 ml), brine (300 ml), dried over anhydrous Na$_2$SO$_4$ and concentrated under reduced pressure. The residue was triturated with 20% DCM-hexane and the resulting solid was dried under reduced pressure to afford CIS-8-ethylamino-8-phenyl-1,3-diaza-spiro[4.5]decane-2,4-dione as white solid. This step was done in 2 batches (12 g & 2.4 g) and the yield is given for 2 combined batches. Yield: 31.2% (5.0 g, 17.421 mmol). LC-MS: m/z [M+1]$^+$=288.0.

Step 6: CIS-8-ethylamino-8-phenyl-1,3-diaza-spiro[4.5]decan-2-one (INT-1008)

To a slurry of LiAlH$_4$ (793 mg, 20.91 mmol, 3.0 eq.) in THF (15 ml) was added a suspension of CIS-8-ethylamino-8-phenyl-1,3-diaza-spiro[4.5]decane-2,4-dione (2.0 g, 6.97 mmol, 1.0 eq.) in THF (60 ml) at 0° C. and the reaction mixture was heated to 65° C. for 16 h. The reaction mixture was cooled to 0° C., quenched with sat. aq. Na$_2$SO$_4$ (20 ml), stirred at RT for 1 h and filtered through celite pad. The residue was washed with 15% MeOH-DCM (500 ml). The combined filtrate was dried over anhydrous Na$_2$SO$_4$ and concentrated under reduced pressure to give crude product which was triturated with 15% DCM-Hexane to afford CIS-8-ethylamino-8-phenyl-1,3-diaza-spiro[4.5]decan-2-one (INT-1008) (1.6 g, 5.86 mmol, 84%) as a white solid. Yield: 84% (1.6 g, 5.86 mmol). LC-MS: m/z [M+1]$^+$=274.2.

Synthesis of INT-1026: CIS-8-(methyl((tetrahydrofuran-3-yl)methyl)amino)-8-phenyl-1,3-diazaspiro[4.5]decan-2-one

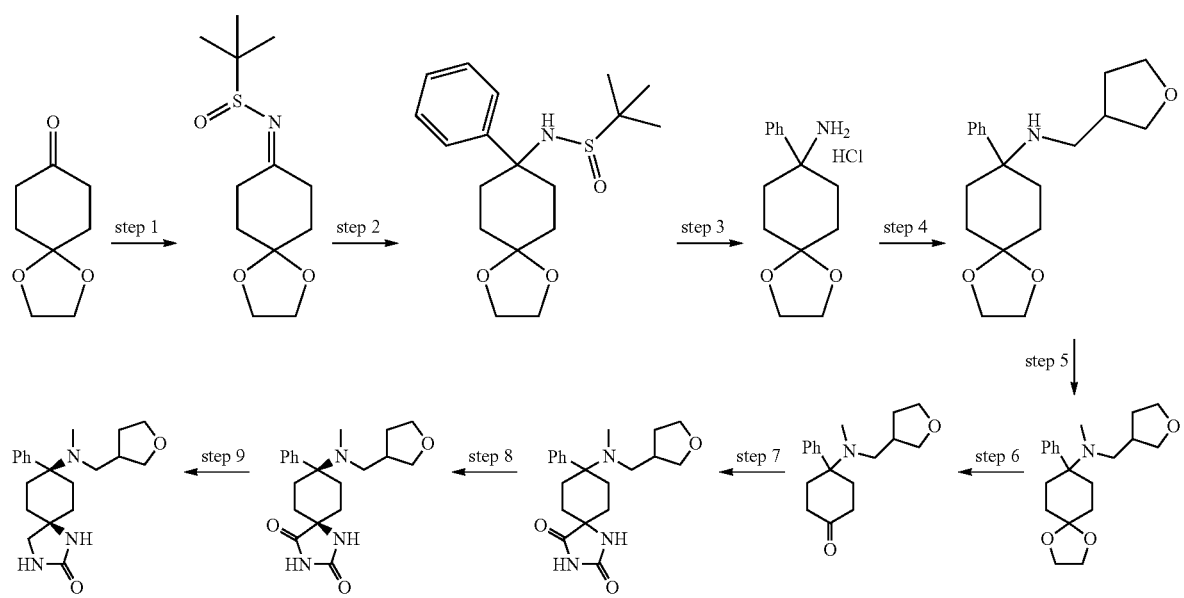

INT-1026

Step 1: 2-methyl-N-(1,4-dioxaspiro[4.5]decan-8-ylidene)propane-2-sulfinamide Titanium ethoxide (58.45 g, 256.4 mmol) was added to a solution of 1,4-dioxaspiro[4.5]decan-8-one (20 g, 128.20 mmol) and 2-methylpropane-2-sulfinamide (15.51 g, 128.20 mmol) in THF (200 mL) at RT and the reaction mixture was stirred at RT for 18 h. The reaction mixture was cooled to 0° C. and quenched by dropwise addition of sat. aq. NaHCO$_3$ (500 mL) over a period of 30 min. The organic product was extracted with EtOAc (3×100 mL). The combined organic extracts were dried over anhydrous Na$_2$SO$_4$ and concentrated in vacuo to afford 10 g (crude) of 2-methyl-N-(1,4-dioxaspiro[4.5]decan-8-ylidene)propane-2-sulfinamide as a white solid (TLC system: 30% Ethyl acetate in hexane; Rf: 0.30).

Step 2: 2-methyl-N-(8-phenyl-1,4-dioxaspiro[4.5]decan-8-yl)propane-2-sulfinamide Phenylmagnesium bromide (1M in THF, 116 mL, 116 mmol) was added dropwise to a solution of 2-methyl-N-(1,4-dioxaspiro[4.5]decan-8-ylidene)propane-2-sulfinamide (10 g, 38.61 mmol) in THF (500 mL) at −10° C. under argon atmosphere. The reaction mixture was stirred for 2 h at −10° C. to 0° C. The reaction completion was monitored by TLC. The reaction mixture was quenched with sat. aq. NH$_4$Cl (50 mL) at 0° C. and the organic product was extracted with EtOAc (3×100 mL). The combined organic extracts were dried over anhydrous Na$_2$SO$_4$ and concentrated in vacuo. The residue was purified by column chromatography (silica gel 230-400 mesh; 40-60% ethyl acetate in hexane) to yield 6.0 g (46%) of 2-methyl-N-(8-phenyl-1,4-dioxaspiro[4.5]decan-8-yl)propane-2-sulfinamide as a liquid (TLC system: 70% Ethyl acetate in hexane; Rf: 0.30).

Step 3: 8-phenyl-1,4-dioxaspiro[4.5]decan-8-amine hydrochloride 2N solution of HCl in diethyl ether (17.80 mL, 35.60 mmol) was added to a solution of 2-methyl-N-(8-phenyl-1,4-dioxaspiro[4.5]decan-8-yl)propane-2-sulfinamide (6.0 g, 17.80 mmol) in DCM (60 mL) at 0° C. The reaction mixture was stirred at RT for 2 h. The reaction mixture was concentrated in vacuo. The residue was washed with diethyl ether to yield 3 g (crude) of 8-phenyl-1,4-dioxaspiro[4.5]decan-8-amine hydrochloride as a brown solid (TLC system: 5% MeOH in DCM; Rf: 0.10).

Step 4: 8-phenyl-N-((tetrahydrofuran-3-yl)methyl)-1,4-dioxaspiro[4.5]decan-8-amine Sodium cyanoborohydride (2.17 g, 33.45 mmol) was added to a solution of 8-phenyl-1,4-dioxaspiro[4.5]decan-8-amine hydrochloride (3.0 g, 11.15 mmol) and tetrahydrofuran-3-carbaldehyde (4.46 mL, 22.30 mmol) and acetic acid (0.05 mL) in methanol (30 mL) at 0° C. The reaction mixture was stirred at RT for 16 h. The reaction mixture was concentrated in vacuo at 30° C. and to the residue sat. aq. NaHCO$_3$ was added. The organic product was extracted with DCM (3×30 mL). The combined organic extracts were dried over anhydrous Na$_2$SO$_4$ and solvent was concentrated under reduced pressure to get 3 g (crude) of 8-phenyl-N-((tetrahydrofuran-3-yl)methyl)-1,4-dioxaspiro[4.5]decan-8-amine as a semi-solid (TLC system: 10% MeOH in DCM; Rf: 0.22).

Step 5: N-methyl-8-phenyl-N-((tetrahydrofuran-3-yl)methyl)-1,4-dioxaspiro[4.5]decan-8-amine)

Sodium cyanoborohydride (1.76 g, 28.39 mmol) was added to a solution of 8-phenyl-N-((tetrahydrofuran-3-yl)methyl)-1,4-dioxaspiro[4.5]decan-8-amine (3.0 g, 9.46 mmol), 37% formaldehyde in water (7.70 mL, 94.60 mmol) and acetic acid (0.05 mL) in methanol (30 mL) at 0° C. The reaction mixture was stirred at RT for 16 h. The reaction mixture was concentrated in vacuo and to the residue sat. aq. NaHCO$_3$ was added. The organic product was extracted with DCM (3×30 mL). The combined organic extracts were dried over anhydrous Na$_2$SO$_4$ and solvent was concentrated under reduced pressure. The resulting residue was purified by column chromatography (silica gel 230-400 mesh; 5-6% MeOH in DCM) to yield 2.50 g (83%) of N-methyl-8-phenyl-N-((tetrahydrofuran-3-yl)methyl)-1,4-dioxaspiro[4.5]decan-8-amine as a semi solid (TLC system: 10% MeOH in DCM; Rf: 0.25).

Step 6: 4-(methyl((tetrahydrofuran-3-yl)methyl)amino)-4-phenylcyclohexanone

5% sulfuric acid in water (25 mL) was added to N-methyl-8-phenyl-N-((tetrahydrofuran-3-yl)methyl)-1,4-dioxaspiro[4.5]decan-8-amine (2.50 g, 7.55 mmol) at 0° C. and the resulting mixture was stirred at RT for 24 h. The reaction mixture was quenched with sat. aq. NaHCO$_3$ and the organic product was extracted with DCM (2×50 mL). The combined organic layers were dried over anhydrous Na$_2$SO$_4$ and concentrated in vacuo to afford 2.0 g (crude) of 4-(methyl((tetrahydrofuran-3-yl)methyl)amino)-4-phenylcyclohexanone as a thick liquid (TLC system: 10% MeOH in DCM, Rf: 0.20).

Step 7: 8-(methyl((tetrahydrofuran-3-yl)methyl)amino)-8-phenyl-1,3-diazaspiro[4.5]decane-2,4-dione 4-(methyl((tetrahydrofuran-3-yl)methyl)amino)-4-phenylcyclohexanone (1.50 g, 5.22 mmol) was suspended in 30 mL of EtOH:H$_2$O (1:1 v/v) at RT under argon atmosphere. (NH$_4$)$_2$CO$_3$ (1.9 g, 13.05 mmol) and KCN (0.34 g, 5.22 mmol) were added. The reaction mixture was heated to 70° C. for 16 h. The reaction mixture was diluted with ice-water and the organic product was extracted with DCM (2×50 mL). The combined organic layer was dried over anhydrous Na$_2$SO$_4$ and concentrated in vacuo to give 1.0 g (crude) of 8-(methyl((tetrahydrofuran-3-yl)methyl)amino)-8-phenyl-1,3-diazaspiro[4.5]decane-2,4-dione as a solid (TLC system: 70% Ethyl acetate in hexane; Rf: 0.18).

Step 8: CIS-8-(methyl((tetrahydrofuran-3-yl)methyl)amino)-8-phenyl-1,3-diazaspiro[4.5]decane-2,4-dione Diastereomeric mixture of 8-(methyl((tetrahydrofuran-3-yl)methyl)amino)-8-phenyl-1,3-diazaspiro[4.5]decane-2,4-dione (1.0 g) was separated by reverse phase preparative HPLC to afford 400 mg of isomer 1 (CIS-8-(methyl((tetrahydrofuran-3-yl)methyl)amino)-8-phenyl-1,3-diazaspiro[4.5]decane-2,4-dione) and 60 mg of isomer 2 (TRANS-8-(methyl((tetrahydrofuran-3-yl)methyl)amino)-8-phenyl-1,3-diazaspiro[4.5]decane-2,4-dione) and 300 mg of mixture of both isomers. Reverse phase preparative HPLC conditions: mobile phase: 10 mM ammonium bicarbonate in H$_2$O/acetonitrile, column: X-BRIDGE-C18 (150*30), 5 μm, gradient (T/B %): 0/35, 8/55, 8.1/98, 10/98, 10.1/35, 13/35, flow rate: 25 ml/min, diluent: mobile phase+ THF.

Step 9: CIS-8-(methyl((tetrahydrofuran-3-yl)methyl) amino)-8-phenyl-1,3-diazaspiro[4.5]decan-2-one (INT-1026)

LiAlH$_4$ (1M in THF) (4.48 mL, 4.48 mmol) was added to a solution of CIS-8-(methyl((tetrahydrofuran-3-yl)methyl) amino)-8-phenyl-1,3-diazaspiro[4.5]decane-2,4-dione (isomer-1) (0.4 g, 1.12 mmol) in THF:Et$_2$O (2:1 v/v, 15 mL) at 0° C. under argon atmosphere. The reaction mixture was stirred at 65° C. for 16 h. The mixture was cooled to 0° C., quenched with sat. aq. Na$_2$SO$_4$ (1000 mL) and filtered through celite pad. The filtrate was dried over anhydrous Na$_2$SO$_4$ and concentrated in vacuo. The residue was purified by column chromatography (silica gel 230-400 mesh; 5-6% MeOH in DCM) to yield 0.3 g (78%) of CIS-8-(methyl ((tetrahydrofuran-3-yl)methyl)amino)-8-phenyl-1,3-diazaspiro[4.5]decan-2-one (INT-1026) as an off white solid. (TLC system: 10% MeOH in DCM, Rf: 0.2). LC-MS: m/z [M+1]$^+$=344.2.

Synthesis of INT-1031: CIS-1-(Cyclobutyl-methyl)-8-dimethylamino-8-(3-fluorophenyl)-1,3-diazaspiro [4.5]decan-2-one

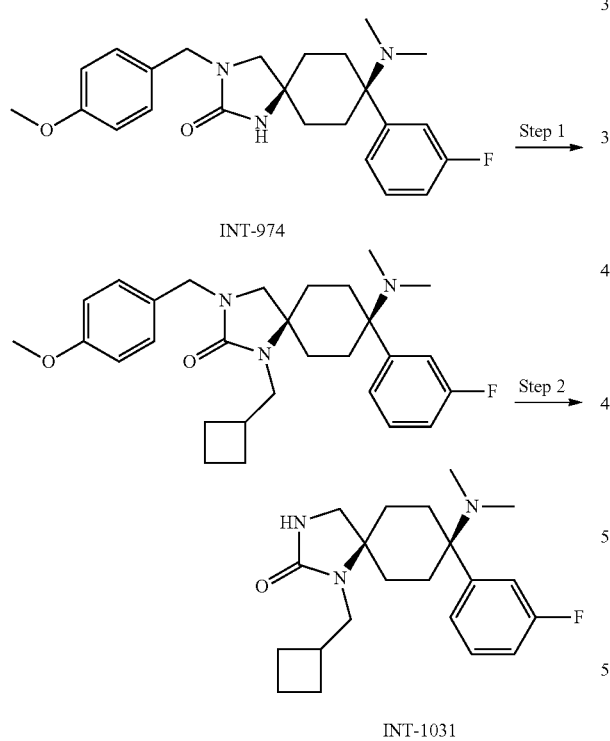

Step 1: CIS-1-(Cyclobutyl-methyl)-8-dimethyl-amino-8-(3-fluorophenyl)-3-[(4-methoxyphenyl)-methyl]-1,3-diazaspiro[4.5]decan-2-one In analogy to the method described for INT-952 CIS-8-dimethylamino-8-(3-fluorophenyl)-3-[(4-methoxyphenyl)-methyl]-1,3-diazaspiro[4.5]decan-2-one (INT-974) was converted into CIS-1-(cyclobutyl-methyl)-8-dimethylamino-8-(3-fluorophenyl)-3-[(4-methoxyphenyl)-methyl]-1,3-diazaspiro[4.5]decan-2-one.

Step 2: CIS-1-(Cyclobutyl-methyl)-8-dimethyl-amino-8-(3-fluorophenyl)-1,3-diazaspiro[4.5]decan-2-one In analogy to the method described for INT-982 step 2 1-(cyclobutyl-methyl)-8-dimethylamino-8-(3-fluorophenyl)-3-[(4-methoxyphenyl)-methyl]-1,3-diazaspiro[4.5]decan-2-one was converted into 1-(cyclobutyl-methyl)-8-dimethylamino-8-(3-fluorophenyl)-1,3-diazaspiro[4.5]decan-2-one (INT-1031).

Synthesis of INT-1037: 8-(dimethylamino)-2-oxo-1,3-diazaspiro[4.5]decane-8-carbonitrile

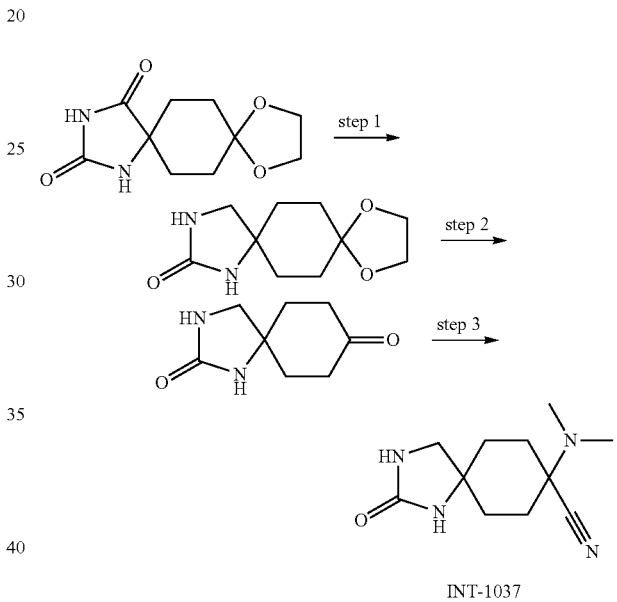

Step 1: 9,12-dioxa-2,4-diazadispiro [4.2.4^{8}0.2^{5}]tetradecan-3-one

Lithiumaluminiumhydride (2.2 equiv., 292 mmol) was suspended in THF (400 mL) and the suspension was cooled to 0° C. 8-(Dimethylamino)-8-(m-tolyl)-1,3-diazaspiro[4.5] decan-2-one (B, 75 mg, 0,261 mmol) (step 1 of INT-965) was added portionwise at 0° C. The reaction mixture was stirred 1.5 h at 0° C., then overnight at RT and then 2 h at 40° C. The reaction mixture was cooled down to 0° C., quenched carefully with sat. aq. Na$_2$SO$_4$, EtOAc (400 mL) was added and the resulting mixture was stirred for 2 h and then left without stirring for 2 h at RT. The precipitate was filtered off and washed with EtOAc and MeOH. The resulting solid residue was suspended in methanol and stirred at RT overnight. The precipitate was filtered off and disposed. The filtrate was concentrated under reduced pressure, the residue was suspended thoroughly in water (50 mL) at 40° C., the precipitate was filtered off and dried under reduced pressure to yield 9,12-dioxa-2,4-diazadispiro [4.2.4^{8}0.2^{5}]tetradecan-3-one (11.4 g, 41%). Mass: m/z 213.2 (M+H)$^+$.

Step 2: 1,3-diazaspiro[4.5]decane-2,8-dione

In analogy to the method described for INT-1003 step 3 9,12-dioxa-2,4-diazadispiro[4.2.4^{8}0.2^{5}]tetradecan-3-one was treated with conc. aq. HCl to be converted into 1,3-diazaspiro[4.5]decane-2,8-dione. Mass: m/z 169.1 (M+H)$^+$.

Step 3: 8-(dimethylamino)-2-oxo-1,3-diazaspiro[4.5]decane-8-carbonitrile (INT-1037)

In analogy to the method described for INT-965 step 1 1,3-diazaspiro[4.5]decane-2,8-dione was treated with dimethyl amine and potassium cyanide to be converted into 8-(dimethylamino)-2-oxo-1,3-diazaspiro[4.5]decane-8-carbonitrile (INT-1037). Mass: m/z 223.2 (M+H)$^+$.

Synthesis of INT-1038: CIS-8-(dimethylamino)-8-(m-tolyl)-1,3-diazaspiro[4.5]decan-2-one

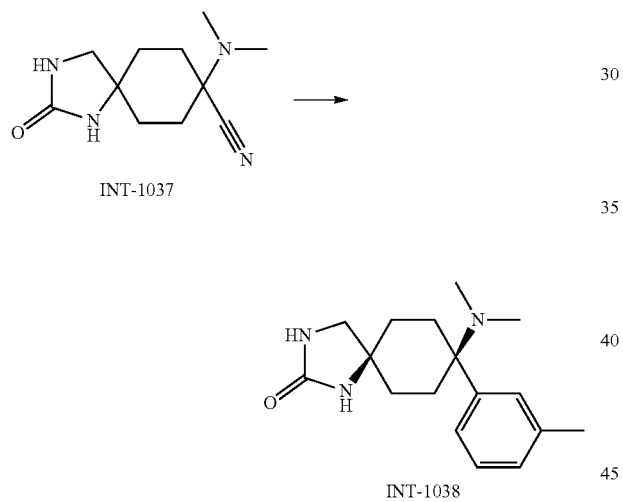

To the suspension of 8-(dimethylamino)-2-oxo-1,3-diazaspiro[4.5]decane-8-carbonitrile (200 mg, 0.90 mmol) in THF (4 mL) at RT was added dropwise 1M bromo(m-tolyl)magnesium in THF (4 equiv., 3.6 mmol, 3.6 mL) and the reaction mixture was stirred for 1 h at RT. Additional portion of 1M bromo(m-tolyl)magnesium in THF (1 equiv., 0.8 mL) was added. The reaction mixture was stirred at RT overnight, then quenched with methanol/water. Solid NH$_4$Cl and DCM were added to the resulting mixture and the precipitate was filtered off. The organic phase of the filtrate was separated and the aqueous phase was extracted with DCM (3×). The combined organic phases were dried over anhydr. Na$_2$SO$_4$ and concentrated under reduced pressure. The residue was purified by flash chromatography on silica gel (DCM/MeOH, 100/0 to 65/35) to yield CIS-8-(dimethylamino)-8-(m-tolyl)-1,3-diazaspiro[4.5]decan-2-one (INT-1038) (81 mg, 31%). Mass: m/z 288.2 (M+H)$^+$.

Synthesis of INT-1052: CIS-3-(2-amino-2-methylpropyl)-1-(cyclopropylmethyl)-8-(dimethylamino)-8-phenyl-1,3-diazaspiro[4.5]decan-2-one

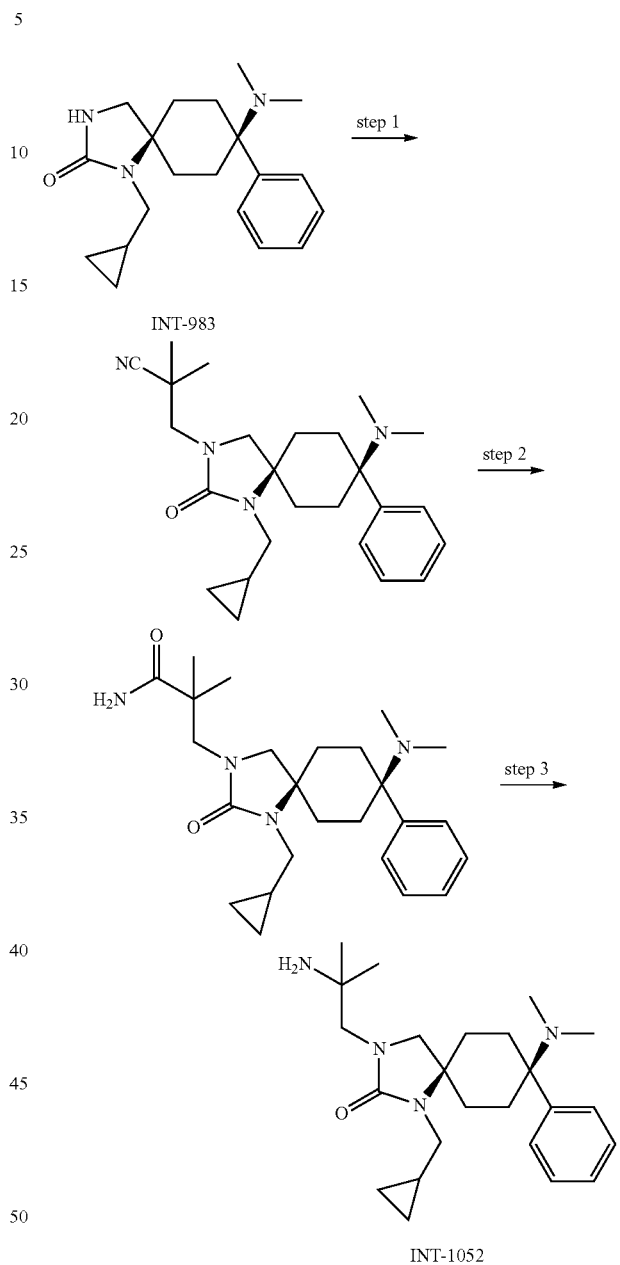

Step 1: CIS-3-(1-(cyclopropylmethyl)-8-(dimethylamino)-2-oxo-8-phenyl-1,3-diazaspiro[4.5]decan-3-yl)-2,2-dimethylpropanenitrile NaH (60% in mineral oil) (1.76 g, 44.04 mmol) was added to the solution of CIS-1-(cyclopropylmethyl)-8-(dimethylamino)-8-phenyl-1,3-diazaspiro[4.5]decan-2-one (INT-983) (3.6 g, 11.01 mmol) in DMSO (150 mL) at RT under argon atmosphere. 2-Cyano-2-methylpropyl 4-methylbenzenesulfonate (113 mg, 0.45 mmol) was added to the reaction mixture in one portion. The reaction mixture was heated at 70° C. for 16 h. The reaction mixture was cooled to 0° C. and quenched with water (20 mL). The organic product was extracted with EtOAc (2×200 mL). The combined organic extracts were dried over anhydr. Na₂SO₄ and concentrated under reduced pressure. The resulting crude product was purified by column chromatography (silica gel 100-200 mesh, 0-10% MeOH in DCM) to get 2.1 g, 46% of CIS-3-(1-(cyclopropylmethyl)-8-(dimethylamino)-2-oxo-8-phenyl-1,3-diazaspiro[4.5]decan-3-yl)-2,2-dimethylpropanenitrile as an off-white solid (TLC system: 5% MeOH in DCM; Rf: 0.60).

Step 2: CIS-3-(1-(cyclopropylmethyl)-8-(dimethylamino)-2-oxo-8-phenyl-1,3-diazaspiro[4.5]decan-3-yl)-2,2-dimethylpropanamide H₂O₂ (30% in water) (8 mL) was added to a solution of CIS-3-(1-(cyclopropylmethyl)-8-(dimethylamino)-2-oxo-8-phenyl-1,3-diazaspiro[4.5]decan-3-yl)-2,2-dimethylpropanenitrile (2.0 g, 4.90 mmol) in DMSO (50 mL) at RT under argon atmosphere. A solution of KOH (1.1 g, 19.6 mmol) in water (10 mL) was added dropwise to the reaction mixture. The reaction mixture was stirred at RT for 16 h. The reaction mixture was diluted with water (300 mL) and the organic product was extracted with EtOAc (2×100 mL). The combined organic extracts were dried over anhydrous Na₂SO₄ and concentrated under reduced pressure. The resulting crude product was purified by column chromatography (silica gel 100-200 mesh, 0-5% MeOH in DCM) to get 0.44 g (21%) of CIS-3-(1-(cyclopropylmethyl)-8-(dimethylamino)-2-oxo-8-phenyl-1,3-diazaspiro[4.5]decan-3-yl)-2,2-dimethylpropanamide as a gummy solid (TLC system: 5% MeOH in DCM; Rf: 0.30) and 1.1 g of CIS-3-(1-(cyclopropylmethyl)-8-(dimethylamino)-2-oxo-8-phenyl-1,3-diazaspiro[4.5]decan-3-yl)-2,2-dimethylpropanenitrile was also reisolated (TLC system: 5% MeOH in DCM; Rf: 0.30).

Step 3: CIS-3-(2-amino-2-methylpropyl)-1-(cyclopropylmethyl)-8-(dimethylamino)-8-phenyl-1,3-diazaspiro[4.5]decan-2-one (INT-1052)

PhI(OCOCF₃)₂ (703.5 mg, 1.636 mmol) was added to a solution of CIS-3-(1-(cyclopropylmethyl)-8-(dimethylamino)-2-oxo-8-phenyl-1,3-diazaspiro[4.5]decan-3-yl)-2,2-dimethylpropanamide (410 mg, 0.962 mmol) in mixture of acetonitrile (15 mL) and water (15 mL) at RT under argon atmosphere. The reaction mixture was stirred for 18 h at RT. The reaction mixture was diluted with water (15 mL) and the aqueous layer was washed with EtOAc (2×20 mL). The water layer was basified with solid NaHCO₃ and the organic product was extracted with EtOAc (2×30 mL). The organic layer was dried over anhydr. Na₂SO₄ and solvent was concentrated under reduced pressure to afford 350 mg, 91% of CIS-3-(2-amino-2-methylpropyl)-1-(cyclopropylmethyl)-8-(dimethylamino)-8-phenyl-1,3-diazaspiro[4.5]decan-2-one as gummy solid (TLC system: 5% MeOH in DCM; Rf: 0.15). Mass: m/z 399.3 (M+H)⁺.

Synthesis of INT-1054: CIS-8-(dimethylamino)-8-(m-tolyl)-1,3-diazaspiro[4.5]decan-2-one

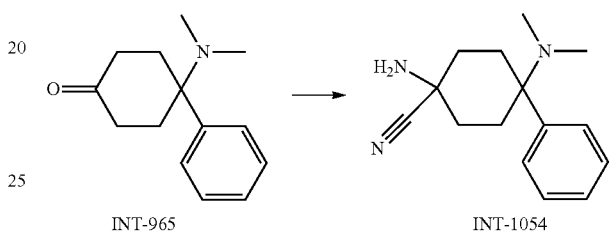

INT-965 INT-1054

To a stirred solution of 4-dimethylamino-4-phenyl-cyclohexanone (50 g, 230.1 mmol) in MeOH (400 mL) was added NH₄Cl (24.6 g, 460.8 mmol) followed by NH₄OH (400 mL) at RT and stirred for 15 min. NaCN (22.5 g, 460.83 mmol) was added to the reaction mixture and stirred for 16 h at RT. The reaction mixture was extracted with DCM (3×750 ml). Organic layer was washed with water (750 ml), brine (750 ml) and dried over Na₂SO₄. The solvent was evaporated under reduced pressure. The residue was triturated with DCM/hexane to get crude 1-amino-4-dimethylamino-4-phenyl-cyclohexanecarbonitrile (50 g, 90%) as off white solid which was used in next step without purification. Yield: 78% (44 g, 181 mmol). Mass: m/z 244.2 (M+H)⁺.

Synthesis of INT-1055 and INT-1056: CIS- and TRANS-3-(2-amino-2-methylpropyl)-1-(cyclopropylmethyl)-8-(dimethylamino)-8-phenyl-1,3-diazaspiro[4.5]decan-2-one

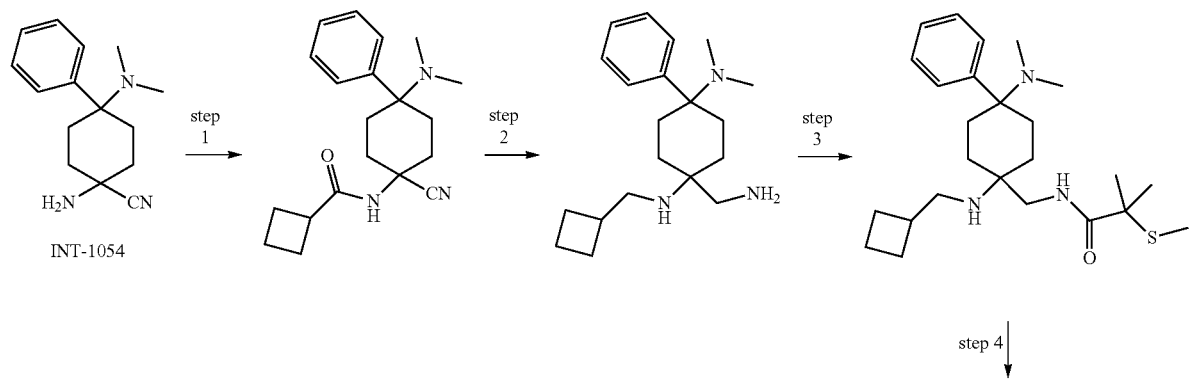

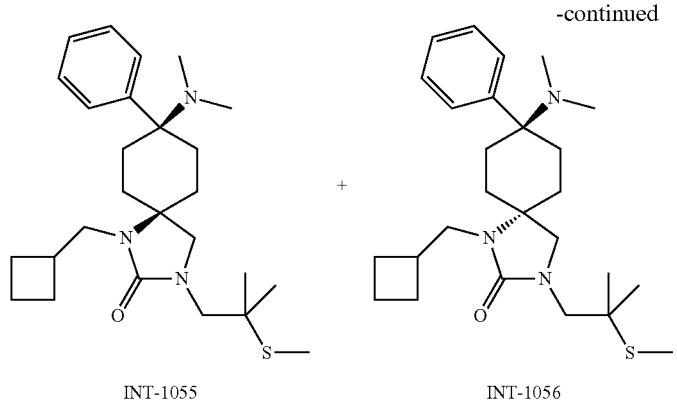

INT-1055 + INT-1056

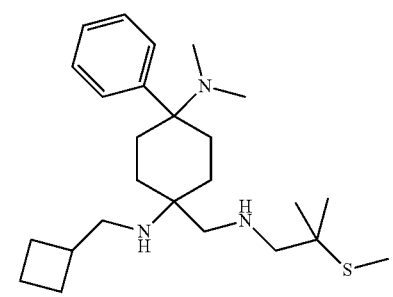

step 5

Step 1: N-(1-cyano-4-(dimethylamino)-4-phenylcyclohexyl)cyclobutanecarboxamide (CIS-/TRANS mixture)

To a solution of 1-amino-4-dimethylamino-4-phenyl-cyclohexanecarbonitrile (INT-1054) (5.0 g, 20.57 mmol, 1.0 eq.) in THF (100 mL) were added cyclobutanecarboxylic acid (2.50 g, 24.69 mmol, 1.2 eq), DIPEA (10.5 mL, 61.71 mmol, 3.0 eq) and T3P (18.38 mL, 30.85 mmol, 1.5 eq). The reaction mixture was stirred at RT for 16 h, diluted with water (100 mL) and extracted with EtOAc (2×200 ml). Combined organic layer was washed with brine (100 mL), dried over $Na_2SO_4$ and concentrated under reduced pressure to get crude cyclobutanecarboxylic acid (1-cyano-4-dimethylamino-4-phenyl-cyclohexyl)-amide as a light yellow sticky material which was used in the next step without further purification. Mass: m/z 326.3 (M+H)$^+$.

Step 2: 1-(aminomethyl)-N'-(cyclobutylmethyl)-N$^4$,N$^4$-dimethyl-4-phenylcyclohexane-1,4-diamine (CIS/TRANS-mixture)

To suspension of $LiAlH_4$ (2.81 g, 73.84 mmol, 6.0 eq.) in dry THF (25 mL) was added a solution cyclobutanecarboxylic acid (1-cyano-4-dimethylamino-4-phenyl-cyclohexyl)-amide (4.0 g, 12.3 mmol, 1.0 eq.) in dry THF (35 mL) dropwise at 0° C. The reaction mixture was stirred at RT for 16 h, then quenched with sat. aq. $Na_2SO_4$ at 0° C., excess THF was added and the resulting mixture stirred at RT for 2 h. The reaction mixture was filtered through celite and washed with THF (100 mL). Filtrate was concentrated under reduced pressure to get crude 1-aminomethyl-N-cyclobutyl-methyl-N',N'-dimethyl-4-phenyl-cyclohexane-1,4-diamine (3.0 g) as a light yellow sticky material which was used in the next step without further purification. Mass: m/z 316.4 (M+H)$^+$.

Step 3: N-((1-(((cyclobutylmethyl)amino)-4-(dimethylamino)-4-phenylcyclohexyl)methyl)-2-methyl-2-(methylthio)propanamide (CIS/TRANS-mixture)

To a solution of crude 1-aminomethyl-N-cyclobutylmethyl-N',N'-dimethyl-4-phenyl-cyclohexane-1,4-diamine (3.0 g, 9.23 mmol, 1.0 eq.) in THF (50 mL) were added 2-methyl-2-methylsulfanyl-propionic acid (1.23 g, 9.23 mmol, 1.0 eq), DIPEA (4.81 mL, 27.69 mmol, 3.0 eq) and T3P (8.3 mL, 13.84 mmol, 1.5 eq, 50% solution in EtOAc) at 0° C. and the resulting mixture was stirred at RT for 16 h. The reaction mixture was diluted with DCM (300 mL), washed with water (100 mL) and brine (100 mL), dried over $Na_2SO_4$ and concentrated under reduced pressure to get crude N-[1-(cyclobutylmethyl-amino)-4-dimethylamino-4-phenyl-cyclohexylmethyl]-2-methyl-2-methylsulfanyl-propionamide as a light yellow sticky material which was used in the next step without further purification. Mass: m/z 432.1 (M+H)$^+$.

Step 4: N'-(cyclobutylmethyl)-N$^4$,N$^4$-dimethyl-1-(((2-methyl-2-(methylthio)propyl)amino)methyl)-4-phenylcyclohexane-1,4-diamine (CIS/TRANS-mixture)

To a solution of crude N-[1-(cyclobutylmethyl-amino)-4-dimethylamino-4-phenyl-cyclohexylmethyl]-2-methyl-2-methylsulfanyl-propionamide (2.5 g, 5.8 mmol, 1.0 eq.) in THF (60 mL) was added $BH_3 \times Me_2S$ (2.75 ml, 29.0 mmol, 5.0 eq.). The reaction mixture was stirred at RT for 16 h, then quenched with MeOH (10 mL) and 2N HCl (10 mL) at 0° C. and stirred at RT for 30 min. The resulting mixture was concentrated under reduced pressure, diluted with water (50 mL), basified with sat. aq. $NaHCO_3$ and extracted with DCM (2×250 mL). Combined organic layer was dried over $Na_2SO_4$ and concentrated under reduced pressure to get crude N-cyclobutylmethyl-N',N'-dimethyl-1-[(2-methyl-2-methylsulfanyl-propylamino)-methyl]-4-phenyl-cyclohexane-1,4-diamine as a light yellow sticky material which was used in the next step without further purification. Mass: m/z 418.4 (M+H)$^+$.

Step 5: CIS- and TRANS-3-(2-amino-2-methylpropyl)-1-(cyclopropylmethyl)-8-(dimethylamino)-8-phenyl-1,3-diazaspiro[4.5]decan-2-one (INT-1055 and INT-1056)

To a solution of crude N-cyclobutylmethyl-N',N'-dimethyl-1-[(2-methyl-2-methylsulfanyl-propylamino)-methyl]-4-phenyl-cyclohexane-1,4-diamine (2.0 g, 4.79 mmol, 1.0 eq.) in toluene (30 ml) was added KOH (1.61 g, 28.77 mmol, 6.0 eq) in water (60 mL) at 0° C. followed by addition of $COCl_2$ (5.84 L 16.76 mmol, 3.5 eq., 20% in toluene). The reaction mixture was stirred at RT for 16 h, then basified with sat. aq. $NaHCO_3$ and extracted with DCM (2×200 mL). Combined organic layer was dried over $Na_2SO_4$ and concentrated under reduced pressure to get crude product which was purified by prep HPLC to get CIS-1-cyclobutylmethyl-8-dimethylamino-3-(2-methyl-2-methylsulfanyl-propyl)-8-phenyl-1,3-diaza-spiro[4.5]decan-2-one (INT-1055) as peak 2 (45 mg) and TRANS-1- cyclobutylmethyl-8-dimethylamino-3-(2-methyl-2-methylsulfanyl-propyl)-8-phenyl-1,3-diaza-spiro[4.5]decan-2-one (INT-1056) as peak 1 (300 mg). Mass: m/z 444.1 (M+H)⁺ (trans), m/z 444.0 (M+H)⁺ (cis).

Synthesis of INT-1059: TRANS-8-(dimethylamino)-8-phenyl-1,3-diazaspiro[4.5]decan-2-one

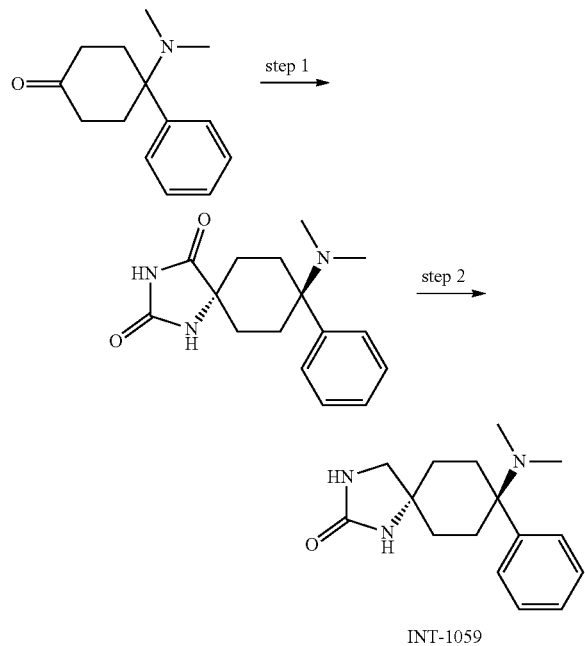

INT-1059

Step 1: TRANS-8-(dimethylamino)-8-phenyl-1,3-diazaspiro[4.5]decane-2,4-dione

To a stirred solution of 4-dimethylamino-4-phenyl-cyclohexanone (250.0 g, 1.15 mol, 1.0 eq.) in EtOH (2.5 L) and water (2.1 L) was added $(NH_4)_2CO_3$ (276.2 g, 2.87 mol, 2.5 eq.) and the reaction mixture was stirred at RT for 15 min. KCN (74.92 g, 1.15 mol, 1.0 eq.) was added. The reaction mixture was stirred at 60° C. for 18 h and then filtered in hot condition to get white solid which was washed with water (2.5 L), ethanol (1 L) and hexane (2.5 L). The resulting solid was dried under reduced pressure to get CIS-8-dimethylamino-8-phenyl-1,3-diaza-spiro[4.5]decane-2,4-dione (223 g, 0.776 mol, 65%) as a white solid. The filtrate was collected from multiple batches (~450 g) which contained a mixture of cis and trans isomers. The filtrate was concentrated under reduced pressure and solid obtained was filtered and washed with water (1 L) and hexane (1 L). Solid material was dried under reduced pressure to get ~100 g of a mixture of cis and trans (major) isomers. Crude material was partially dissolved in hot MeOH (600 mL) and cooled to RT, filtered through sintered funnel, washed with MeOH (200 mL) followed by ether (150 mL) and dried to get TRANS-8-dimethylamino-8-phenyl-1,3-diaza-spiro[4.5]decane-2,4-dione (50 g, 0.174 mmol, -9-10%).

Step 2: TRANS-8-(dimethylamino)-8-phenyl-1,3-diazaspiro[4.5]decan-2-one (INT-1059)

In analogy to the method described for INT-976 step 2 TRANS-8-dimethylamino-8-phenyl-1,3-diaza-spiro[4.5]decane-2,4-dione was treated with $LiAlH_4$ to be converted into TRANS-8-(dimethylamino)-8-phenyl-1,3-diazaspiro[4.5]decan-2-one (INT-1059). Mass: m/z 274.2 (M+H)⁺.

Synthesis of INT-1068 and INT-1069: CIS- and TRANS-8-(dimethylamino)-8-phenyl-1-(2,2,2-trifluoroethyl)-1,3-diazaspiro[4.5]decan-2-one

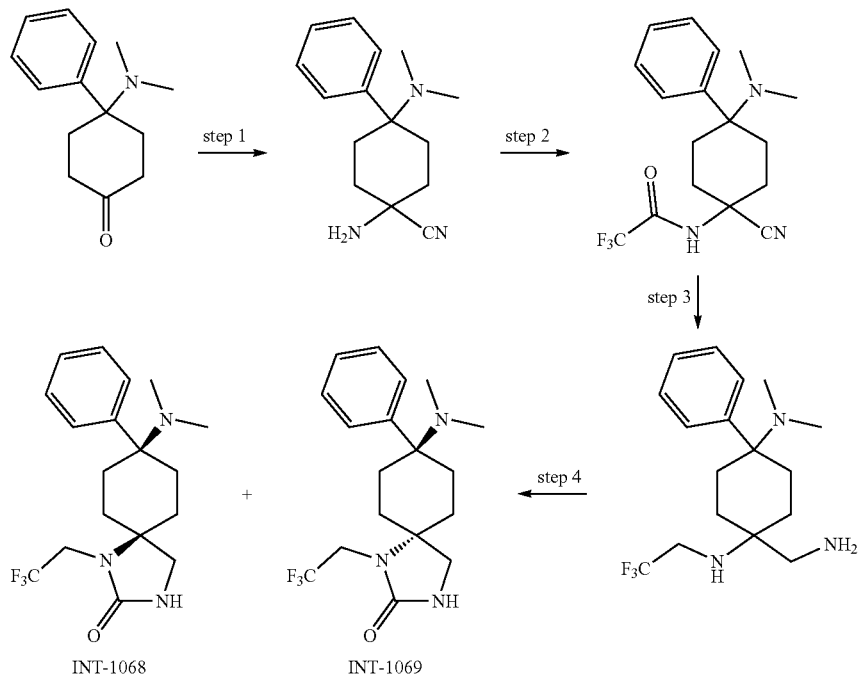

INT-1068        INT-1069

Step 1: 1-amino-4-dimethylamino-4-phenyl-cyclohexanecarbonitril

To a stirred solution of 4-dimethylamino-4-phenyl-cyclohexanone (50 g, 230.096 mmol) in MeOH (400 mL) was added NH$_4$Cl (24.6 g, 460.8 mmol) followed by NH$_4$OH (400 mL) at RT and the reaction mixture was stirred for 15 min. NaCN (22.5 g, 460.83 mmol) was added and the resulting mixture was stirred for 16 h at RT. The reaction mixture was extracted with DCM (3×750 mL). Combined organic layer was washed with water (750 mL), brine (750 mL), dried over Na$_2$SO$_4$ and concentrated under reduced pressure. The residue was triturated with DCM/hexane to get crude 1-amino-4-dimethylamino-4-phenyl-cyclohexanecarbonitrile (50 g, 90%) as an off white solid which was used in next step without further purification. LC-MS: m/z [M+H]$^+$=244.2 (MW calc. 244.09).

Step 2: N-(1-cyano-4-dimethylamino-4-phenyl-cyclohexyl)-2,2,2-trifluoroacetamide To a solution of 1-amino-4-dimethylamino-4-phenyl-cyclohexanecarbonitrile (5.0 g, 20.57 mmol, 1.0 eq.) in THF (100 ml) were added DIPEA (10.72 ml, 61.71 mmol, 3.0 eq), trifluoroacetic acid (1.89 ml, 24.69 mmol, 1.2 eq) and T3P (18.2 ml, 30.85 mmol, 1.5 eq) at 0° C. The reaction mixture was stirred at RT for 16 h, then diluted with water (100 ml) and extracted with 10% MeOH in DCM (2×250 mL). Combined organic layer was washed with brine (100 mL), dried over Na$_2$SO$_4$ and concentrated under reduced pressure to get crude N-(1-cyano-4-dimethylamino-4-phenyl-cyclohexyl)-2,2,2-trifluoroacetamide as a light yellow sticky material which was used in the next step without further purification. LC-MS: m/z [M+1]$^+$=339.9 (MW calc. 339.36).

Step 3: 1-aminomethyl-N',N'-dimethyl-4-phenyl-N-(2,2,2-trifluoroethyl)cyclohexane-1,4-diamine To suspension of LiAlH$_4$ (4.03 g, 106.19 mmol, 6.0 eq.) in dry THF (40 mL) was added N-(1-cyano-4-dimethylamino-4-phenyl-cyclohexyl)-2,2,2-trifluoro-acetamide (6.0 g, 17.69 mmol, 1.0 eq.) in dry THF (100 mL) dropwise at 0° C. The reaction mixture was stirred at RT for 16 h, then quenched with sat. aq. Na$_2$SO$_4$ at 0° C., excess THF was added and the resulting mixture was stirred at RT for 2 h. The resulting suspension was filtered through celite and the filter cake was washed with 10% MeOH in DCM (150 mL). Combined filtrate was concentrated under reduced pressure to yield crude 1-aminomethyl-N',N'-dimethyl-4-phenyl-N-(2,2,2-trifluoro-ethyl)-cyclohexane-1,4-diamine (4.2 g, crude) as a light yellow sticky material which was directly used in the next step without further purification. LC-MS: m/z [M+1]$^+$=330.0 (MW calc. 329.40).

Step 4: CIS- and TRANS-8-dimethylamino-8-phenyl-1-(2,2,2-trifluoro-ethyl)-1,3-diaza-spiro[4.5]decan-2-one (INT-1068 and INT-1069)

To a solution of 1-aminomethyl-N',N'-dimethyl-4-phenyl-N-(2,2,2-trifluoro-ethyl)-cyclohexane-1,4-diamine (4.2 g, 12.76 mmol, 1.0 eq.) in toluene (60 ml) was added KOH (4.29 g, 76.56 mmol, 6.0 eq.) in water (120 ml) at 0° C. followed by addition of COCl$_2$ (15.6 ml, 44.66 mmol, 3.5 eq., 20% in toluene) at 0° C. and stirred at RT for 16 h. Reaction mixture was basified with sat NaHCO$_3$ solution and extracted with DCM (2×200 ml). Combined organic layer was dried over Na$_2$SO$_4$ and concentrated under reduced pressure to get crude product which was purified by prep HPLC to get CIS-8-dimethylamino-8-phenyl-1-(2,2,2-trifluoro-ethyl)-1,3-diaza-spiro[4.5]decan-2-one (INT-1068) (1.5 g) (major isomer, polar spot on TLC) and TRANS-8-dimethylamino-8-phenyl-1-(2,2,2-trifluoro-ethyl)-1,3-diaza-spiro[4.5]decan-2-one (INT-1069) as minor isomer (non-polar spot on TLC) (120 mg, 92.93% by HPLC) as off-white solids. CIS-isomer: LC-MS: m/z [M+1]$^+$=356.2 (MW calc.=355.40). HPLC: 98.53%, Column: Xbridge C-18 (100×4.6), 5 g, Diluent: MeOH, Mobile phase: A) 0.05% TFA in water; B) ACN flow rate: 1 ml/min, R$_t$=5.17 min. $^1$HNMR (DMSO-d$_6$, 400 MHz), δ (ppm)=7.43-7.27 (m, 5H), 6.84 (s, 1H), 3.30-3.25 (m, 4H), 2.66-2.63 (d, 2H, J=12.72 Hz), 1.89 (s, 6H), 1.58-1.51 (m, 2H), 1.46-1.43 (m, 2H), 1.33-1.23 (m, 2H).

Synthesis of INT-1071: CIS-8-(dimethylamino)-8-phenyl-1-(2,2,2-trifluoroethyl)-1,3-diazaspiro[4.5]decan-2-one

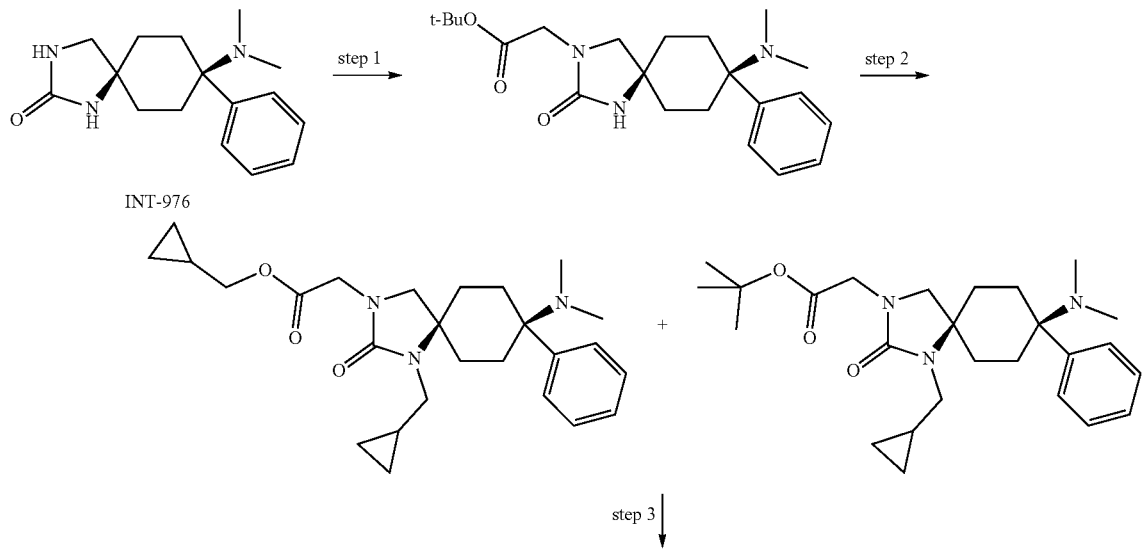

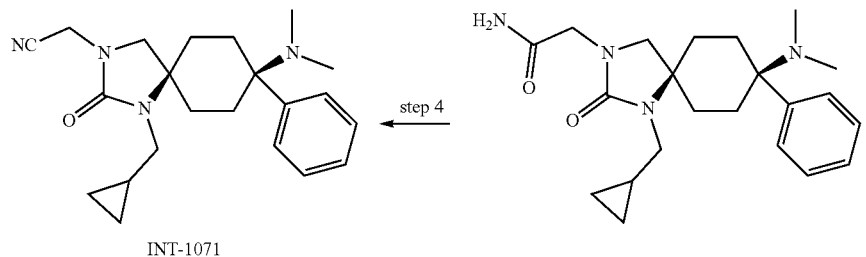

INT-1071

Step 1: tert-butyl CIS-2-(8-(dimethylamino)-2-oxo-8-phenyl-1,3-diazaspiro[4.5]decan-3-yl)acetate To a solution of CIS-8-dimethylamino-8-phenyl-1,3-diaza-spiro[4.5]decan-2-one (INT-976) (10.0 g, 36.63 mmol, 1.0 eq.) in dry THF (1.5 L) was added potassium tert-butoxide (7.14 mg, 36.63 mmol, 1.1 eq.) at RT. The reaction mixture was stirred for 30 min followed by addition of tert-butyl bromo acetate (4.51 g, 40.293 mmol, 1.1 eq.). The reaction mixture was stirred at RT for 4 h, poured into ice-water and extracted with EtOAc (2×700 mL). The organic layer was washed with water (400 mL), brine (400 mL) and dried over $Na_2SO_4$ and concentrated under reduced pressure. The resulting crude product was purified by column chromatography (neutral alumina; 1% MeOH/Hexane) to yield CIS-(8-dimethylamino-2-oxo-8-phenyl-1,3-diaza-spiro[4.5]dec-3-yl)-acetic acid tert-butyl ester (7 g, 18.06 mmol, 49%) as a white solid. LC-MS: m/z $[M+1]^+$=387.9 (MW calc.=387.52).

Step 2: mixture of CIS-(1-cyclopropylmethyl-8-dimethylamino-2-oxo-8-phenyl-1,3-diaza-spiro[4.5]dec-3-yl)-acetic acid cyclopropylmethyl ester and CIS-(1-cyclopropylmethyl-8-dimethylamino-2-oxo-8-phenyl-1,3-diaza-spiro[4.5]dec-3-yl)-acetic acid tert-butyl ester To a solution of CIS-(8-dimethylamino-2-oxo-8-phenyl-1,3-diaza-spiro[4.5]dec-3-yl)-acetic acid tert-butyl ester (2.0 g, 5.16 mmol, 1.0 eq.) in dry DMF (40 mL) was added 60 wt % NaH (413 mg, 10.33 mmol, 2 eq.) at RT. The reaction mixture was stirred for 30 min followed by addition of bromomethylcyclopropane (1.74 g, 12.91 mmol, 2.5 eq.). The reaction mixture was stirred at RT for 20 h, poured slowly into ice-water and extracted with EtOAc (2×400 mL). The organic layer was washed with water (2×200 mL), brine (200 mL) and dried over $Na_2SO_4$ and concentrated under reduced pressure to get crude product which was purified by column chromatography (neutral alumina; 30% EA/Hexane) to yield a mixture of CIS-(1-cyclopropylmethyl-8-dimethylamino-2-oxo-8-phenyl-1,3-diaza-spiro[4.5]dec-3-yl)-acetic acid cyclopropylmethyl ester and CIS-(1-cyclopropylmethyl-8-dimethylamino-2-oxo-8-phenyl-1,3-diaza-spiro[4.5]dec-3-yl)-acetic acid tert-butyl ester (3:2) (1.1 g, 2.505 mmol, 48%) as a light brown sticky liquid. LC-MS: m/z $[M+1]^+$=440.0, 442.0 (MW calc.=439.59, 441.61).

Step 3: CIS-2-(1-cyclopropylmethyl-8-dimethyl-amino-2-oxo-8-phenyl-1,3-diaza-spiro[4.5]dec-3-yl)-acetamide To a mixture of CIS-(1-cyclopropylmethyl-8-dimethyl-amino-2-oxo-8-phenyl-1,3-diaza-spiro[4.5]dec-3-yl)-acetic acid cyclopropylmethyl ester and CIS-(1-cyclopropylmethyl-8-dimethylamino-2-oxo-8-phenyl-1,3-diaza-spiro[4.5]dec-3-yl)-acetic acid tert-butyl ester (2.0 g, 4.55 mmol, 1.0 eq.) in dry MeOH (5 mL) was added 7M $NH_3$ in MeOH (15 mL) and the reaction mixture was stirred in a sealed tube at 95° C. for 48 h. Solvent was evaporated under reduced pressure to get crude product which was purified by column chromatography (neutral alumina; 2% MeOH/DCM) to yield CIS-2-(1-cyclopropylmethyl-8-dimethylamino-2-oxo-8-phenyl-1,3-diaza-spiro[4.5]dec-3-yl)-acetamide (1.2 g, 3.15 mmol, 68%) as an off-white solid. LC-MS (Method 1): m/z $[M+H]^+$=385.2 (MW calc.=384.52).

Step 4: CIS-(1-cyclopropylmethyl-8-dimethyl-amino-2-oxo-8-phenyl-1,3-diaza-spiro[4.5]dec-3-yl) acetonitrile (INT-1071)

To a solution of CIS-2-(1-cyclopropylmethyl-8-dimethyl-amino-2-oxo-8-phenyl-1,3-diaza-spiro[4.5]dec-3-yl)-acetamide (1.7 g, 4.42 mmol, 1.0 eq.) in dry DMF (40 mL) was added cyanuric chloride (2.4 g, 13.28 mmol, 3 eq.) at RT. The reaction mixture was stirred at RT for 1.5 h, basified (pH~9) with sat. aq. $NaHCO_3$ and extracted with EtOAc (2×400 mL). The combined organic layer was washed with water (2×300 mL), brine (300 mL), dried over $Na_2SO_4$ and concentrated under reduced pressure to get crude product which was purified by column chromatography (neutral alumina; 80% DCM/Hexane) to yield CIS-(1-cyclopropylmethyl-8-dimethylamino-2-oxo-8-phenyl-1,3-diaza-spiro[4.5]dec-3-yl) acetonitrile (1.1 g, 3.00 mmol, 68%) as an off-white solid. LC-MS: m/z $[M+1]^+$=367.3 (MW calc.=366.50).

For further intermediates the synthesis in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Intermediate | Chemical Name | Chemical Structure | in analogy to method | m/z [M + H]+ |
|---|---|---|---|---|
| INT-794 | CIS-3-(3,4-dimethoxybenzyl)-8-(dimethylamino)-8-phenyl-1,3-diazaspiro[4.5]decan-2-one | 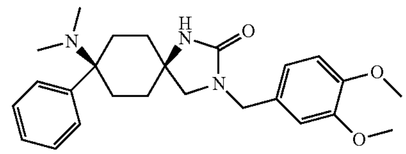 [SMILES: COc1ccc(CN2C[C@]3(CC[C@](c4ccccc4)(N(C)C)CC3)NC2=O)cc1OC] | INT-975 | 424.3 |
| INT-796 | CIS-8-Dimethylamino-3-[(4-methoxyphenyl)-methyl]-8-(3-methoxy-propyl)-1,3-diazaspiro[4.5]decan-2-one | 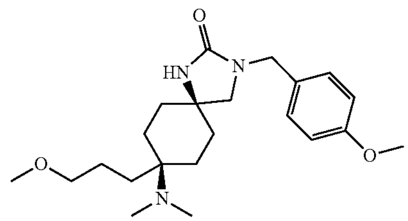 | INT-974 | 390.3 |
| INT-797 | CIS-8-(Ethyl-methyl-amino)-8-phenyl-1,3-diazaspiro[4.5]decan-2-one | 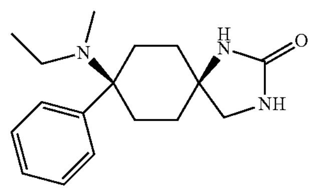 [SMILES: CCN(C)[C@]1(c2ccccc2)CC[C@]2(CC1)CNC(=O)N2] | INT-976 | 288.2 |
| INT-949 | CIS-8-Dimethylamino-1-ethyl-8-phenyl-1,3-diazaspiro[4.5]decan-2-one | 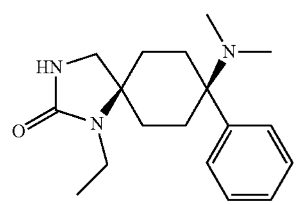 [SMILES: CCN1C(=O)NC[C@]12CC[C@](c1ccccc1)(N(C)C)CC2] | INT-984 | 302.2 |
| INT-950 | CIS-1-(Cyclobutyl-methyl)-8-dimethylamino-8-phenyl-3-[phenyl-methyl]-1,3-diazaspiro[4.5]decan-2-one | 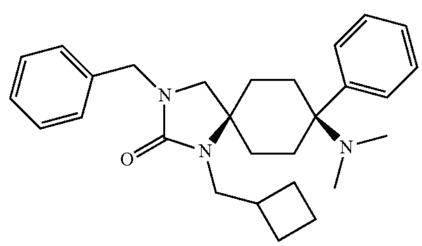 [SMILES: CN(C)[C@]1(c2ccccc2)CC[C@]2(CC1)CN(Cc1ccccc1)C(=O)N2CC1CCC1] | INT-952 | 432.3 |
| INT-954 | 4-Dimethylamino-4-(5-methyl-thiophen-2-yl)-cyclohexan-1-one | 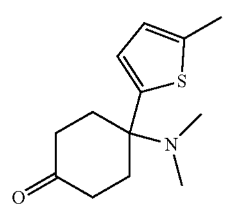 [SMILES: Cc1ccc(C2(N(C)C)CCC(=O)CC2)s1] | INT-965 | 238.1 |
| INT-955 | 4-Dimethylamino-4-thiophen-2-yl-cyclohexan-1-one | 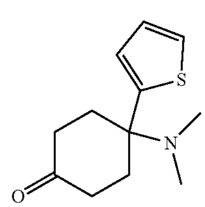 | INT-965 | 224.1 |

-continued

| Inter-mediate | Chemical Name | Chemical Structure | in analogy to method | m/z [M + H]+ |
|---|---|---|---|---|
| INT-956 | 1-(1-Methyl-1H-pyrazol-3-yl)-4-oxo-cyclohexane-1-carbonitrile | 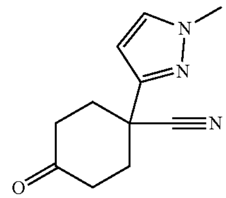 | INT-958 | 204.1 |
| INT-957 | 4-Oxo-1-pyrazin-2-yl-cyclohexane-1-carbonitrile | 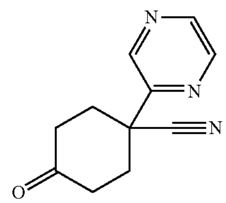 [SMILES: N#CC1(c2cnccn2)CCC(=O)CC1] | INT-958 | 202.1 |
| INT-959 | 4-Dimethylamino-4-(1-methyl-1H-pyrazol-3-yl)-cyclohexan-1-one | 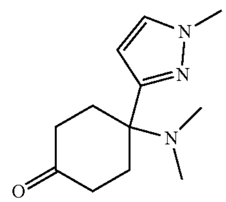 [SMILES: CN(C)C1(c2ccn(C)n2)CCC(=O)CC1] | INT-961 | 222.2 |
| INT-960 | 4-Dimethylamino-4-pyrazin-2-yl-cyclohexan-1-one | 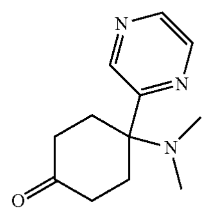 [SMILES: CN(C)C1(c2cnccn2)CCC(=O)CC1] | INT-961 | 220.1 |
| INT-962 | 4-Dimethylamino-4-(3-methoxyphenyl)-cyclohexan-1-one | 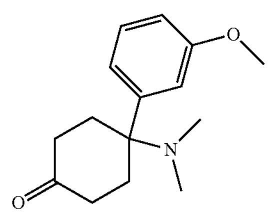 [SMILES: COc1cccc(C2(N(C)C)CCC(=O)CC2)c1] | INT-965 | 248.2 |
| INT-963 | CIS-3-Benzyl-8-dimethylamino-8-phenyl-1,3-diazaspiro[4.5]decan-2-one | 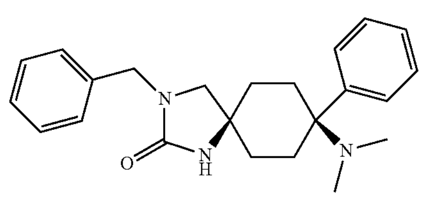 [SMILES: CN(C)[C@]1(c2ccccc2)CC[C@]2(CC1)CN(Cc1ccccc1)C(=O)N2] | INT-975 | 364.2 |
| INT-964 | 4-(Ethyl-methyl-amino)-4-phenyl-cyclohexan-1-one | 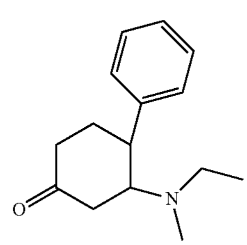 [SMILES: CCN(C)C1CC(=O)CCC1c1ccccc1] | INT-965 | 232.2 |

-continued

| Intermediate | Chemical Name | Chemical Structure | in analogy to method | m/z [M + H]+ |
|---|---|---|---|---|
| INT-967 | CIS-8-Dimethylamino-8-[4-(methoxymethyloxy)-phenyl]-3-[(4-methoxyphenyl)-methyl]-1,3-diazaspiro[4.5]decan-2-one | 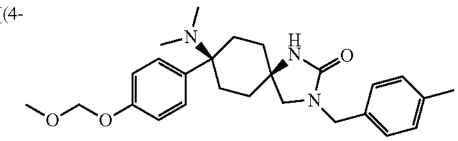 | INT-974 | 454.3 |
| INT-968 | CIS-8-Dimethylamino-8-[3-(methoxymethyloxy)-phenyl]-3-[(4-methoxyphenyl)-methyl]-1,3-diazaspiro[4.5]decan-2-one | 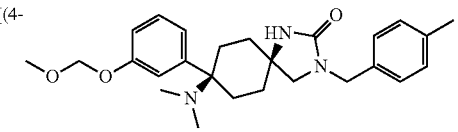 | INT-974 | 454.3 |
| INT-969 | CIS-1-(Cyclobutyl-methyl)-8-dimethylamino-8-(4-hydroxyphenyl)-3-[(4-methoxyphenyl)-methyl]-1,3-diazaspiro[4.5]decan-2-one | 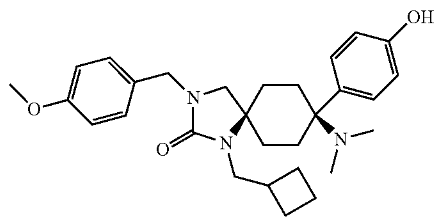 [SMILES: COc1ccc(CN2C[C@]3(CC[C@](c4ccc(O)cc4)(N(C)C)CC3)N(CC3CCC3)C2=O)cc1] | INT-971 | 478.3 |
| INT-970 | CIS-8-Dimethylamino-8-(4-methoxyphenyl)-3-[(4-methoxyphenyl)-methyl]-1,3-diazaspiro[4.5]decan-2-one | 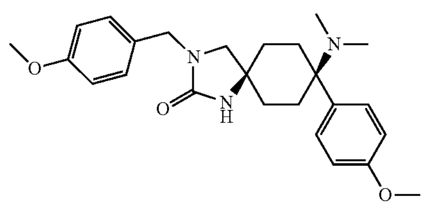 | SC_2017 | 424.3 |
| INT-972 | CIS-8-Dimethylamino-8-(3-methoxyphenyl)-3-[(4-methoxyphenyl)-methyl]-1,3-diazaspiro[4.5]decan-2-one | 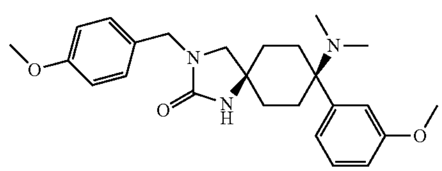 | SC_2017 | 424.3 |
| INT-973 | CIS-8-Dimethylamino-8-(4-fluorophenyl)-3-[(4-methoxyphenyl)-methyl]-1,3-diazaspiro[4.5]decan-2-one | 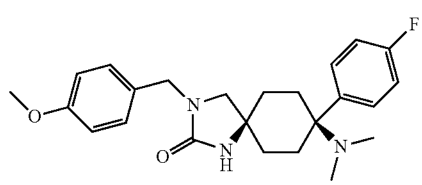 [SMILES: COc1ccc(CN2C[C@]3(CC[C@](c4ccc(F)cc4)(N(C)C)CC3)NC2=O)cc1] | INT-974 | 412.2 |
| INT-979 | CIS-8-Dimethylamino-1-(3-methoxy-propyl)-8-phenyl-1,3-diazaspiro[4.5]decan-2-one | 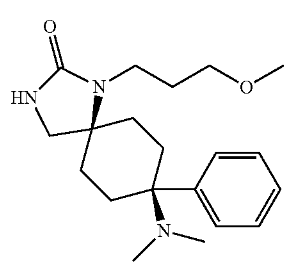 [SMILES: COCCCN1C(=O)NC[C@]12CC[C@](c1ccccc1)(N(C)C)CC2] | INT-984 | 346.2 |

-continued

| Intermediate | Chemical Name | Chemical Structure | in analogy to method | m/z [M + H]+ |
|---|---|---|---|---|
| INT-980 | CIS-8-Dimethylamino-1-(2-methoxy-ethyl)-8-phenyl-1,3-diazaspiro[4.5]decan-2-one | 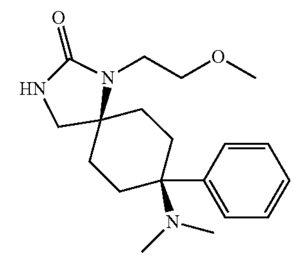 [SMILES: COCCN1C(=O)NC[C@]12CC[C@](c1ccccc1)(N(C)C)CC2] | INT-984 | 332.2 |
| INT-981 | CIS-8-Dimethylamino-8-phenyl-1-propyl-1,3-diazaspiro[4.5]decan-2-one | 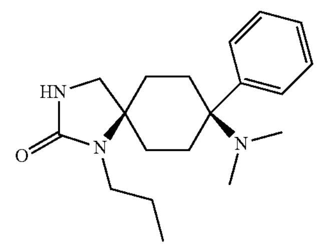 [SMILES: CCCN1C(=O)NC[C@]12CC[C@](c1ccccc1)(N(C)C)CC2] | INT-984 | 316.2 |
| INT-983 | CIS-1-(Cyclopropyl-methyl)-8-dimethylamino-8-phenyl-1,3-diazaspiro[4.5]decan-2-one | 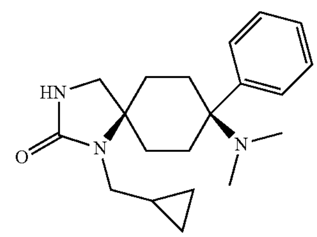 [SMILES: CN(C)[C@]1(c2ccccc2)CC[C@]2(CC1)CNC(=O)N2CC1CC1] | INT-984 | 328.2 |
| INT-985 | CIS-1-(Cyclobutyl-methyl)-8-(methyl-propyl-amino)-8-phenyl-1,3-diazaspiro[4.5]decan-2-one | 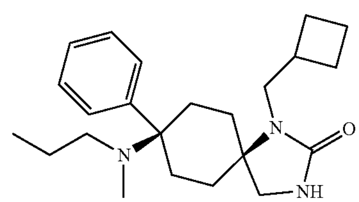 [SMILES: CCCN(C)[C@]1(c2ccccc2)CC[C@]2(CC1)CNC(=O)N2CC1CCC1] | INT-986 | 370.3 |
| INT-993 | 4-benzyl-4-(dimethylamino)cyclohexanone | 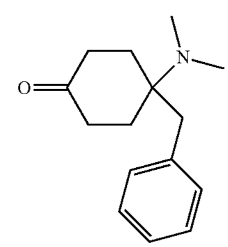 [SMILES: CN(C)C1(Cc2ccccc2)CCC(=O)CC1] | INT-965 | 232.3 |
| INT-994 | CIS-8-benzyl-8-(dimethylamino)-1,3-diazaspiro[4.5]decan-2-one | 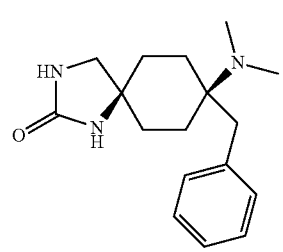 [SMILES: CN(C)[C@]1(Cc2ccccc2)CC[C@]2(CC1)CNC(=O)N2] | INT-976 | 288.2 |

-continued

| Intermediate | Chemical Name | Chemical Structure | in analogy to method | m/z [M + H]+ |
|---|---|---|---|---|
| INT-995 | TRANS-8-benzyl-8-(dimethylamino)-1,3-diazaspiro[4.5]decan-2-one | 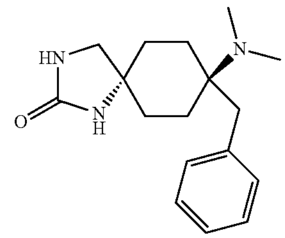 [SMILES: CN(C)[C@]1(Cc2ccccc2)CC[C@@]2(CC1)CNC(=O)N2] | INT-976 | 288.2 |
| INT-997 | CIS-8-(dimethylamino)-8-(thiophen-2-yl)-1,3-diazaspiro[4.5]decan-2-one | 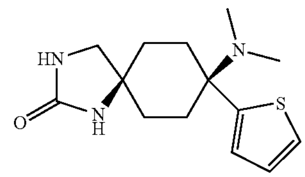 [SMILES: CN(C)[C@]1(c2cccs2)CC[C@]2(CC1)CNC(=O)N2] | INT-976 | 280.1 |
| INT-998 | TRANS-8-(dimethylamino)-8-(thiophen-2-yl)-1,3-diazaspiro[4.5]decan-2-one | 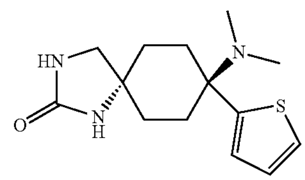 [SMILES: CN(C)[C@]1(c2cccs2)CC[C@@]2(CC1)CNC(=O)N2] | INT-976 | 280.1 |
| INT-999 | 4-(dimethylamino)-4-(1-methyl-1H-benzo[d]imidazol-2-yl)cyclohexanone | 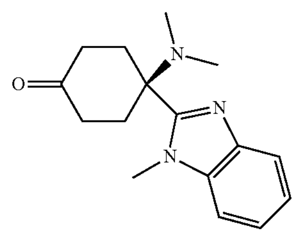 | INT-965 | 272.2 |
| INT-1000 | CIS-8-(dimethylamino)-8-(1-methyl-1H-benzo[d]imidazol-2-yl)-1,3-diazaspiro[4.5]decan-2-one | 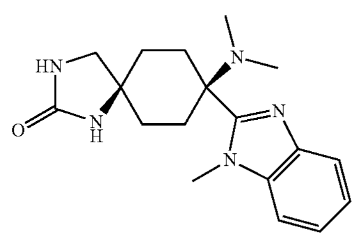 [SMILES: Cn1c2ccccc2nc1[C@]1(N(C)C)CC[C@@]2(CC1)CNC(=O)N2] | INT-976 | 328.2 |
| INT-1001 | TRANS-8-(dimethylamino)-8-(1-methyl-1H-benzo[d]imidazol-2-yl)-1,3-diazaspiro[4.5]decan-2-one | 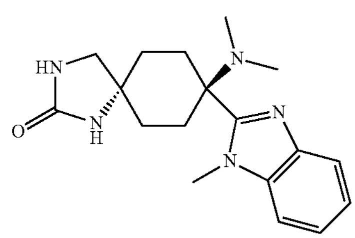 [SMILES: Cn1c2ccccc2nc1[C@]1(N(C)C)CC[C@]2(CC1)CNC(=O)N2] | INT-976 | 328.2 |
| INT-1009 | TRANS-8-ethylamino-8-phenyl-1,3-diaza-spiro[4.5]decan-2-one | 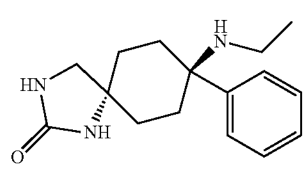 [SMILES: CCN[C@]1(c2ccccc2)CC[C@@]2(CC1)CNC(=O)N2] | INT-1008 | 274.2 |

-continued

| Intermediate | Chemical Name | Chemical Structure | in analogy to method | m/z [M + H]+ |
|---|---|---|---|---|
| INT-1024 | CIS-8-(dimethylamino)-8-(3-fluorophenyl)-1,3-diazaspiro[4.5]decan-2-one | 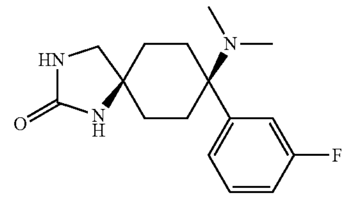 [SMILES: CN(C)[C@]1(c2cccc(F)c2)CC[C@]2(CC1)CNC(=O)N2] | INT-977 (step 2) | 292.2 |
| INT-1025 | CIS-8-(dimethylamino)-8-(4-fluorophenyl)-1,3-diazaspiro[4.5]decan-2-one | 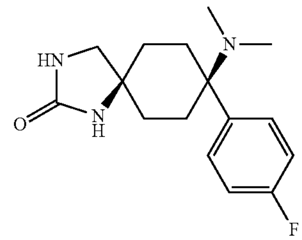 [SMILES: CN(C)[C@]1(c2ccc(F)cc2)CC[C@]2(CC1)CNC(=O)N2] | INT-974 INT-977 (step 2) | 292.2 |
| INT-1039 | CIS-8-(dimethylamino)-8-(3-(trifluoromethoxy)phenyl)-1,3-diazaspiro[4.5]decan-2-one | 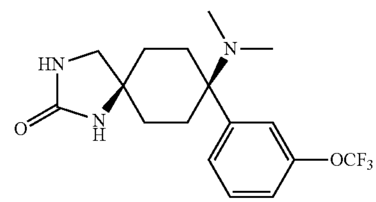 [SMILES: CN(C)[C@]1(c2cccc(OC(F)(F)F)c2)CC[C@]2(CC1)CNC(=O)N2] | INT-1038 | 358.2 |
| INT-1040 | (CIS)-8-(dimethylamino)-8-(3-(trifluoromethyl)phenyl)-1,3-diazaspiro[4.5]decan-2-one | 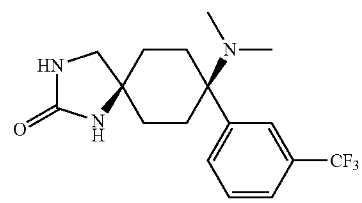 [SMILES: CN(C)[C@]1(c2cccc(C(F)(F)F)c2)CC[C@]2(CC1)CNC(=O)N2] | INT-1038 | 342.2 |
| INT-1041 | (CIS)-8-(dimethylamino)-8-(3-methoxyphenyl)-1,3-diazaspiro[4.5]decan-2-one | 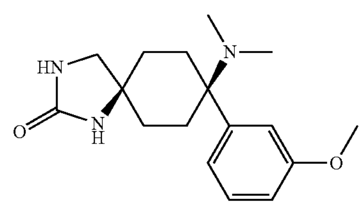 [SMILES: COc1cccc([C@]2(N(C)C)CC[C@@]3(CC2)CNC(=O)N3)c1] | INT-1038 | 304.2 |
| INT-1042 | (CIS)-8-(5-chlorothiophen-2-yl)-8-(dimethylamino)-1,3-diazaspiro[4.5]decan-2-one | 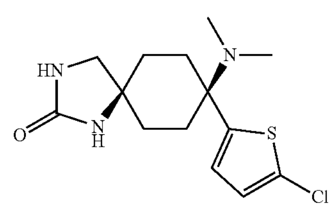 [SMILES: CN(C)[C@]1(c2ccc(Cl)s2)CC[C@]2(CC1)CNC(=O)N2] | INT-1038 | 314.1 |
| INT-1043 | (CIS)-8-(dimethylamino)-8-(3-fluoro-5-methylphenyl)-1,3-diazaspiro[4.5]decan-2-one | 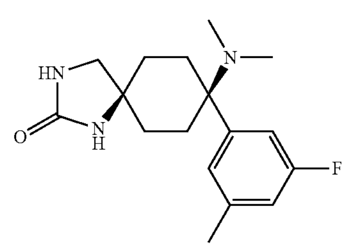 [SMILES: Cc1cc(F)cc([C@]2(N(C)C)CC[C@@]3(CC2)CNC(=O)N3)c1] | INT-1038 | 306.2 |

-continued

| Intermediate | Chemical Name | Chemical Structure | in analogy to method | m/z [M + H]+ |
|---|---|---|---|---|
| INT-1044 | (CIS)-8-(3-chlorophenyl)-8-(dimethylamino)-1,3-diazaspiro[4.5]decan-2-one | 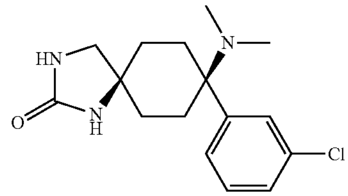 [SMILES: CN(C)[C@]1(c2cccc(Cl)c2)CC[C@]2(CC1)CNC(=O)N2] | INT-1038 | 308.2 |
| INT-1047 | (CIS)-8-(methyl(oxetan-3-ylmethyl)amino)-8-phenyl-1,3-diazaspiro[4.5]decan-2-one | 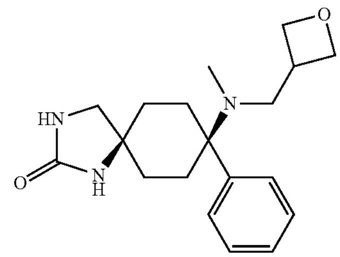 [SMILES: CN(CC1COC1)[C@]1(c2ccccc2)CC[C@]2(CC1)CNC(=O)N2] | INT-1026 | 330.5 |
| INT-1050 | (CIS)-8-(dimethylamino)-8-phenyl-3-(piperidin-4-yl)-1,3-diazaspiro[4.5]decan-2-one | 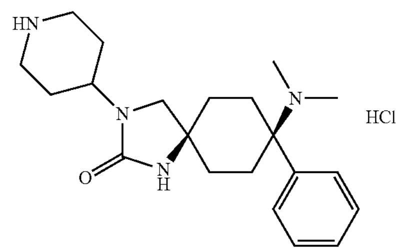 [SMILES: CN(C)[C@]1(c2ccccc2)CC[C@]2(CC1)CN(C1CCNCC1)C(=O)N2 ; Cl] | SC_4054 | 357.3 |
| INT-1051 | (CIS)-8-(dimethylamino)-8-phenyl-3-(piperidin-4-ylmethyl)-1,3-diazaspiro[4.5]decan-2-one | 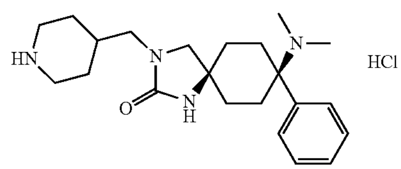 [SMILES: CN(C)[C@]1(c2ccccc2)CC[C@]2(CC1)CN(CC1CCNCC1)C(=O)N2 ; Cl] | SC_4058 | 371.5 |
| INT-1053 | (CIS)-3-(2-amino-2-methylpropyl)-8-(dimethylamino)-1-((1-hydroxycyclobutyl)methyl)-8-phenyl-1,3-diazaspiro[4.5]decan-2-one | 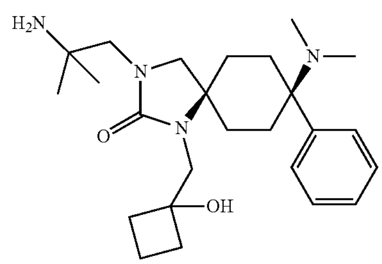 [SMILES: CN(C)[C@]1(c2ccccc2)CC[C@]2(CC1)CN(CC(C)(C)N)C(=O)N2CC1(O)CCC1] | INT-1052 | 429.3 |
| INT-1061 | TRANS-1-(cyclopropyl-methyl)-8-dimethylamino-8-phenyl-1,3-diazaspiro[4.5]decan-2-one | 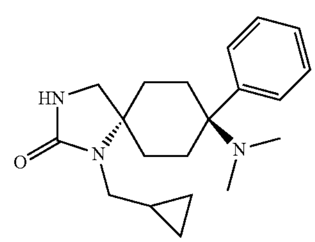 [SMILES: CN(C)[C@]1(c2ccccc2)CC[C@@]2(CC1)CNC(=O)N2CC1CC1] | INT-984 | 328.2 |

| Intermediate | Chemical Name | Chemical Structure | in analogy to method | m/z [M + H]+ |
|---|---|---|---|---|
| INT-1063 | CIS-1-(cyclopropylmethyl)-8-(dimethylamino)-8-(3-fluorophenyl)-1,3-diazaspiro[4.5]decan-2-one | 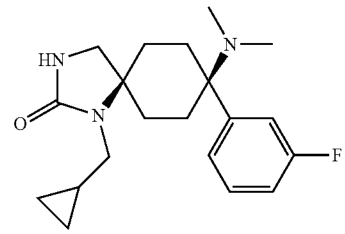 [SMILES: CN(C)[C@]1(c2cccc(F)c2)CC[C@]2(CC1)CNC(=O)N2CC1CC1] | INT-1031 | 346.2 |
| INT-1066 | TRANS-1-(cyclobutylmethyl)-8-(dimethylamino)-8-phenyl-1,3-diazaspiro[4.5]decan-2-one | 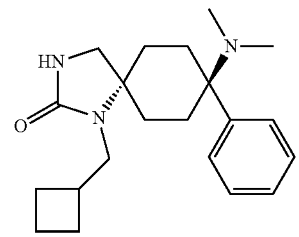 [SMILES: CN(C)[C@]1(c2ccccc2)CC[C@@]2(CC1)CNC(=O)N2CC1CCC1] | INT-987 | 342.3 |
| INT-1070 | CIS-8-(dimethylamino)-8-phenyl-1-(3,3,3-trifluoropropyl)-1,3-diazaspiro[4.5]decan-2-one | 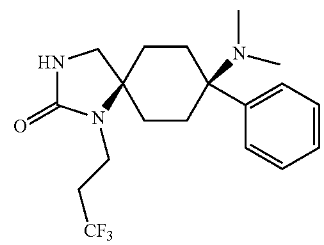 [SMILES: CN(C)[C@]1(c2ccccc2)CC[C@]2(CC1)CNC(=O)N2CCC(F)(F)F] | INT-1068 | 360.2 |
| INT-1072 | CIS-8-(dimethylamino)-1-((1-hydroxycyclobutyl)methyl)-8-phenyl-3-(piperidin-4-yl)-1,3-diazaspiro[4.5]decan-2-one | 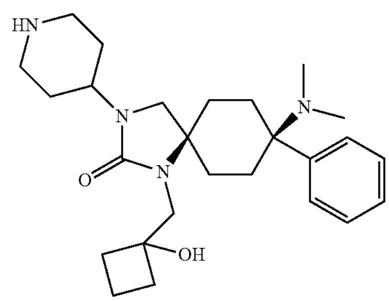 | SC_4054 | 441.3 |
| INT-1073 | CIS-8-(dimethylamino)-1-((1-hydroxycyclobutyl)methyl)-8-phenyl-3-(piperidin-4-yl)-1,3-diazaspiro[4.5]decan-2-one | 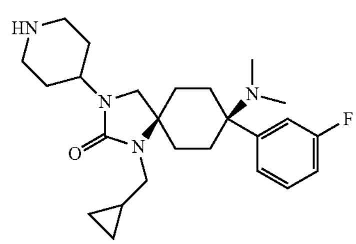 | SC_4054 | 429.3 |
| INT-1074 | CIS-8-(dimethylamino)-8-(3-fluorophenyl)-1-((1-hydroxycyclobutyl)methyl)-1,3-diazaspiro[4.5]decan-2-one | 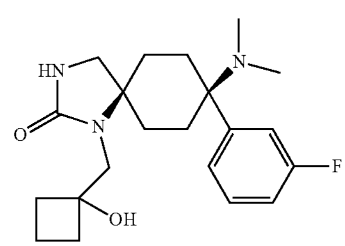 [SMILES: CN(C)[C@]1(c2cccc(F)c2)CC[C@]2(CC1)CNC(=O)N2CC1(O)CCC1] | INT-1031 | 376.2 |

Synthesis of exemplary compounds

Synthesis of SC_4001: CIS-4-[1-(Cyclobutyl-methyl)-8-dimethylamino-2-oxo-8-phenyl-1,3-diazaspiro[4.5]decan-3-yl]-butyramide

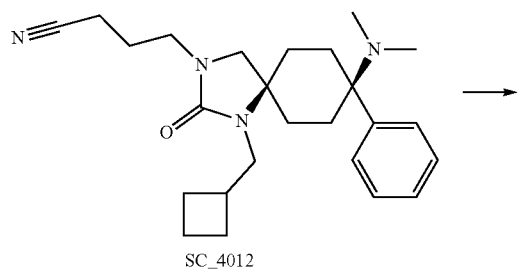

SC_4012

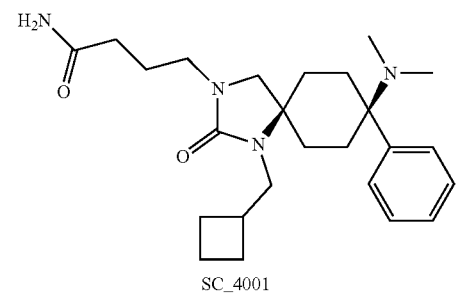

SC_4001

CIS-4-[1-(cyclobutyl-methyl)-8-dimethylamino-2-oxo-8-phenyl-1,3-diazaspiro[4.5]decan-3-yl]-butyronitrile (SC_4012) (201 mg, 0.5 mmol) was dissolved in DMSO (7 mL) and K$_2$CO$_3$ (136 mg, 1 mmol) and hydrogen peroxide (30% in water, 0.7 mL) were added. The resulting mixture was stirred at RT for 18 h, then quenched with 2N aq. NaOH (5 mL) and extracted with ethyl acetate (3×5 mL). The combined organic layers were dried over Na$_2$SO$_4$, concentrated in vacuo and purified by flash chromatography to yield CIS-4-[1-(cyclobutyl-methyl)-8-dimethylamino-2-oxo-8-phenyl-1,3-diazaspiro[4.5]decan-3-yl]-butyramide SC_4001 (58 mg) as a white solid. [M+H]$^+$ 427.3

Synthesis of SC_4003: CIS-1-(Cyclobutyl-methyl)-8-dimethylamino-3-[2-[2-(2-methoxy-ethoxy)-ethoxy]-ethyl]-8-phenyl-1,3-diazaspiro[4.5]decan-2-one

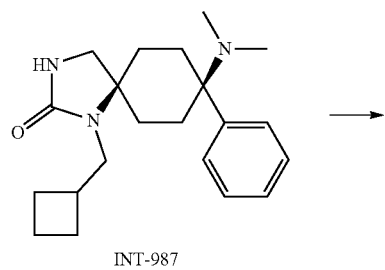

INT-987

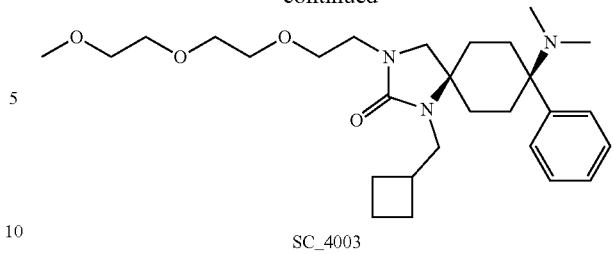

SC_4003

In an oven dried flask, sodium hydroxide powder (28 mg, 0.7 mmol) was added to DMSO (0.25 mL) at RT. The mixture was stirred for 5 min, then CIS-1-(cyclobutyl-methyl)-8-dimethylamino-8-phenyl-1,3-diazaspiro[4.5]decan-2-one (INT-987) (60 mg, 0.18 mmol) was added and the reaction mixture was stirred for 10 min at RT. 1-[2-(2-Bromo-ethoxy)ethoxy]-2-methoxy-ethane (120 mg, 0.53 mmol) was added and the resulting mixture was stirred for 30 min at RT and for 2 h at 60° C. Water was added and the aqueous layer was extracted with DCM (3×10 mL). The combined organic layers were dried over Na$_2$SO$_4$ and concentrated in vacuo. The residue was purified by flash chromatography to yield CIS-1-(cyclobutyl-methyl)-8-dimethylamino-3-[2-[2-(2-methoxy-ethoxy)-ethoxy]-ethyl]-8-phenyl-1,3-diazaspiro[4.5]decan-2-one (SC_4003) (38 mg) as a white solid. [M+H]$^+$ 488.3

Synthesis of SC_4010: CIS-1-(Cyclobutyl-methyl)-8-methylamino-3-(2-methylsulfonyl-ethyl)-8-phenyl-1,3-diazaspiro[4.5]decan-2-one

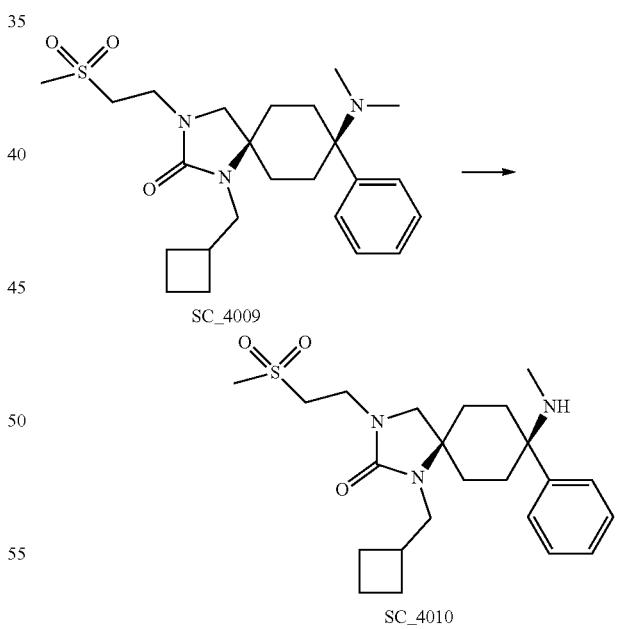

SC_4009

SC_4010

N-Iodosuccinimide (30 mg, 0.14 mmol) was added to a suspension of CIS-1-(cyclobutyl-methyl)-8-dimethylamino-3-(2-methylsulfonyl-ethyl)-8-phenyl-1,3-diazaspiro[4.5]decan-2-one (SC_4009) (40 mg, 0.09 mmol) in a mixture of acetonitrile and THF (1:1 v/v, 20 mL) at RT and the resultant mixture was stirred at RT for 16 h. The reaction mixture was basified with 2N aq. NaOH to pH~10 and the organic product was extracted with DCM (3×10 mL). The combined organic extracts were dried over anhydrous Na₂SO₄ and concentrated under reduced pressure. The residue was stirred vigorously with a mixture of 10 wt % aq. citric acid (5 mL) and DCM (10 mL) at RT for 10 min. The reaction mixture was basified with 5N aq. NaOH to pH~10 and extracted with DCM (3×10 mL). The combined organic layer was dried over anhydrous Na₂SO₄ and concentrated in vacuo. The residue was purified by flash chromatography and prep. HPLC to give 16 mg of CIS-1-(cyclobutyl-methyl)-8-methylamino-3-(2-methylsulfonyl-ethyl)-8-phenyl-1,3-diazaspiro[4.5]decan-2-one (SC_4010). [M+H]+ 434.2

Synthesis of SC_4012: CIS-4-[1-(Cyclobutyl-methyl)-8-dimethylamino-2-oxo-8-phenyl-1,3-diazaspiro[4.5]decan-3-yl]-butyronitrile

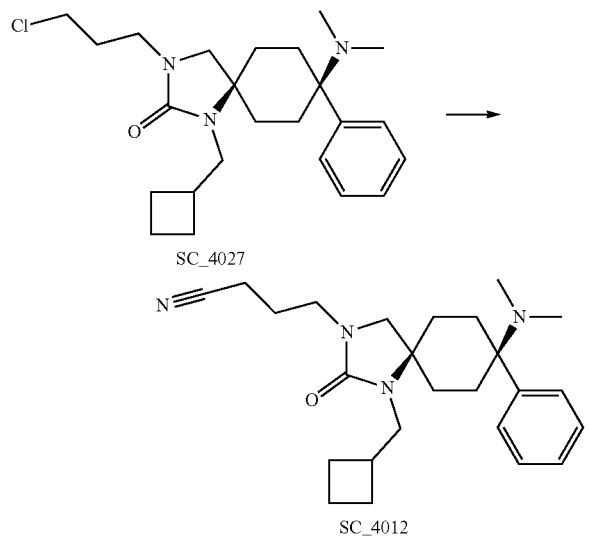

Potassium cyanide (131 mg, 2 mmol) and sodium iodide (202 mg, 1.4 mmol) were added to a solution of CIS-3-(3-chloro-propyl)-1-(cyclobutyl-methyl)-8-dimethylamino-8-phenyl-1,3-diazaspiro[4.5]decan-2-one (SC_4027) (57 mg, 1.4 mmol) in DMSO (5 mL) at RT and the resulting mixture was stirred at 90° C. for 18 h. The reaction mixture was quenched with water (5 mL) and extracted with ethyl acetate (5×25 mL). The combined organic layers were dried over Na₂SO₄ and concentrated in vacuo. The residue was purified by flash chromatography to yield CIS-4-[1-(cyclobutyl-methyl)-8-dimethylamino-2-oxo-8-phenyl-1,3-diazaspiro[4.5]decan-3-yl]-butyronitrile (SC_4012) (38 mg) as a white solid. [M+H]+ 409.3

Synthesis of SC_4013: CIS-4-[1-(Cyclobutyl-methyl)-8-dimethylamino-2-oxo-8-phenyl-1,3-diazaspiro[4.5]decan-3-yl]-N-methyl-butyramide

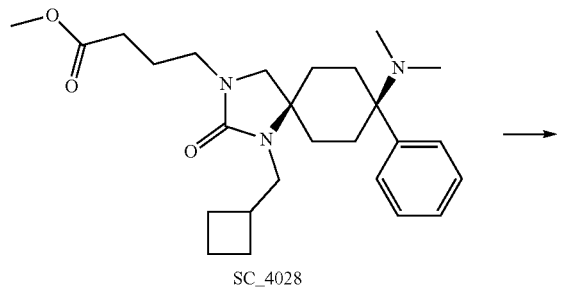

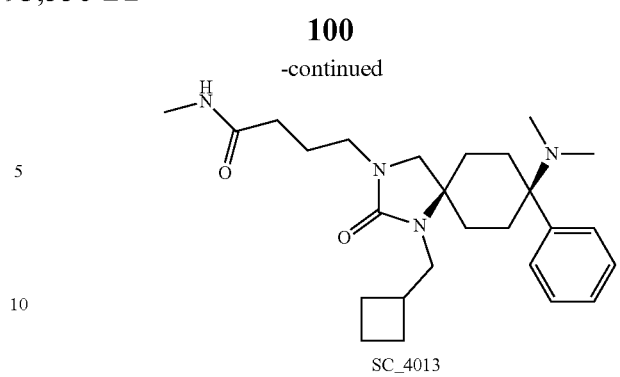

CIS-4-[1-(cyclobutyl-methyl)-8-dimethylamino-2-oxo-8-phenyl-1,3-diazaspiro[4.5]decan-3-yl]-butyric acid methyl ester (SC_4028) (59 mg, 0.13 mmol) was treated with 2M methylamine in methanol (1.5 mL) and heated for 100 min at 100° C. in a closed vessel. Volatiles were removed under a stream of nitrogen, the residue was taken up in 2M methylamine in methanol (1.5 mL) and heated for 50 min at 120° C. in a closed vessel. All volatiles were removed under a stream of nitrogen to afford the crude product, which was purified by column chromatography to yield 49 mg of CIS-4-[1-(cyclobutyl-methyl)-8-dimethylamino-2-oxo-8-phenyl-1,3-diazaspiro[4.5]decan-3-yl]-N-methyl-butyramide (SC_4013) as a white solid. [M+H]441.3

Synthesis of SC_4025: CIS-8-Dimethylamino-1-[(1-hydroxy-cyclobutyl)-methyl]-8-phenyl-3-(tetrahydro-pyran-4-yl-methyl)-1,3-diazaspiro[4.5]decan-2-one

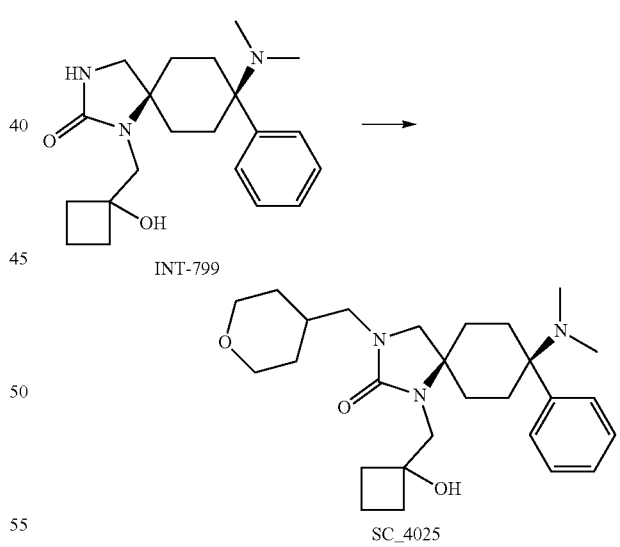

KOtBu (1M in THF) (0.5 mL, 0.504 mmol) was added to a suspension of CIS-8-dimethylamino-1-[(1-hydroxy-cyclobutyl)-methyl]-8-phenyl-1,3-diazaspiro[4.5]decan-2-one (INT-799) (0.15 g, 0.42 mmol) in THF (4 mL) at 0° C. The reaction mixture was stirred for 10 min and a solution of 4-(bromomethyl)tetrahydro-2H-pyran (90 mg, 0.504 mmol) in THF (2 mL) was added. The reaction mixture was stirred at 70° C. for 16 h, then quenched with sat. aq. NH₄Cl (5 mL) and extracted with ethyl acetate (2×20 mL). The combined organic extracts were washed with water, brine, dried over Synthesis of SC_4027: CIS-3-(3-Chloro-propyl)-1-(cyclobutyl-methyl)-8-dimethylamino-8-phenyl-1,3-diazaspiro[4.5]decan-2-one

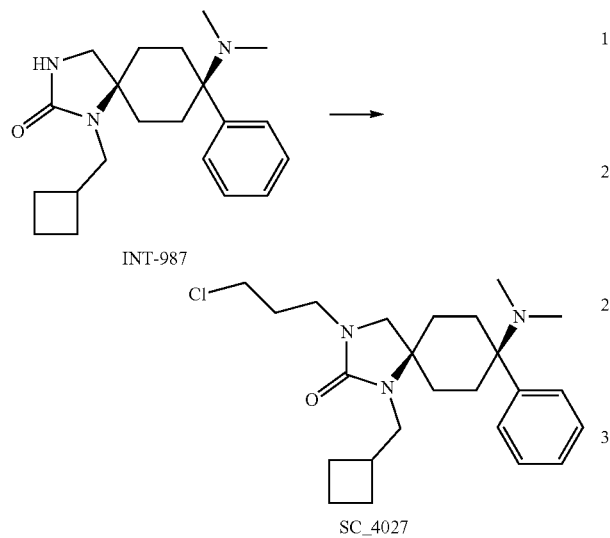

Sodium hydride (60% suspension in mineral oil, 23 mg, 0.6 mmol) was added to a solution of CIS-1-(cyclobutyl-methyl)-8-dimethylamino-8-phenyl-1,3-diazaspiro[4.5]decan-2-one (INT-987) (100 mg, 0.3 mmol) in THF (3 mL) at 0° C. and the resulting mixture was stirred for 30 min at 50° C. A solution of 1-bromo-3-chloro-propane (0.14 mL, 1.5 mmol) in THF (0.7 mL) was added at 50° C. and stirring was continued at 80° C. for 18 h. The reaction mixture was quenched with cold water (10 mL) and extracted with ethyl acetate (3×10 mL). The combined organic layers were dried over Na$_2$SO$_4$ and concentrated in vacuo. The residue was purified by flash chromatography to yield CIS-3-(3-chloro-propyl)-1-(cyclobutyl-methyl)-8-dimethylamino-8-phenyl-1,3-diazaspiro[4.5]decan-2-one (SC_4027) (50 mg) as a white powder. [M+H]+ 418.3

Synthesis of SC_4028: CIS-4-[1-(Cyclobutyl-methyl)-8-dimethylamino-2-oxo-8-phenyl-1,3-diazaspiro[4.5]decan-3-yl]-butyric acid methyl ester

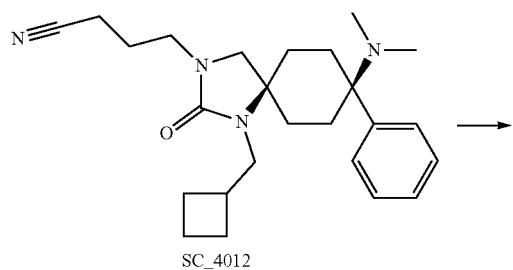

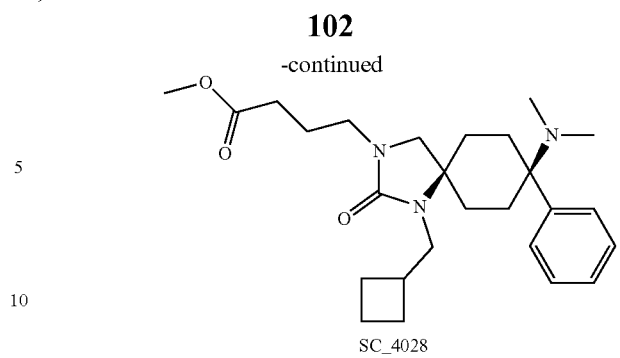

CIS-4-[1-(Cyclobutyl-methyl)-8-dimethylamino-2-oxo-8-phenyl-1,3-diazaspiro[4.5]decan-3-yl]-butyronitrile SC_4012 (345 mg, 0.85 mmol) was dissolved in 5 mL conc. HCl and stirred for 6 h at 100° C. Volatiles were removed under reduced pressure to afford the crude product as hydrochloride salt. This salt was dissolved in MeOH/toluene and concentrated under reduced pressure. The latter dissolution/evaporation cycle was repeated, yielding 380 mg of CIS-4-[1-(Cyclobutyl-methyl)-8-dimethylamino-2-oxo-8-phenyl-1,3-diazaspiro[4.5]decan-3-yl]-butyric acid methyl ester SC_4028. [M+H]+ 442.

Synthesis of SC_4031: CIS-3-acetyl-8-(dimethylamino)-8-phenyl-1,3-diazaspiro[4.5]decan-2-one

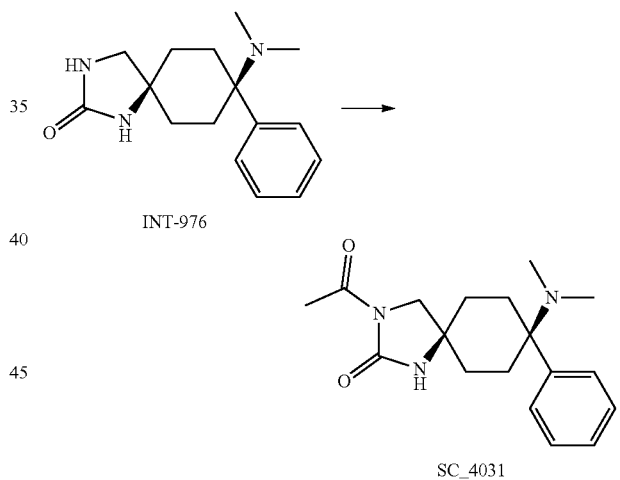

To the mixture of CIS-8-dimethylamino-8-phenyl-1,3-diaza-spiro[4.5]decan-2-one (INT-976) (3.5 g, 12.83 mmol, 1.0 eq.) and K$_2$CO$_3$ (3.54 g, 25.66 mmol, 2.0 eq.) in THF (200 ml) at 0° C. was added acetyl chloride (1.4 ml, 19.23 mmol, 1.5 eq.). The reaction mixture was stirred at RT for 3 h, diluted with DCM (300 ml) and filtered through Celite. The filtrate was washed with sat. aq. NaHCO$_3$ (100 ml), water (100 ml) and brine (100 ml). The organic layer was dried over Na$_2$SO$_4$ and concentrated under reduced pressure. The resulting residue was purified by column chromatography (silica gel neutralized with ammonia, 5% MeOH/DCM) to yield CIS-3-acetyl-8-dimethylamino-8-phenyl-1,3-diazaspiro[4.5]decan-2-one (SC_4031) as an off white solid. Note: This reaction was done in two parallel batches of 3.5 g scale and yield given for two combined batches. Yield: 63% (5.1 g, 16.19 mmol). $^1$HNMR (DMSO-d6, 400 MHz), δ (ppm)

=8.05 (bs, 1H), 7.36-7.25 (m, 5H), 3.44 (s, 2H), 2.31 (s, 5H, CH$_3$+CH$_2$), 1.92 (s, 6H), 1.83-1.76 (m, 4H), 1.39 (bs, 2H). Mass: m/z 316.1 [M+H]$^+$

Synthesis of SC_4032: CIS-8-(dimethylamino)-3-(2-(methylsulfonyl)ethyl)-8-phenyl-1,3-diazaspiro[4.5]decan-2-one

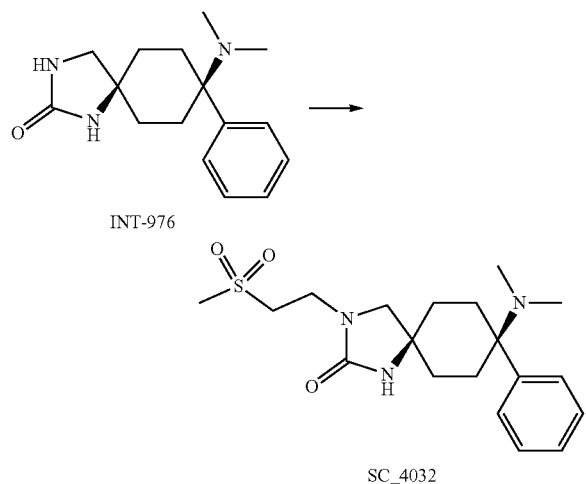

SC_4032

KOtBu (1M in THF) (1.1 mL, 0.11 mmol) was added to the suspension of CIS-8-(dimethylamino)-8-phenyl-1,3-diazaspiro[4.5]decan-2-one (INT-976) (0.3 g, 0.11 mmol) in THF (10 mL) at 0° C. The reaction mixture was stirred for 10 min and 1-bromo-2-(methylsulfonyl)ethane (0.16 g, 0.09 mmol) was added. The reaction mixture was stirred at 0° C. for 4 h, then quenched with sat. aq. NH$_4$Cl (15 mL) and the organic product was extracted with DCM (3×20 mL). The combined organic extracts were washed with brine, dried over anhydr. Na$_2$SO$_4$ and concentrated under reduced pressure. Purification of the residue by reverse phase preparative HPLC afforded 180 mg (43%) of CIS-8-(dimethylamino)-3-(2-(methylsulfonyl)ethyl)-8-phenyl-1,3-diazaspiro[4.5]decan-2-one (SC_4032) as an off white solid (TLC system: 10% MeOH in DCM Rf: 0.3.). $^1$H NMR (DMSO-d6): δ 7.37-7.23 (m, 5H), 6.90 (br s, 1H), 3.43 (t, 2H), 3.26 (t, 2H), 3.10 (s, 2H), 2.95 (s, 3H), 2.32 (br m, 2H), 1.93 (s, 6H), 1.79-1.76 (m, 4H), 1.38-1.36 (m, 2H). Mass: m/z 380.2 [M+H]$^+$

Synthesis of SC_4033: CIS-1-acetyl-8-(dimethylamino)-8-phenyl-1,3-diazaspiro[4.5]decan-2-one

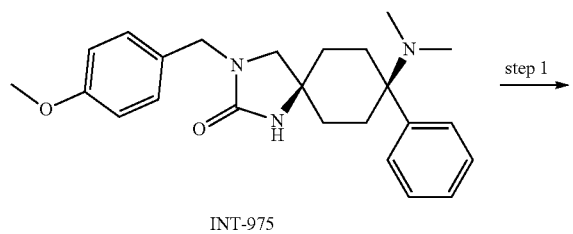

INT-975

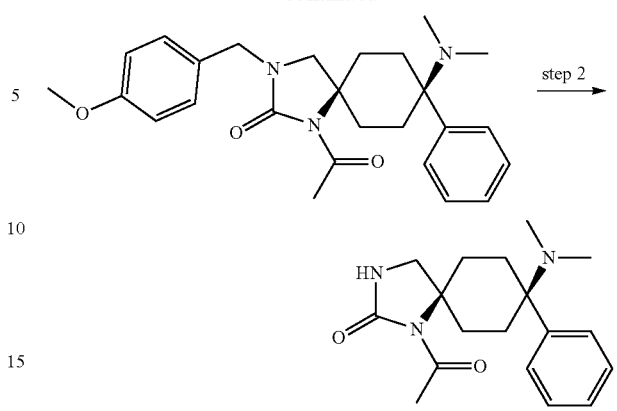

SC_4033

Step 1: CIS-1-acetyl-8-(dimethylamino)-3-(4-methoxybenzyl)-8-phenyl-1,3-diazaspiro[4.5]decan-2-one To a solution of CIS-8-dimethylamino-3-(4-methoxy-benzyl)-8-phenyl-1,3-diaza-spiro[4.5]decan-2-one (INT-975) (19.5 g, 49.6 mmol, 1.0 eq.) in THF (180 ml) was added 2.5M solution of n-BuLi in hexane (39.7 ml, 99.23 mmol, 2.0 eq.) at 0° C. and the resulting mixture was stirred for 1 h. A solution of acetyl chloride (7.7 g, 99.23 mmol, 2.0 eq.) in THF (20 ml) was added dropwise at 0° C. The cooling bath was removed, the reaction mixture was stirred at RT for 16 h, then cooled down to 0° C. again, quenched with water and extracted with ethyl acetate (2×200 ml). The combined organic extracts were washed with brine (250 ml), dried over Na$_2$SO$_4$ and concentrated under reduced pressure. The residue was purified by column chromatography (silica gel; 30% EtOAc/Hexane) to yield CIS-1-acetyl-8-dimethyl-amino-3-(4-methoxy-benzyl)-8-phenyl-1,3-diaza-spiro[4.5]decan-2-one (6.1 g, 14.02 mmol, 28%) as a light yellow sticky solid. Mass: m/z 436.3 [M+H]$^+$

Step 2: CIS-1-acetyl-8-(dimethylamino)-8-phenyl-1,3-diazaspiro[4.5]decan-2-one (SC_4033)

To a solution of CIS-1-acetyl-8-dimethylamino-3-(4-methoxy-benzyl)-8-phenyl-1,3-diaza-spiro[4.5]decan-2-one (5.0 g, 11.5 mmol, 1.0 eq.) in acetonitrile (60 ml) was added a solution cerium(IV) ammonium nitrate (18.98 g, 34.5 mmol, 3.0 eq.) in water (60 ml) at 0° C. and the reaction mixture was stirred at RT for 2 h. The reaction mixture was quenched with aq. NaHCO$_3$ solution (50 ml) and extracted with ethyl acetate (2×100 ml). The combined organic layer was washed with brine (2×100 ml), dried over Na$_2$SO$_4$ and concentrated under reduced pressure. The residue was purified by column chromatography (silica gel neutralized with TEA; 2/3 v/v EtOAc/Hexane) to yield CIS-1-acetyl-8-dimethylamino-8-phenyl-1,3-diaza-spiro[4.5]decan-2-one (SC_4033) as an off white solid. Yield: 61% (4.9 g, 15.55 mmol). $^1$HNMR (DMSO-d6, 400 MHz), δ (ppm)=7.57 (s, 1H), 7.33-7.23 (m, 5H), 3.21 (s, 2H), 3.03 (t, 2H, J=12.78 Hz), 2.60 (d, 2H, J=13.32 Hz), 2.32 (s, 3H), 1.89 (s, 6H), 1.37-1.32 (m, 4H). Mass: m/z 316.2 [M+H]$^+$

Synthesis of SC_4034: CIS-1-(cyclopropylmethyl)-8-(dimethylamino)-3-(2-(methylsulfonyl)ethyl)-8-phenyl-1,3-diazaspiro[4.5]decan-2-one

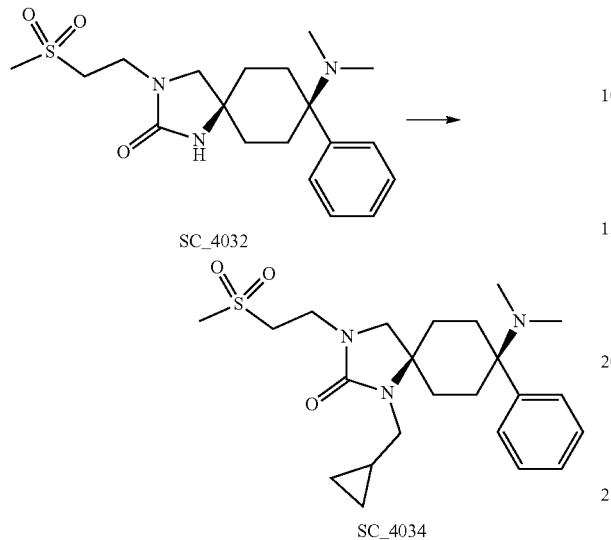

To a solution of CIS-8-dimethylamino-3-(2-methanesulfonyl-ethyl)-8-phenyl-1,3-diaza-spiro[4.5]decan-2-one (SC_4032) (150 mg, 0.395 mmol, 1.0 eq.) in dry DMF (5 ml) was added 60% NaH (47 mg, 1.18 mmol, 3.0 eq.) at RT and the reaction mixture was stirred for 20 min. Bromomethylcyclopropane (160 mg, 1.18 mmol, 3.0 eq.) was added and the reaction mixture was stirred for 16 h. The reaction mixture was quenched with ice-water (20 ml) and extracted with EtOAc (2×20 ml). The combined organic layers were washed with water (20 ml) and brine (20 ml), dried over anhydr. $Na_2SO_4$ and concentrated under reduced pressure. The residue was purified by column chromatography (silica gel; 3% MeOH/DCM) to yield CIS-1-cyclopropylmethyl-8-dimethylamino-3-(2-methanesulfonyl-ethyl)-8-phenyl-1,3-diaza-spiro[4.5]decan-2-one (80 mg, 0.18 mmol, 47%) (SC_4034) as a white solid. $^1$HNMR (CDCl3, 400 MHz), δ (ppm)=7.36-7.24 (m, 5H, merged with CDCl3), 3.65 (t, 2H, J=6.46 Hz), 3.27 (t, 2H, J=6.46 Hz), 3.23 (s, 2H), 3.04 (d, 2H, J=6.7 Hz), 2.94 (s, 3H), 2.65-2.62 (m, 2H), 2.30-2.23 (m, 2H), 2.02 (s, 6H), 1.46-1.40 (m, 4H), 1.02-0.98 (m, 1H), 0.53-0.49 (m, 2H), 0.33-0.29 (2H). Mass: m/z 434.0 $(M+H)^+$ (MW calc.=433.61).

Synthesis of SC_4037: CIS-8-(dimethylamino)-8-phenyl-1-tosyl-1,3-diazaspiro[4.5]decan-2-one

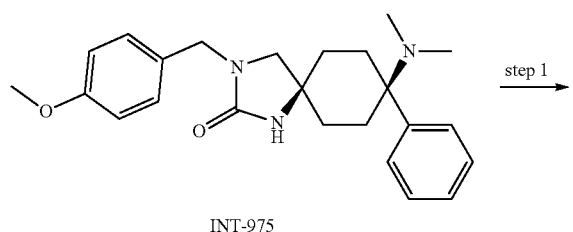

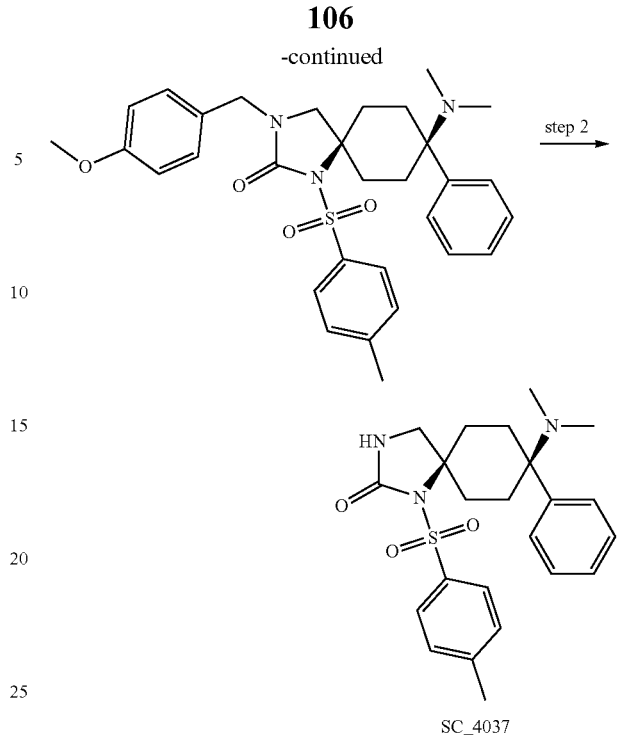

Step 1: CIS-8-(dimethylamino)-3-(4-methoxybenzyl)-8-phenyl-1-tosyl-1,3-diazaspiro[4.5]decan-2-one CIS-8-(dimethylamino)-3-[(4-methoxyphenyl)methyl]-8-phenyl-1,3-diazaspiro[4.5]decan-2-one (INT-975) (500 mg, 1.271 mmol) was dissolved in THF (8 mL) under nitrogen atmosphere and the solution was cooled down to −78° C. [Bis(trimethylsilyl)amino]lithium (1M in THF, 1.5 equiv., 1.906 mmol, 1.9 mL) was added dropwise and the reaction mixture was stirred at −78° C. for 30 min, then at 0° C. for 30 min. The reaction mixture was cooled down to −78° C. again and the solution of p-toluenesulfonyl chloride (1.5 equiv., 1.906 mmol) in THF (5 mL) was added. The reaction mixture was stirred further 2.5 h at −78° C. and then the temperature was allowed to increase to RT overnight. The reaction mixture was quenched by the addition of sat. aq. $NaHCO_3$ (20 mL). The aqueous phase was extracted with EtOAc (3×40 mL). The combined organic extracts were washed with brine (30 mL), dried over $MgSO_4$ and concentrated under reduced pressure. Purification of the residue by flash chromatography on silica gel (elution with gradient DCM/EtOH 100/0 to 97/3) yielded 281 mg (40%) of CIS-8-(dimethylamino)-3-(4-methoxybenzyl)-8-phenyl-1-tosyl-1,3-diazaspiro[4.5]decan-2-one. $^1$H NMR (600 MHz, DMSO) δ 7.90-7.84 (m, 2H), 7.47-7.40 (m, 2H), 7.42-7.27 (m, 4H), 7.27-7.22 (m, 1H), 7.15-7.06 (m, 2H), 6.92-6.83 (m, 2H), 4.16 (s, 2H), 3.72 (s, 3H), 3.24 (s, 2H), 2.99 (ddd, 2H), 2.70-2.62 (m, 2H), 2.42 (s, 3H), 2.01 (s, 6H), 1.56-1.49 (m, 2H), 1.31 (td, 2H). Mass: m/z 548.3 $(M+H)^+$.

Step 2: CIS-8-(dimethylamino)-8-phenyl-1-tosyl-1,3-diazaspiro[4.5]decan-2-one (SC_4037)

In analogy to the method described for INT-982 (step 2) CIS-8-(dimethylamino)-3-(4-methoxybenzyl)-8-phenyl-1-tosyl-1,3-diazaspiro[4.5]decan-2-one was reacted with trifluoroacetic acid to be converted into CIS-8-(dimethylamino)-8-phenyl-1-tosyl-1,3-diazaspiro[4.5]decan-2-one (SC_4037). ¹HNMR (DMSO-d6, 400 MHz), δ (ppm)=7.82 (d, 2H, J=8.0 Hz), 7.48 (s, 1H), 7.40 (d, 2H, J=7.88 Hz), 7.35-7.24 (m, 5H), 3.27 (s, 2H), 2.97 (t, 2H, J=11.88 Hz), 2.66 (d, 2H, J=12.76 Hz), 2.39 (s, 3H), 2.0 (s, 6H), 1.60 (d, 2H, J=11.04 Hz), 1.38 (t, 2H, J=13.56 Hz). Mass: m/z 427.9 (M+H)⁺.

Synthesis of SC_4038: CIS-8-(dimethylamino)-3-((1,1-dioxidotetrahydro-2H-thiopyran-4-yl)methyl)-1-((1-hydroxycyclobutyl)methyl)-8-phenyl-1,3-diazaspiro[4.5]decan-2-one

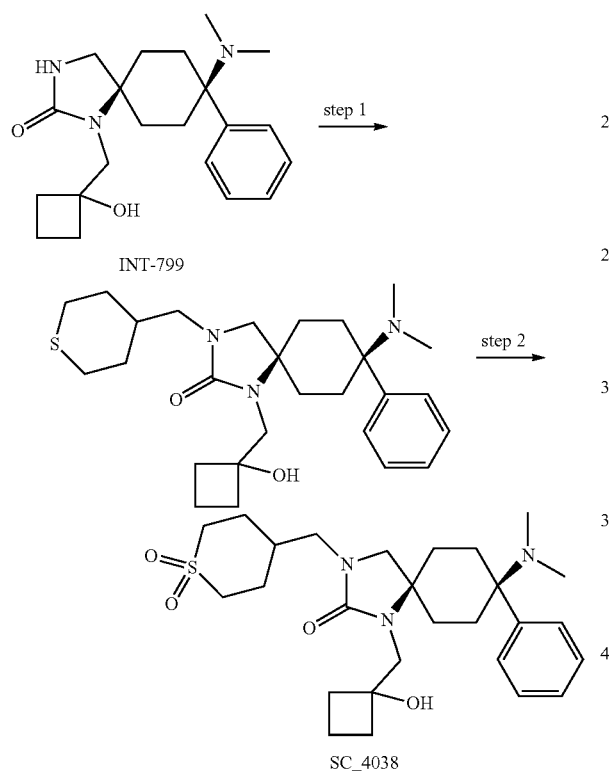

Step 1: CIS-8-(dimethylamino)-1-((1-hydroxycyclobutyl)methyl)-8-phenyl-3-((tetrahydro-2H-thiopyran-4-yl)methyl)-1,3-diazaspiro[4.5]decan-2-one NaH (60% in mineral oil) (84.03 mg, 2.101 mmol) was added to an ice cold solution of CIS-8-(methylamino)-8-phenyl-3-(2-(trifluoromethyl)pyrimidin-5-yl)-1,3-diazaspiro[4.5]decan-2-one (INT-799) (500 mg, 1.401 mmol) in DMF (5 mL) under argon atmosphere and the resulting mixture was stirred for 2 min. The reaction mixture was allowed to warm up to RT and a solution of (tetrahydro-2H-thiopyran-4-yl)methyl 4-methylbenzenesulfonate (481.5 mg, 1.681 mmol) in DMF (4.8 mL) was added. The reaction mixture was stirred at RT for 16 h. The reaction progress was monitored by LCMS. The reaction mixture was diluted with water (50 mL) and the organic product was extracted with EtOAc (3×40 mL). The combined organic extracts were dried over anhydrous Na₂SO₄ and concentrated under reduced pressure to give 550 mg of crude product. The crude product was purified by prep-HPLC (column LUNA-PHE-NYL HEXYL-C18 (150*30 mm) 5 μm, detection at 215 nm, eluent 10 mM ammonium bicarbonate in water/Acetonitrile gradient 45/55 to 2/98, flow rate: 25 ml/min) to afford 235 mg (35%) of CIS-8-(dimethylamino)-1-((1-hydroxycyclobutyl)methyl)-8-phenyl-3-((tetrahydro-2H-thiopyran-4-yl)methyl)-1,3-diazaspiro[4.5]decan-2-one as an off white solid (TLC system: 5% MeOH in DCM Rf: 0.63.). Mass: m/z 472.3 (M+H)+.

Step 2: CIS-8-(dimethylamino)-3-((1,1-dioxidotetrahydro-2H-thiopyran-4-yl)methyl)-1-((1-hydroxycyclobutyl)methyl)-8-phenyl-1,3-diazaspiro[4.5]decan-2-one (SC_4038)

A solution of oxone (599.53 mg, 0.975 mmol) in water (6 mL) was added to a solution of CIS-8-(dimethylamino)-1-((1-hydroxycyclobutyl)methyl)-8-phenyl-3-((tetrahydro-2H-thiopyran-4-yl)methyl)-1,3-diazaspiro[4.5]decan-2-one (230 mg, 0.488 mmol) in MeOH (8 mL) at RT under argon atmosphere. The reaction mixture was stirred for 16 h. The reaction progress was monitored by LCMS. The reaction mixture was filtered and the filtrate was concentrated under reduced pressure to give 330 mg of crude product, which was purified by prep. HPLC (column LUNA-PHENYL HEXYL-C18 (150*30 mm) 5 μm, detection at 215 nm, eluent 10 mM ammonium bicarbonate in water/Acetonitrile gradient 45/55 to 2/98, flow rate: 25 ml/min) to get 128 mg (52%) of CIS-8-(dimethylamino)-3-(4-(bromomethyl)-1-λ6-thiane-1,1-dione)-1-((1-hydroxycyclobutyl)methyl)-8-phenyl-1,3-diazaspiro[4.5]decan-2-one (SC_4038) as an off white solid (TLC system: 10% MeOH in DCM Rf: 0.53). ¹H NMR (DMSO-d6): δ 7.37-7.25 (m, 5H), 6.01 (s, 1H), 3.26 (s, 2H), 3.09-2.99 (m, 8H), 2.69-2.65 (m, 2H), 2.09-1.82 (m, 15H), 1.66-1.51 (m, 3H), 1.41-1.33 (m, 5H). Mass: m/z 504.2 (M+H)⁺.

Synthesis of SC_4044: CIS-8-(dimethylamino)-1-((1-hydroxycyclobutyl)methyl)-3-((4-hydroxytetrahydro-2H-pyran-4-yl)methyl)-8-phenyl-1,3-diazaspiro[4.5]decan-2-one

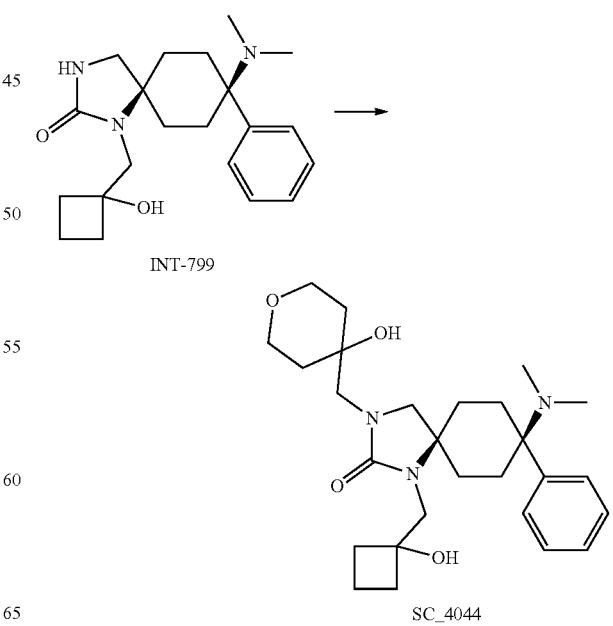

NaH (0.14 g, 3.501 mmol, 60% dispersion in mineral oil) was added to a solution of CIS-8-(dimethylamino)-1-((1-hydroxycyclobutyl)methyl)-8-phenyl-1,3-diazaspiro[4.5]decan-2-one (INT-799) (0.25 g, 0.700 mmol) in THF (40 mL) at 0° C. under argon atmosphere. The solution of 1,6-dioxaspiro[2.5]octane (0.479 g, 4.200 mmol) in THF (2 mL) was added dropwise and the reaction mixture was stirred at 85° C. for 16 h. The reaction mixture was cooled to 0° C. and quenched with water (50 mL). The organic product was extracted with ethyl acetate (2×50 mL). Combined organic layer was dried over anhydrous Na$_2$SO$_4$ and concentrated under reduced pressure. The residue was purified by column chromatography (silica gel 230-400 mesh size, 0-60% EtOAc in pet ether as eluent) followed by reverse phase prep HPLC to get 0.180 g of CIS-8-(dimethylamino)-1-((1-hydroxycyclobutyl)methyl)-3-((4-hydroxytetrahydro-2H-pyran-4-yl)methyl)-8-phenyl-1,3-diazaspiro[4.5]decan-2-one formiate. The product formiate salt was taken in water (20 mL), basified with solid NaHCO$_3$ and extracted with ethyl acetate (2×20 mL). The combined organic layer was dried over anhydrous Na$_2$SO$_4$ and concentrated under reduced pressure to afford 0.130 g (39%) of CIS-8-(dimethylamino)-1-((1-hydroxycyclobutyl)methyl)-3-((4-hydroxytetrahydro-2H-pyran-4-yl)methyl)-8-phenyl-1,3-diazaspiro[4.5]decan-2-one (SC_4044) as an off white solid. (TLC system: 5% MeOH in DCM; Rf: 0.3). $^1$H NMR (DMSO-d6): δ 7.37-7.34 (m, 4H), 7.27-7.26 (m, 1H), 6.04 (s, 1H), 4.51 (s, 1H), 3.61-3.56 (m, 4H), 3.43 (s, 2H), 3.09-3.05 (m, 4H), 2.70-2.67 (m, 2H), 2.07-1.82 (m, 12H), 1.63-1.61 (m, 1H), 1.51-1.30 (m, 9H). Mass: m/z 472.3 (M+H)$^+$.

Synthesis of SC_4049: CIS-(5s,8s)-3-(1-benzoylpiperidin-4-yl)-1-(cyclopropylmethyl)-8-(dimethylamino)-8-phenyl-1,3-diazaspiro[4.5]decan-2-one amino)-8-phenyl-3-(piperidin-4-yl)-1,3-diazaspiro[4.5]decan-2-one hydrochloride (0.3 g, 0.73 mmol) in DCM (10 mL) at 0° C. under argon atmosphere. After 10 min, acetyl chloride (86 mg, 1.09 mmol) was added dropwise at 0° C. and the reaction mixture was stirred at RT for 16 h. The reaction mixture was quenched with sat. aq. NaHCO$_3$. The organic product was extracted with DCM (2×50 mL), the combined organic layer was dried over anhydr. Na$_2$SO$_4$ and concentrated under reduced pressure. The residue was purified by reverse phase prep. HPLC to afford 0.133 g (40%) of CIS-3-(1-acetylpiperidin-4-yl)-1-(cyclopropylmethyl)-8-(dimethylamino)-8-phenyl-1,3-diazaspiro[4.5]decan-2-one (SC_4049) as a white solid. (TLC system: 10% MeOH in DCM; Rf: 0.55). $^1$H NMR (DMSO-d6): δ 7.36-7.33 (m, 2H), 7.28-7.25 (m, 3H), 4.70-4.67 (m, 1H), 3.98-3.81 (m, 2H), 3.12-3.04 (m, 5H), 2.65-2.57 (m, 3H), 2.26 (t, 2H), 2.06-2.04 (m, 9H), 1.79-1.70 (m, 2H), 1.50-1.39 (m, 6H), 1.02 (m, 1H), 0.53-0.50 (m, 2H), 0.34-0.31 (m, 2H). Mass: m/z 453.3 (M+H)$^+$.

Synthesis of SC_4052: CIS-1-(cyclobutylmethyl)-8-(dimethylamino)-3-(2-(1-hydroxycyclohexyl)ethyl)-8-phenyl-1,3-diazaspiro[4.5]decan-2-one

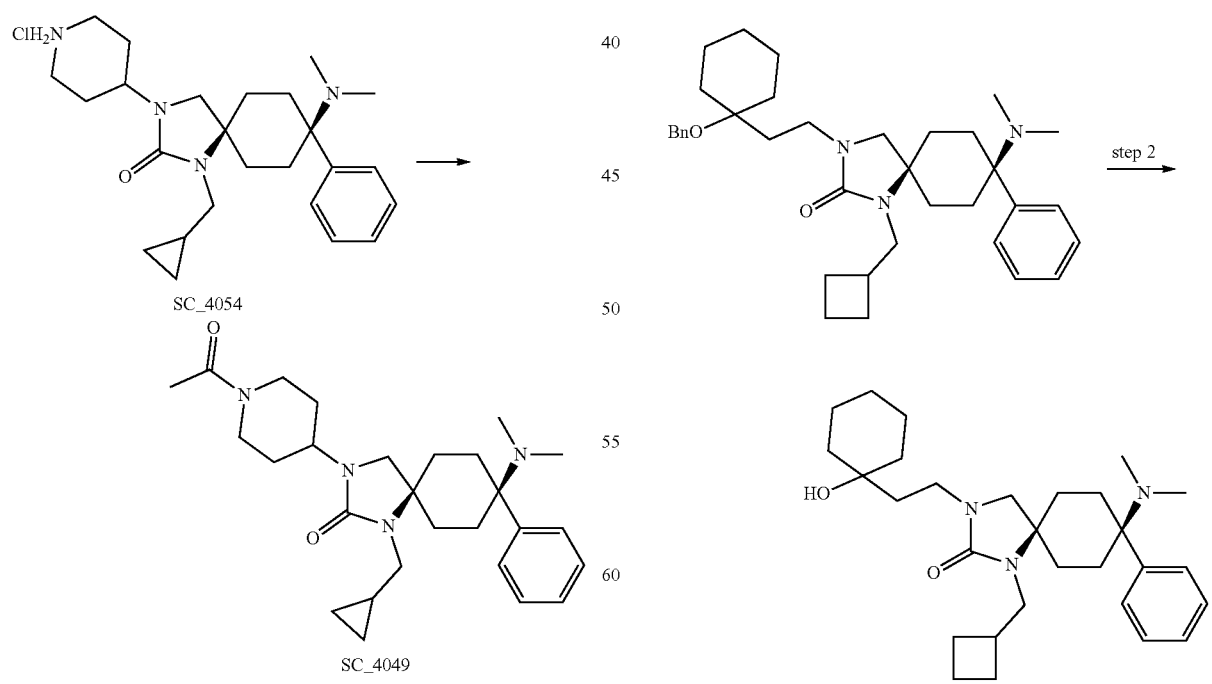

Triethylamine (0.51 mL, 3.65 mmol) was added to a stirred solution of CIS-1-(cyclopropylmethyl)-8-(dimethyl- Step 1: CIS-3-(2-(1-(benzyloxy)cyclohexyl)ethyl)-1-(cyclobutylmethyl)-8-(dimethylamino)-8-phenyl-1,3-diazaspiro[4.5]decan-2-one In analogy to the method described for SC_4034 CIS-1-(cyclobutylmethyl)-8-(dimethylamino)-8-phenyl-1,3-diazaspiro[4.5]decan-2-one (INT-787) was reacted with 2-(4-(benzyloxy)tetrahydro-2H-pyran-4-yl)ethyl 4-methylbenzenesulfonate to be converted into CIS-3-(2-(1-(benzyloxy)cyclohexyl)ethyl)-1-(cyclobutylmethyl)-8-(dimethylamino)-8-phenyl-1,3-diazaspiro[4.5]decan-2-one. Mass: m/z 558.4 (M+H)$^+$.

Step 2: CIS-1-(cyclobutylmethyl)-8-(dimethylamino)-3-(2-(1-hydroxycyclohexyl)ethyl)-8-phenyl-1,3-diazaspiro[4.5]decan-2-one (SC_4052)

Trifluoroacetic acid (20 mL) was added to CIS-3-(2-(1-(benzyloxy)cyclohexyl)ethyl)-1-(cyclobutylmethyl)-8-(dimethylamino)-8-phenyl-1,3-diazaspiro[4.5]decan-2-one (0.4 g, 0.71 mmol) at RT. The reaction mixture was stirred at RT for 16 h and then concentrated under reduced pressure. To the residue sat. aq. NaHCO$_3$ was added and the organic product was extracted with dichloromethane (3×150 mL). The combined organic extract was dried over anhydrous Na$_2$SO$_4$ and concentrated under reduced pressure. The residue was purified by column chromatography (230-400 mesh silica gel; 4-8% MeOH in DCM as eluent) and further by reverse phase prep HPLC to afford 0.112 g (40%) of CIS-1-(cyclobutylmethyl)-8-(dimethylamino)-3-(2-(1-hydroxycyclohexyl)ethyl)-8-phenyl-1,3-diazaspiro[4.5]decan-2-one (SC_4052) as a white solid. (TLC system: 10% MeOH in DCM; Rf: 0.45). $^1$H NMR (DMSO-d6): δ 7.37-7.32 (m, 4H), 7.27-7.23 (m, 1H), 4.25 (s, 1H), 3.62-3.49 (m, 4H), 3.17-3.13 (m, 2H), 3.09 (s, 2H), 3.01 (d, 2H), 2.66-2.63 (m, 2H), 2.05-2.02 (m, 1H), 1.97-1.91 (m, 9H), 1.80-1.65 (m, 4H), 1.53-1.43 (m, 5H), 1.38-1.35 (m, 6H). Mass: m/z 470.4 (M+H)$^+$.

Synthesis of SC_4054: CIS-1-(cyclopropylmethyl)-8-(dimethylamino)-8-phenyl-3-(piperidin-4-yl)-1,3-diazaspiro[4.5]decan-2-one

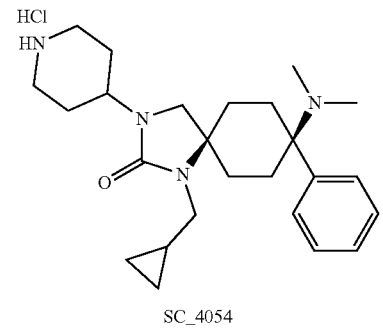

SC_4054

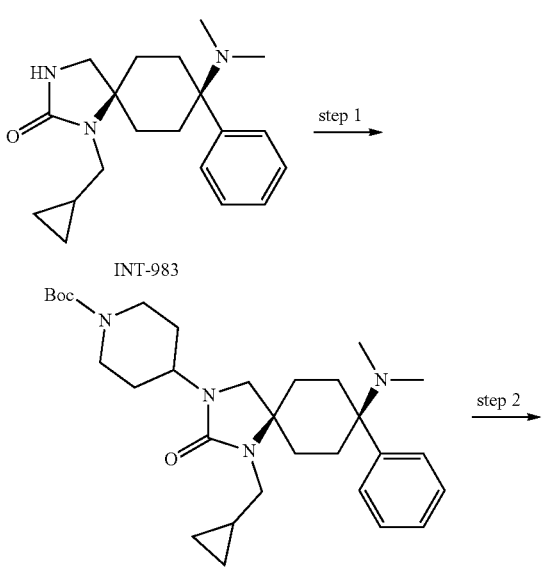

Step 1: CIS-tert-butyl 4-(1-(cyclopropylmethyl)-8-(dimethylamino)-2-oxo-8-phenyl-1,3-diazaspiro[4.5]decan-3-yl)piperidine-1-carboxylate In analogy to the method described for SC_4044 CIS-1-(cyclopropylmethyl)-8-(dimethylamino)-8-phenyl-1,3-diazaspiro[4.5]decan-2-one (INT-983) was reacted with tert-butyl 4-(tosyloxy)piperidine-1-carboxylate to be converted into CIS-tert-butyl 4-(1-(cyclopropylmethyl)-8-(dimethylamino)-2-oxo-8-phenyl-1,3-diazaspiro[4.5]decan-3-yl)piperidine-1-carboxylate. Mass: m/z 511.4 (M+H)$^+$.

Step 2: CIS-1-(cyclopropylmethyl)-8-(dimethylamino)-8-phenyl-3-(piperidin-4-yl)-1,3-diazaspiro[4.5]decan-2-one (SC_4054)

4N HCl in dioxane (20 mL) was added to a solution of CIS-tert-butyl 4-(1-(cyclopropylmethyl)-8-(dimethylamino)-2-oxo-8-phenyl-1,3-diazaspiro[4.5]decan-3-yl)piperidine-1-carboxylate (1.9 g, 3.7 mmol) in DCM (30 mL) at 0° C. under argon atmosphere. The reaction was stirred at 0° C. for 2 h and then concentrated under reduced pressure to get CIS-1-(cyclopropylmethyl)-8-(dimethylamino)-8-phenyl-3-(piperidin-4-yl)-1,3-diazaspiro[4.5]decan-2-one hydrochloride as gummy, which was triturated with diethyl ether to get CIS-1-(cyclopropylmethyl)-8-(dimethylamino)-8-phenyl-3-(piperidin-4-yl)-1,3-diazaspiro[4.5]decan-2-one hydrochloride (SC 4054) as an off-white solid. (TLC system: 10% MeOH in DCM; Rf: 0.15). $^1$H NMR (DMSO-d6): δ 7.37-7.32 (m, 4H), 7.28-7.23 (m, 1H), 3.58-3.50 (m, 2H), 3.10 (s, 2H), 2.94-2.89 (m, 4H), 2.66-2.62 (m, 2H), 2.46-2.41 (m, 2H), 2.13 (t, 2H), 1.97 (s, 6H), 1.49-1.41 (m, 6H), 1.32-1.29 (m, 2H), 0.93-0.88 (m, 1H), 0.46-0.42 (m, 2H), 0.25-0.24 (m, 2H). Mass: m/z 411.3 (M+H)$^+$.

Synthesis of SC_4055: CIS-1-(cyclopropylmethyl)-8-(dimethylamino)-3-(2-hydroxy-2-methylpropyl)-8-phenyl-1,3-diazaspiro[4.5]decan-2-one

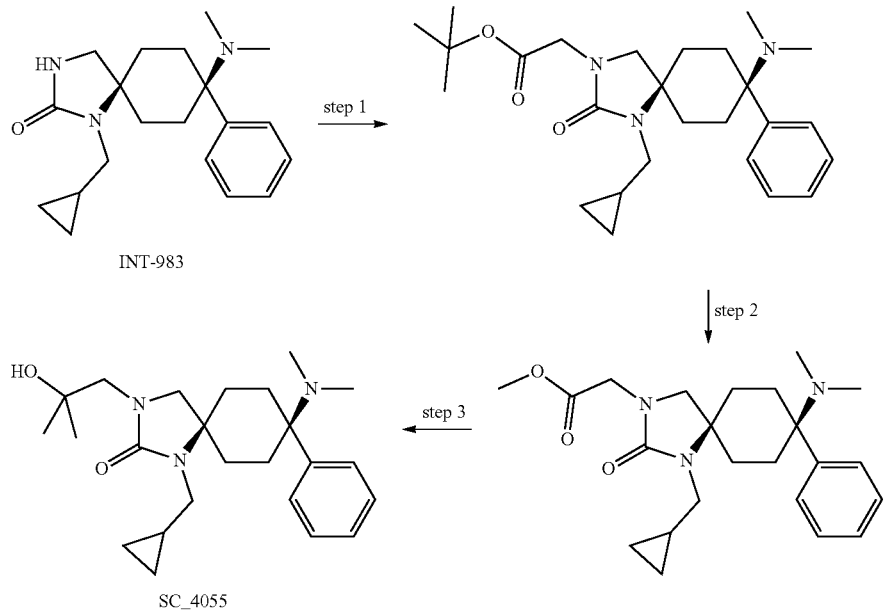

Step 1: tert-butyl 2-(CIS-1-(cyclopropylmethyl)-8-(dimethylamino)-2-oxo-8-phenyl-1,3-diazaspiro[4.5]decan-3-yl)acetate In analogy to the method described for SC_4027 CIS-1-(cyclopropylmethyl)-8-(dimethylamino)-8-phenyl-1,3-diazaspiro[4.5]decan-2-one (INT-983) was reacted with tert-butyl bromoacetate to be converted into tert-butyl 2-(CIS-1-(cyclopropylmethyl)-8-(dimethylamino)-2-oxo-8-phenyl-1,3-diazaspiro[4.5]decan-3-yl)acetate. Mass: m/z 442.3 (M+H)$^+$.

Step 2: methyl CIS-2-(1-(cyclopropylmethyl)-8-(dimethylamino)-2-oxo-8-phenyl-1,3-diazaspiro[4.5]decan-3-yl)acetate 4M HCl in dioxane (8 mL) was added to tert-butyl CIS-2-(1-(cyclopropylmethyl)-8-(dimethylamino)-2-oxo-8-phenyl-1,3-diazaspiro[4.5]decan-3-yl)acetate (800 mg, 1.81 mmol) in DCM (6 mL) at 0° C. The reaction mixture was stirred at RT for 16 h and then concentrated under reduced pressure. The residue was suspended in DCM and the resulting mixture was concentrated under reduced pressure again. The residue was washed with diethyl ether (5 mL) to give CIS-2-(8-(dimethylamino)-3-oxo-8-phenyl-2-azaspiro[4,5]decan-2-yl)acetic acid hydrochloride which was dissolved in methanol (10 mL) and refluxed for 2 h. The reaction mixture was cooled down to RT and concentrated under reduced pressure. The residue was partitioned between EtOAc and sat. aq. NaHCO₃. The organic layer was separated and washed with water, brine, dried over anhydr. Na₂SO₄ and concentrated under reduced pressure. Purification of the residue by column chromatography (silica gel 100-200 mesh, 0-3% MeOH in DCM) yielded 500 mg (56%) of methyl CIS-2-(1-(cyclopropylmethyl)-8-(dimethylamino)-2-oxo-8-phenyl-1,3-diazaspiro[4.5]decan-3-yl)acetate as a solid. (TLC system: 10% MeOH in DCM Rf: 0.20). Mass: m/z 400.3 (M+H)$^+$.

Step 3: CIS-1-(cyclopropylmethyl)-8-(dimethylamino)-3-(2-hydroxy-2-methylpropyl)-8-phenyl-1,3-diazaspiro[4.5]decan-2-one (SC_4055)

Methylmagnesium bromide (3M in Et₂O, 2.1 mL, 6.25 mmol) was added to a solution of methyl CIS-2-(1-(cyclopropylmethyl)-8-(dimethylamino)-2-oxo-8-phenyl-1,3-diazaspiro[4.5]decan-3-yl)acetate (500 mg, 1.25 mmol) in THF (10 mL) at 0° C. The reaction mixture was warmed to RT and stirred for 2 h. The reaction mixture was quenched with sat. aq. NH₄Cl and the organic product was extracted with DCM (3×25 mL). The combined organic extracts were washed with water, brine, dried over anhydr. Na₂SO₄ and concentrated under reduced pressure. Purification of the resulting residue by column chromatography (silica gel 100-200 mesh, 0-3% MeOH in DCM) followed by preparative HPLC yielded 80 mg (16%) of CIS-1-(cyclopropylmethyl)-8-(dimethylamino)-3-(2-hydroxy-2-methylpropyl)-8-phenyl-1,3-diazaspiro[4.5]decan-2-one (SC_4055) as a solid. (TLC system: 10% MeOH in DCM Rf: 0.20). $^1$H NMR (DMSO d6): δ 7.36-7.33 (m, 4H), 7.26-7.24 (m, 1H), 4.39 (s, 1H), 3.30 (m, 2H), 2.95-2.91 (m, 4H), 2.69-2.66 (m, 2H), 2.18-2.13 (m, 2H), 1.97 (s, 6H), 1.37-1.31 (m, 4H), 1.03 (s, 6H), 0.92-0.91 (m, 1H), 0.46-0.43 (m, 2H), 0.26-0.23 (m, 2H). Mass: m/z 400.3 (M+H)$^+$.

115

Synthesis of SC_4056: CIS-1-(cyclopropylmethyl)-8-(dimethylamino)-8-phenyl-3-(1-(pyrimidin-5-yl)piperidin-4-yl)-1,3-diazaspiro[4.5]decan-2-one

116

Synthesis of SC_4057: CIS-1-(cyclopropylmethyl)-8-(dimethylamino)-8-phenyl-3-(1-(pyrimidin-5-yl)piperidin-4-yl)-1,3-diazaspiro[4.5]decan-2-one

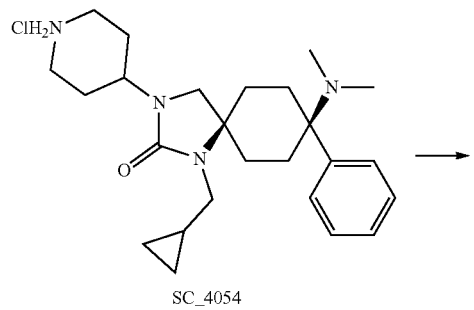

SC_4054

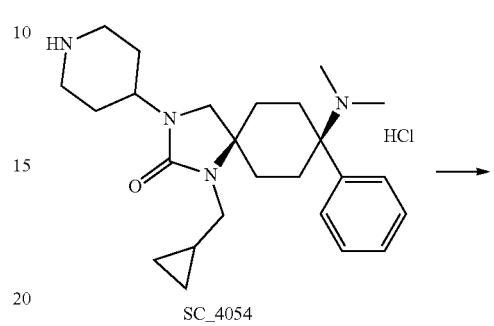

SC_4054

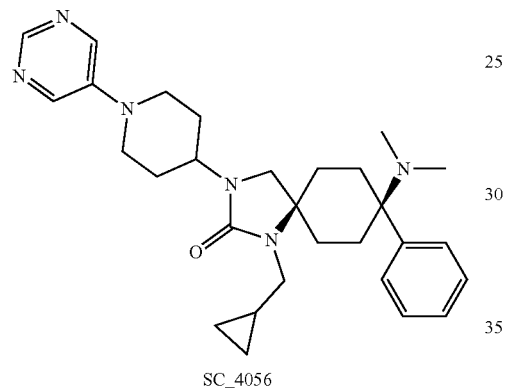

SC_4056

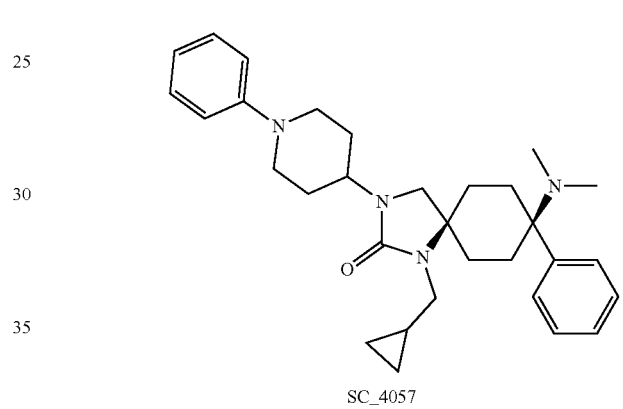

SC_4057

CsCO$_3$ (1.27 g, 3.90 mmol) was added to a solution of CIS-1-(cyclopropylmethyl)-8-(dimethylamino)-8-phenyl-3-(piperidin-4-yl)-1,3-diazaspiro[4.5]decan-2-one hydrochloride (SC_4054) (0.4 g, 0.97 mmol), XanthPhos (85 mg, 0.146 mmol), Pd$_2$(dba)$_3$ (89 mg, 0.097 mmol) and 5-bromopyrimidine (0.31 g, 1.95 mmol) in 1,4-dioxane (20 mL). The mixture was purged with argon for 5 min and then stirred for 16 h at 120° C. The reaction mixture was cooled to RT and concentrated under reduced pressure. The residue was diluted with DCM (20 mL), filtered through a pad of celite and concentrated under reduced pressure. The crude product was purified by flash chromatography (silica gel 230-400 mesh size, 5-10% methanol in DCM as eluent) to afford 0.4 g of the desired product, which was further purified by reverse phase prep HPLC to afford 172 mg (36%) of CIS-1-(cyclopropylmethyl)-8-(dimethylamino)-8-phenyl-3-(1-(pyrimidin-5-yl)piperidin-4-yl)-1,3-diazaspiro[4.5]decan-2-one (SC_4056) as off-white solid. (TLC system: 10% MeOH in DCM; Rf: 0.35). $^1$H NMR (CDCl3): δ 8.64 (s, 1H), 8.34 (s, 2H), 7.36-7.33 (m, 2H), 7.29-7.27 (m, 2H), 7.24 (m, 1H), 4.00-3.96 (m, 1H), 3.78-3.76 (m, 2H), 3.09-3.06 (m, 4H), 2.96-2.90 (m, 2H), 2.66-2.63 (m, 2H), 2.30-2.24 (m, 2H), 2.04 (s, 6H), 1.83-1.81 (m, 2H), 1.73-1.61 (m, 2H), 1.45-1.40 (m, 4H), 1.04-1.01 (m, 1H), 0.54-0.50 (m, 2H), 0.35-0.32 (m, 2H). Mass: m/z 489.3 (M+H)$^+$.

Triethylamine (0.23 mL, 1.70 mmol) was added to a solution of CIS-1-(cyclopropylmethyl)-8-(dimethylamino)-8-phenyl-3-(piperidin-4-yl)-1,3-diazaspiro[4.5]decan-2-one hydrochloride (SC_4054) (0.35 g, 0.85 mmol) and phenylboronic acid (0.21 g, 1.70 mmol) in acetonitrile (15 mL). Copper(II) acetate (155 mg, 0.85 mmol) was added and the reaction mixture was stirred at 100° C. for 24 h. The reaction mixture was cooled to RT, filtered through a pad of celite and concentrated under reduced pressure. The residue was purified by silica gel flash chromatography (3% MeOH/DCM) to give 100 mg of CIS-1-(cyclopropylmethyl)-8-(dimethylamino)-8-phenyl-3-(1-phenylpiperidin-4-yl)-1,3-diazaspiro[4.5]decan-2-one, which was further purified by reverse phase prep HPLC to afford 38 mg (9%) of CIS-1-(cyclopropylmethyl)-8-(dimethylamino)-8-phenyl-3-(1-phenylpiperidin-4-yl)-1,3-diazaspiro[4.5]decan-2-one (SC_4057) as an off-white solid. (TLC system: 10% MeOH in DCM; Rf: 0.65). $^1$H NMR (DMSO-d6): δ 7.36-7.33 (m, 2H), 7.29-7.27 (m, 2H), 7.24-7.21 (m, 3H), 6.91 (d, 2H), 6.81 (t, 1H), 3.95-3.91 (m, 1H), 3.72-3.69 (m, 2H), 3.11-3.06 (m, 4H), 2.84-2.79 (m, 2H), 2.65-2.62 (m, 2H), 2.26 (t, 2H), 2.04 (s, 6H), 1.79-1.70 (m, 4H), 1.45-1.40 (m, 4H), 1.05-1.01 (m, 1H), 0.53-0.51 (m, 2H), 0.34-0.32 (m, 2H). Mass: m/z 487.4 (M+H)$^+$.

Synthesis of SC_4064: CIS-3-((1-aminocyclopropyl)methyl)-1-(cyclopropylmethyl)-8-(dimethylamino)-8-phenyl-1,3-diazaspiro[4.5]decan-2-one

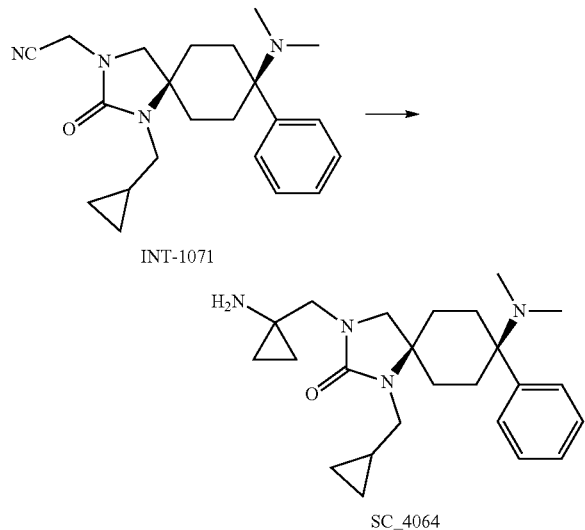

To a solution titanium isopropoxide (0.89 mL, 3.0 mmol, 2 eq.) in dry THF (15 mL) was added EtMgBr (3 M in Et$_2$O) (2 mL, 6.0 mmol, 4 eq.) at −78° C. and the resulting mixture was stirred for 1.5 h at −78° C. A solution of CIS-(1-cyclopropylmethyl-8-dimethylamino-2-oxo-8-phenyl-1,3-diaza-spiro[4.5]dec-3-yl)-acetonitrile (INT-1071) (550 mg, 1.50 mmol, 1.0 eq.) in THF (5 mL) was added dropwise at −78° C. The reaction mixture was stirred at same temperature for 10 min, then warmed to RT and stirred for 1.5 h. The reaction mixture was cooled again to −78° C., BF$_3$.Et$_2$O (0.37 mL, 3.0 mmol, 2 eq.) was added and the resulting mixture was stirred at -78° C. for 10 min and at RT for 1.5 h. The reaction mixture was basified (pH~9-10) with 10 wt % aq. NaOH, stirred for 30 min and extracted with EtOAc (2×250 mL). The combined organic layer was washed with water (2×150 mL), brine (200 mL), dried over Na$_2$SO$_4$ and concentrated under reduced pressure to get crude product which was purified by column chromatography (neutral alumina; 2.5% MeOH/DCM) to yield CIS-3-(1-amino-cyclopropylmethyl)-1-cyclopropylmethyl-8-dimethylamino-8-phenyl-1,3-diaza-spiro[4.5]decan-2-one (SC_4064) as off white solid. This step was done in two batches of 550 mg scale and yield is given for combined batches. Yield: 16% (200 g, 0.25 mmol). LC-MS: m/z [M+H]$^+$=397.1 (MW calc.=396.57). $^1$HNMR (DMSO-d$_6$, 400 MHz), δ (ppm)=7.35-7.25 (5H), 3.24 (s, 2H), 3.00 (s, 2H), 2.92 (d, 2H, J=6.48 Hz), 2.68-2.65 (m, 2H), 2.19-2.07 (m, 2H), 1.97 (s, 6H), 1.75 (bs, 2H), 1.43-1.36 (m, 4H), 0.93 (bs, 1H), 0.46-0.36 (m, 6H), 0.25-0.23 (m, 2H).

Synthesis of SC_4071: CIS-1-(cyclobutylmethyl)-8-(dimethylamino)-3-(2-(3-hydroxyoxetan-3-yl)ethyl)-8-phenyl-1,3-diazaspiro[4.5]decan-2-one

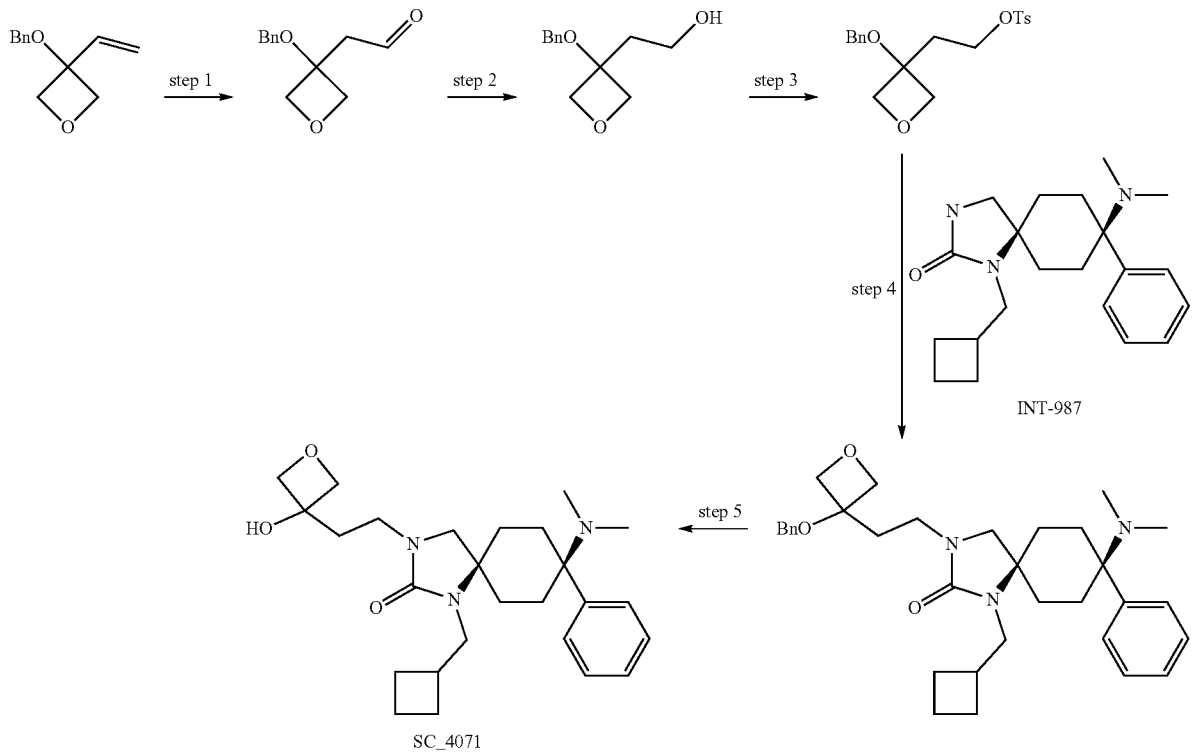

Step 1: 2-(3-(benzyloxy)oxetan-3-yl)acetaldehyde

To a stirred solution of 3-allyl-3-(benzyloxy)oxetane (10.0 g, 49.01 mmol, prepared from 3-allyl-3-hydroxyoxetane and benzyl bromide) in acetone (300 mL) and water (200 mL) was added potassium osmate(VI) dihydrate (0.61 g, 1.66 mmol). The reaction mixture was cooled to 0° C. and sodium periodate (41.93 g, 916.07 mmol) was added portionwise over a period of 15 min. The reaction mixture was allowed to stir for 1 h at 0° C. The reaction mixture was filtered and the filter cake was washed with acetone (300 mL). The combined filtrate was concentrated under reduced pressure and the aqueous layer was extracted with dichloromethane (2×300 mL). The combined organic layer was washed with water (2×200 mL), brine (300 mL), dried was over anhydr. $Na_2SO_4$ and concentrated under reduced pressure. The resulting crude product was purified by column chromatography (silica gel 230-400 mesh size 30-40% EtOAc in Pet. ether as eluent) to afford 2-(3-(benzyloxy) oxetan-3-yl)acetaldehyde (4.5 g, 43%) as a liquid. (TLC system: 40% EtOAc in Pet. ether; Rf: 0.4).

Step 2: 2-(3-(benzyloxy)oxetan-3-yl)ethanol

To a cold stirred solution of 2-(3-(benzyloxy)oxetan-3-yl)ethanol (4.50 g, 21.84 mmol) in methanol (50 mL) was added portionwise $NaBH_4$ (1.24 g, 32.76 mmol). The reaction mixture was stirred at 0° C. for 1 h. The reaction mixture was quenched with water (30 mL), concentrated under reduced pressure and the residue was taken in DCM (150 mL). The organic layer was washed with water (100 mL) and brine (100 mL), dried over anhydr. $Na_2SO_4$ and concentrated under reduced pressure to get 5.0 g of crude 2-(3-(benzyloxy)oxetan-3-yl)ethanol which was used in the next step without further purification.

Step 3: 2-(3-(benzyloxy)oxetan-3-yl)ethyl 4-methylbenzenesulfonate

To a stirred solution of 2-(3-(benzyloxy)oxetan-3-yl)ethanol (5.0 g, 24.03 mmol) in DCM (15 mL) were added triethylamine (13.4 mL, 96.15 mmol) and DMAP (0.29 g, 2.40 mmol). The reaction mixture was cooled to 0° C. and tosyl chloride (9.13 g, 48.07 mmol) was added to the reaction mixture portionwise. The reaction mixture was stirred at RT for 16 h, then diluted with sat. aq. $NaHCO_3$ and the organic product was extracted with DCM (200 mL). The organic layer was dried over anhydr. $Na_2SO_4$ and concentrated under reduced pressure. The resulting crude product was purified by column chromatography (230-400 mesh silica gel; 20-40% EtOAc in Pet. ether as eluent) to afford 2-(3-(benzyloxy)oxetan-3-yl)ethyl 4-methylbenzenesulfonate (4.0 g, 50% over 2 steps) as an off-white solid.

Step 4: CIS-3-(2-(3-(benzyloxy)oxetan-3-yl)ethyl)-1-(cyclobutylmethyl)-8-(dimethylamino)-8-phenyl-1,3-diazaspiro[4.5]decan-2-one NaH (0.29 g, 7.33 mmol, 60% dispersion in mineral oil) was added to a solution of CIS-1-(cyclobutylmethyl)-8-(dimethylamino)-8-phenyl-1,3-diazaspiro[4.5]decan-2-one (INT-987) (0.50 g, 1.46 mmol) in DMF (15 mL) at RT under argon atmosphere and the resulting mixture was stirred for 10 min. 2-(3-(Benzyloxy)oxetan-3-yl)ethyl 4-methylbenzenesulfonate (1.58 g, 4.39 mmol) was added and the reaction mixture was stirred at 120° C. for 16 h. The reaction progress was monitored by LCMS. The reaction mixture was cooled to 0° C. and quenched with sat. aq. $NaHCO_3$ (50 mL). The organic product was extracted with DCM (2×100 mL), the combined organic phase was dried over anhydr. $Na_2SO_4$ and concentrated under reduced pressure. The resulting crude product was purified by flash chromatography (silica gel 230-400 mesh size 2-5% methanol in DCM as eluent) to afford 0.40 g (51%) of CIS-3-(2-(3-(benzyloxy) oxetan-3-yl)ethyl)-1-(cyclobutylmethyl)-8-(dimethyl-amino)-8-phenyl-1,3-diazaspiro[4.5]decan-2-one as a brown oil. (TLC system: 10% MeOH in DCM; Rf: 0.6).

Step 5: CIS-1-(cyclobutylmethyl)-8-(dimethyl-amino)-3-(2-(3-hydroxyoxetan-3-yl)ethyl)-8-phenyl-1,3-diazaspiro[4.5]decan-2-one (SC_4071)

CIS-3-(2-(3-(benzyloxy)oxetan-3-yl)ethyl)-1-(cyclobutylmethyl)-8-(dimethylamino)-8-phenyl-1,3-diazaspiro[4.5] decan-2-one (0.38 g, 0.71 mmol) in THF (4 mL) was added to sodium metal (0.32 g, 14.31 mmol) in liquid ammonia (5 mL) at −78° C. The reaction mixture was stirred for 20 min at −78° C., then quenched with saturated $NH_4Cl$ solution and the organic product was extracted with EtOAc (2×20 mL). The combined organic layer was dried over anhydr. $Na_2SO_4$ and concentrated under reduced pressure. The resulting crude product was purified by flash chromatography (silica gel 230-400 mesh 2-5% methanol in DCM as eluent) to afford 0.155 g (49%) of CIS-1-(cyclobutylmethyl)-8-(dimethylamino)-3-(2-(3-hydroxyoxetan-3-yl) ethyl)-8-phenyl-1,3-diazaspiro[4.5]decan-2-one (SC_4071) as an off-white solid. (TLC system: 5% MeOH in DCM; Rf: 0.4). $^1H$ NMR (DMSO-d6): δ 7.36-7.32 (m, 4H), 7.26-7.23 (m, 1H), 5.62 (s, 1H), 4.38-4.31 (m, 4H), 3.14-3.10 (m, 4H), 3.01 (d, 2H), 2.64-2.63 (m, 2H), 2.49 (m, 1H), 2.02-1.96 (m, 10H), 1.87-1.77 (m, 6H), 1.39 (t, 2H), 1.28 (d, 2H). Mass: m/z 442.3 (M+H)$^+$.

Synthesis of SC_4072: CIS-1-(cyclopropylmethyl)-8-(dimethylamino)-3-(2-methyl-2-(2-oxopyrrolidin-1-yl)propyl)-8-phenyl-1,3-diazaspiro[4.5]decan-2-one

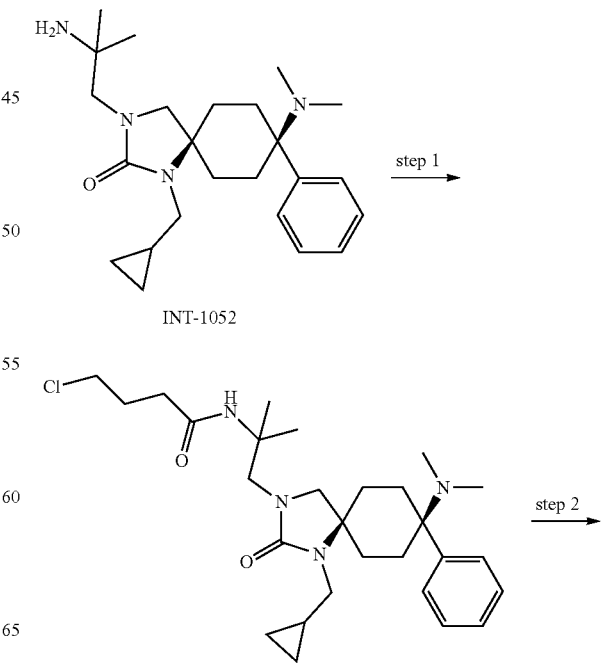

-continued

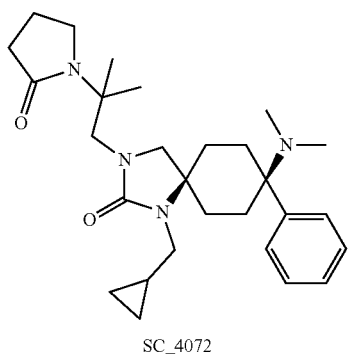

SC_4072

Step 1: CIS-4-chloro-N-(1-(1-(cyclopropylmethyl)-8-(dimethylamino)-2-oxo-8-phenyl-1,3-diazaspiro[4.5]decan-3-yl)-2-methylpropan-2-yl)butanamide In analogy to the method described for SC_4049 CIS-3-(2-amino-2-methylpropyl)-1-(cyclopropylmethyl)-8-(dimethylamino)-8-phenyl-1,3-diazaspiro[4.5]decan-2-one (INT-1052) was reacted with 4-chlorobutanoyl chloride to be converted into CIS-4-chloro-N-(1-(1-(cyclopropylmethyl)-8-(dimethylamino)-2-oxo-8-phenyl-1,3-diazaspiro[4.5]decan-3-yl)-2-methylpropan-2-yl)butanamide. Mass: m/z 503.3 (M+H)$^+$.

Step 2: CIS-1-(cyclopropylmethyl)-8-(dimethylamino)-3-(2-methyl-2-(2-oxopyrrolidin-1-yl)propyl)-8-phenyl-1,3-diazaspiro[4.5]decan-2-one (SC_4072)

NaH (60% in mineral oil) (95.62 mg, 2.390 mmol) was added to a solution of CIS-4-chloro-N-(1-(1-(cyclopropylmethyl)-8-(dimethylamino)-2-oxo-8-phenyl-1,3-diazaspiro[4.5]decan-3-yl)-2-methylpropan-2-yl)butanamide (0.3 g, 0.598 mmol) in THF (30 mL) at 0° C. under argon atmosphere. The reaction mixture was stirred at 70° C. for 4 h, then cooled to 0° C. and quenched with water (15 mL). The organic product was extracted with EtOAc (2×30 mL). The combined organic extracts were dried over anhydr. Na$_2$SO$_4$ and concentrated under reduced pressure. The resulting crude product was purified by column chromatography (silica gel 230-400 mesh, 0-10% MeOH in DCM) and reverse phase HPLC to yield 80 mg (28%) of CIS-1-(cyclopropylmethyl)-8-(dimethylamino)-3-(2-methyl-2-(2-oxopyrrolidin-1-yl)propyl)-8-phenyl-1,3-diazaspiro[4.5]decan-2-one (SC_4072) as a white solid (TLC system: 5% MeOH in DCM; Rf: 0.30). $^1$H NMR (DMSO-d6): δ 7.37-7.32 (m, 4H), 7.27-7.24 (m, 1H), 3.34-3.27 (m, 4H), 3.16-3.13 (m, 4H), 2.93 (d, 2H), 2.67-2.64 (m, 2H), 2.16-2.05 (m, 4H), 1.97 (s, 6H), 1.40-1.36 (m, 4H), 1.29 (s, 6H), 0.93-0.92 (m, 1H), 0.46-0.44 (m, 2H), 0.26-0.24 (m, 2H). Mass: m/z 503.3 (M+H)$^+$.

Synthesis of SC_4080: CIS-8-(dimethylamino)-8-phenyl-3-(1-phenylpiperidin-4-yl)-1,3-diazaspiro[4.5]decan-2-one

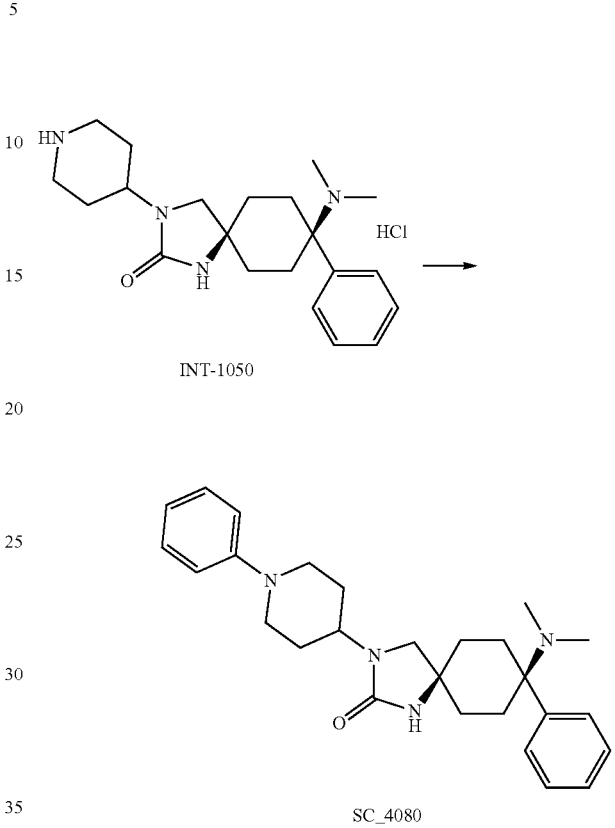

KOtBu (94.26 mg, 0.840 mmol) was added to a solution of CIS-8-(dimethylamino)-8-phenyl-3-(piperidin-4-yl)-1,3-diazaspiro[4.5]decan-2-one (INT-1050) (0.25 g, 0.70 mmol), bromobenzene (109.9 mg, 0.70 mmol), BINAP (65.38 mg, 0.105 mmol) and Pd$_2$(dba)$_3$ (96.15 mg, 0.105 mmol) in toluene (40 mL). The mixture was purged with argon for 5 min and stirred for 16 h at 90° C. The reaction mixture was cooled to RT and diluted with DCM (20 mL), filtered through a pad of celite and the filtrate was concentrated under reduced pressure. The resulting crude product was purified by flash chromatography (silica gel 230-400 mesh, 5-10% methanol in DCM as eluent) followed by reverse phase prep. HPLC to afford 57 mg (18%) of CIS-8-(dimethylamino)-8-phenyl-3-(1-phenylpiperidin-4-yl)-1,3-diazaspiro[4.5]decan-2-one (SC_4080) as an off-white solid. (TLC system: 10% MeOH in DCM; Rf: 0.40). Reverse prep HPLC condition: mobile phase: 10 mM ammonium bicarbonate in H$_2$O/acetonitrile; column: INERTSIL-ODS (250*19 mm) 5 μm; gradient (% B): 0/65, 8/80, 8.1/98, 12/98, 12.1/65, 15/65; flow rate: 18 ml/min; diluent: ACN+THF+MeOH+H$_2$O. $^1$H NMR (DMSO-d6): δ 7.36-7.30 (m, 4H), 7.23 (t, 1H), 7.18-7.14 (m, 2H), 6.90 (d, 2H), 6.72 (t, 2H), 3.72-3.69 (m, 2H), 3.65-3.60 (m, 1H), 3.01 (s, 2H), 2.70-2.65 (m, 2H), 2.28 (br s, 2H), 1.93 (s, 6H), 1.78 (br m, 4H), 1.68-1.60 (m, 2H), 1.57-1.55 (m, 2H), 1.34-1.31 (m, 2H). Mass: m/z 433.3 (M+H)$^+$.

Synthesis of SC_4084: CIS-1-(1-(1-(cyclopropylmethyl)-8-(dimethylamino)-2-oxo-8-phenyl-1,3-diazaspiro[4.5]decan-3-yl)-2-methylpropan-2-yl)pyrrolidine-2,5-dione

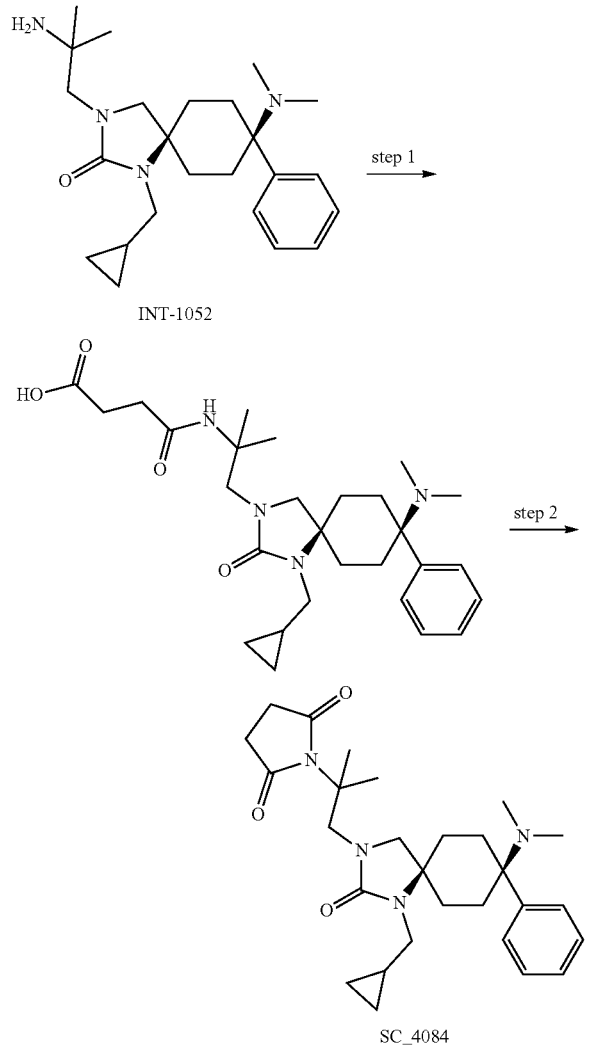

Step 1: CIS-4-(1-(1-(cyclopropylmethyl)-8-(dimethylamino)-2-oxo-8-phenyl-1,3-diazaspiro[4.5]decan-3-yl)-2-methylpropan-2-ylamino)-4-oxobutanoic acid Succinic anhydride (233.3 mg, 2.330 mmol) was added to a stirred solution of CIS-3-(2-amino-2-methylpropyl)-1-(cyclopropylmethyl)-8-(dimethylamino)-8-phenyl-1,3-diazaspiro[4.5]decan-2-one (0.58 g, 1.457 mmol) in DCM (15 mL) at RT under argon atmosphere. The reaction mixture was stirred at RT for 4 h and then concentrated under reduced pressure to yield 440 mg of crude CIS-4-(1-(1-(cyclopropylmethyl)-8-(dimethylamino)-2-oxo-8-phenyl-1,3-diazaspiro[4.5]decan-3-yl)-2-methylpropan-2-ylamino)-4-oxobutanoic acid as an off-white solid (TLC system: 5% MeOH in DCM; Rf: 0.35).

Step 2: CIS-1-(1-(1-(cyclopropylmethyl)-8-(dimethylamino)-2-oxo-8-phenyl-1,3-diazaspiro[4.5]decan-3-yl)-2-methylpropan-2-yl)pyrrolidine-2,5-dione (SC_4084)

Acetyl chloride (2.2 mL) was added to a solution of CIS-4-(1-(1-(cyclopropylmethyl)-8-(dimethylamino)-2-oxo-8-phenyl-1,3-diazaspiro[4.5]decan-3-yl)-2-methylpropan-2-ylamino)-4-oxobutanoic acid (0.44 g, 0.883 mmol) in EtOAc (30 mL) at 0° C. under argon atmosphere. The reaction mixture was stirred at 80° C. for 16 h. The reaction mixture was cool to RT, concentrated under reduced pressure, quenched with sat. aq. NaHCO$_3$ and the organic product was extracted with EtOAc (2×30 mL). The combined organic extracts were dried over anhydrous Na$_2$SO$_4$ and concentrated under reduced pressure. The resulting crude product was purified by column chromatography (silica gel 230-400 mesh, 0-8% MeOH in DCM) followed by reverse phase prep HPLC to get 50 mg (9%) of CIS-1-(1-(1-(cyclopropylmethyl)-8-(dimethylamino)-2-oxo-8-phenyl-1,3-diazaspiro[4.5]decan-3-yl)-2-methylpropan-2-yl)pyrrolidine-2,5-dione (SC_4084) as a white solid (TLC system: 5% MeOH in DCM; Rf: 0.30). Reverse prep HPLC condition: mobile phase: 10 mM ammonium bicarbonate in H$_2$O/acetonitrile; column: INERTSIL-ODS (250*19 mm) 5 µm; gradient (% B): 0/80, 9/90, 9.1/80, 12/80; flow rate: 18 ml/min; diluent: ACN+THF+H$_2$O. $^1$H NMR (DMSO-d6): δ 7.35-7.34 (m, 4H), 7.27-7.24 (m, 1H), 3.34 (s, 2H), 3.19 (s, 2H), 2.87 (d, 2H), 2.66-2.64 (m, 2H), 2.43 (s, 4H), 2.13-2.08 (m, 2H), 1.97 (s, 6H), 1.51 (s, 6H), 1.37-1.32 (m, 4H), 0.89-0.87 (m, 1H), 0.45-0.42 (m, 2H), 0.27-0.24 (m, 2H). Mass: m/z 481.3 (M+H)$^+$.

Synthesis of SC_4096: CIS-1-(cyclopropylmethyl)-8-(dimethylamino)-8-phenyl-3-(1-(pyridazin-4-yl)piperidin-4-yl)-1,3-diazaspiro[4.5]decan-2-one

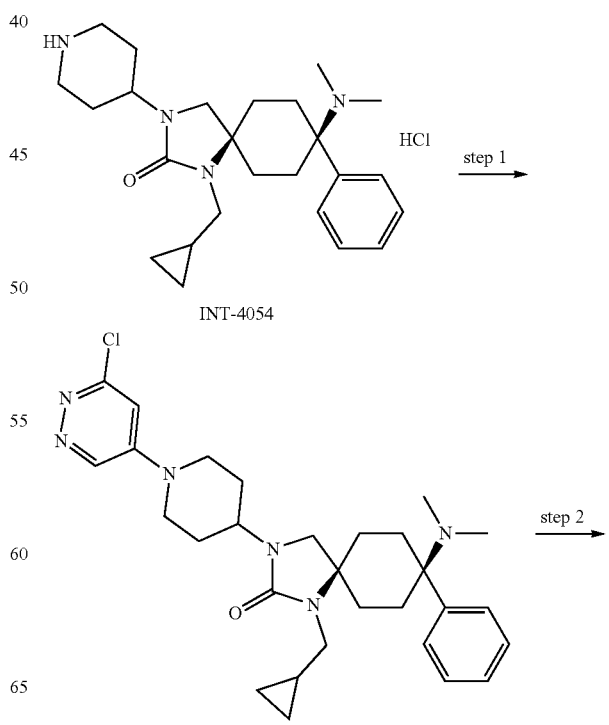

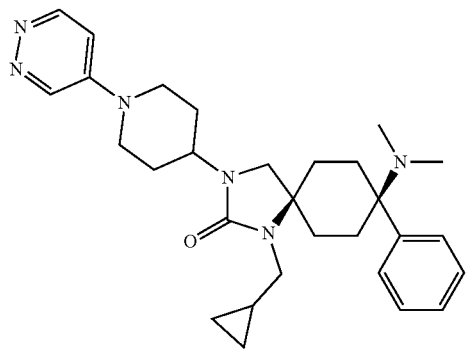

SC_4096

Step 1: CIS-3-(1-(6-chloropyridazin-4-yl)piperidin-4-yl)-1-(cyclopropylmethyl)-8-(dimethylamino)-8-phenyl-1,3-diazaspiro[4.5]decan-2-one DIPEA (0.566 g, 4.3 mmol) was added to a solution of CIS-1-(cyclopropylmethyl)-8-(dimethylamino)-8-phenyl-3-(piperidin-4-yl)-1,3-diazaspiro[4.5]decan-2-one (SC_4054) (0.6 g, 1.4 mmol) and 3,5-dichloropyridazine (310 mg, 2.10 mmol) in N-methyl-2-pyrrolidone (30 mL). The reaction mixture was purged with argon for 10 min and stirred for 16 h at 80° C. The reaction mixture was quenched with water and extracted with EtOAc (3×20 mL). The combined organic layer was concentrated under reduced pressure and the crude product was purified by flash chromatography (silica gel 230-400 mesh size, 5-10% methanol in dichloromethane as eluent) to afford 250 mg of CIS-3-(1-(6-chloropyridazin-4-yl)piperidin-4-yl)-1-(cyclopropylmethyl)-8-(dimethylamino)-8-phenyl-1,3-diazaspiro[4.5]decan-2-one) as a light brown solid. (TLC system: 10% MeOH in DCM; Rf: 0.35).

Step 2: CIS-1-(cyclopropylmethyl)-8-(dimethylamino)-8-phenyl-3-(1-(pyridazin-4-yl)piperidin-4-yl)-1,3-diazaspiro[4.5]decan-2-one (SC_4096)

10% Pd—C (125 mg) was added to a solution of CIS-3-(1-(6-chloropyridazin-4-yl)piperidin-4-yl)-1-(cyclopropylmethyl)-8-(dimethylamino)-8-phenyl-1,3-diazaspiro[4.5]decan-2-one) (0.25 g, 0.47 mmol) and triethylamine (96 mg, 0.95 mmol) in ethanol. The resultant mixture was hydrogenated under balloon pressure for 4 h. The reaction mixture was diluted with EtOH (10 mL); filtered through a pad of celite and the filtrate was concentrated under reduced pressure. The crude product was purified by flash chromatography (silica gel 230-400 mesh, 5-10% methanol in DCM as eluent) and further purified by reverse phase prep HPLC to afford 85 mg (17%) of CIS-1-(cyclopropylmethyl)-8-(dimethylamino)-8-phenyl-3-(1-(pyridazin-4-yl)piperidin-4-yl)-1,3-diazaspiro[4.5]decan-2-one (SC_4096) as an off-white solid. (TLC system: 10% MeOH in DCM; Rf: 0.35). Reverse prep HPLC condition: column X-BRIDGE C18 (4.6×150 mm) 3.5 μm; mobile phase: 10 mM ammonium acetate in water (A)/acetonitrile (B); gradient time (min)/% B: 0/5, 1.2/5, 3/55, 5/70, 7/95, 10/95, 12/100, 14/5, 16/5; flow rate: 1 ml/min; diluent: (acetonitrile/water). $^1$H NMR (DMSO): δ 8.92 (m, 1H), 8.55-8.54 (m, 1H), 7.34-7.30 (m, 4H), 7.24-7.21 (m, 1H), 6.91-6.89 (m, 1H), 4.09-4.07 (d, 2H), 3.84 (m, 1H), 3.09 (s, 2H), 2.95-2.90 (m, 4H), 2.62-2.59 (d, 2H), 2.12-2.09 (t, 2H), 1.96 (s, 6H), 1.60-1.56 (m, 4H), 1.42-1.39 (m, 2H), 1.31-1.28 (m, 2H), 0.91 (m, 1H), 0.46-0.43 (m, 2H), 0.26-0.23 (m, 2H). Mass: m/z 489.4 (M+H)+.

Synthesis of SC_4091: CIS-1-(cyclobutylmethyl)-8-(dimethylamino)-3-(2-methyl-2-(methylsulfonyl)propyl)-8-phenyl-1,3-diazaspiro[4.5]decan-2-one

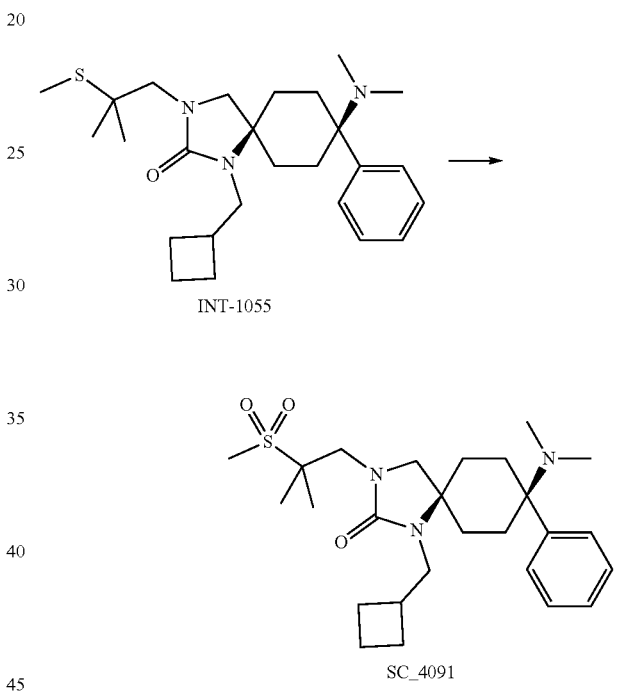

To a solution of 1-cyclobutylmethyl-8-dimethylamino-3-(2-methyl-2-methylsulfanyl-propyl)-8-phenyl-1,3-diazaspiro[4.5]decan-2-one (45 mg, 0.1 mmol, 1.0 eq) in THF/H$_2$O (6 ml, 5:1) was added oxone (119 mg, 0.19 mmol, 1.9 eq.) at 0° C. The reaction mixture was stirred at RT for 16 h, then quenched with sat. aq. NaHSO$_3$, diluted with EtOAc (50 mL) and washed with sat. aq. NaHCO$_3$ (25 ml). Organic layer was dried over Na$_2$SO$_4$ and concentrated under reduced pressure. The resulting crude product was purified by column chromatography (neutral alumina; 1.5% MeOH in DCM) to yield 1-cyclobutylmethyl-8-dimethylamino-3-(2-methanesulfonyl-2-methyl-propyl)-8-phenyl-1,3-diazaspiro[4.5]decan-2-one (SC_4091) (100 mg, 0.17 mmol, 94%) as an off-white solid. $^1$HNMR at 100° C. (DMSO-d6, 400 MHz), δ (ppm)=7.33-7.24 (m, 5H), 3.41 (s, 2H), 3.29 (s, 2H), 3.10 (d, 2H, J=7.04 Hz), 2.87 (s, 3H), 2.63-2.56 (m, 3H), 2.12-2.01 (m, 10H), 1.83-1.81 (m, 4H), 1.47-1.27 (m, 10H). Mass: m/z 576.0 (M+H)$^+$.

Synthesis of SC_4098: TRANS-8-(dimethylamino)-1-((1-hydroxycyclobutyl)methyl)-3-(2-(methylsulfonyl)ethyl)-8-phenyl-1,3-diazaspiro[4.5]decan-2-one

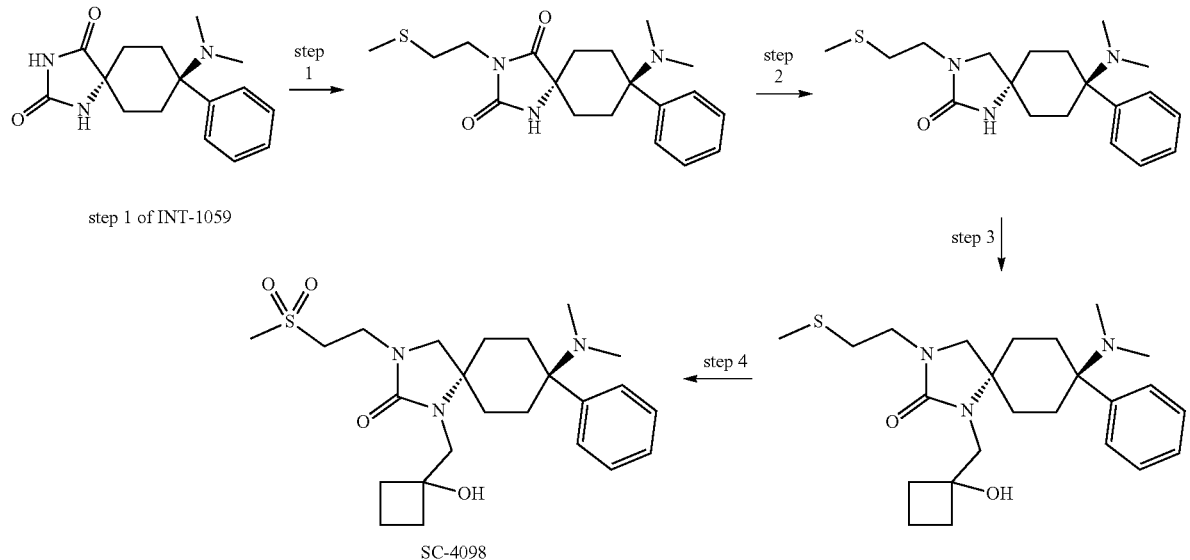

SC-4098

Step 1: TRANS-8-(dimethylamino)-3-(2-(methylthio)ethyl)-8-phenyl-1,3-diazaspiro[4.5]decane-2,4-dione In analogy to the method described for SC_4034 TRANS-8-(dimethylamino)-8-phenyl-1,3-diazaspiro[4.5]decane-2,4-dione (step 1 of INT-1059) was reacted with 1-bromo-2-methylsulfanyl-ethane to be converted into TRANS-8-(dimethylamino)-3-(2-(methylthio)ethyl)-8-phenyl-1,3-diazaspiro[4.5]decane-2,4-dione. Mass: m/z 362.2 (M+H)$^+$.

Step 2: TRANS-8-(dimethylamino)-3-(2-(methylthio)ethyl)-8-phenyl-1,3-diazaspiro[4.5]decan-2-one To a slurry of LiAlH$_4$ (315 mg, 8.31 mmol, 6.0 eq.) in THF (10 mL) was added a solution of TRANS-8-dimethylamino-3-(2-methylsulfanyl-ethyl)-8-phenyl-1,3-diaza-spiro[4.5]decane-2,4-dione (500 mg, 1.38 mmol, 1.0 eq.) in THF (10 mL) at 0° C. under argon atmosphere and the reaction mixture was stirred at reflux for 16 h. The reaction mixture was cooled to 0° C. and quenched with sat. aq. Na$_2$SO$_4$ (10 mL). The resulting suspension was stirred at RT for 30 min. The reaction mixture was filtered through celite and filter cake was washed with 10% MeOH in DCM (30 mL). The combined filtrate was dried over anhydr. Na$_2$SO$_4$ and concentrated under reduced pressure and residue was dissolved in HCOOH (15 mL) and NaBH$_4$ (314 mg, 8.31 mmol, 6.0 eq.) was added portionwise at 0° C. The reaction mixture was stirred at RT for 3 h, then basified with sat. aq. NaHCO$_3$ up to pH~8 and extracted with EtOAc (2×50 mL). Combined organic layer was washed with brine (30 mL), dried over Na$_2$SO$_4$ and concentrated under reduced pressure to get crude TRANS-8-dimethylamino-3-(2-methylsulfanyl-ethyl)-8-phenyl-1,3-diaza-spiro[4.5]decan-2-one (400 mg, 1.29 mmol, 83%) as a brown solid which was used in the next step without further purification. LC-MS: m/z [M+1]$^+$=348.4 (MW calc. 347.52).

Step 3: TRANS-8-dimethylamino-1-(1-hydroxy-cyclobutylmethyl)-3-(2-methylsulfanyl-ethyl)-8-phenyl-1,3-diaza-spiro[4.5]decan-2-one To a solution of TRANS-8-dimethylamino-3-(2-methylsulfanyl-ethyl)-8-phenyl-1,3-diaza-spiro[4.5]decan-2-one (450 mg, 1.29 mmol, 1.0 eq.) in DMSO (10 mL) was added NaOH (363 mg, 9.07 mmol, 7.0 eq.) at RT. The reaction mixture was heated to 60° C. for 30 min, then cooled to RT and 1-oxa-spiro[2.3]hexane (435 mg, 5.18 mmol, 4.0 eq.) was added. The reaction mixture was stirred at 60° C. for 48 h, then quenched with ice water (25 mL), extracted with EtOAc (2×50 mL). Combined organic layer was washed with brine (25 ml), dried over Na$_2$SO$_4$, filtered and concentrated under reduced pressure to get the crude product which was purified by column chromatography (neutral alumina; 4% MeOH/DCM) to yield TRANS-8-dimethylamino-1-(1-hydroxy-cyclobutylmethyl)-3-(2-methylsulfanyl-ethyl)-8-phenyl-1,3-diaza-spiro[4.5]decan-2-one (120 mg, 0.27 mmol, 21%) as a brown liquid. LC-MS: m/z [M+1]$^+$=432.0 (MW calc. 431.64.

Step 4: TRANS-8-(dimethylamino)-1-((1-hydroxy-cyclobutyl)methyl)-3-(2-(methylsulfonyl)ethyl)-8-phenyl-1,3-diazaspiro[4.5]decan-2-one (SC_4098)

In analogy to the method described for step 2 of SC_4038 TRANS-8-dimethylamino-1-(1-hydroxy-cyclobutylmethyl)-3-(2-methylsulfanyl-ethyl)-8-phenyl-1,3-diaza-spiro[4.5]decan-2-one was reacted with oxone to be converted into TRANS-8-(dimethylamino)-1-((1-hydroxycyclobutyl)methyl)-3-(2-(methylsulfonyl)ethyl)-8-phenyl-1,3-diazaspiro[4.5]decan-2-one (SC_4098). Mass: m/z 464.3 (M+H)$^+$. $^1$HNMR (DMSO-d$_6$, 400 MHz), δ (ppm)=7.39-7.28 (m, 5H), 5.35 (s, 1H), 3.59-3.56 (m, 2H), 3.42-3.34 (m, 4H), 2.97-2.95 (m, 3H), 2.66 (s, 2H), 2.67 (bs, 2H), 2.59-2.56 (m, 2H), 2.00 (s, 6H), 1.77-0.163 (m, 6H), 1.50-1.27 (m, 5H), 1.05-0.98 (m, 1H).

Synthesis of SC_5063: CIS-2,2-dimethyl-3-(8-(methylamino)-2-oxo-8-phenyl-1,3-diazaspiro[4.5]decan-3-yl)propanenitrile

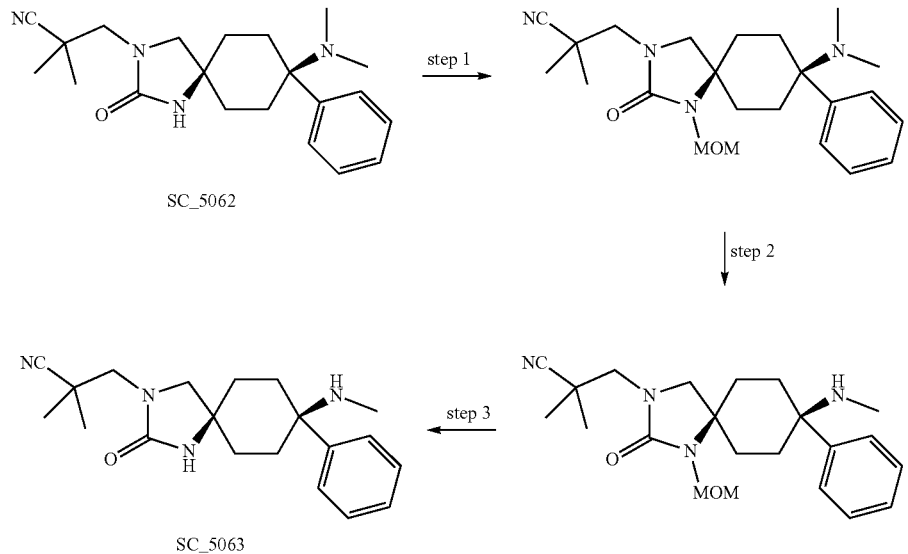

Step 1: CIS-3-(8-(dimethylamino)-1-(methoxymethyl)-2-oxo-8-phenyl-1,3-diazaspiro[4.5]decan-3-yl)-2,2-dimethylpropanenitrile To a solution of CIS-3-(8-dimethylamino-2-oxo-8-phenyl-1,3-diaza-spiro[4.5]dec-3-yl)-2,2-dimethyl-propionitrile (SC_5062) (1.8 g, 5.08 mmol, 1.0 eq.) in THF (20 ml) was added NaH (95%, 366 mg, 15.25 mmol, 3.0 eq.) at 0° C. and the reaction mixture was stirred for 20 min at RT. A solution of methoxymethyl chloride (0.57 ml, 7.62 mmol, 1.5 eq.) in THF (5 ml) was added at 0° C. and the resulting mixture was stirred at RT for 16 h. The reaction mixture was diluted with water (20 ml) and extracted with EtOAc (2×50 ml). The combined organic layers were washed with water (50 ml) and brine (50 ml), dried over anhydr. $Na_2SO_4$ and concentrated under reduced pressure. The resulting crude product was purified by column chromatography (neutral alumina; 0.2% MeOH/DCM) to yield CIS-3-(8-(dimethylamino)-1-(methoxymethyl)-2-oxo-8-phenyl-1,3-diazaspiro[4.5]decan-3-yl)-2,2-dimethylpropanenitrile (700 mg, 1.75 mmol, 34%) as an off-white sticky solid. LC-MS: m/z $[M+H]^+$=399.3 (MW calc.=398.54).

Step 2: CIS-3-(1-(methoxymethyl)-8-(methylamino)-2-oxo-8-phenyl-1,3-diazaspiro[4.5]decan-3-yl)-2,2-dimethylpropanenitrile To a solution of CIS-3-(8-(dimethylamino)-1-(methoxymethyl)-2-oxo-8-phenyl-1,3-diazaspiro[4.5]decan-3-yl)-2,2-dimethylpropanenitrile (700 mg, 1.75 mmol, 1.0 eq.) in acetonitrile (20 ml) and THF (10 ml) was added N-iodosuccinimide (590 mg, 2.63 mmol, 1.5 eq.) at 0° C. and the mixture was stirred at RT for 3 h. The reaction mixture was diluted with water (20 ml) and 1N aq. NaOH (5 ml) and extracted with DCM (2×30 ml). The combined organic layers were washed with brine (40 ml), dried over anhydr. $Na_2SO_4$ and concentrated under reduced pressure to give CIS-3-(1-(methoxymethyl)-8-(methylamino)-2-oxo-8-phenyl-1,3-diazaspiro[4.5]decan-3-yl)-2,2-dimethylpropanenitrile (350 mg, 0.911 mmol, 52%) which was used directly for next step without further purification. LC-MS: m/z $[M+H]^+$=385.2 (MW calc.=384.52).

Step 3: CIS-2,2-dimethyl-3-(8-(methylamino)-2-oxo-8-phenyl-1,3-diazaspiro[4.5]decan-3-yl)propanenitrile (SC_5063)

To a solution of CIS-3-(1-(methoxymethyl)-8-(methylamino)-2-oxo-8-phenyl-1,3-diazaspiro[4.5]decan-3-yl)-2,2-dimethylpropanenitrile (400 mg, 1.04 mmol, 1.0 eq.) in MeOH (10 ml) was added 2M aq. HCl (30 ml) at 0° C. and the mixture was stirred at RT for 16 h. The reaction mixture was basified with 2M aq. NaOH and extracted with DCM (2×25 ml). The combined organic layers were washed with brine (30 ml), dried over anhydr. $Na_2SO_4$ and concentrated under reduced pressure to give CIS-2,2-dimethyl-3-(8-(methylamino)-2-oxo-8-phenyl-1,3-diazaspiro[4.5]decan-3-yl)propanenitrile (SC_5063) (300 mg, 0.882 mmol, 84%) which was 95.72% pure according to HPLC. LC-MS: m/z $[M+H]^+$=341.27 (MW calc.=340.46). $^1$HNMR (DMSO-d6, 400 MHz), δ (ppm)=7.42-7.19 (m, 5H), 6.78 (bs, 1H), 3.36 (s, 2H), 3.18 (s, 2H), 1.96-1.85 (m, 7H), 1.66 (bs, 2H), 1.46-1.43 (m, 2H), 1.25 (s, 6H).

For further exemplary compounds the last synthesis step in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Example | Chemical Name | Reactant I | Reactant II | in analogy to method | m/z [M + H]+ |
|---|---|---|---|---|---|
| SC_4002 | CIS-1-(Cyclobutyl-methyl)-8-dimethylamino-3-[2-[2-[2-[2-[2-(2-methoxy-ethoxy)-ethoxy]-ethoxy]-ethoxy]-ethyl]-8-phenyl-1,3-diazaspiro[4.5]decan-2-one | INT-987 | 19-bromo-2,5,8,11,14,17-hexaoxanonadecane | SC_4003 | 620.4 |
| SC_4004 | CIS-1-(Cyclobutyl-methyl)-8-dimethylamino-3-[2-[2-[2-[2-[2-[2-(2-methoxy-ethoxy)-ethoxy]-ethoxy]-ethoxy]-ethoxy]-ethyl]-8-phenyl-1,3-diazaspiro[4.5]decan-2-one | INT-987 | 22-bromo-2,5,8,11,14,17,20-heptaoxadocosane | SC_4003 | 664.4 |
| SC_4005 | CIS-1-(Cyclobutyl-methyl)-8-dimethylamino-3-[2-[2-[2-[2-(2-methoxy-ethoxy)-ethoxy]-ethoxy]-ethoxy]-ethyl]-8-phenyl-1,3-diazaspiro[4.5]decan-2-one | INT-987 | 16-bromo-2,5,8,11,14-pentaoxahexadecane | SC_4003 | 576.4 |
| SC_4006 | CIS-1-(Cyclobutyl-methyl)-8-dimethylamino-3-[2-(2-methoxy-ethoxy)-ethyl]-8-phenyl-1,3-diazaspiro[4.5]decan-2-one | INT-987 | 1-bromo-2-(2-methoxyethoxy)ethane | SC_4003 | 444.3 |
| SC_4007 | CIS-1-(Cyclobutyl-methyl)-8-dimethylamino-3-(2-methoxy-ethyl)-8-phenyl-1,3-diazaspiro[4.5]decan-2-one | INT-987 | 1-bromo-2-methoxyethane | SC_4003 | 400.3 |
| SC_4008 | CIS-1-(Cyclobutyl-methyl)-8-dimethylamino-3-[2-[2-[2-(2-methoxy-ethoxy)-ethoxy]-ethoxy]-ethyl]-8-phenyl-1,3-diazaspiro[4.5]decan-2-one | INT-987 | 13-bromo-2,5,8,11-tetraoxatridecane | SC_4003 | 532.4 |
| SC_4009 | CIS-1-(Cyclobutyl-methyl)-8-dimethylamino-3-(2-methylsulfonyl-ethyl)-8-phenyl-1,3-diazaspiro[4.5]decan-2-one | INT-987 | 1-bromo-2-(methylsulfonyl)ethane | SC_4025 | 448.3 |
| SC_4011 | CIS-8-Dimethylamino-1-[(1-hydroxy-cyclobutyl)-methyl]-3-(2-methylsulfonyl-ethyl)-8-phenyl-1,3-diazaspiro[4.5]decan-2-one | INT-799 | 1-bromo-2-(methylsulfonyl)ethane | SC_4025 | 464.3 |
| SC_4014 | CIS-3-[1-(Cyclobutyl-methyl)-8-dimethylamino-2-oxo-8-phenyl-1,3-diazaspiro[4.5]decan-3-yl]-2,2-dimethyl-propionitrile | INT-799 | 3-bromo-2,2-dimethylpropanenitrile | SC_4025 | 423.3 |
| SC_4017 | CIS-1-(Cyclobutyl-methyl)-8-dimethylamino-3-[2-[2-[2-[2-[2-[2-(2-methoxy-ethoxy)-ethoxy]-ethoxy]-ethoxy]-ethoxy]-ethoxy]-ethyl]-8-phenyl-1,3-diazaspiro[4.5]decan-2-one | INT-987 | 25-bromo-2,5,8,11,14,17,20,23-octaoxapentacosane | SC_4003 | 708.5 |
| SC_4018 | CIS-1-(Cyclobutyl-methyl)-8-dimethylamino-3-methyl-8-phenyl-1,3-diazaspiro[4.5]decan-2-one | INT-987 | Methyliodide | SC_4025 | 356.3 |
| SC_4021 | CIS-1-[(1-Hydroxy-cyclobutyl)-methyl]-8-methylamino-3-(2-methylsulfonyl-ethyl)-8-phenyl-1,3-diazaspiro[4.5]decan-2-one | SC_4011 | — | SC_4010 | 450.2 |
| SC_4022 | CIS-3-[1-[(1-Hydroxy-cyclobutyl)-methyl]-8-methylamino-2-oxo-8-phenyl-1,3-diazaspiro[4.5]decan-3-yl]-propionitrile | SC_4029 | — | SC_4010 | 397.3 |
| SC_4024 | CIS-2-[1-[(1-Hydroxy-cyclobutyl)-methyl]-8-methylamino-2-oxo-8-phenyl-1,3-diazaspiro[4.5]decan-3-yl]-acetonitrile | SC_4030 | — | SC_4010 | 383.2 |
| SC_4026 | CIS-8-Dimethylamino-1-[(1-hydroxy-cyclobutyl)-methyl]-3-(2-morpholin-4-yl-ethyl)-8-phenyl-1,3-diazaspiro[4.5]decan-2-one | INT-799 | 4-(2-bromoethyl)morpholine | SC_4025 | 471.3 |
| SC_4029 | CIS-3-[8-Dimethylamino-1-[(1-hydroxy-cyclobutyl)-methyl]-2-oxo-8-phenyl-1,3-diazaspiro[4.5]decan-3-yl]-propionitrile | INT-799 | 3-bromopropanenitrile | SC_4025 | 411.3 |
| SC_4030 | CIS-2-[8-Dimethylamino-1-[(1-hydroxy-cyclobutyl)-methyl]-2-oxo-8-phenyl-1,3-diazaspiro[4.5]decan-3-yl]-acetonitrile | INT-799 | 2-bromoacetonitrile | SC_4025 | 397.3 |

| Example | Reactant I | Reactant II | Chemical name | in analogy to method | ¹H NMR data | m/z (M + H)⁺ |
|---|---|---|---|---|---|---|
| SC_4035 | SC_4032 | toluene-4-sulfonic acid oxetan-3-ylmethyl ester | CIS-8-Dimethylamino-3-(2-methylsulfonyl-ethyl)-1-(oxetan-3-yl-methyl)-8-phenyl-1,3-diazaspiro[4.5]decan-2-one | SC_4034 | ¹HNMR (DMSO-d6, 400 MHz, δ (ppm) = 7.34-7.25 (m, 5H), 4.59 (t, 2H, 6.64 Hz) 4.35 (bs, 2H), 3.48 (bs, 2H), 3.21 (s, 2H), 3.13 (bs, 1H), 2.95 (s, 3H), 2.67-2.65 (m, 2H), 1.97 (s, 8H), 1.41-1.30 (m, 4H). | 450.1 |
| SC_4036 | SC_4032 | 1-bromo-3-methoxy-propane | CIS-8-Dimethylamino-1-(3-methoxy-propyl)-3-(2-methylsulfonyl-ethyl)-8-phenyl-1,3-diazaspiro[4.5]decan-2-one | SC_4034 | ¹HNMR (CDCl3, 400 MHz), δ (ppm) = 7.35-7.25 (m, 5H, merged with CDCl3), 3.64 (t, 2H, J = 6.32 Hz), 3.44 (t, 2H, J = 6.08 Hz), 3.34 (s, 3H), 3.28-3.19 m, 6H), 2.95 (s, 3H), 2.64-2.61 (m, 2H), 2.22-2.16 (m, 2H), 2.01 (s, 6H), 1.89-1.86 (m, 2H), 1.29-1.27 (m, 4H). | 452.3 |
| SC_4039 | INT-987 | 1,6-dioxaspiro[2.5]octane | CIS-1-(Cyclobutyl-methyl)-8-dimethylamino-3-[(4-hydroxy-tetrahydro-pyran-4-yl)-methyl]-8-phenyl-1,3-diazaspiro[4.5]decan-2-one | SC_4027 | ¹H NMR (DMSO-d6): δ 7.26-7.23 (m, 1H), 4.52 (s, 1H), 3.60-3.56 (m, 4H), 3.28 (s, 2H), 3.03-3.01 (m, 4H), 2.68-2.65 (m, 2H), 2.49-2.46 (m, 1H), 2.06-1.92 (m, 10H), 1.82-1.65 (m, 4H), 1.49-1.44 (m, 2H), 1.34-1.31 (m, 6H). | 456.3 |
| SC_4040 | INT-983 | tetrahydro-2H-pyran-4-yl 4-methylbenzenesulfonate | CIS-1-(Cyclopropyl-methyl)-8-dimethylamino-8-phenyl-3-tetrahydro-pyran-4-yl-1,3-diazaspiro[4.5]decan-2-one | SC_4027 | ¹H NMR (DMSO-d6): δ 7.34-7.25 (m, 5H), 3.86-3.84 (m, 2H), 3.76-3.70 (m, 1H), 3.35 (m, 2H), 3.13 (s, 2H), 2.91 (d, 2H), 2.66-2.62 (m, 2H), 2.14 (t, 2H), 1.97 (s, 6H), 1.66-1.58 (m, 2H), 1.46-1.23 (m, 6H), 0.91 (m, 1H), 0.44 (m, 2H), 0.24 (m, 2H). | 412.3 |
| SC_4041 | INT-987 | 1-oxa-6-thiaspiro[2.5]octane (step 1) | CIS-1-(Cyclobutyl-methyl)-8-dimethylamino-1,1-dioxo-thian-4-yl)-methyl]-8-phenyl-1,3-diazaspiro[4.5]decan-2-one | SC_4027 (for step 1), SC_4038 (for step 2) | ¹H NMR (DMSO-d6): δ 7.37-7.23 (m, 5H), 5.02 (s, 1H), 3.27 (s, 2H), 3.17-3.03 (m, 6H), 2.97-2.94 (m, 2H), 2.68-2.65 (m, 2H), 2.54-2.46 (m, 1H), 2.07-1.92 (m, 10H), 1.87-1.84 (m, 4H), 1.80-1.66 (m, 4H), 1.34-1.31 (m, 4H). | 504.3 |
| SC_4042 | INT-799 | tetrahydro-2H-pyran-4-yl 4-methylbenzenesulfonate | CIS-1-(1-hydroxy-cyclobutyl)-methyl]-8-phenyl-3-tetrahydro-pyran-4-yl-1,3-diazaspiro[4.5]decan-2-one | SC_4027 | ¹H NMR (DMSO-d6): δ 7.37-7.25 (m, 5H), 6.05 (s, 1H), 3.87-3.84 (m, 2H), 3.74-3.73 (m, 1H), 3.36-3.35 (m, 2H), 3.24 (s, 2H), 3.07 (s, 2H), 2.66-2.63 (m, 2H), 2.06-1.83 (m, 12H), 1.65-1.58 (m, 3H), 1.48-1.32 (m, 7H). | 442.3 |
| SC_4043 | SC_4032 | toluene-4-sulfonic acid 1-cyano-cyclobutylmethyl ester | CIS-1-[[8-Dimethylamino-3-(2-methylsulfonyl-ethyl)-2-oxo-8-phenyl-1,3-diazaspiro[4.5]decan-1-yl]-methyl]-cyclobutane-1-carbonitrile | SC_4034 | ¹HNMR (DMSO-d6, 400 MHz), δ (ppm) = 7.33-7.32 (m, 2H), 7.25 (s, 3H), 3.69-3.66 (t, 2H, J = 5), 3.41 (s, 2H), 3.30-3.25 (m, 4H), 2.95 (s, 3H), 2.67-2.64 (d, 2H, J = 13.4), 2.45 (bs, 4H), 2.19-2.08 (m, 4H), 2.02 (s, 6H), 1.46-1.39 (m, 2H). | 473.2 |
| SC_4045 | INT-799 | 1-oxa-6-thiaspiro[2.5]octane (step 1) | CIS-8-Dimethylamino-1-[(1-hydroxy-cyclobutyl)-methyl]-3-[(4-hydroxy-1,1-dioxo-thian-4-yl)-methyl]-8-phenyl-1,3-diazaspiro[4.5]decan-2-one | SC_4044 (for step 1), step 2 of SC_4038 (for step 2) | ¹H NMR (DMSO-d6): δ 7.37-7.25 (m, 5H), 5.93 (s, 1H), 5.01 (s, 1H), 3.41 (s, 2H), 3.16-3.09 (m, 6H), 2.98-2.95 (m, 2H), 2.70-2.66 (m, 2H), 2.06-2.03 (m, 4H), 1.97 (s, 6H), 1.89-1.87 (m, 6H), 1.64-1.61 (m, 1H), 1.45-1.31 (m, 5H). | 520.3 |

| Example | Chemical name | Reactant I | Reactant II | in analogy to method | 1H NMR data | m/z (M + H)+ |
|---|---|---|---|---|---|---|
| SC_4046 | CIS-1-(Cyclopropyl-methyl)-8-dimethylamino-3-(1,1-dioxo-thian-4-yl)-8-phenyl-1,3-diazaspiro[4.5]decan-2-one | INT-983 | tetrahydro-2H-thiopyran-4-yl 4-methylbenzenesulfonate (step 1) | SC_4044 (for step 1), step 2 of SC_4038 (for step 2) | 1H NMR (DMSO-d6): δ 7.37-7.26 (m, 5H), 4.08-4.02 (m, 1H), 3.17-3.03 (m, 8H), 2.67-2.63 (m, 2H), 2.32-2.04 (m,12H), 1.46-1.39 (m, 4H), 1.02-0.99 (m, 1H), 0.54-0.50 (m, 2H), 0.34-0.30 (m, 2H). | 460.3 |
| SC_4047 | CIS-8-Dimethylamino-3-(1,1-dioxo-thian-4-yl)-1-((1-hydroxy-cyclobutyl)-methyl]-8-phenyl-1,3-diazaspiro[4.5]decan-2-one | INT-799 | tetrahydro-2H-thiopyran-4-yl 4-methylbenzenesulfonate (step 1) | SC_4044 (for step 1), step 2 of SC_4038 (for step 2) | 1H NMR (DMSO-d6): δ 7.37-7.32 (m, 4H), 7.27-7.23 (m, 1H), 5.94 (s, 1H), 3.97-3.91 (m, 1H), 3.33-3.31 (m, 2H), 3.27 (s, 2H), 3.07 (s, 2H), 3.02-2.99 (m, 2H), 2.64-2.61 (m, 2H), 2.12-2.02 (m, 6H), 1.97 (s, 6H), 1.88-1.85 (m, 4H), 1.66-1.61 (m, 1H), 1.50-1.29 (m, 5H). | 490.3 |
| SC_4049 | CIS-3-(1-Benzoyl-piperidin-4-yl)-1-(cyclopropyl-methyl)-8-dimethylamino-8-phenyl-1,3-diazaspiro[4.5]decan-2-one | SC_4054 | benzoyl chloride | SC_4048 | 1H NMR (CDCl3): δ 7.40-7.34 (m, 7H), 7.30-7.27 (m, 3H), 4.79 (m, 1H), 4.06-4.00 (m, 1H), 3.78 (br m, 1H), 3.90-3.05 (m, 5H), 2.80-2.77 (br m, 1H), 2.65 (d, 2H), 2.27 (t, 2H), 2.05 (s, 6H), 1.82-1.62 (m, 3H), 1.46-1.41 (m, 5H), 1.04-0.99 (m, 1H), 0.53-0.50 (m, 2H), 0.33-0.30 (m, 2H). | 515.4 |
| SC_4050 | CIS-1-(Cyclopropyl-methyl)-8-dimethylamino-8-phenyl-3-[1-(pyridine-4-carbonyl)-piperidin-4-yl]-1,3-diazaspiro[4.5]decan-2-one | SC_4054 | isonicotinoyl chloride hydrochloride | SC_4048 | 1H NMR (CDCl3): δ 8.67-8.66 (m, 2H), 7.36-7.35 (m, 2H), 7.30-7.27 (m, 3H), 7.25-7.24 (m, 2H), 4.80-4.77 (m, 1H), 4.06-4.01 (m, 1H), 3.65-3.62 (m, 1H), 3.14-3.05 (m, 5H), 2.82 (t, 1H), 2.67-2.65 (m, 2H), 2.28 (m, 2H), 2.05 (s, 6H), 1.86-1.84 (m, 1H), 1.71-1.62 (m, 1H), 1.46-1.39 (m, 5H), 1.03-0.99 (m, 1H), 0.53-0.50 (m, 2H), 0.34-0.33 (m, 2H). | 516.3 |
| SC_4051 | CIS-1-(Cyclopropyl-methyl)-8-dimethylamino-34(4-hydroxy-tetrahydro-pyran-4-yl)-methyl]-8-phenyl-1,3-diazaspiro[4.5]octane | INT-983 | 1,6-dioxaspiro[2.5]octane | SC_4044 | 1H NMR (DMSO-d6): δ 7.37-7.33 (m, 4H), 7.27-7.23 (m, 1H), 4.54 (s, 1H), 3.60-3.53 (m, 4H), 3.32 (m, 2H), 3.03 (s, 2H), 2.91 (d, 2H), 2.67 (d, 2H), 2.15 (t, 2H), 1.97 (s, 6H), 1.49-1.44 (m, 2H), 1.40-1.31 (m, 6H), 0.95-0.90 (m, 1H), 0.46-0.43 (m, 2H), 0.30-0.21 (m, 2H). | 442.3 |
| SC_4053 | CIS-3-[(1-Acetyl-piperidin-4-yl)-methyl]-1-(cyclopropyl-methyl)-8-dimethylamino-8-phenyl-1,3-diazaspiro[4.5]decan-2-one | SC_4058 | acetyl chloride | SC_4048 | 1H NMR (DMSO d6): δ 7.35-7.34 (m, 4H), 7.25 (m, 1H), 4.31-4.28 (m, 1H), 3.77-3.74 (m, 1H), 3.15 (s, 2H), 2.97-2.90 (m, 5H), 2.68-2.64 (m, 2H), 2.19-2.13 (m, 2H), 1.97-1.95 (m, 9H), 1.76 (m, 1H), 1.59-1.52 (m, 2H), 1.43-1.31 (m, 4H), 1.03-0.87 (m, 3H), 0.45-0.44 (m, 2H), 0.25-0.24 (m, 2H). | 467.3 |
| SC_4058 | CIS-1-(Cyclopropyl-methyl)-8-dimethylamino-8-phenyl-3-(piperidin-4-yl-methyl)-1,3-diazaspiro[4.5]decan-2-one | INT-983 | tert-butyl 4-((tosyloxy)methyl)piperidine-1-carboxylate (step 1) | SC_4034 (for step 1), step 2 of SC_4054 (for step 2) | 1H NMR (DMSO d6): δ 7.37-7.34 (m, 4H), 7.27-7.23 (m, 1H), 3.13 (s, 2H), 2.91-2.87 (m, 6H), 2.67-2.64 (m, 2H), 2.39-2.33 (m, 2H), 2.18-2.12 (m, 2H), 1.97 (s, 6H), 1.58-1.54 (m, 1H), 1.47-1.30 (m, 6H), 0.98-0.88 (m, 3H), 0.46-0.42 (m, 2H), 0.26-0.22 (m, 2H). | 425.3 |

| Example | Chemical name | Reactant I | Reactant II | in analogy to method | ¹H NMR data | m/z (M + H)⁺ |
|---|---|---|---|---|---|---|
| SC_4059 | CIS-3-(1-Benzoyl-piperidin-4-yl)-8-dimethylamino-8-phenyl-1,3-diazaspiro[4.5]decan-2-one | INT-976 | tert-butyl 4-(tosyloxy)piperidine-1-carboxylate (step 1), benzoyl chloride (step 3) | SC_4054 (for steps 1,2), SC_4048 (for step 3) | ¹H NMR (DMSO d6): δ 7.42-7.23 (m, 10H), 6.67 (br s, 1H), 4.51 (m, 1H), 3.75 (m, 1H), 3.54 (m, 1H), 3.05 (s, 3H), 2.75 (m, 1H), 2.34 (m, 2H), 1.93 (s, 6H), 1.77 (m, 4H), 1.55-1.35 (m, 6H). | 461.3 |
| SC_4060 | CIS-8-Dimethylamino-8-phenyl-3-[1-(pyridine-4-carbonyl)-piperidin-4-yl]-1,3-diazaspiro[4.5]decan-2-one | INT-976 | isonicotinoyl chloride hydrochloride | SC_4054 (for steps 1, 2), SC_4048 (for step 3) | ¹H NMR (DMSO d6): δ 8.64-8.62 (m, 2H), 7.37-7.32 (m, 6H), 7.26-7.23 (m, 1H), 6.67 (br s, 1H), 4.50 (d, 1H), 3.80-3.73 (m, 1H), 3.40-3.37 (m, 1H), 3.11-3.05 (m, 3H), 2.78 (t, 1H), 2.36-2.33 (m, 2H), 1.93 (s, 6H), 1.80-1.65 (m, 4H), 1.61-1.52 (m, 3H), 1.49-1.35 (m, 3H). | 462.3 |
| SC_4061 | CIS-3-(1-Acetyl-piperidin-4-yl)-8-dimethylamino-8-phenyl-1,3-diazaspiro[4.5]decan-2-one | INT-976 | acetyl chloride | SC_4054 (for steps 1, 2), SC_4048 (for step 3) | ¹H NMR (DMSO-d6): δ 7.36-7.23 (m, 5H), 6.68 (br, s, 1H), 4.40 (d, 1H), 3.80 (d, 1H), 3.69 (m, 1H), 3.05-2.99 (m, 3H), 2.32 (m, 3H), 1.95-1.92 (m, 9H), 1.78-1.76 (m, 4H), 1.50-1.46 (m, 3H), 1.33-1.30 (m, 3H). | 399.3 |
| SC_4062 | CIS-1-(Cyclopropyl-methyl)-8-dimethylamino-3-[(4-hydroxy-1,1-dioxo-thian-4-yl)-methyl]-8-phenyl-1,3-diazaspiro[4.5]decan-2-one | INT-983 | 1-oxa-6-thiaspiro[2.5]octane (step 1) | SC_4044 (for step 1), step 2 of SC_4038 (for step 2) | ¹H NMR (DMSO-d6): δ 7.37-7.33 (m, 4H), 7.27-7.24 (m, 1H), 5.04 (s, 1H), 3.30 (m, 2H), 3.15-3.07 (m, 4H), 2.97-2.92 (m, 4H), 2.69-2.66 (m, 2H), 2.18-2.13 (m, 2H), 1.97 (s, 6H), 1.87-1.84 (m, 4H), 1.38-1.31 (m, 4H), 0.94-0.91 (m, 1H), 0.47-0.43 (m, 2H), 0.26-0.24 (m, 2H). | 490.3 |
| SC_4063 | CIS-8-Dimethylamino-1-[(1-hydroxy-cyclobutyl)-methyl]-3-(2-hydroxy-2-methyl-propyl)-8-phenyl-1,3-diazaspiro[4.5]decan-2-one | INT-799 | tert-butyl bromoacetate (step 1), methylmagnesium bromide (step 3) | SC_4055 | ¹H NMR (DMSO-d6): δ 7.37-7.33 (m, 4H), 7.26-7.23 (m, 1H), 6.11 (s, 1H), 4.41 (s, 1H), 3.42 (s, 2H), 3.09 (s, 2H), 2.98 (s, 2H), 2.70-2.67 (m, 2H), 2.07-2.02 (m, 4H), 1.97 (s, 6H), 1.91-1.83 (m, 3H), 1.63-1.61 (m, 1H), 1.45-1.42 (m, 2H), 1.36-1.32 (m, 3H), 1.04 (s, 6H). | 430.3 |
| SC_4066 | CIS-8-Dimethylamino-1,3-bis(2-methylsulfonyl-ethyl)-8-phenyl-1,3-diazaspiro [4.5]decan-2-one | INT-976 | 1-bromo-2-methylsulfonyl-ethane | SC_4003 | 1H NMR (600 MHz, DMSO) δ 7.40-7.32 (m, 4H), 7.30-7.23 (m, 1H), 3.52 (t, 2H), 3.46-3.31 (m, 1H), 3.27 (s, 2H), 3.05 (s, 3H), 2.97 (s, 3H), 2.72-2.63 (m, 2H), 2.11-2.01 (m, 2H), 1.99 (s, 6H), 1.45-1.36 (m, 4H). | 380.2 |
| SC_4067 | CIS-N-[1-[[1-Cyclopropyl-methyl)-8-dimethylamino-2-oxo-8-phenyl-1,3-diazaspiro[4.5]decan-3-yl]-methyl]-cyclopropyl]-acetamide | SC_4064 | acetyl chloride | SC_4048 | [0375] 1HNMR (DMSO-d6, 400 MHz), δ (ppm) = 7.98 (s, 1H), 7.36-7.25 (m, 5H), 3.25 (s, 2H), 3.12 (s, 2H), 2.89 (d, 2H, J = 6.48 Hz), 2.67-2.64 (m, 2H), 2.16-2.07 (m, 2H), 1.97 (s, 6H), 1.67 (s, 3H), 1.44-1.36 (m, 4H), 0.91 (bs, 1H), 0.62-0.42 (m, 6H), 0.25-0.23 (m, 2H). | 439.1 |

| Example | Chemical name | Reactant I | Reactant II | in analogy to method | 1H NMR data | m/z (M + H)+ |
|---|---|---|---|---|---|---|
| SC_4068 | CIS-1-(Cyclopropyl-methyl)-8-dimethylamino-8-phenyl-3-[(1-pyrimidin-5-yl-piperidin-4-yl)-methyl]-1,3-diazaspiro[4.5]decan-2-one | SC_4058 | 5-bromo-2-(trifluoromethyl)pyrimidine | SC_4056 | 1H NMR (DMSO d6): δ 8.52 (s, 1H), 8.45 (s, 2H), 7.37-7.33 (m, 4H), 7.27-7.23 (m, 1H), 3.83-3.80 (m, 2H), 3.17 (s, 2H), 2.96-2.75 (m, 4H), 2.73-2.65 (m, 4H), 2.16 (m, 2H), 1.98 (s, 6H), 1.65 (m, 1H), 1.65-1.63 (m, 2H), 1.40-1.32 (m, 4H), 1.20-1.17 (m, 2H), 0.94 (m, 1H), 0.46-0.44 (m, 2H), 0.26-0.24 (m, 2H). | 503.4 |
| SC_4069 | CIS-8-Dimethylamino-8-phenyl-3-[(1-pyrimidin-5-yl-piperidin-4-yl)-methyl]-1,3-diazaspiro[4.5]decan-2-one | INT-1051 | 5-bromopyrimidine | SC_4056 | 1H NMR (DMSO d6): δ 8.52 (s, 1H), 8.45 (s, 2H), 7.37-7.33 (m, 4H), 7.26-7.23 (m, 1H), 6.72 (broad s, 1H), 3.82-3.79 (m, 2H), 3.18 (s, 2H), 2.30 (m, 2H), 2.90-2.89(m, 2H), 2.72-2.69 (m, 2H), 1.92 (s, 6H), 1.79-1.69 (m, 5H), 1.64-1.61 (m, 2H), 1.35 (m, 2H), 1.20-1.12 (m, 2H). | 449.3 |
| SC_4070 | CIS-8-Dimethylamino-8-phenyl-3-(1-pyrimidin-5-yl-piperidin-4-yl)-1,3-diazaspiro[4.5]decan-2-one | INT-1050 | 5-bromopyrimidine | SC_4056 | 1H NMR (DMSO d6): δ 8.46 (s, 2H), 7.36-7.30 (m, 4H), 7.24-7.22 (m, 1H), 6.71 (br s, 1H), 3.90-3.88 (m, 2H), 3.71-3.67 (m, 1H), 3.00 (s, 2H), 2.84-2.79 (br m, 4H), 1.66-1.55 (m, 4H), 1.34-1.33 (m, 2H), 2.28 (br s, 2H), 1.92 (s, 6H), 1.78 (m, 2H). | 435.3 |
| SC_4072 | CIS-1-(Cyclopropyl-methyl)-8-dimethylamino-3-[2-methyl-2-(2-oxo-pyrrolidin-1-yl)-propyl]-8-phenyl-1,3-diazaspiro[4.5]decan-2-one | INT-1052 | 4-chlorobutanoyl chloride (step 1) | SC_4048 (step 1), procedure described (step 2) | 1H NMR (DMSO d6): δ 7.37-7.32 (m, 4H), 7.27-7.24 (m, 1H), 3.40-3.36 (m, 4H), 3.16 (s, 2H), 2.92 (d, 2H), 2.69-2.66 (m, 2H), 2.19-2.07 (m, 4H), 1.97 (s, 6H), 1.79-1.75 (m, 2H), 1.37-1.29 (m, 4H), 1.26 (s, 6H), 0.93-0.92 (m, 1H), 0.47-0.42 (m, 2H), 0.27-0.24 (m, 2H). | 467.3 |
| SC_4073 | CIS-1-(Cyclopropyl-methyl)-8-dimethylamino-3-[2-(1,1-dioxo-[1,2]thiazolidin-2-yl)-2-methyl-propyl]-8-phenyl-1,3-diazaspiro[4.5]decan-2-one | INT-1052 | 3-chloropropane-1-sulfonyl chloride (step 1) | SC_4072 | 1H NMR (DMSO d6): δ 7.37-7.32 (m, 4H), 7.27-7.24 (m, 1H), 3.34-3.27 (m, 4H), 3.16-3.13 (m, 4H), 2.93 (d, 2H), 2.67-2.64 (m, 2H), 2.16-2.05 (m, 4H), 1.97 (s, 6H), 1.40-1.36 (m, 4H), 1.29 (s, 6H), 0.93-0.92 (m, 1H), 0.46-0.44 (m, 2H), 0.26-0.24 (m, 2H). | 503.3 |
| SC_4074 | CIS-8-Dimethylamino-1-[(1-hydroxy-cyclobutyl)-methyl]-3-[2-(4-hydroxy-tetrahydro-pyran-4-yl)-ethyl]-8-phenyl-1,3-diazaspiro[4.5]decan-2-one | INT-799 | 2-(4-(benzyloxy)tetrahydro-2H-pyran-4-yl)ethyl 4-methylbenzenesulfonate | SC_4052 | 1H NMR (DMSO d6): δ 7.37-7.34 (m, 4H), 7.27-7.24 (m, 1H), 6.17 (s, 1H), 4.28 (br s, 1H), 3.61-3.51 (m, 4H), 3.25 (s, 2H), 3.22-3.18 (m, 2H), 3.07 (s, 2H), 2.68-2.65 (m, 2H), 2.06-2.03 (m, 4H), 1.97 (s, 6H), 1.91-1.83 (m, 2H), 1.64-1.61 (m, 1H), 1.57-1.50 (m, 2H), 1.47-1.29 (m, 9H). | 486.4 |
| SC_4075 | CIS-1-(Cyclobutyl-methyl)-8-dimethylamino-3-[2-(4-hydroxy-1,1-dioxo-thian-4-yl)-ethyl]-8-phenyl-1,3-diazaspiro[4.5]decan-2-one | INT-987 | 4-allyl-4-(benzyloxy)tetrahydro-2H-thiopyran | SC_4071 | 1H NMR (DMSO d6): δ 7.37-7.23 (m, 5H), 4.76 (s, 1H), 3.16-3.10 (m, 6H), 3.01 (d, 2H), 2.91-2.88 (m, 2H), 2.67-2.63 (m, 2H), 2.02-1.82 (m, 14H), 1.80-1.65 (m, 5H), 1.58 (m, 2H), 1.42-1.35 (m, 2H), 1.28-1.26 (m, 2H), | 518.3 |

| Example | Chemical name | Reactant I | Reactant II | in analogy to method | ¹H NMR data | m/z (M + H)⁺ |
|---|---|---|---|---|---|---|
| SC_4076 | CIS-3-[(1-Acetyl-piperidin-4-yl)-methyl]-8-dimethylamino-8-phenyl-1,3-diazaspiro[4.5]decan-2-one | INT-1051 | acetyl chloride | SC_4048 | 1H NMR (DMSO d6): δ 7.37-7.23 (m, 5H), 6.72 (b s, 1H), 4.30-4.27 (m, 1H), 3.76-3.73 (m, 1H), 3.03 (s, 2H), 2.96-2.91 (m, 1H), 2.86-2.81 (m, 2H), 2.44 (m, 1H), 2.32 (m, 2H), 1.95-1.92 (m, 9H), 1.79-1.68 (m, 5H), 1.58-1.50 (m, 2H), 1.36-1.34 (m, 2H), 1.05-1.01 (m, 1H), 0.98-0.92 (m, 1H). | 413.3 |
| SC_4077 | CIS-8-Dimethylamino-3-(2-methylsulfonyl-ethyl)-1-(2-oxo-2-pyrrolidin-1-yl-ethyl)-8-phenyl-1,3-diazaspiro[4.5]decan-2-one | SC_4032 | 2-chloro-1-pyrrolidin-1-yl-ethanone | SC_4003 | 1H NMR (600 MHz, DMSO) δ 7.38-7.30 (m, 4H), 7.29-7.22 (m, 1H), 3.79 (s, 2H), 3.53-3.48 (m, 5H), 3.35-3.27 (m, 5H), 2.96 (s, 3H), 2.67-2.59 (m, 2H), 1.98-1.87 (m, 10H), 1.77 (p, 2H), 1.44-1.34 (m, 4H) | 491.3 |
| SC_4078 | TRANS-8-Dimethylamino-3-(2-methylsulfonyl-ethyl)-8-phenyl-1,3-diazaspiro[4.5]decan-2-one | INT-1059 | 1-bromo-2-methylsulfonyl-ethane | SC_4003 | 1HNMR (DMSO-d6, 400 MHz at 100 0 C.), δ (ppm) = 7.35-7.24 (m, 5H), 6.43 (s, 1H), 3.50 (t, 2H, J = 6.46 Hz), 3.31-3.22 (m, 4H), 2.95 (3H, merged with DMSO-water), 2.17 (bs, 2H), 1.99 (bs, 8H), 1.72 (bs, 2H), 1.45-1.39 (m, 2H). | 380.2 |
| SC_4079 | CIS-8-Dimethylamino-1-[(1-hydroxy-cyclobutyl)-methyl]-3-[2-(4-hydroxy-1,1-dioxo-thian-4-yl)-ethyl]-8-phenyl-1,3-diazaspiro[4.5]decan-2-one | INT-799 | 4-allyl-4-(benzyloxy)tetrahydro-2H-thiopyran | SC_4071 | 1H NMR (DMSO-d6): δ 7.37-7.33 (m, 4H), 7.27-7.24 (m, 1H), 6.13 (br s, 1H), 3.26 (s, 2H), 3.20-3.11 (m, 4H), 3.07 (s, 2H), 2.92-2.89 (m, 2H), 2.68-2.65 (m, 2H), 2.05-2.01 (m, 4H), 1.97 (s, 6H), 1.89-1.85 (m, 8H), 1.64-1.60 (m, 3H), 1.43-1.32 (m, 4H). | 534.3 |
| SC_4081 | CIS-N-[2-[1-(Cyclopropyl-methyl)-8-dimethylamino-2-oxo-8-phenyl-1,3-diazaspiro[4.5]decan-3-yl]-1,1-dimethyl-ethyl]-acetamide | INT-1052 | acetyl chloride | SC_4048 | 1H NMR (CDCl3, 400 MHz) = 7.53 (s, 1H), 7.36-7.28 (m, 5H), 3.28 (s, 2H), 3.08-3.04 (m, 4H), 2.66-2.63 (m, 2H), 2.31-2.25 (m, 2H), 2.03 (s, 6H), 1.87 (s, 3H), 1.51-1.41 (m, 4H), 1.35 (s, 6H), 1.02 (bs, 1H), 0.53-0.51 (m, 2H), 0.33-0.32 (m, 2H). | 441.3 |
| SC_4082 | CIS-N-[2-[1-(Cyclopropyl-methyl)-8-dimethylamino-2-oxo-8-phenyl-1,3-diazaspiro[4.5]decan-3-yl]-1,1-dimethyl-ethyl]-methanesulfonic acid amide | INT-1052 | methanesulfonyl chloride | SC_4048 | 1HNMR (CDCl3, 400 MHz), δ (ppm) = 7.34-7.25 (m, 5H), 6.16 (s, 1H), 3.31 (s, 2H), 3.10-3.05 (m, 4H), 2.97 (s, 3H), 2.67-2.63 (m, 2H), 2.32-2.25 (m, 2H), 2.03 (s, 6H), 1.51-1.43 (m, 4H), 1.37 (s, 6H), 1.01-0.99 (m, 1H), 0.52-0.50 (m, 2H), 0.32 (m, 2H). | 477.2 |
| SC_4083 | CIS-8-Dimethylamino-1-[(1-hydroxy-cyclobutyl)-methyl]-3-[2-(3-hydroxy-oxetan-3-yl)-ethyl]-8-phenyl-1,3-diazaspiro[4.5]decan-2-one | INT-799 | 3-(benzyloxy)-3-vinyloxetane | SC_4071 | 1H NMR (DMSO-d6): δ 7.36-7.33 (m, 4H), 7.26-7.25 (m, 1H), 6.12 (s, 1H), 5.65 (s, 1H), 4.39 (d, 2H), 4.33 (d, 2H), 3.29 (s, 2H), 3.17-3.14 (m, 2H), 3.08 (s, 2H), 2.68-2.65 (m, 2H), 1.91-1.86 (m, 4H), 1.69-1.59 (m, 1H), 1.43-1.40 (m, 4H), 1.38-1.31 (m, 1H). | 458.3 |
| SC_4085 | CIS-N-[2-[8-Dimethylamino-1-[(1-hydroxy-cyclobutyl)-methyl]-2-oxo-8-phenyl-1,3-diazaspiro[4.5]decan-3-yl]-1,1-dimethyl-ethyl]-acetamide | INT-1053 | acetyl chloride | SC_4048 | 1HNMR (DMSO-d6, 400 MHz), δ (ppm) = 7.48 (s, 1H), 7.32 (m, 5H), 5.95 (s, 1H), 3.29-3.26 (m, 4H), 3.06 (s, 2H), 2.65-2.62 (m, 2H), 2.05-1.99 (m, 4H), 1.93 (s, 6H), 1.85-1.82 (m, 2H), 1.67 (s, 3H), 1.60-1.59 (m, 1H), 1.43-1.26 (m, 5H), 1.13 (m, 6H). | 471.3 |

| Example | Chemical name | Reactant I | Reactant II | in analogy to method | 1H NMR data | m/z (M + H)+ |
|---|---|---|---|---|---|---|
| SC_4086 | CIS-N-[2-[8-Dimethylamino-1-[(1-hydroxy-cyclobutyl)-methyl]-2-oxo-8-phenyl-1,3-diazaspiro[4.5]decan-3-yl]-1,1-dimethyl-ethyl]-methanesulfonic acid amide | INT-1053 | methanesulfonyl chloride | SC_4048 | 1HNMR (DMSO-d6, 400 MHz), δ (ppm) = 7.35-7.25 (m, 5H), 6.90 (s, 1H), 5.95 (s, 1H), 3.44 (s, 2H), 3.14 (s, 2H), 2.92 (s, 3H), 2.68-2.66 (m, 3H), 2.08-2.03 (m, 4H), 1.97 (s, 6H), 1.88-1.85 (m, 2H), 1.47-1.31 (m, 7H), 1.21 (s, 6H). | 507.1 |
| SC_4087 | CIS-1-(Cyclopropyl-methyl)-8-dimethylamino-8-phenyl-3-(1-pyridin-3-yl-piperidin-4-yl)-1,3-diazaspiro[4.5]decan-2-one | SC_4054 | 3-bromopyridine | SC_4056 | 1H NMR (DMSO d6): δ 8.26 (d, 1H), 7.93 (m, 1H), 7.35-7.27 (m, 4H), 7.25-7.23 (m, 2H), 7.17-7.15 (m, 1H), 3.80 (d, 2H), 3.77-3.68 (m, 1H), 3.29-3.27 (m, 1H), 3.13 (s, 2H), 2.91 (d, 2H), 2.77 (t, 2H), 2.64-2.62 (m, 1H), 2.14 (t, 2H), 1.97 (s, 6H), 1.72-1.68 (m, 2H), 1.61-1.59 (m, 2H), 1.44 (t, 2H), 1.32 (d, 2H), 0.94-0.90 (m, 1H), 0.47-0.44 (m, 2H), 0.28-0.25 (m, 2H). | 488.4 |
| SC_4088 | CIS-1-(Cyclopropyl-methyl)-8-dimethylamino-8-(3-fluorophenyl)-3-(2-methylsulfonyl-ethyl)-1,3-diazaspiro[4.5]decan-2-one | INT-1063 | 1-bromo-2-methylsulfonyl-ethane | SC_4032 | 1H NMR (600 MHz, DMSO) δ 7.44-7.36 (m, 1H), 7.18 (d, 1H), 7.15 (dt, 1H), 7.10 (td, 1H), 3.51 (t, 2H), 3.32 (t, 2H), 3.23 (s, 2H), 2.96 (s, 3H), 2.93 (d, 2H), 2.68-2.60 (m, 2H), 2.18-2.10 (m, 2H), 2.00 (s, 6H), 1.45-1.33 (m, 4H), 0.93 (tdd, 1H), 0.50-0.41 (m, 2H), 0.31-.022 (m, 2H). | 452.2 |
| SC_4089 | CIS-1-(Cyclopropyl-methyl)-8-dimethylamino-8-phenyl-3-(1-pyridin-4-yl-piperidin-4-yl)-1,3-diazaspiro[4.5]decan-2-one | SC_4054 | 4-bromopyridine | SC_4056 | 1H NMR (DMSO d6): δ 8.09-8.08 (d, 2H), 7.33-7.30 (m, 4H), 7.24-7.23 (m, 1H), 6.77-76 (d, 2H), 3.98-3.96 (d, 2H), 3.80 (m, 1H), 3.09 (s, 2H), 2.91-2.84 (m, 4H), 2.62-2.59 (m, 2H), 2.15-2.10 (m, 2H), 1.94 (m, 6H), 1.59-1.56 (m, 4H), 1.42-1.37 (m, 2H), 1.33-1.29 (m, 2H), 0.91-0.90 (m, 1H), 0.46-0.43 (m, 2H), 0.26 (m, 2H). | 488.4 |
| SC_4090 | CIS-8-Dimethylamino-1-(1-hydroxy-cyclobutyl)-methyl]-3-[2-methyl-2-(2-oxo-pyrrolidin-1-yl)-propyl]-8-phenyl-1,3-diazaspiro[4.5]decan-2-one | INT-1053 | 4-chlorobutanoyl chloride (step 1) | SC_4072 | 1H NMR (DMSO-d6): δ 7.37-7.32 (m, 4H), 7.27-7.25 (m, 1H), 6.03 (s, 1H), 3.43 (s, 2H), 3.39 (t, 2H), 3.27 (s, 2H), 2.09 (s, 2H), 2.69-2.66 (m, 2H), 2.12 (t, 2H), 2.07-2.03 (m, 4H), 1.96 (s, 6H), 1.90-1.86 (m, 2H), 1.84-1.76 (m, 2H), 1.63-1.61 (m, 1H), 1.45-1.43 (m, 2H), 1.41 (m, 3H), 1.35-1.31 (m, 2H). | 497.4 |
| SC_4092 | TRANS-1-(Cyclobutyl-methyl)-8-dimethylamino-3-(2-methyl-2-methylsulfonyl-propyl)-8-phenyl-1,3-diazaspiro[4.5]decan-2-one | INT-1056 | — | SC_4091 | 1HNMR (DMSO-d6, 400 MHz), δ (ppm) 7.44-7.29 (m, 5H), 3.38 (s, 2H), 3.34 (s, 2H), 2.94 (s, 3H), 2.87 (s, 3H), 2.64 (d, 2H, J = 12.24 Hz), 2.60 (d, 2H, J = 7.24 Hz), 2.10-2.06 (m, 1H), 1.90 (s, 6H), 1.73-1.49 (m, 6H), 1.42-1.33 (m, 6H), 1.27 (s, 6H). | 476.3 |

| Example | Chemical name | Reactant I | Reactant II | in analogy to method | 1H NMR data | m/z (M + H)+ |
|---|---|---|---|---|---|---|
| SC_4093 | CIS-8-Dimethylamino-3-[2-(1,1-dioxo-[1,2]thiazolidin-2-yl)-2-methyl-propyl]-1-[(1-hydroxy-cyclobutyl)-methyl]-8-phenyl-1,3-diazaspiro[4.5]decan-2-one | INT-799 | 3-chloropropane-1-sulfonyl chloride (step 1) | SC_4072 | 1H NMR (DMSO-d6): δ 7.37-7.32 (m, 4H), 7.27-7.23 (m, 1H), 6.01 (s, 1H), 3.42 (s, 2H), 3.36-3.31 (m, 2H), 3.18-3.13 (m, 4H), 3.10 (s, 2H), 2.68-2.64 (m, 2H), 2.10-2.03 (m, 6H), 1.96 (s, 6H), 1.90-1.84 (m, 2H), 1.70-1.60 (m,1H), 1.47-1.44 (m, 2H), 1.41-1.35 (m, 3H), 1.32 (s, 6H). | 533.3 |
| SC_4094 | CIS-1-(Cyclopropyl-methyl)-8-dimethylamino-8-(3-fluorophenyl)-3-[(4-hydroxy-tetrahydro-pyran-4-yl)-methyl)]-1,3-diazaspiro[4.5]decan-2-one | INT-1063 | 1,6-dioxaspiro[2.5]octane | SC_4044 | 1H NMR (DMSO-d6): δ 7.34-7.29 (m, 1H), 7.06-7.04 (m, 1H), 6.99-6.95 (m, 2H), 4.43 (s, 1H), 3.82-3.78 (m, 2H), 3.74-3.71 (m, 2H), 3.28 (s, 2H), 3.14 (s, 2H), 3.06 (d, 2H), 2.59 (d, 2H),2.26 (t, 2H),2.05 (s, 6H),1.58-1.49 (m, 4H),1.47-1.42 (m, 4H),1.02 (m, 1H), 0.54-0.51 (m, 2H), 0.33-031 (m, 2H) | 460.3 |
| SC_4095 | CIS-8-Dimethylamino-1-[(1-hydroxy-cyclobutyl)-methyl]-8-phenyl-3-(1-pyrimidin-5-yl-piperidin-4-yl)-1,3-diazaspiro[4.5]decan-2-one | INT-1072 | 5-bromopyrimidine | SC_4056 | | 519.3 |
| SC_4097 | CIS-2-[8-Dimethylamino-3-(2-methylsulfonyl-ethyl)-2-oxo-8-phenyl-1,3-diazaspiro[4.5]decan-1-yl]-N,N-dimethyl-acetamide | SC_4032 | 2-chloro-N,N-dimethyl-acetamide | SC_4003 | 1H NMR (600 MHz, DMSO) δ 7.35 (d, 4H), 7.29-7.22 (m, 1H), 3.86 (s, 2H), 3.51 (t, 2H), 3.32 (t, 2H), 3.29 (s, 2H), 3.03 (s, 3H), 2.97 (s, 3H), 2.84 (s, 3H), 2.64 (d, 2H), 2.02-1.86 (m, 8H), 1.44-1.35 (m, 4H). | 465.3 |
| SC_4099 | CIS-1-(Cyclopropyl-methyl)-8-dimethylamino-8-(3-fluorophenyl)-3-(1-pyrimidin-5-yl)-1,3-diazaspiro[4.5]decan-2-one | INT-1073 | 5-bromopyrimidine | SC_4056 | | 507.3 |
| SC_4100 | CIS-1-(cyclopropylmethyl)-8-(3-fluorophenyl)-8-(methylamino)-3-(2-(methylsulfonyl)ethyl)-1,3-diazaspiro[4.5]decan-2-one | SC_4088 | | SC_4010 | | 438.2 |
| SC_4101 | CIS-1-(cyclopropylmethyl)-8-(dimethylamino)-3-((1-hydroxycyclobutyl)methyl)-8-phenyl-1,3-diazaspiro[4.5]decan-2-one | INT-983 | 1-oxaspiro[2.3]hexane | SC_4044 | | |
| SC_4102 | CIS-8-(dimethylamino)-8-(3-fluorophenyl)-3-((4-hydroxy-1,1-dioxidotetrahydro-2H-thiopyran-4-yl)methyl)-1-((1-hydroxycyclobutyl)methyl)-1,3-diazaspiro[4.5]decan-2-one | INT-1074 | 1-oxa-6-thiaspiro[2.5]octane (step 1) | SC_4044 (for step 1), step 2 of SC_4038 (for step 2) | | |
| SC_4103 | CIS-8-(dimethylamino)-1-((1-hydroxycyclobutyl)methyl)-3-(((4-hydroxytetrahydro-2H-pyran-4-yl)methyl)-1,3-diazaspiro[4.5]decan-2-one | INT-1074 | 1,6-dioxaspiro[2.5]octane | SC_4044 | | |

-continued

| Example | Chemical name | Reactant I | Reactant II | in analogy to method | 1H NMR data | m/z (M + H)+ |
|---|---|---|---|---|---|---|
| SC_4104 | CIS-1-(cyclopropylmethyl)-8-(dimethylamino)-8-(3-fluorophenyl)-3-((4-hydroxy-1,1-dioxidotetrahydro-2H-thiopyran-4-yl)methyl)-1,3-diazaspiro[4.5]decan-2-one | INT-1063 | 1-oxa-6-thiaspiro[2.5]octane (step 1) | SC_4044 (for step 1), step 2 of SC_4038 (for step 2) | | |
| SC_4105 | CIS-1-(cyclopropylmethyl)-8-(dimethylamino)-3-(oxetan-3-ylmethyl)-8-phenyl-1,3-diazaspiro[4.5]decan-2-one | INT-983 | 3-(bromomethyl)oxetane | SC_4032 | | |
| SC_4106 | CIS-8-(dimethylamino)-8-phenyl-3-((S)-1-(thiophen-3-yl)propan-2-yl)-1,3-diazaspiro[4.5]decan-2-one | INT-976 | (R)-1-(thiophen-3-yl)propan-2-yl methanesulfonate | SC_4032 | | 398.2 |
| SC_4107 | CIS-8-(dimethylamino)-8-phenyl-1,3-bis((1-(trifluoromethyl)cyclopropyl)methyl)-1,3-diazaspiro[4.5]decan-2-one | INT-976 | (1-(trifluoromethyl)cyclopropyl)methyl 4-methylbenzenesulfonate | SC_4032 | | |
| SC_4108 | CIS-8-(dimethylamino)-1,3-bis((1-fluorocyclopropyl)methyl)-8-phenyl-1,3-diazaspiro[4.5]decan-2-one | INT-976 | (1-fluorocyclopropyl)methyl 4-methylbenzenesulfonate | SC_4032 | | |
| SC_4109 | CIS-1-(cyclopropylmethyl)-8-(dimethylamino)-3-((3-(hydroxymethyl)oxetan-3-yl)methyl)-8-phenyl-1,3-diazaspiro[4.5]decan-2-one | INT-983 | (3-(bromomethyl)oxetan-3-yl)methanol | SC_4032 | | |
| SC_4110 | CIS-3-(3-aminooxetan-3-yl)methyl)-1-(cyclopropylmethyl)-8-(dimethylamino)-8-phenyl-1,3-diazaspiro[4.5]decan-2-one | INT-983 | tert-butyl (3-(bromomethyl)oxetan-3-yl)carbamate | SC_4034 (for step 1), step 2 of SC_4054 (for step 2) | | |
| SC_4111 | CIS-3-(8-(dimethylamino)-1-((1-fluorocyclopropyl)methyl)-2-oxo-8-phenyl-1,3-diazaspiro[4.5]decan-3-yl)-1,4-methylbenzenesulfonate | INT-983 | (1-cyanocyclobutyl)methyl 1,4-methylbenzenesulfonate | SC_4032 | | |
| SC_4112 | CIS-3-(8-(dimethylamino)-1-((1-fluorocyclopropyl)methyl)-2-oxo-8-phenyl-1,3-diazaspiro[4.5]decan-3-yl)-2,2-dimethylpropanenitrile | INT-976 | 2-cyano-2-methylpropyl 4-methylbenzenesulfonate (step 1), (1-fluorocyclopropyl)methyl 4-methylbenzenesulfonate (step 2) | SC_4032 (step 1), SC_4034 (step 2) | | |
| SC_5061 | CIS-3-[8-(Ethyl-methyl-amino)-2-oxo-8-phenyl-1,3-diazaspiro[4.5]decan-3-yl]-2,2-dimethyl-propionitrile | INT-797 | 3-bromo-2,2-dimethyl-propionitrile | step 1 of INT-897 | 1HNMR (DMSO-d6, 400 MHz, at 100 0 C.), δ (ppm) = 7.34-7.21 (m, 5H), 6.70 (bs, 1H), 3.28 (s, 2H), 3.19 (s, 2H), 2.32-2.24 (m, 4H), 2.06 (s, 3H), 1.87-1.82 (m, 4H), 1.45-1.37 (bs, 2H), 1.27 (s, 6H), 0.93 (t, 3H, 6.8 Hz). | 369.2 |

-continued

| Example | Chemical name | Reactant I | Reactant II | in analogy to method | 1H NMR data | m/z (M + H)+ |
|---|---|---|---|---|---|---|
| SC_5062 | CIS-3-(8-Dimethylamino-2-oxo-8-phenyl-1,3-diazaspiro[4.5]decan-3-yl)-2,2-dimethyl-propionitrile | INT-976 | 3-bromo-2,2-dimethyl-propionitrile | step 1 of INT-897 | 1HNMR (DMSO-d6, 400 MHz), δ (ppm) = 7.35-7.24 (m, 5H), 7.03 (bs, 1H), 3.25 (s, 2H), 3.15 (s, 2H), 2.32 (bs, 2H), 1.92 (s, 6H), 1.82 (bs, 4H), 1.38 (bs, 2H), 1.24 (s, 6H). | 355.2 |
| SC_5065 | CIS-3-[8-(Ethyl-methyl-amino)-1-methyl-2-oxo-8-phenyl-1,3-diazaspiro[4.5]decan-3-yl]-2,2-dimethyl-propionitrile | SC_5061 | methyl iodide | step 1 of INT-953 | 1HNMR (DMSO-d6, 400 MHz), δ (ppm) = 7.34-7.22 (m, 5H), 3.38 (s, 2H), 3.21 (s, 2H), 2.71-2.64 (m, 5H), 2.19-2.16 (m, 4H), 1.96 (s, 3H), 1.37-1.30 (m, 4H), 1.25 (s, 6H), 0.98 (t, 3H, J = 6.48 Hz). | 383.2 |
| SC_5068 | CIS-3-(8-Ethylamino-2-oxo-8-phenyl-1,3-diazaspiro[4.5]decan-3-yl)-2,2-dimethyl-propionitrile | INT-1008 | 3-bromo-2,2-dimethyl-propionitrile | step 1 of INT-897 | 1HNMR (DMSO-d6, 400 MHz), δ (ppm) = 7.42 (d, 12H, J = 7.32 Hz), 7.30 (t, 2H, J = 7.20 Hz), 7.17 (t, 1H, J = 7.12 Hz), 6.78 (s, 1H), 3.35 (s, 2H), 3.17 (s, 2H), 2.05 (m, 7H), 1.67-1.43 (m, 4H), 1.25 (s, 6H), 0.91 (t, 3H, J = 6.78 Hz). | 355.1 |
| SC_5080 | TRANS-3-[1-(Cyclopropyl-methyl)-8-dimethylamino-2-oxo-8-phenyl-1,3-diazaspiro[4.5]decan-3-yl]-2,2-dimethyl-propionitrile | INT 1059 | 3-bromo-2,2-dimethyl-propionitrile (step 1), cyclopropylmethyl-bromide (step 2) | step 1 of INT-897 (for step 1), step 1 of INT-953 (for step 2) | 1HNMR at 20° C. (DMSO-d6, 400 MHz), δ (ppm) = 7.44-7.28 (m, 5H), 3.46 (s, 2H), 3.23 (s, 2H), 2.72-2.66 (m, 2H), 2.57-2.55 (m, 2H), 1.91 (s, 6H), 1.55-1.45 (m, 6H), 1.27 (s, 6H), 0.51 (bs, 1H), 0.19-0.14 (m, 2H), (−0.22)-(−0.26) (m, 2H). | 409.2 |

Chemical Structure of All Examples
SC_4001
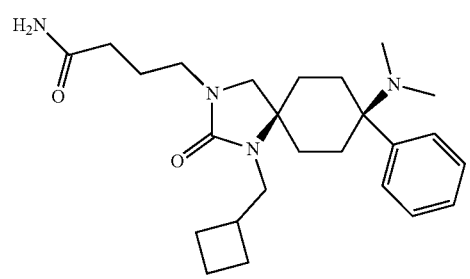
SC_4002
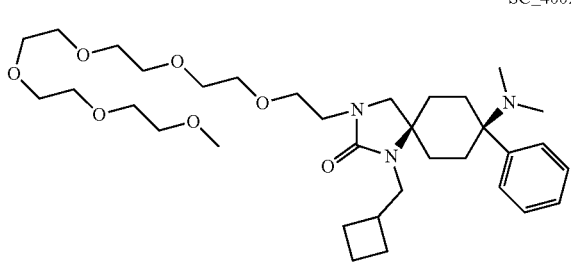
SC_4003
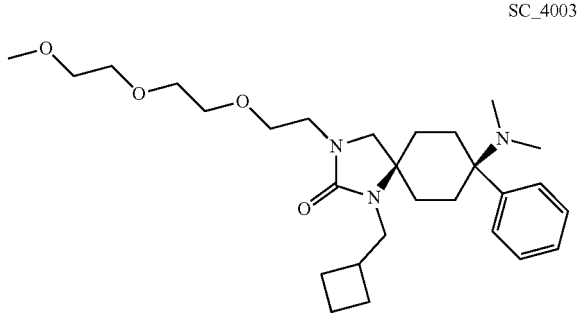
SC_4004
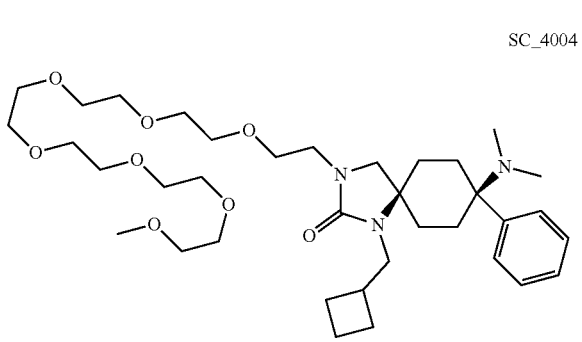
SC_4005
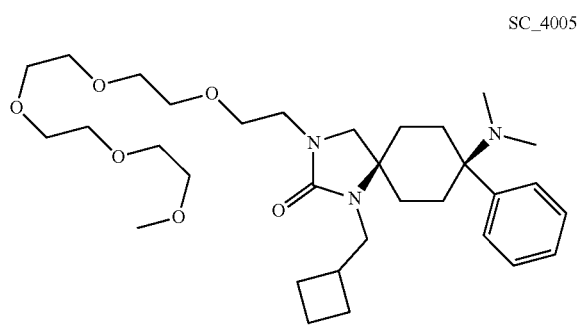
SC_4006
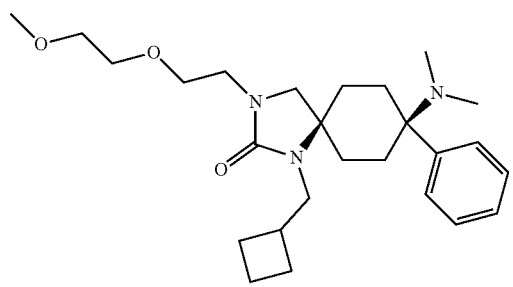
SC_4007
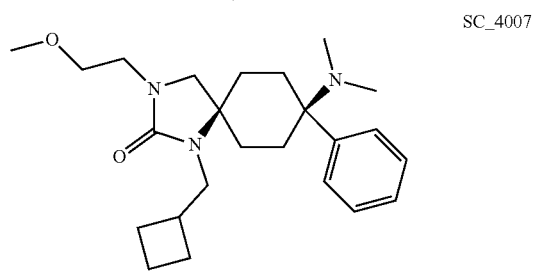
SC_4008
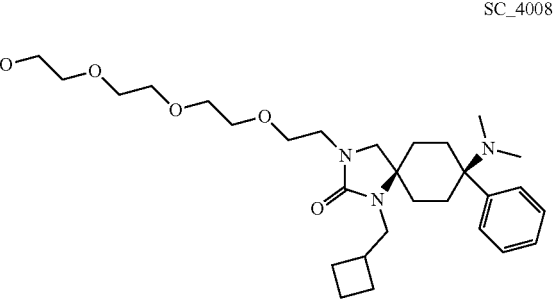
SC_4009
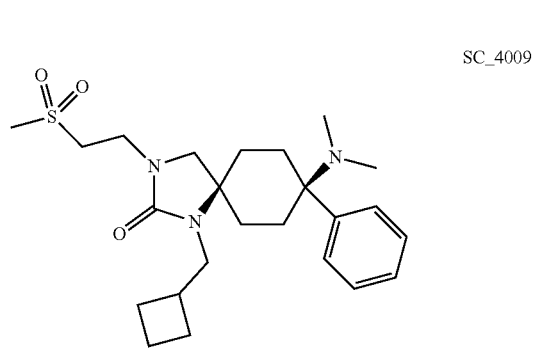
SC_4010
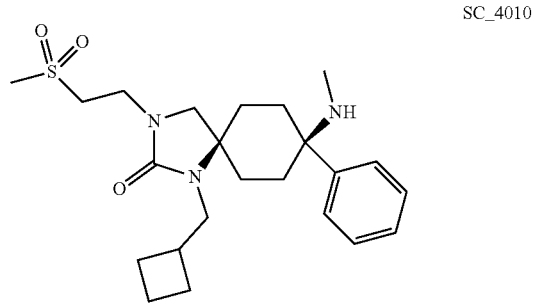

SC_4011 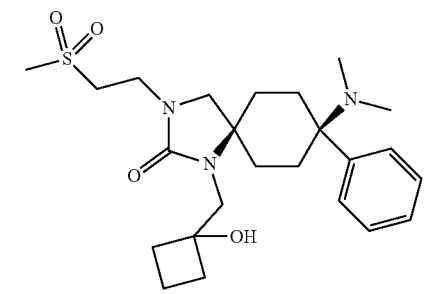
SC_4012 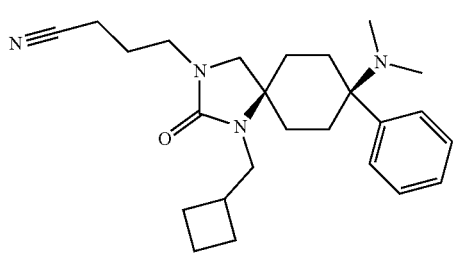
SC_4013 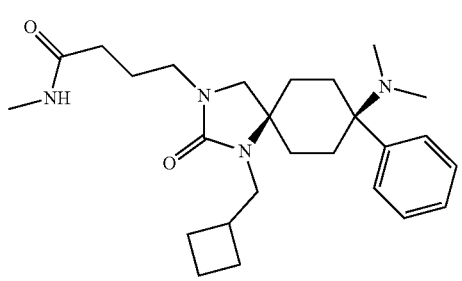
SC_4014 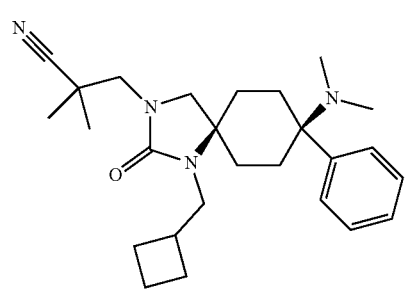
SC_4017 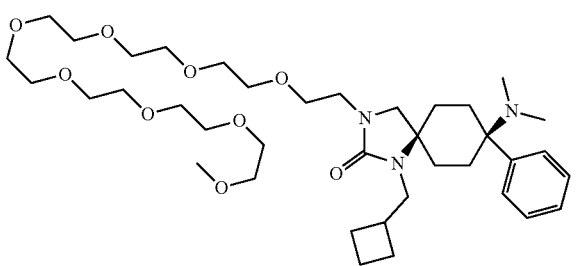
SC_4018 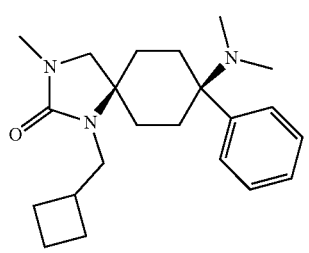
SC_4021 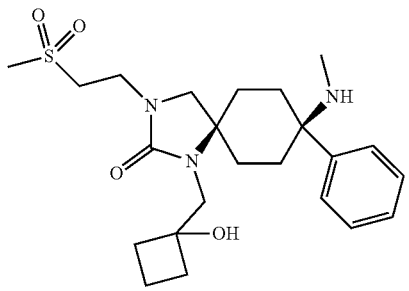
SC_4022 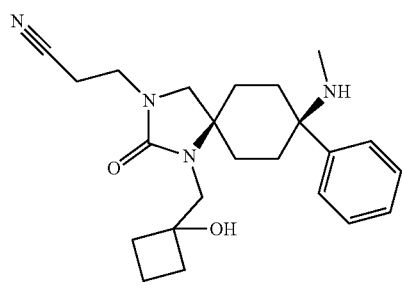
SC_4024 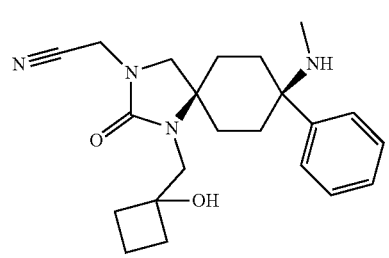
SC_4025 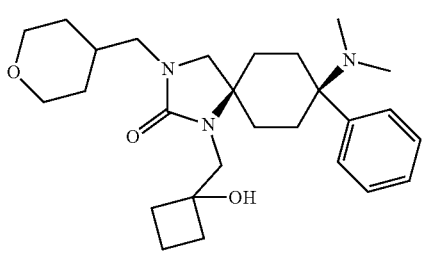
SC_4026 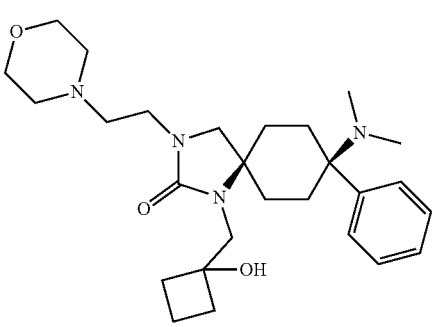
SC_4027 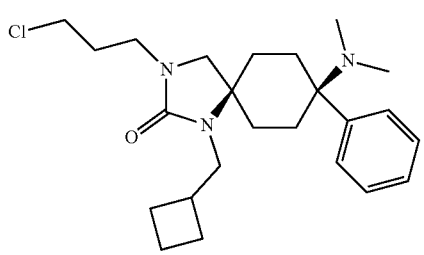

SC_4028
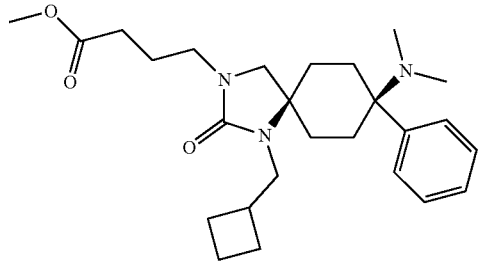
SC_4029
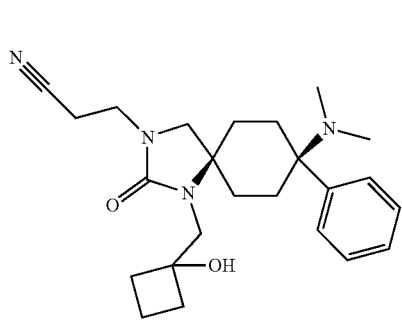
SC_4030
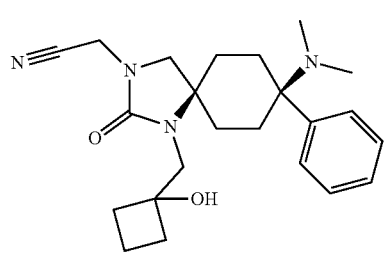
SC_4031
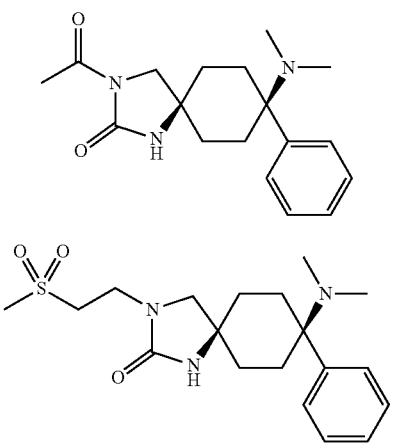
SC_4032
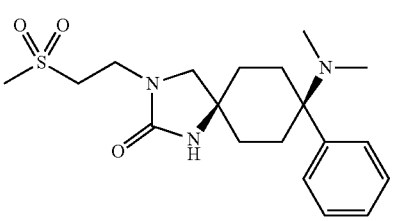
SC_4033
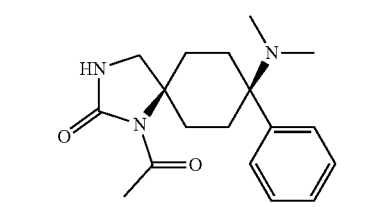
SC_4034
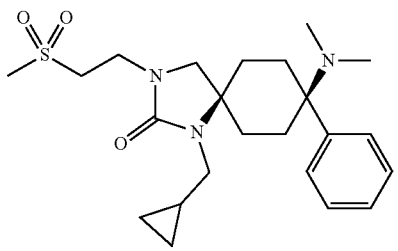
SC_4035
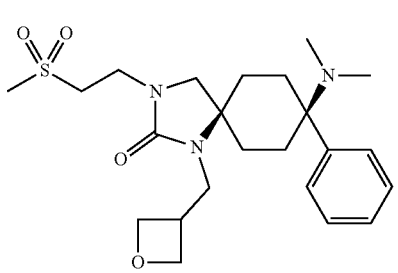
SC_4036
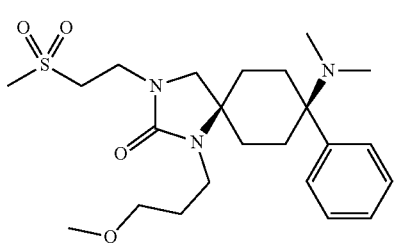
SC_4037
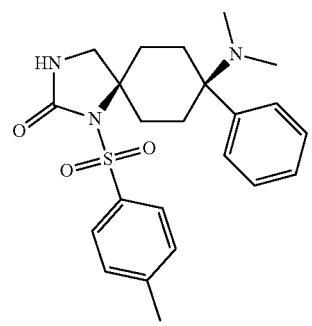
SC_4038
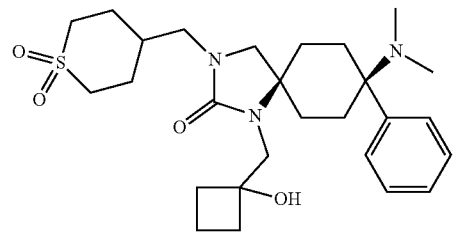

-continued
SC_4039
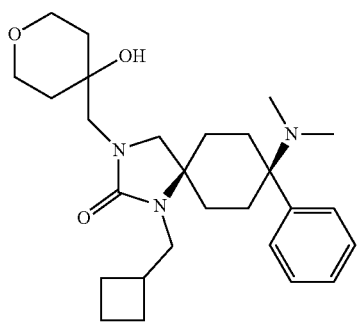
SC_4040
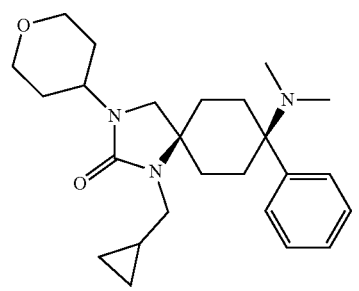
SC_4041
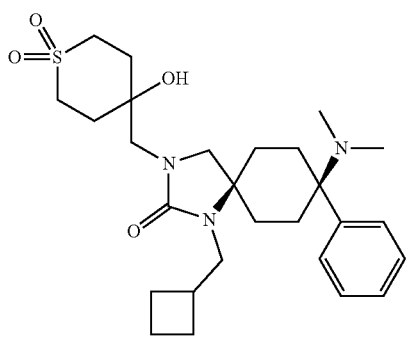
SC_4042
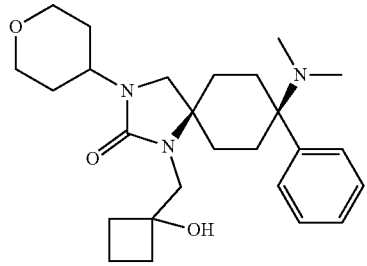
SC_4043
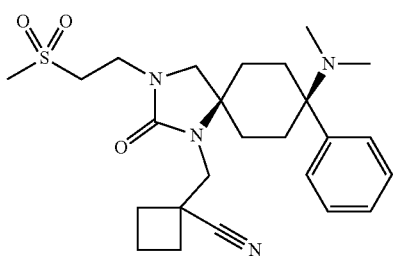
-continued
SC_4044
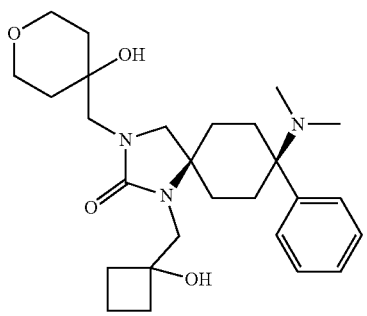
SC_4045
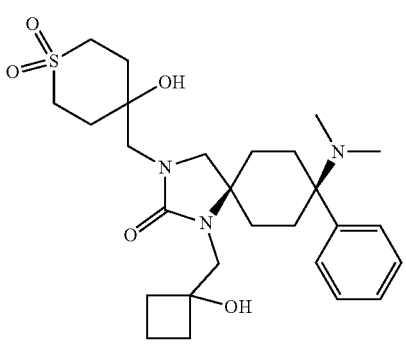
SC_4046
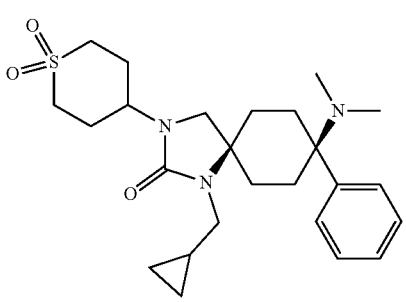
SC_4047
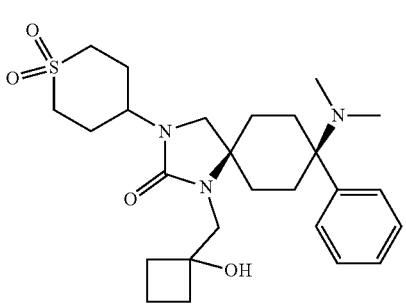
SC_4048
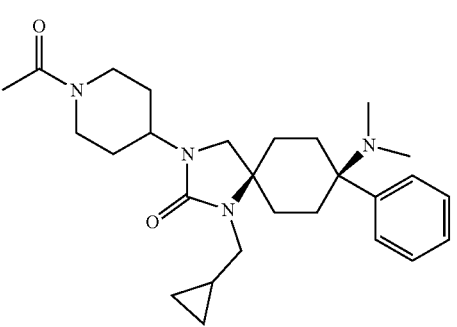

SC_4049
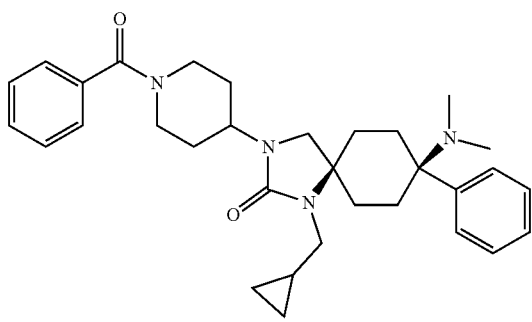
SC_4054
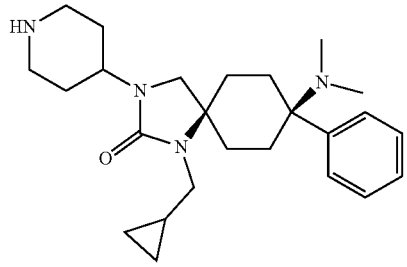
SC_4050
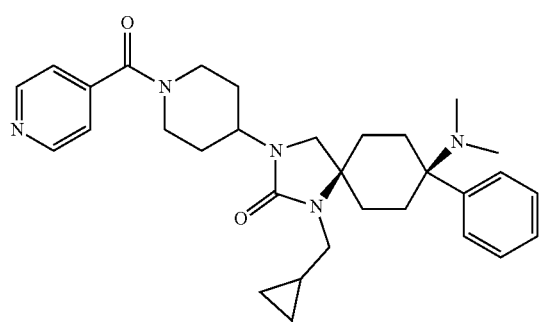
SC_4055
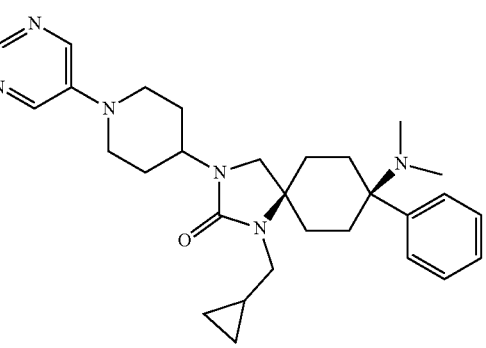
SC_4051
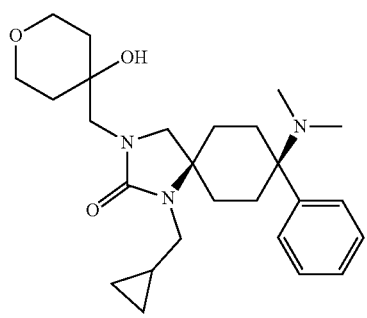
SC_4056
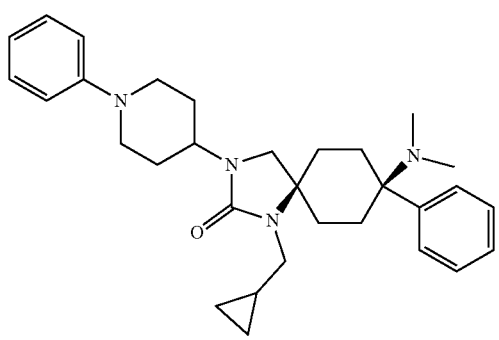
SC_4052
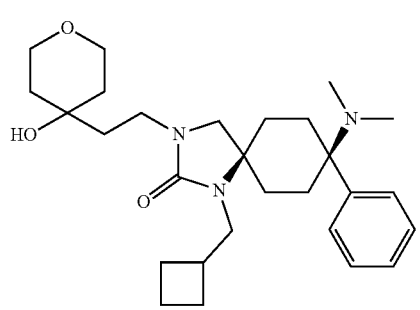
SC_4057
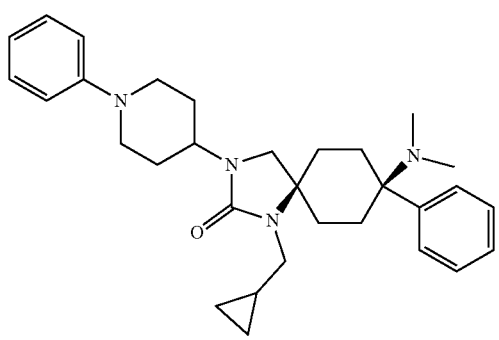
SC_4053
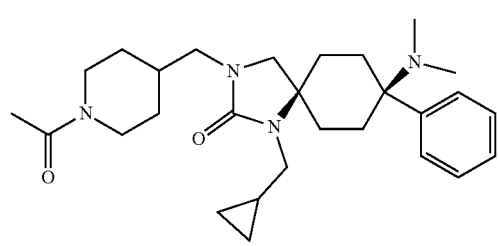
SC_4058
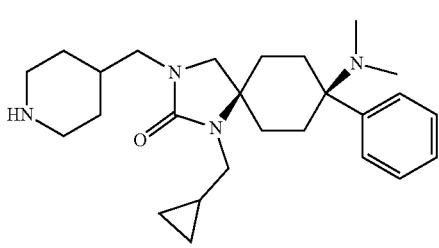

SC_4059
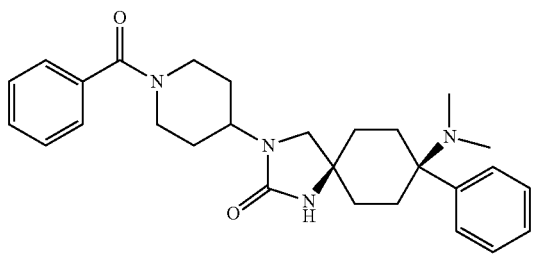
SC_4060
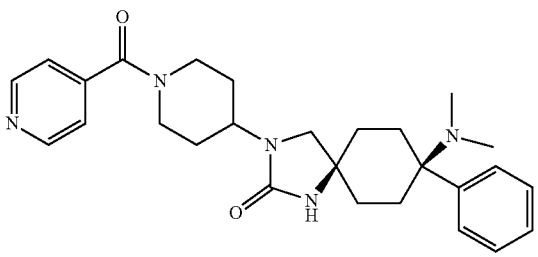
SC_4061
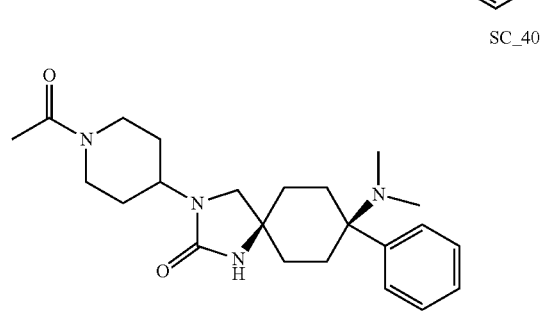
SC_4062
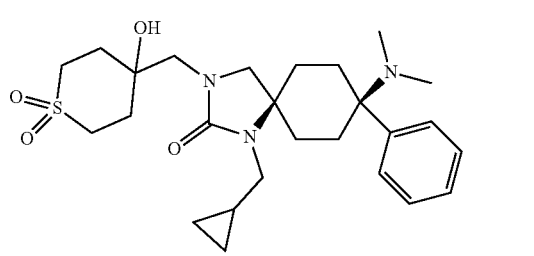
SC_4063
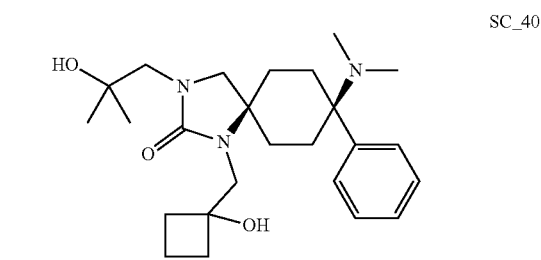
SC_4064
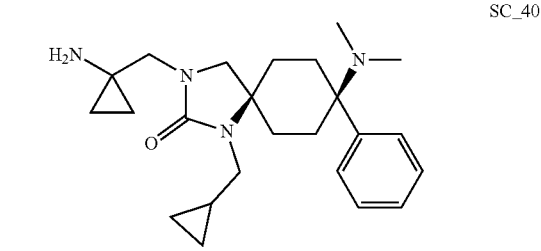
SC_4066
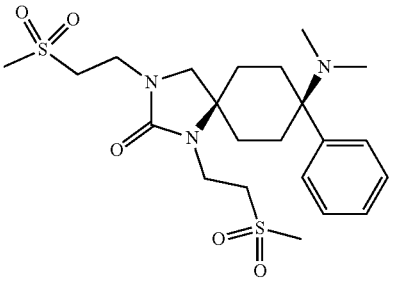
SC_4067
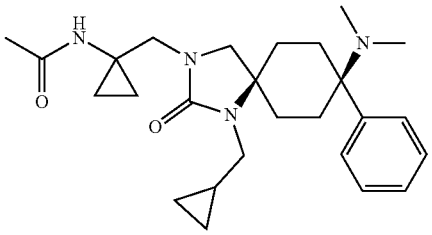
SC_4068
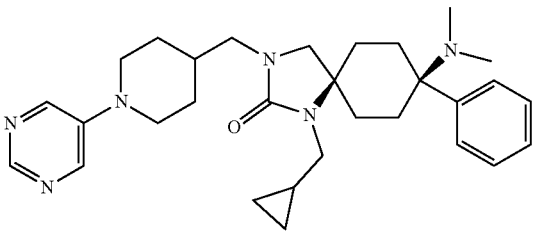
SC_4069
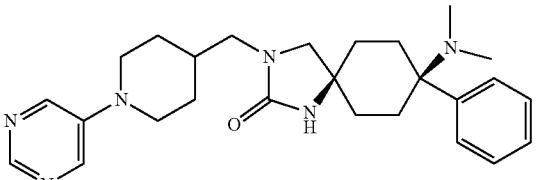
SC_4070
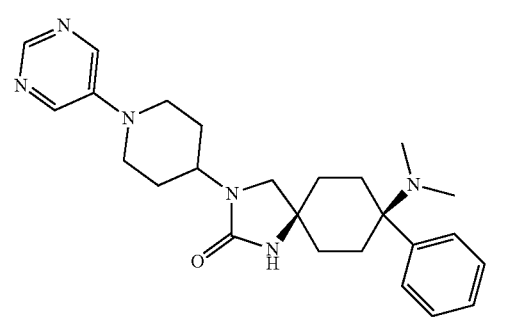
SC_4071
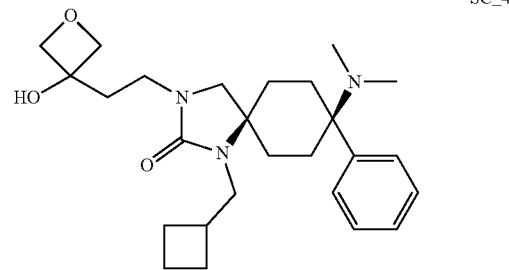

-continued
SC_4072
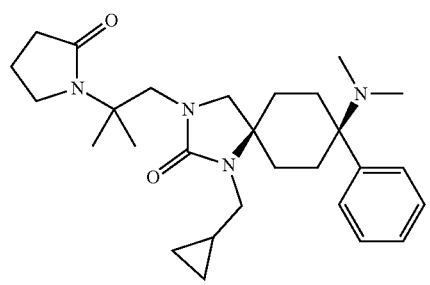
SC_4073
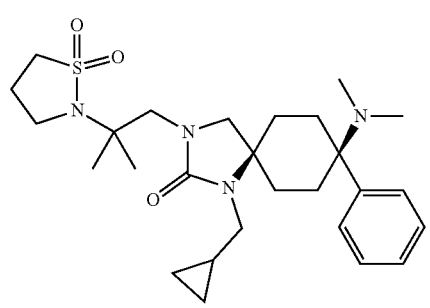
SC_4074
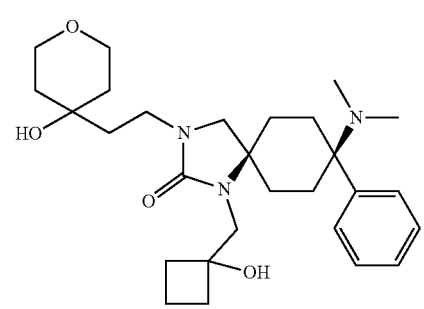
SC_4075
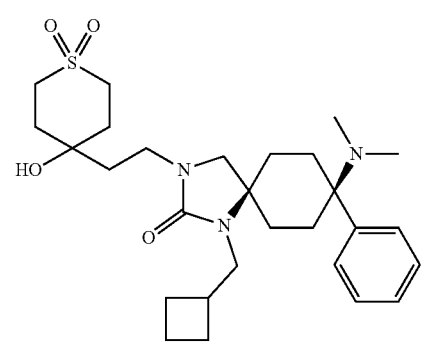
SC_4076
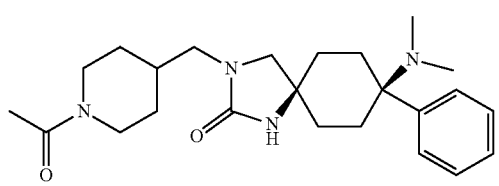
-continued
SC_4077
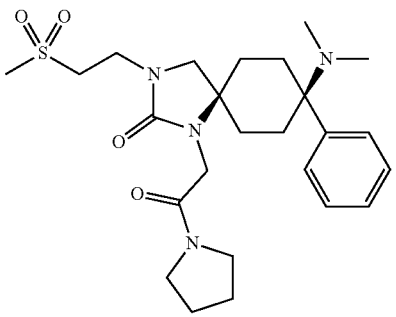
SC_4078
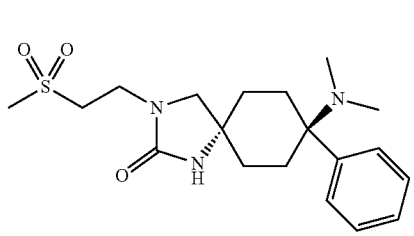
SC_4079
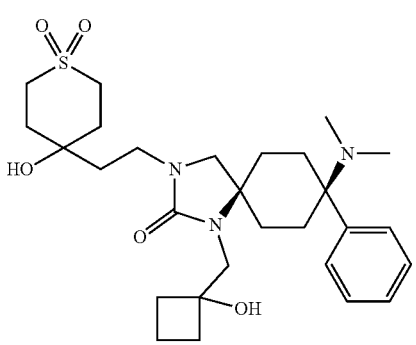
SC_4080
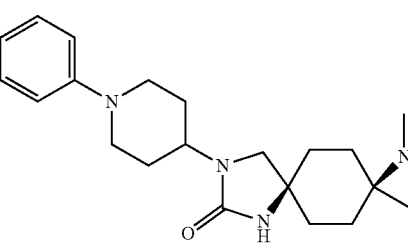
SC_4081
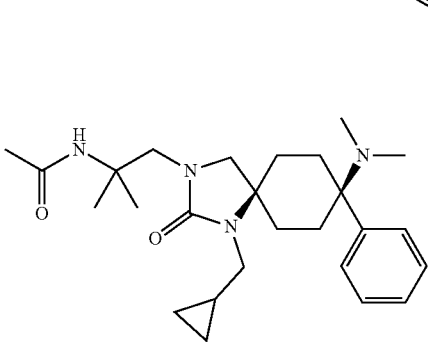

SC_4082
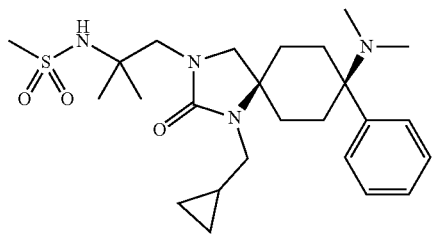
SC_4083
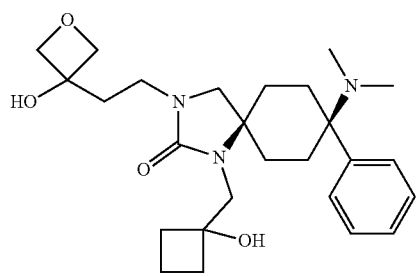
SC_4084
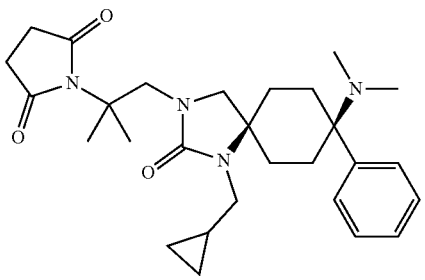
SC_4085
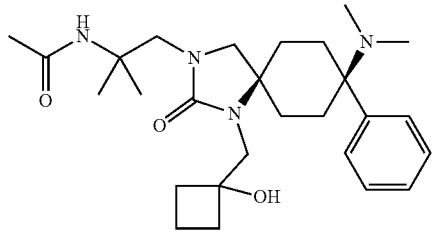
SC_4086
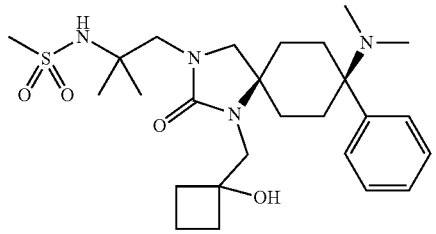
SC_4087
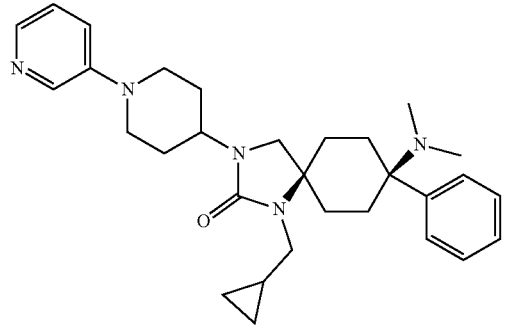
SC_4088
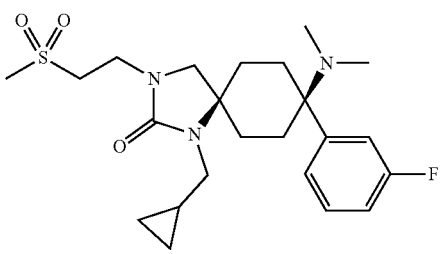
SC_4089
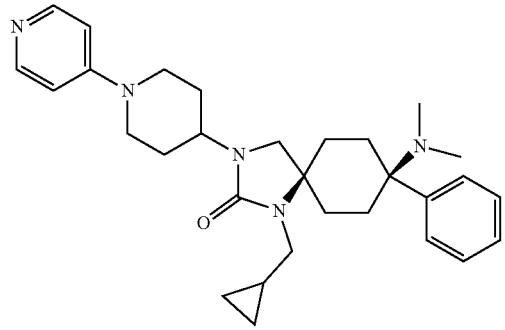
SC_4090
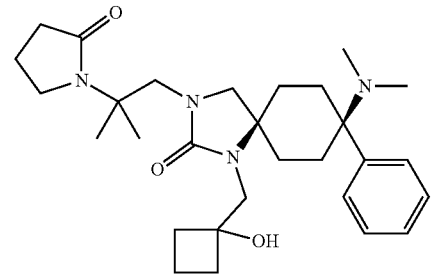
SC_4091
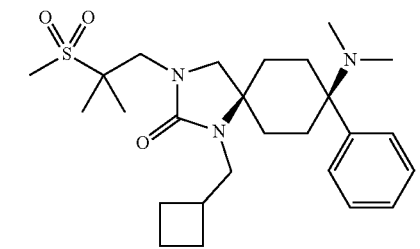

-continued
SC_4092
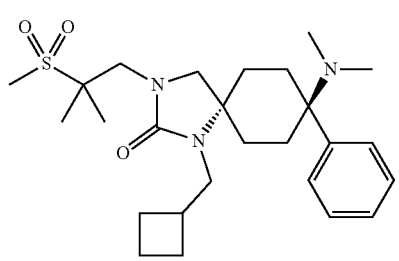
SC_4097
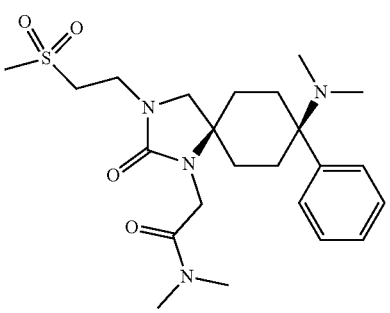
SC_4093
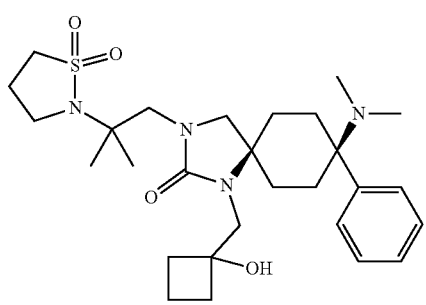
SC_4098
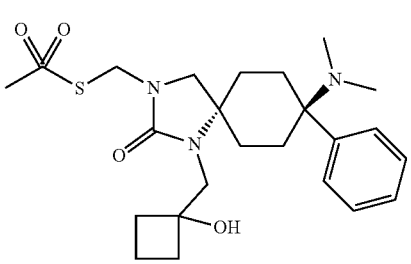
SC_4094
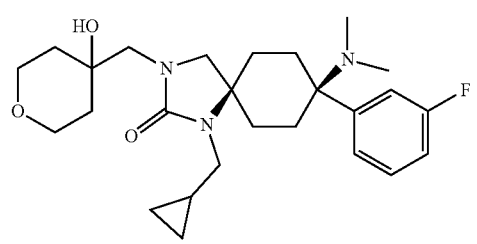
SC_4099
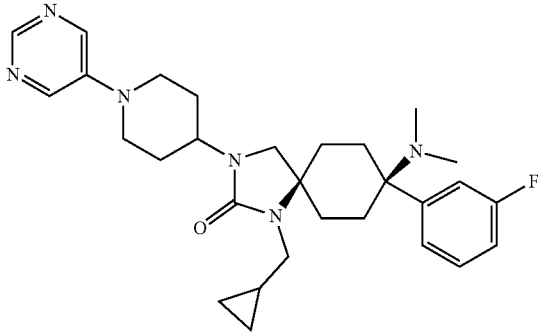
SC_4095
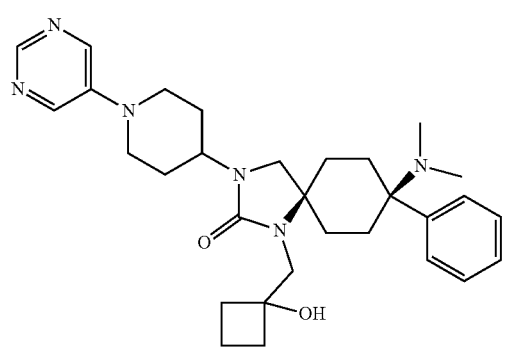
SC_4100
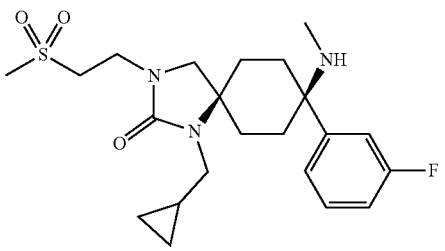
SC_4096
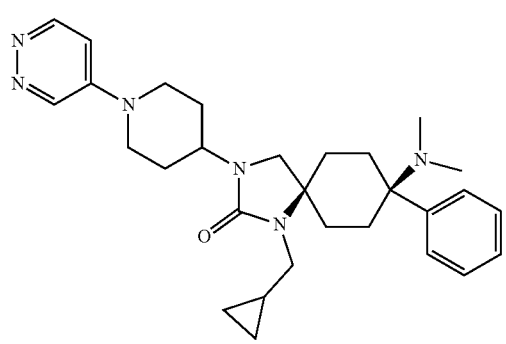
SC_4101
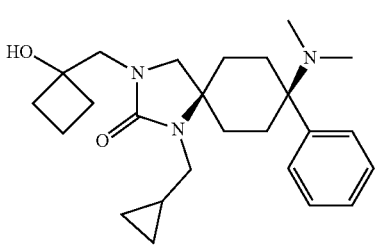

SC_4102
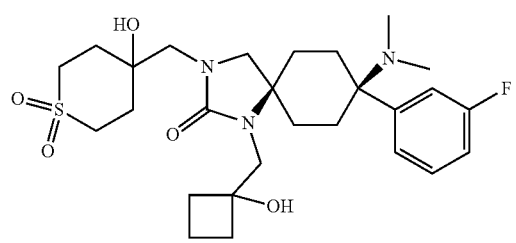
SC_4103
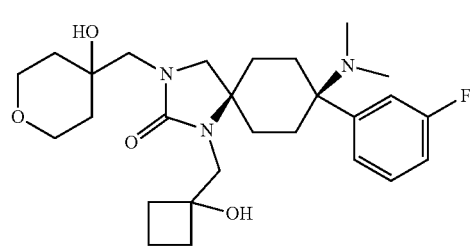
SC_4104
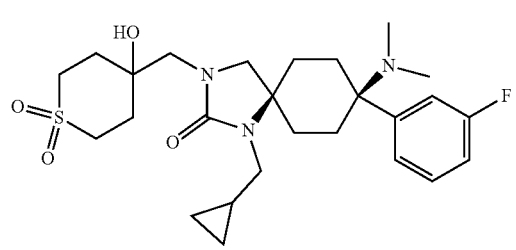
SC_4105
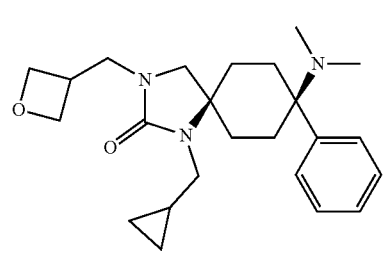
SC_4106
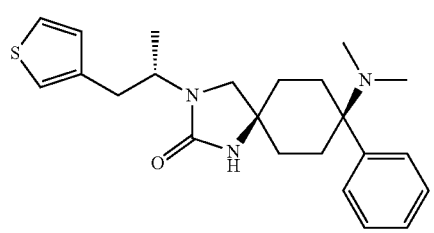
SC_4107
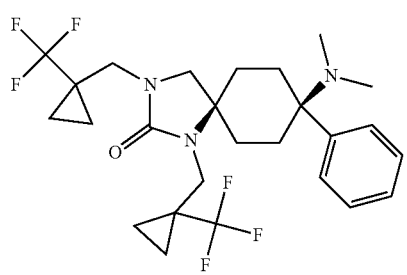
SC_4108
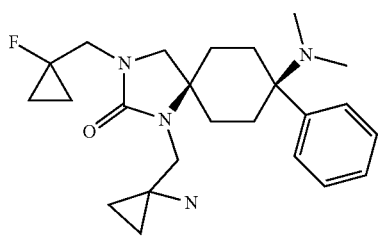
SC_4109
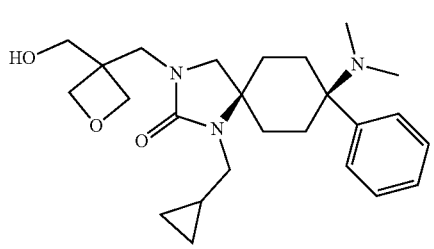
SC_4110
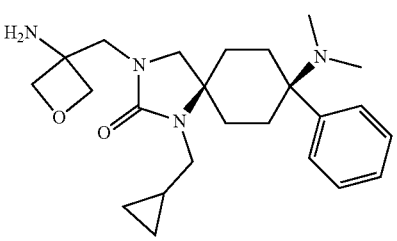
SC_4111
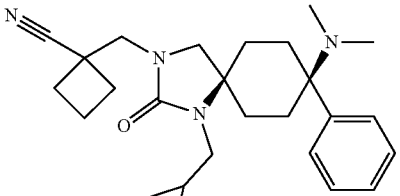
SC_4112
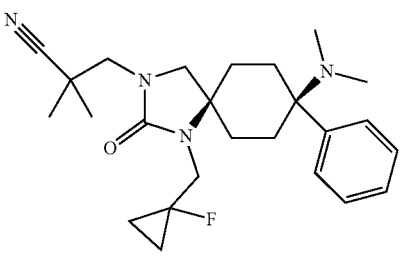
SC_5061
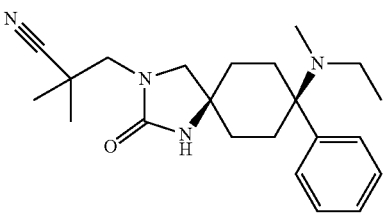

-continued

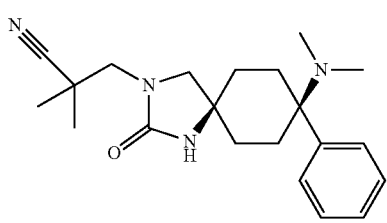
SC_5062

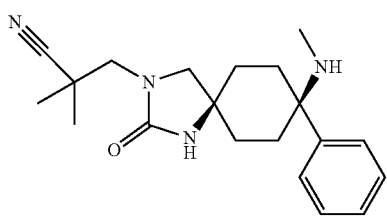
SC_5063

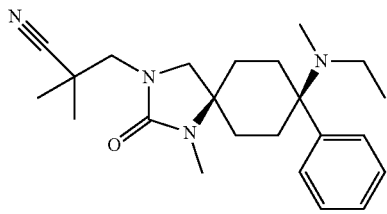
SC_5065

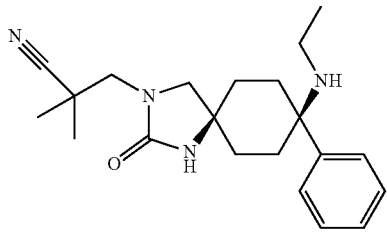
SC_5068

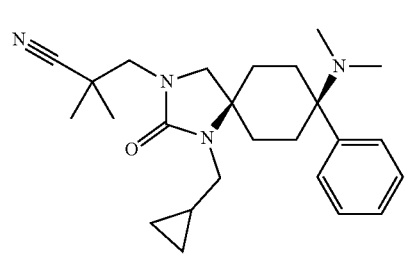
SC_5075

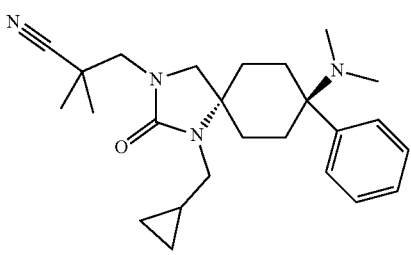
SC_5080

Pharmacological Investigations

Functional investigation on the human mu-opioid receptor (hMOP), human kappa-opioid receptor (hKOP), human delta-opioid receptor (hDOP), and human nociceptin/orphanin FQ peptide receptor (hNOP)

Human Mu-Opioid Peptide (hMOP) Receptor Binding Assay

The hMOP receptor binding assay was performed as homogeneous SPA-assay (scintillation proximity assay) using the assay buffer 50 mM TRIS-HCl (pH 7.4) supplemented with 0.052 mg/ml bovine serum albumin (Sigma-Aldrich Co. St. Louis. Mo.). The final assay volume (250 µl/well) included 1 nM of [N-allyl-2.3-$^3$H]naloxone as ligand (PerkinElmer Life Sciences. Inc. Boston. Mass. USA). and either test compound in dilution series or 25 µM unlabelled naloxone for determination of unspecific binding. The test compound was diluted with 25% DMSO in H$_2$O to yield a final 0.5% DMSO concentration. which also served as a respective vehicle control. The assay was started by adding wheat germ agglutinin coated SPA beads (GE Healthcare UK Ltd. Buckinghamshire. UK) which had been preloaded with hMOP receptor membranes (PerkinElmer Life Sciences. Inc. Boston. Mass. USA). After incubation for 90 minutes at RT and centrifugation for 20 minutes at 500 rpm the signal rate was measured by means of a 1450 Microbeta Trilux ß-counter (PerkinElmer Life Sciences/ Wallac. Turku. Finland). Half-maximal inhibitory concentration (IC50) values reflecting 50% displacement of [$^3$H] naloxone-specific receptor binding were calculated by nonlinear regression analysis and Ki values were calculated by using the Cheng-Prusoff equation. (Cheng and Prusoff. 1973).

Human Kappa-Opioid Peptide (hKOP) Receptor Binding Assay

The hKOP receptor binding assay is run as homogeneous SPA-assay (scintillation proximity assay) using the assay buffer 50 mM TRIS-HCl (pH 7.4) supplemented with 0.076 mg BSA/ml. The final assay volume of 250 µl per well includes 2 nM of [$^3$H]U69,593 as ligand, and either test compound in dilution series or 100 µM unlabelled naloxone for determination of unspecific binding. The test compound is diluted with 25% DMSO in H$_2$O to yield a final 0.5% DMSO concentration which serves as respective vehicle control, as well. The assays are started by the addition of wheat germ agglutinin coated SPA beads (1 mg SPA beads/ 250 µl final assay volume per well) which has been preloaded for 15 minutes at room temperature with hKOP receptor membranes (14.8 µg/250 µl final assay volume per well). After short mixing on a mini-shaker, the microtiter plates are covered with a lid and the assay plates are incubated for 90 minutes at room temperature. After this incubation, the microtiter plates are sealed with a topseal and centrifuged for 20 minutes at 500 rpm. The signal rate is measured after a short delay of 5 minutes by means of a 1450 Microbeta Trilux ß-counter (PerkinElmer Life Sciences/ Wallac, Turku, Finland). Half-maximal inhibitory concentration (IC50) values reflecting 50% displacement of [$^3$H] U69.593-specific receptor binding are calculated by nonlinear regression analysis and $K_i$ values are calculated by using the Cheng-Prusoff equation, (Cheng and Prusoff, 1973).

Human Delta-Opioid Peptide (hDOP) Receptor Binding Assay

The hDOP receptor binding assay is performed as homogeneous SPA-assay using the assay buffer 50 mM TRIS-HCl, 5 mM MgCl$_2$ (pH 7.4). The final assay volume (250 µl/well) includes 1 nM of [Tyrosyl-3,5-$^3$H]2-D-Ala-deltorphin II as ligand, and either test compound in dilution series or 10 µM unlabelled naloxone for determination of unspecific binding. The test compound is diluted with 25% DMSO in H$_2$O to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hDOP receptor membranes (15.2 µg/250 µl final assay volume per well). After short mixing on a mini-shaker, the microtiter plates are covered with a lid and the assay plates are incubated for 120 minutes at room temperature and centrifuged for 20 minutes at 500 rpm. The signal rate is measured by means of a 1450 Microbeta Trilux ß-counter (PerkinElmer Life Sciences/Wallac, Turku, Finland). Half-maximal inhibitory concentration (IC50) values reflecting 50% displacement of [Tyrosyl-3,5-$^3$H]2-D-Ala-deltorphin II-specific receptor binding are calculated by nonlinear regression analysis and $K_i$ values are calculated by using the Cheng-Prusoff equation, (Cheng and Prusoff, 1973).

Human Nociceptin/Orphanin FQ Peptide (hNOP) Receptor Binding Assay

The hNOP receptor binding assay was performed as homogeneous SPA-assay (scintillation proximity assay) using the assay buffer 50 mM TRIS-HCl. 10 mM $MgCl_2$. 1 mM EDTA (pH 7.4). The final assay volume (250 µl/well) included 0.5 nM of [leucyl-$^3$H]nociceptin as ligand (PerkinElmer Life Sciences. Inc. Boston. Mass. USA). and either test compound in dilution series or 1 µM unlabelled nociceptin for determination of unspecific binding. The test compound was diluted with 25% DMSO in $H_2O$ to yield a final 0.5% DMSO concentration. which also served as a respective vehicle control. The assay was started by adding wheat germ agglutinin coated SPA beads (GE Healthcare UK Ltd. Buckinghamshire. UK) which had been preloaded with hMOP receptor membranes (PerkinElmer Life Sciences. Inc. Boston. Mass. USA).

After incubation for 60 minutes at RT and centrifugation for 20 minutes at 500 rpm the signal rate was measured by means of a 1450 Microbeta Trilux ß-counter (PerkinElmer Life Sciences/Wallac. Turku. Finland). Half-maximal inhibitory concentration (IC50) values reflecting 50% displacement of [$^3$H]nociceptin-specific receptor binding were calculated by nonlinear regression analysis and $K_i$ values were calculated by using the Cheng-Prusoff equation. (Cheng and Prusoff. 1973).

| Example | hNOP Ki [nM] | hMOP Ki [nM] or % µinhibition at 1M |
|---|---|---|
| SC_4001 | 2.3 | 80.5 |
| SC_4002 | 28 | 755 |
| SC_4003 | 7.7 | 39.5 |
| SC_4004 | 44 | 305 |
| SC_4005 | 19 | 64.5 |
| SC_4006 | 3.6 | 16 |
| SC_4007 | 2.6 | 58 |
| SC_4008 | 7.3 | 69.8 |
| SC_4009 | 1.1 | 37.4 |
| SC_4010 | 9.5 | 87 |
| SC_4011 | 13 | 210 |
| SC_4012 | 1.6 | 99.7 |
| SC_4013 | 5.8 | 40.5 |
| SC_4014 | 2.1 | 84 |
| SC_4017 | 45 | 375 |
| SC_4018 | 1.3 | 19.7 |
| SC_4021 | 83 | 636.7 |
| SC_4022 | 140 | 555 |
| SC_4024 | 155 | 285 |
| SC_4025 | 26 | 206 |
| SC_4026 | 57 | 643 |
| SC_4031 | 119 | 1430 |
| SC_4032 | 345 | 8530 |
| SC_4033 | — | 15%@1 µM |
| SC_4034 | 11 | 245 |
| SC_4035 | 69 | 1580 |
| SC_4036 | 8 | 210 |
| SC_4037 | 815 | 185 |
| SC_4038 | 69 | 1290 |
| SC_4039 | 3 | 165 |
| SC_4040 | 19 | 270 |
| SC_4041 | 4 | 125 |
| SC_4042 | 11 | 290 |
| SC_4043 | 4 | 124 |
| SC_4044 | 19 | 1065 |
| SC_4045 | 17 | 415 |
| SC_4046 | 15 | 655 |
| SC_4047 | 8 | 265 |
| SC_4048 | 46 | 805 |
| SC_4049 | 11 | 220 |
| SC_4050 | 19 | 255 |
| SC_4051 | 21 | 770 |
| SC_4052 | 3 | 175 |
| SC_4053 | 34 | 1350 |
| SC_4054 | 26 | 1305 |
| SC_4055 | 54 | 1865 |
| SC_4056 | 10 | 1755 |
| SC_4057 | 3 | 1050 |
| SC_4058 | 15 | 540 |
| SC_4059 | 710 | 9%@1 µM |
| SC_4060 | 1170 | 5%@1 µM |
| SC_4061 | 710 | 9%@1 µM |
| SC_4062 | 27 | 1810 |
| SC_4063 | 15 | 2910 |
| SC_4064 | 5 | 495 |
| SC_4066 | 40 | 3045 |
| SC_4067 | 12 | 615 |
| SC_4068 | 13 | 985 |
| SC_4069 | 140 | 6900 |
| SC_4070 | 140 | 8% |
| SC_4071 | 1 | 63 |
| SC_4072 | 10 | 255 |
| SC_4073 | 6 | 300 |
| SC_4074 | 12 | 460 |
| SC_4075 | 1 | 39 |
| SC_4076 | 235 | 17% |
| SC_4077 | 75 | 3230 |
| SC_4078 | 125 | 74 |
| SC_4079 | 6 | 415 |
| SC_4080 | 145 | 4145 |
| SC_4081 | 10 | 765 |
| SC_4082 | 10 | 270 |
| SC_4083 | 10 | 235 |
| SC_4084 | 118 | 2465 |
| SC_4085 | 3 | 495 |
| SC_4086 | 6 | 570 |
| SC_4087 | 12 | 535 |
| SC_4088 | 6 | 935 |
| SC_4089 | 64 | 275 |
| SC_4090 | 6 | 520 |
| SC_4091 | 0.4 | 76 |
| SC_4092 | 16 | 17 |
| SC_4093 | 17 | 1000 |
| SC_4094 | 23 | 1980 |
| SC_4095 | 8 | 630 |
| SC_4096 | 36 | 330 |
| SC_4097 | 114 | 4355 |
| SC_4098 | 395 | 96 |
| SC_5061 | 705 | 6%@1 µM |
| SC_5062 | 84 | 2925 |
| SC_5063 | 690 | 4%@1 µM |
| SC_5065 | 0%@1 µM (DOP 40%) | 13%@1 µM |
| SC_5068 | 0%@1 µM (KOP 40%) | 8%@1 µM |
| SC_5075 | 10 | 305 |
| SC_5080 | 24 | 230 |

Protocol for [$^{35}$S]GTPγS Functional NOP/MOP/KOP/DOP Assays

Cell membrane preparations of CHO-K1 cells transfected with the human MOP receptor (Art.-No. RBHOMM) or the human DOP receptor (Art.-No. RBHODM), and HEK293 cells transfected with the human NOP receptor (Art.-No. RBHORLM) or the human KOP receptor (Art.-No. 6110558) are available from PerkinElmer (Waltham, Mass.). Membranes from CHO-K1 cells transfected with the human nociceptin/orphanin FQ peptide (hNOP) receptor (Art.-No. 93-0264C$_2$, DiscoveRx Corporation, Freemont, Calif.) are also used. [$^{35}$S]GTPγS (Art.-No. NEG030H; Lot-No. #0112, #0913, #1113 calibrated to 46.25 TBq/mmol) is available from PerkinElmer (Waltham, Mass.).

The [$^{35}$S]GTPγS assays are carried out essentially as described by Gillen et al (2000). They are run as homogeneous scintillation proximity (SPA) assays in microtiter luminescence plates, where each well contains 1.5 mg of WGA-coated SPA-beads. To test the agonistic activity of test compounds on recombinant hNOP, hMOP, hDOP, and hKOP receptor expressing cell membranes from CHO-K1 or HEK293 cells, 10 or 5 μg membrane protein per assay are incubated with 0.4 nM [$^{35}$S]GTPγS and serial concentrations of receptor-specific agonists in buffer containing 20 mM HEPES pH 7.4, 100 mM NaCl, 10 mM MgCl2, 1 mM EDTA, 1 mM dithiothreitol, 1.28 mM NaN$_3$, and 10 μM GDP for 45 min at room temperature. The microtiter plates are then centrifuged for 10 min at 830 to sediment the SPA beads. The microtiter plates are sealed and the bound radioactivity [cpm] is determined after a delay of 15 min by means of a 1450 Microbeta Trilux (PerkinElmer, Waltham, Mass.).

The unstimulated basal binding activity (UBS$_{obs}$ [cpm]) is determined from 12 unstimulated incubates and is set as 100% basal binding. For determination of the potency and the efficacy, the arithmetic mean of the observed total [$^{35}$S]GTPγS binding (TB$_{obs}$ [cpm]) of all incubates (duplicates) stimulated by the receptor-specific agonists (i.e. N/OFQ, SNC80, DAMGO, or U69,593) are transformed in percent total binding (TB$_{obs}$ [%]) relative to the basal binding activity (i.e. 100% binding). The potency (EC$_{50}$) of the respective agonist and its maximal achievable total [$^{35}$S]GTPγS binding (TB$_{calc}$ [%]) above its calculated basal binding (UBS$_{calc}$ [%]) are determined from its transformed data (TB$_{obs}$ [%]) by means of nonlinear regression analysis with XLfit for each individual concentration series. Then the difference between the calculated unstimulated [$^{35}$S]GTPγS binding (UBS$_{calc}$ [%]) and the maximal achievable total [$^{35}$S]GTPγS binding (TB$_{calc}$ [%]) by each tested agonist is determined (i.e. B1$_{calc}$ [%]). This difference (B1$_{calc}$[%]) as a measure of the maximal achievable enhancement of [$^{35}$S] GTPγS binding by a given agonist is used to calculate the relative efficacy of test compounds versus the maximal achievable enhancement by a receptor-specific full agonist, e.g. N/OFQ (B1$_{calc-N/OFQ}$ [%]) which is set as 100% relative efficacy for the hNOP receptor. Likewise, the percentage efficacies of test compounds at the hDOP, hMOP, or hKOP receptor are determined versus the calculated maximal enhancement of [$^{35}$S]GTPγS binding by the full agonists SNC80 (B1$_{calc-SNC80}$ [%]), DAMGO (B1$_{calc-DAMGO}$ [%]) and U69,593 (B1$_{calc-U69,593}$ [%]) which are set as 100% relative efficacy at each receptor, respectively.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A compound according to general formula (I)

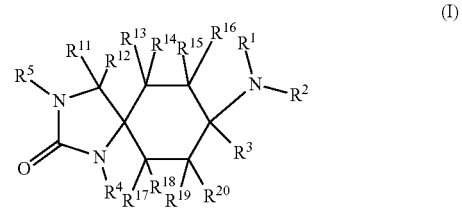

wherein
R$^1$ and R$^2$ independently of one another mean
—H;
—C$_1$-C$_6$-alkyl, linear or branched, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$;
a 3-12-membered cycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered cycloalkyl moiety is optionally connected through —C$_1$-C$_6$-alkylene-, linear or branched, saturated or unsaturated, unsubstituted; or
a 3-12-membered heterocycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered heterocycloalkyl moiety is optionally connected through —C$_1$-C$_6$-alkylene-, linear or branched, saturated or unsaturated, unsubstituted;
or
R$^1$ and R$^2$ together with the nitrogen atom to which they are attached form a ring and mean —(CH$_2$)$_{3-6}$—; —(CH$_2$)$_2$—O—(CH$_2$)$_2$—; or —(CH$_2$)$_2$—NR$^A$—(CH$_2$)$_2$—, wherein R$^A$ means —H or —C$_1$-C$_6$-alkyl, linear or branched, saturated or unsaturated, unsubstituted or substituted with one, two, three or four substituents independently of one another selected from the group consisting of —F, —Cl, —Br and —I;
R$^3$ means
C$_1$-C$_6$-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —C$_1$-C$_6$-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is optionally connected through —C$_1$-C$_6$-alkylene-, linear or branched, saturated or unsaturated, unsubstituted, mono- or polysubstituted;

R$^4$ means

—H;

—C$_1$-C$_6$-alkyl, linear or branched, saturated or unsaturated, unsubstituted, mono- or polysubstituted; wherein said —C$_1$-C$_6$-alkyl is optionally connected through —C(=O)—, —C(=O)O—, or —S(=O)$_2$—;

a 3-12-membered cycloalkyl moiety, saturated or unsaturated, unsubstituted, mono- or polysubstituted; wherein said 3-12-membered cycloalkyl moiety is optionally connected through —C$_1$-C$_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH$_2$—, or —S(=O)$_2$—;

a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH$_2$—, or —S(=O)$_2$—;

a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH$_2$—, or —S(=O)$_2$—; or a 5-14-membered heteroaryl moiety, unsubstituted, mono- or polysubstituted; wherein said 5-14-membered heteroaryl moiety is optionally connected through —C$_1$-C$_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—CH$_2$—, or —S(=O)$_2$—;

R$^5$ means

—H;

—C$_1$-C$_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —C$_1$-C$_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted; or a moiety according to general formula (X);

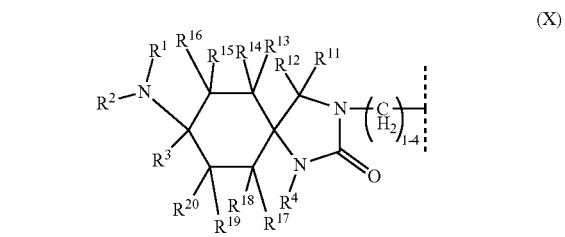

(X)

R$^{11}$, R$^{12}$, R$^{13}$, R$^{14}$, R$^{15}$, R$^{16}$, R$^{17}$, R$^{18}$, R$^{19}$, and R$^{20}$ independently of one another mean —H, —F, —Cl, —Br, —I, —OH, or —C$_1$-C$_6$-alkyl, linear or branched, saturated or unsaturated, unsubstituted, mono- or polysubstituted;

wherein "mono- or polysubstituted" means that one or more hydrogen atoms are replaced by a substituent independently of one another selected from the group consisting of —F, —Cl, —Br, —I, —CN, —R$^{21}$, —C(=O)R$^{21}$, —C(=O)OR$^{21}$, —C(=O)NR$^{21}$R$^{22}$, —O—(CH$_2$CH$_2$—O)$_{1-30}$—H, —O—(CH$_2$CH$_2$—O)$_{1-30}$—CH$_3$, =O, —OR$^{21}$, —OC(=O)R$^{21}$, —OC(=O)OR$^{21}$, —OC(=O)NR$^{21}$R$^{22}$, —NO$_2$, —NR$^{21}$R$^{22}$, —NR$^{21}$—(CH$_2$)$_{1-6}$—C(=O)R$^{22}$, —NR$^{21}$—(CH$_2$)$_{1-6}$—C(=O)OR$^{22}$, —NR$^{23}$—(CH$_2$)$_{1-6}$—C(=O)NR$^{21}$R$^{22}$, —NR$^{21}$C(=O)R$^{22}$, —NR$^{21}$C(=O)—OR$^{22}$, —NR$^{23}$C(=O)NR$^{21}$R$^{22}$, —NR$_{21}$S(=O)$_2$R$^{22}$, —SR$^{21}$, —S(=O)R$^{21}$, —S(=O)$_2$R$^{21}$, —S(=O)$_2$OR$^{21}$, and —S(=O)$_2$NR$^{21}$R$^{22}$;

wherein

R$^{21}$, R$^{22}$ and R$^{23}$ independently of one another mean

—H;

—C$_1$-C$_6$-alkyl, linear or branched, saturated or unsaturated, unsubstituted or substituted with one, two, three or four substituents independently of one another selected from the group consisting of —F, —Cl, —Br, —I, —CN, —OH, —NH$_2$, and —O—C$_1$-C$_6$-alkyl;

a 3-12-membered cycloalkyl moiety, saturated or unsaturated, unsubstituted; wherein said 3-12-membered cycloalkyl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 3-12-membered heterocycloalkyl moiety, saturated or unsaturated, unsubstituted; wherein said 3-12-membered heterocycloalkyl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted or substituted with one, two, three or four substituents independently of one another selected from the group consisting of —F, —Cl, —Br, —I, —CN, —OH, —NH$_2$, —C$_1$-C$_6$-alkyl and —O—C$_1$-C$_6$-alkyl;

a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

or $R^{21}$ and $R^{22}$ within —C(=O)$NR^{21}R^{22}$, —OC(=O)$NR^{21}R^{22}$, —$NR^{21}R^{22}$, —$NR^{23}$—$(CH_2)_{1-6}$—C(=O)$NR^{21}R^{22}$, —$NR^{23}$C(=O)$NR^{21}R^{22}$, or —S(=O)$_2$$NR^{21}R^{22}$ together with the nitrogen atom to which they are attached form a ring and mean —$(CH_2)_{3-6}$—; —$(CH_2)_2$—O—$(CH_2)_2$—; or —$(CH_2)_2$—$NR^B$—$(CH_2)_2$—, wherein $R^B$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

or a physiologically acceptable salt thereof.

2. The compound according to claim 1, wherein $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —OH, or —$C_1$-$C_6$-alkyl.

3. The compound according to claim 1, wherein R' means —H; and $R^2$ means —$C_1$-$C_6$-alkyl, linear or branched, saturated or unsaturated, unsubstituted, mono- or polysubstituted.

4. The compound according to claim 1, wherein $R^1$ means —$CH_3$; and $R^2$ means —$C_1$-$C_6$-alkyl, linear or branched, saturated or unsaturated, unsubstituted, mono- or polysubstituted.

5. The compound according to claim 1, wherein $R^1$ means —H or —$CH_3$; and wherein $R^2$ means —$CH_2$-cycloalkyl, —$CH_2$-cyclobutyl, —$CH_2$-cyclopentyl, —$CH_2$-oxetanyl or —$CH_2$-tetrahydrofuranyl.

6. The compound according to claim 1, wherein $R^1$ and $R^2$ together with the nitrogen atom to which they are attached form a ring and mean —$(CH_2)_{3-6}$—.

7. The compound according to claim 1, wherein $R^3$ means —$C_1$-$C_6$-alkyl, linear or branched, saturated or unsaturated, unsubstituted, mono- or polysubstituted.

8. The compound according to claim 1, wherein $R^3$ means a 6-14-membered aryl moiety, unsubstituted, mono- or polysubstituted.

9. The compound according to claim 1, wherein $R^3$ means a 5-14-membered heteroaryl moiety, unsubstituted, mono- or polysubstituted.

10. The compound according to claim 1, wherein $R^4$ means —H.

11. The compound according to claim 1, wherein $R^4$ means —$C_1$-$C_6$-alkyl, linear or branched, saturated or unsaturated, unsubstituted, mono- or polysubstituted.

12. The compound according to claim 1, wherein $R^4$ means a 3-12-membered cycloalkyl moiety, saturated or unsaturated, unsubstituted, mono- or polysubstituted; wherein the 3-12-membered cycloalkyl moiety is connected through —$C_1$-$C_6$-alkylene-, linear or branched, saturated or unsaturated, unsubstituted, mono- or polysubstituted.

13. The compound according to claim 1, wherein $R^4$ means a 3-12-membered heterocycloalkyl moiety, saturated or unsaturated, unsubstituted, mono- or polysubstituted; wherein said 3-12-membered heterocycloalkyl moiety is connected through —$C_1$-$C_6$-alkylene-, linear or branched, saturated or unsaturated, unsubstituted, mono- or polysubstituted.

14. The compound according to claim 1, wherein $R^4$ means a 6-14-membered aryl moiety, unsubstituted, mono- or polysubstituted; wherein said 6-14-membered aryl moiety is connected through —$C_1$-$C_6$-alkylene-, linear or branched, saturated or unsaturated, unsubstituted, mono- or polysubstituted.

15. The compound according to claim 1, wherein $R^4$ means a 5-14-membered heteroaryl moiety, unsubstituted, mono- or polysubstituted; wherein said 5-14-membered heteroaryl moiety is connected through —$C_1$-$C_6$-alkylene-, linear or branched, saturated or unsaturated, unsubstituted, mono- or polysubstituted.

16. The compound according to claim 1, wherein $R^5$ means —H.

17. The compound according to claim 1, wherein $R^5$ means —$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —O—$C_1$-$C_4$-alkyl, —O—$(CH_2CH_2$—O$)_{1-30}$—H, —O—$(CH_2CH_2$—O$)_{1-30}$—$CH_3$, —C(=O)OH, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl and —S(=O)$_2$$C_1$-$C_4$-alkyl.

18. The compound according to claim 1, wherein $R^5$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —$C_1$-$C_4$-alkyl-OH, —O—$C_1$-$C_4$-alkyl, —O—$(CH_2CH_2$—O$)_{1-30}$—H, —O—$(CH_2CH_2$—O$)_{1-30}$—$CH_3$, —C(=O)OH, —C(=O)$C_1$-$C_4$-alkyl, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —$NH_2$, —NH$C_1$-$C_4$-alkyl, N($C_1$-$C_4$-alkyl)$_2$, —NHC(=O)—$C_1$-$C_4$-alkyl, —N$C_1$-$C_4$-alkylC(=O)$C_1$-$C_4$-alkyl, —S(=O)$C_1$-$C_4$-alkyl and —S(=O)$_2$$C_1$-$C_4$-alkyl; wherein said 3-12-membered cycloalkyl moiety is optionally connected through —$C_1$-$C_6$-alkylene-, linear or branched, saturated or unsaturated, unsubstituted.

19. The compound according to claim 1, wherein $R^5$ means a 3-12-membered heterocycloalkyl moiety, saturated or unsaturated, unsubstituted or substituted with one, two, three or four substituents independently of one another selected from the group consisting of —F, —Cl, —Br, —I, —CN, —OH, —$C_1$-$C_4$-alkyl, —$C_1$-$C_4$-alkyl-OH, —O—$C_1$-$C_4$-alkyl, —O—$(CH_2CH_2$—O$)_{1-30}$—H, —O—$(CH_2CH_2$—O$)_{1-30}$—$CH_3$, —C(=O)OH, —C(=O)$C_1$-$C_4$-alkyl, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —$NH_2$, —NH$C_1$-$C_4$-alkyl, N($C_1$-$C_4$-alkyl)$_2$, —NHC(=O)—$C_1$-$C_4$-alkyl, —N$C_1$-$C_4$-alkylC(=O)$C_1$-$C_4$-alkyl, —S(=O)$C_1$-$C_4$-alkyl and —S(=O)$_2$$C_1$-$C_4$-alkyl; wherein said 3-12-membered heterocycloalkyl moiety is optionally connected through —$C_1$-$C_6$-alkylene-, linear or branched, saturated or unsaturated, unsubstituted.

20. The compound according to claim 1, which has a structure according to any of general formulas (II-A) to (VIII-C):

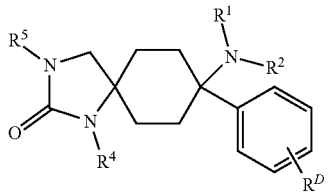
(II-A)
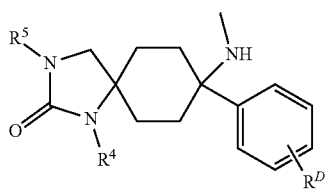
(II-B)
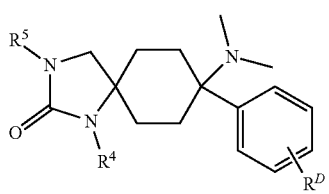
(II-C)
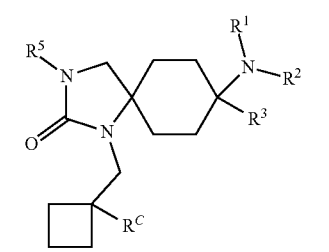
(III-A)
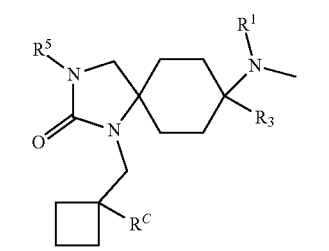
(III-B)
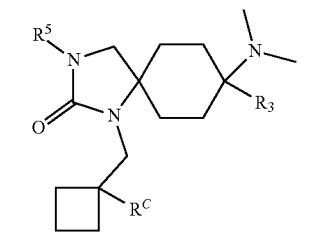
(III-C)
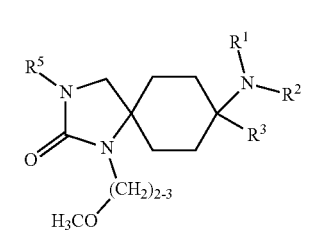
(IV-A)
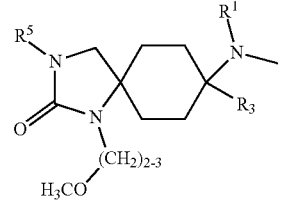
(IV-B)
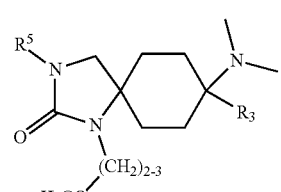
(IV-C)
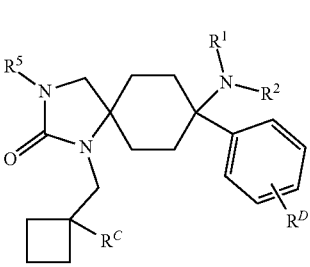
(V-A)
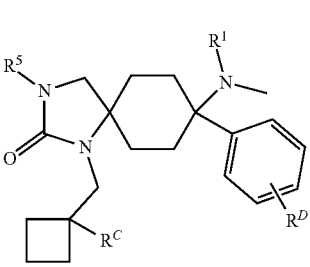
(V-B)
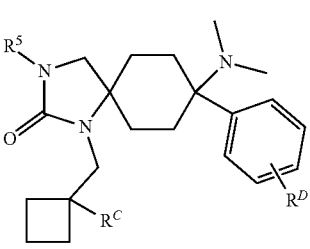
(V-C)
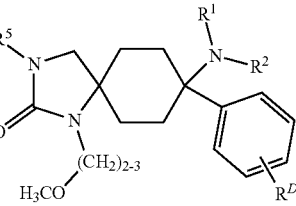
(VI-A)
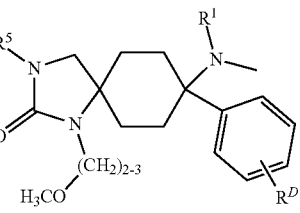
(VI-B)

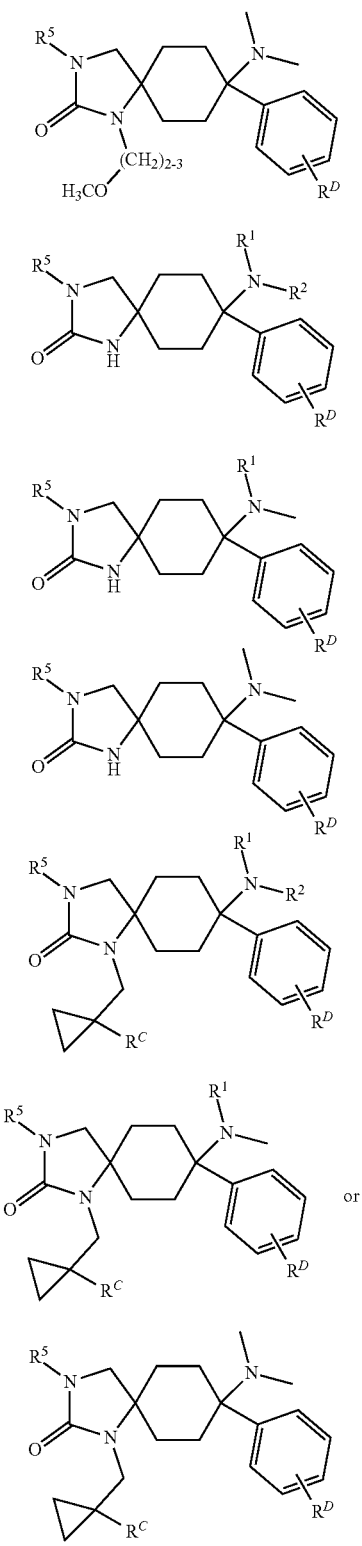
wherein in each case
R¹, R², R³, R⁴, and R⁵ are defined as in claim 1,
R^C means —H, —OH, —F, —CN or —C₁-C₄-alkyl;
R^D means —H or —F;
or a physiologically acceptable salt thereof.
21. The compound according to claim 1, wherein $R^5$ is selected from the group consisting of:
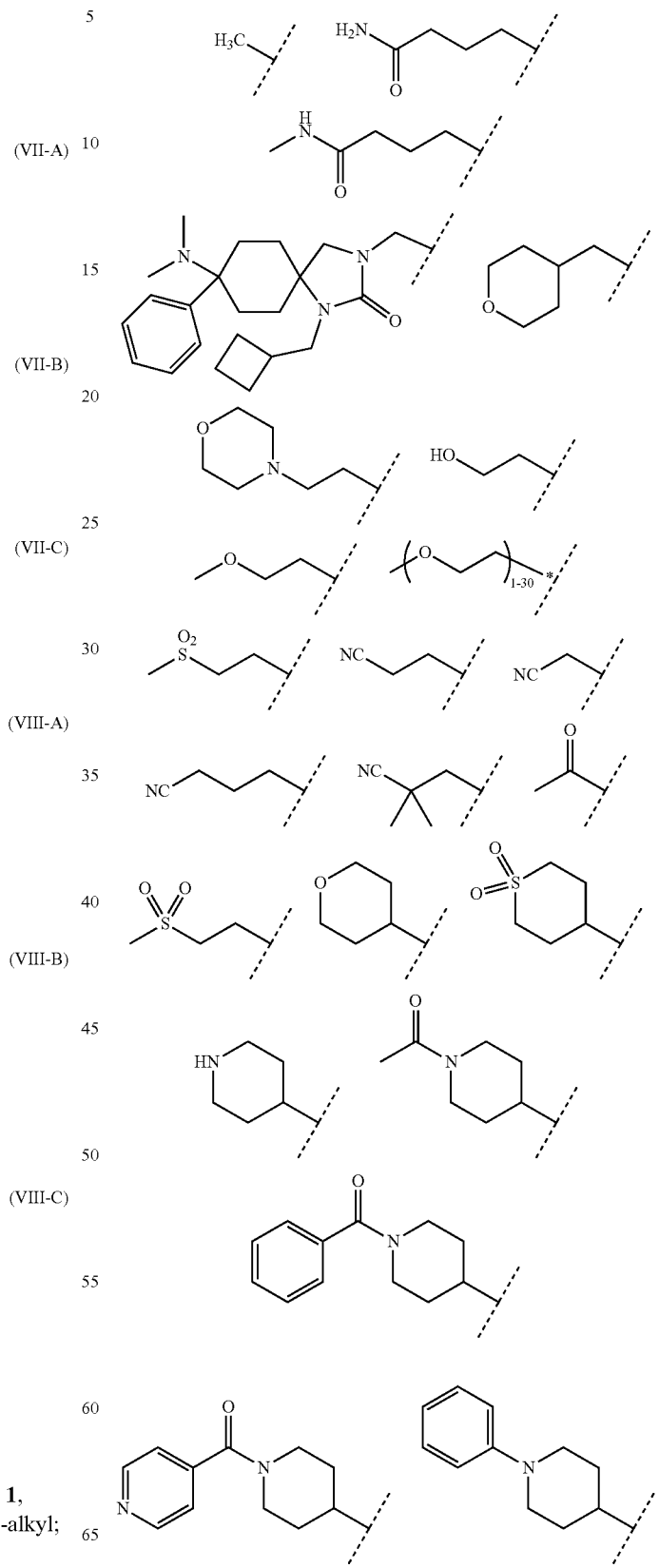

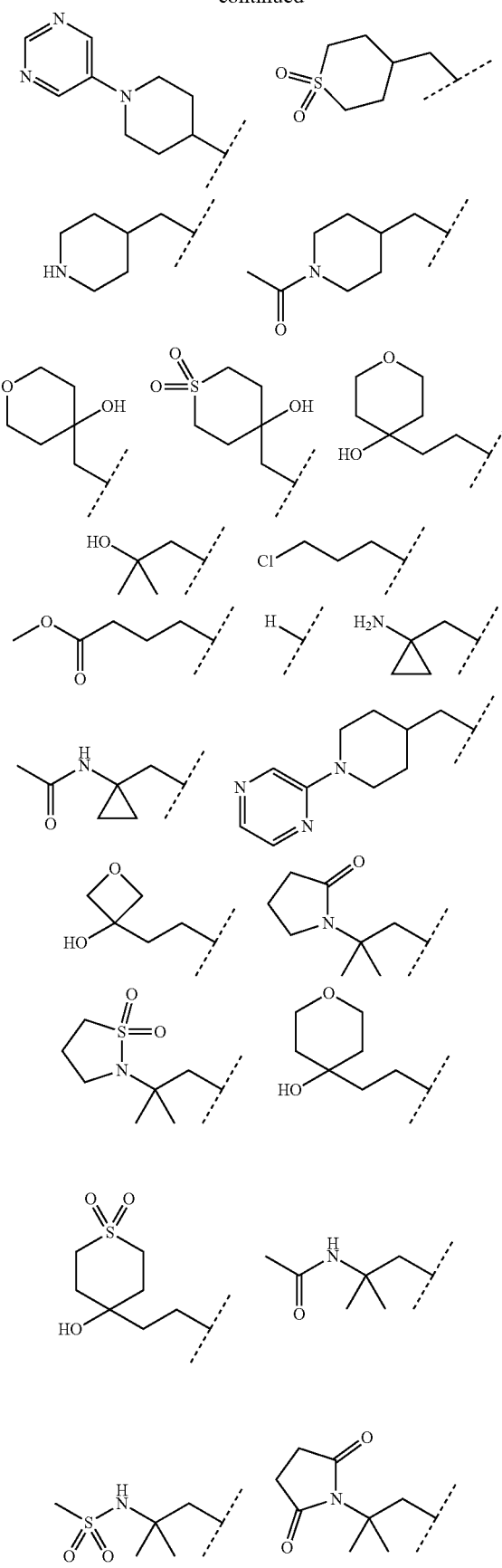
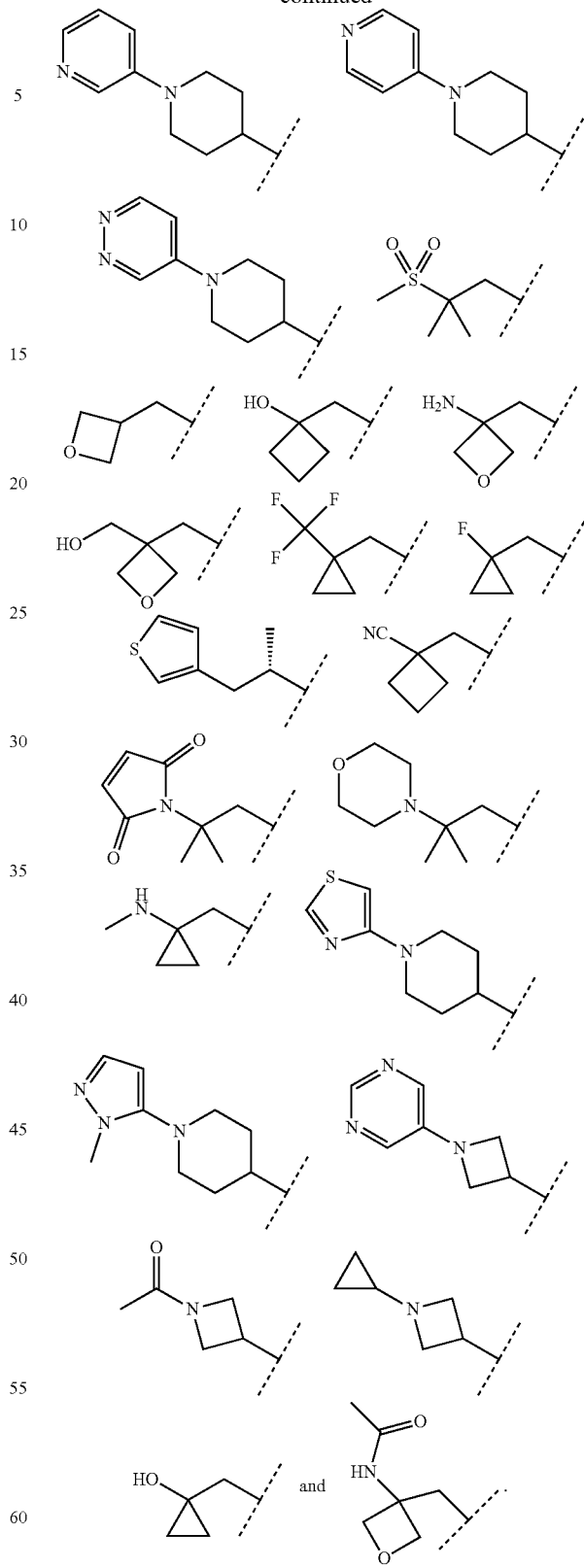
22. The compound according to claim 1, wherein
R¹ means —H or —CH₃;
R² means —C₁-C₆-alkyl, linear or branched, saturated, unsubstituted;

$R^3$ means -phenyl, -thienyl or -pyridinyl, in each case unsubstituted or substituted with one, two, three or four substituents independently of one another selected from the group consisting of —F, —CN, —$CH_3$, —$CH_2CH_3$, —$CH_2F$, —$CHF_2$, —$CF_3$, —$OCF_3$, —OH, —$OCH_3$, —C(=O)$NH_2$, C(=O)$NHCH_3$, —C(=O)N($CH_3$)$_2$, —$NH_2$, —$NHCH_3$, —N($CH_3$)$_2$, —NHC(=O)$CH_3$, —$CH_2$OH, $SOCH_3$ and $SO_2CH_3$; or $R^4$ means
—H;
—$C_1$-$C_6$-alkyl, linear or branched, saturated, unsubstituted or substituted with one, two, three or four substituents independently of one another selected from the group consisting of —F, —Cl, —Br, —I, —CN, —OH, =O, —S(=O)$_2$—$C_1$-$C_4$-alkyl and —O—$C_1$-$C_4$-alkyl;

3-6-membered cycloalkyl, unsubstituted or substituted with one, two, three or four substituents independently of one another selected from the group consisting of —F, —Cl, —Br, —I, —CN, —OH, and —O—$C_1$-$C_4$-alkyl, wherein said 3-6-membered cycloalkyl is connected through —$C_1$-$C_6$-alkylene;

3-12-membered heterocycloalkyl, saturated or unsaturated, unsubstituted or substituted with one, two, three or four substituents independently of one another selected from the group consisting of —F, —Cl, —Br, —I, —CN, —OH, and —O—$C_1$-$C_4$-alkyl; wherein said 3-12-membered heterocycloalkyl is optionally connected through —$C_1$-$C_6$-alkylene-, unsubstituted or substituted with =O;

6-14-membered aryl, unsubstituted or substituted with one, two, three or four substituents independently of one another selected from the group consisting of —F, —Cl, —Br, —I, —CN, —OH, and —O—$C_1$-$C_4$-alkyl; wherein said 6-14-membered aryl is optionally connected through —$C_1$-$C_6$-alkylene- or —S(=O)$_2$—;

$R^5$ means
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —CN, =O, —OH, —O—$C_1$-$C_4$-alkyl, —O—($CH_2CH_2$—O)$_{1-30}$—H, —O—($CH_2CH_2$—O)$_{1-30}$—$CH_3$, —C(=O)OH, —C(=O)O$C_1$-$C_4$-alkyl, —C(=O)O$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl, —S(=O)$_2C_1$-$C_4$-alkyl, —$NH_2$, —NH—$C_1$-$C_4$-alkyl, —N($C_1$-$C_4$-alkyl)$_2$, —NHC(=O)—$C_1$-$C_4$-alkyl-NH—S(=O)$_2C_1$-$C_4$-alkyl; or 3-12-membered cycloalkyl, saturated or unsaturated, unsubstituted or substituted with one, two, three or four substituents independently of one another selected from the group consisting of —F, —Cl, —Br, —I, —CN, =O, —OH, —$C_1$-$C_4$-alkyl, —$C_1$-$C_4$-alkyl-OH, —$NH_2$, —NH—$C_1$-$C_4$-alkyl, —N($C_1$-$C_4$-alkyl)$_2$, —NHC(=O)—$C_1$-$C_4$-alkyl, —NHS(=O)$_2$—$C_1$-$C_4$-alkyl, —O—$C_1$-$C_4$-alkyl, —O—($CH_2CH_2$—O)$_{1-30}$—H, —O—($CH_2CH_2$—O)$_{1-30}$—$CH_3$, —C(=O)OH, —C(=O)O$C_1$-$C_4$-alkyl, —C(=O)$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl, —S(=O)$_2C_1$-$C_4$-alkyl, -phenyl, —C(=O)-phenyl, —C(=O)-pyridyl, -pyridyl, -thiazolyl, —N-methyldiazolyl, -pyrimidinyl, and -pyridazinyl; wherein said 3-12-membered cycloalkyl moiety is optionally connected through —$C_1$-$C_6$-alkylene-, linear or branched, saturated or unsaturated, unsubstituted; or 3-12-membered heterocycloalkyl, saturated or unsaturated, unsubstituted or substituted with one, two, three or four substituents independently of one another selected from the group consisting of —F, —Cl, —Br, —I, —CN, =O, —OH, —$C_1$-$C_4$-alkyl, —$NH_2$, —NH—$C_1$-$C_4$-alkyl, —N($C_1$-$C_4$-alkyl)$_2$, —NHC(=O)—$C_1$-$C_4$-alkyl, —NHS(=O)$_2$—$C_1$-$C_4$-alkyl, —O—$C_1$-$C_4$-alkyl, —O—($CH_2CH_2$—O)$_{1-30}$—H, —O—($CH_2CH_2$—O)$_{1-30}$—$CH_3$, —C(=O)OH, —C(=O)O$C_1$-$C_4$-alkyl, —C(=O)$C_1$-$C_4$-alkyl, —C(=O)$NH_2$, —C(=O)NH$C_1$-$C_4$-alkyl, —C(=O)N($C_1$-$C_4$-alkyl)$_2$, —S(=O)$C_1$-$C_4$-alkyl, —S(=O)$_2C_1$-$C_4$-alkyl, -phenyl, —C(=O)-phenyl, —C(=O)-pyridyl, -pyridyl, -thiazolyl, —N-methyldiazolyl, -pyrimidinyl, and -pyridazinyl; wherein said 3-12-membered heterocycloalkyl moiety is optionally connected through —$C_1$-$C_6$-alkylene-, linear or branched, saturated or unsaturated, unsubstituted; and $R^{11}$, $R^{12}$, $R^{13}$, $R^{14}$, $R^{15}$, $R^{16}$, $R^{17}$, $R^{18}$, $R^{19}$, and $R^{20}$ mean —H.

23. The compound according to claim 1, which has a structure according to general formula (I')

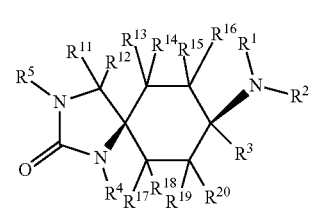

wherein $R^1$ to $R^5$, $R^{11}$ to $R^{20}$ are defined as in claim 1, or a physiologically acceptable salt thereof.

24. The compound according to claim 1, which has a structure according to general formula (IX)

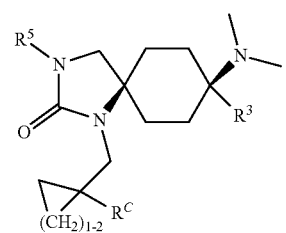

wherein
$R^C$ means —H or —OH;
$R^3$ means -phenyl or -3-fluorophenyl;
$R^5$ means
$C_1$-$C_6$-alkyl, linear or branched, saturated, unsubstituted or monosubstituted with —OH, —CN, —$NH_2$, —NHC(=O)$C_1$-$C_4$-alkyl, —NHS(=O)$_2$—$C_1$-$C_4$-alkyl, or —S(=O)$_2$—$C_1$-$C_4$-alkyl; or 3-6-membered heterocycloalkyl, saturated, unsubstituted or substituted with —OH; wherein said 3-6-membered heterocycloalkyl is optionally connected through —$CH_2$— or —($CH_2$)$_2$—;

or a physiologically acceptable salt thereof.

25. The compound according to claim 24, wherein the 3-6-membered heterocycloalkyl is selected from the group consisting of oxetanly, tetrahydrofuranyl and tetrahydropyranyl.

26. The compound according to claim 1, which is selected from the group consisting of
CIS-4-[1-(Cyclobutyl-methyl)-8-dimethylamino-2-oxo-8-phenyl-1,3-diazaspiro[4.5]decan-3-yl]-butyramide;
CIS-1-(Cyclobutyl-methyl)-8-dimethylamino-3-[2-[2-[2-[2-[2-(2-methoxy-ethoxy)-ethoxy]-ethoxy]-ethoxy]-ethyl]-8-phenyl-1,3-diazaspiro[4.5]decan-2-one;
CIS-1-(Cyclobutyl-methyl)-8-dimethylamino-3-[2-[2-(2-methoxy-ethoxy)-ethoxy]-ethyl]-8-phenyl-1,3-diazaspiro[4.5]decan-2-one;
CIS-1-(Cyclobutyl-methyl)-8-dimethylamino-3-[2-[2-[2-[2-[2-[2-(2-methoxy-ethoxy)-ethoxy]-ethoxy]-ethoxy]-ethoxy]-ethyl]-8-phenyl-1,3-diazaspiro[4.5]decan-2-one;
CIS-1-(Cyclobutyl-methyl)-8-dimethylamino-3-[2-[2-[2-[2-(2-methoxy-ethoxy)-ethoxy]-ethoxy]-ethoxy]-ethyl]-8-phenyl-1,3-diazaspiro[4.5]decan-2-one;
CIS-1-(Cyclobutyl-methyl)-8-dimethylamino-3-[2-(2-methoxy-ethoxy)-ethyl]-8-phenyl-1,3-diazaspiro[4.5]decan-2-one;
CIS-1-(Cyclobutyl-methyl)-8-dimethylamino-3-(2-methoxy-ethyl)-8-phenyl-1,3-diazaspiro[4.5]decan-2-one;
CIS-1-(Cyclobutyl-methyl)-8-dimethylamino-3-[2-[2-[2-(2-methoxy-ethoxy)-ethoxy]-ethoxy]-ethyl]-8-phenyl-1,3-diazaspiro[4.5]decan-2-one;
CIS-1-(Cyclobutyl-methyl)-8-dimethylamino-3-(2-methylsulfonyl-ethyl)-8-phenyl-1,3-diazaspiro[4.5]decan-2-one;
CIS-1-(Cyclobutyl-methyl)-8-methylamino-3-(2-methylsulfonyl-ethyl)-8-phenyl-1,3-diazaspiro[4.5]decan-2-one;
CIS-8-Dimethylamino-1-[(1-hydroxy-cyclobutyl)-methyl]-3-(2-methylsulfonyl-ethyl)-8-phenyl-1,3-diazaspiro[4.5]decan-2-one;
CIS-4-[1-(Cyclobutyl-methyl)-8-dimethylamino-2-oxo-8-phenyl-1,3-diazaspiro[4.5]decan-3-yl]-butyronitrile;
CIS-4-[1-(Cyclobutyl-methyl)-8-dimethylamino-2-oxo-8-phenyl-1,3-diazaspiro[4.5]decan-3-yl]-N-methyl-butyramide;
CIS-3-[1-(Cyclobutyl-methyl)-8-dimethylamino-2-oxo-8-phenyl-1,3-diazaspiro[4.5]decan-3-yl]-2,2-dimethyl-propionitrile;
CIS-1-(Cyclobutyl-methyl)-8-dimethylamino-3-[2-[2-[2-[2-[2-[2-(2-methoxy-ethoxy)-ethoxy]-ethoxy]-ethoxy]-ethoxy]-ethoxy]-ethyl]-8-phenyl-1,3-diazaspiro[4.5]decan-2-one;
CIS-1-(Cyclobutyl-methyl)-8-dimethylamino-3-methyl-8-phenyl-1,3-diazaspiro[4.5]decan-2-one;
CIS-1-[(1-Hydroxy-cyclobutyl)-methyl]-8-methylamino-3-(2-methylsulfonyl-ethyl)-8-phenyl-1,3-diazaspiro[4.5]decan-2-one;
CIS-3-[1-[(1-Hydroxy-cyclobutyl)-methyl]-8-methylamino-2-oxo-8-phenyl-1,3-diazaspiro[4.5]decan-3-yl]-propionitrile;
CIS-2-[1-[(1-Hydroxy-cyclobutyl)-methyl]-8-methylamino-2-oxo-8-phenyl-1,3-diazaspiro[4.5]decan-3-yl]-acetonitrile;
CIS-8-Dimethylamino-1-[(1-hydroxy-cyclobutyl)-methyl]-8-phenyl-3-(tetrahydro-pyran-4-yl-methyl)-1,3-diazaspiro[4.5]decan-2-one;
CIS-8-Dimethylamino-1-[(1-hydroxy-cyclobutyl)-methyl]-3-(2-morpholin-4-yl-ethyl)-8-phenyl-1,3-diazaspiro[4.5]decan-2-one;
CIS-3-(3-Chloro-propyl)-1-(cyclobutyl-methyl)-8-dimethylamino-8-phenyl-1,3-diazaspiro[4.5]decan-2-one;
CIS-4-[1-(Cyclobutyl-methyl)-8-dimethylamino-2-oxo-8-phenyl-1,3-diazaspiro[4.5]decan-3-yl]-butyric acid methyl ester;
CIS-3-[8-Dimethylamino-1-[(1-hydroxy-cyclobutyl)-methyl]-2-oxo-8-phenyl-1,3-diazaspiro[4.5]decan-3-yl]-propionitrile;
CIS-2-[8-Dimethylamino-1-[(1-hydroxy-cyclobutyl)-methyl]-2-oxo-8-phenyl-1,3-diazaspiro[4.5]decan-3-yl]-acetonitrile;
CIS-3-Acetyl-8-dimethylamino-8-phenyl-1,3-diazaspiro[4.5]decan-2-one;
CIS-8-Dimethylamino-3-(2-methylsulfonyl-ethyl)-8-phenyl-1,3-diazaspiro[4.5]decan-2-one
CIS-1-Acetyl-8-dimethylamino-8-phenyl-1,3-diazaspiro[4.5]decan-2-one;
CIS-1-(Cyclopropyl-methyl)-8-dimethylamino-3-(2-methylsulfonyl-ethyl)-8-phenyl-1,3-diazaspiro[4.5]decan-2-one;
CIS-8-Dimethylamino-3-(2-methylsulfonyl-ethyl)-1-(oxetan-3-yl-methyl)-8-phenyl-1,3-diazaspiro[4.5]decan-2-one;
CIS-8-Dimethylamino-1-(3-methoxy-propyl)-3-(2-methylsulfonyl-ethyl)-8-phenyl-1,3-diazaspiro[4.5]decan-2-one;
CIS-8-Dimethylamino-8-phenyl-1-(p-tolylsulfonyl)-1,3-diazaspiro[4.5]decan-2-one;
CIS-8-Dimethylamino-3-[(1,1-dioxo-thian-4-yl)-methyl]-1-[(1-hydroxy-cyclobutyl)-methyl]-8-phenyl-1,3-diazaspiro[4.5]decan-2-one;
CIS-1-(Cyclobutyl-methyl)-8-dimethylamino-3-[(4-hydroxy-tetrahydro-pyran-4-yl)-methyl]-8-phenyl-1,3-diazaspiro[4.5]decan-2-one;
CIS-1-(Cyclopropyl-methyl)-8-dimethylamino-8-phenyl-3-tetrahydro-pyran-4-yl-1,3-diazaspiro[4.5]decan-2-one;
CIS-1-(Cyclobutyl-methyl)-8-dimethylamino-3-[(4-hydroxy-1,1-dioxo-thian-4-yl)-methyl]-8-phenyl-1,3-diazaspiro[4.5]decan-2-one;
CIS-8-Dimethylamino-1-[(1-hydroxy-cyclobutyl)-methyl]-8-phenyl-3-tetrahydro-pyran-4-yl-1,3-diazaspiro[4.5]decan-2-one;
CIS-1-[[8-Dimethylamino-3-(2-methylsulfonyl-ethyl)-2-oxo-8-phenyl-1,3-diazaspiro[4.5]decan-1-yl]-methyl]-cyclobutane-1-carbonitrile;
CIS-8-Dimethylamino-1-[(1-hydroxy-cyclobutyl)-methyl]-3-[(4-hydroxy-tetrahydro-pyran-4-yl)-methyl]-8-phenyl-1,3-diazaspiro[4.5]decan-2-one;
CIS-8-Dimethylamino-1-[(1-hydroxy-cyclobutyl)-methyl]-3-[(4-hydroxy-1,1-dioxo-thian-4-yl)-methyl]-8-phenyl-1,3-diazaspiro[4.5]decan-2-one;
CIS-1-(Cyclopropyl-methyl)-8-dimethylamino-3-(1,1-dioxo-thian-4-yl)-8-phenyl-1,3-diazaspiro[4.5]decan-2-one;
CIS-8-Dimethylamino-3-(1,1-dioxo-thian-4-yl)-1-[(1-hydroxy-cyclobutyl)-methyl]-8-phenyl-1,3-diazaspiro[4.5]decan-2-one;
CIS-3-(1-Acetyl-piperidin-4-yl)-1-(cyclopropyl-methyl)-8-dimethylamino-8-phenyl-1,3-diazaspiro[4.5]decan-2-one;
CIS-3-(1-Benzoyl-piperidin-4-yl)-1-(cyclopropyl-methyl)-8-dimethylamino-8-phenyl-1,3-diazaspiro[4.5]decan-2-one;

CIS-1-(Cyclopropyl-methyl)-8-dimethylamino-8-phenyl-3-[1-(pyridine-4-carbonyl)-piperidin-4-yl]-1,3-diazaspiro[4.5]decan-2-one;
CIS-1-(Cyclopropyl-methyl)-8-dimethylamino-3-[(4-hydroxy-tetrahydro-pyran-4-yl)-methyl]-8-phenyl-1,3-diazaspiro[4.5]decan-2-one;
CIS-1-(Cyclobutyl-methyl)-8-dimethylamino-3-[2-(4-hydroxy-tetrahydro-pyran-4-yl)-ethyl]-8-phenyl-1,3-diazaspiro[4.5]decan-2-one;
CIS-3-[(1-Acetyl-piperidin-4-yl)-methyl]-1-(cyclopropyl-methyl)-8-dimethylamino-8-phenyl-1,3-diazaspiro[4.5]decan-2-one;
CIS-1-(Cyclopropyl-methyl)-8-dimethylamino-8-phenyl-3-piperidin-4-yl-1,3-diazaspiro[4.5]decan-2-one;
CIS-1-(Cyclopropyl-methyl)-8-dimethylamino-3-(2-hydroxy-2-methyl-propyl)-8-phenyl-1,3-diazaspiro[4.5]decan-2-one;
CIS-1-(Cyclopropyl-methyl)-8-dimethylamino-8-phenyl-3-(1-pyrimidin-5-yl-piperidin-4-yl)-1,3-diazaspiro[4.5]decan-2-one;
CIS-1-(Cyclopropyl-methyl)-8-dimethylamino-8-phenyl-3-(1-phenyl-piperidin-4-yl)-1,3-diazaspiro[4.5]decan-2-one;
CIS-1-(Cyclopropyl-methyl)-8-dimethylamino-8-phenyl-3-(piperidin-4-yl-methyl)-1,3-diazaspiro[4.5]decan-2-one;
CIS-3-(1-Benzoyl-piperidin-4-yl)-8-dimethylamino-8-phenyl-1,3-diazaspiro[4.5]decan-2-one
CIS-8-Dimethylamino-8-phenyl-3-[1-(pyridine-4-carbonyl)-piperidin-4-yl]-1,3-diazaspiro[4.5]decan-2-one;
CIS-3-(1-Acetyl-piperidin-4-yl)-8-dimethylamino-8-phenyl-1,3-diazaspiro[4.5]decan-2-one;
CIS-1-(Cyclopropyl-methyl)-8-dimethylamino-3-[(4-hydroxy-1,1-dioxo-thian-4-yl)-methyl]-8-phenyl-1,3-diazaspiro[4.5]decan-2-one;
CIS-8-Dimethylamino-1-[(1-hydroxy-cyclobutyl)-methyl]-3-(2-hydroxy-2-methyl-propyl)-8-phenyl-1,3-diazaspiro[4.5]decan-2-one;
and the physiologically acceptable salts thereof.

27. A medicament comprising a compound according to claim 1.

28. A compound according to general formula (IIIa) or (IIIb),

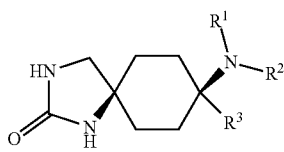

(IIIa)

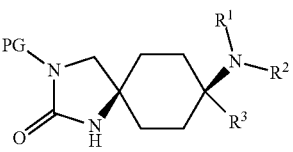

(IIIb)

wherein
$R^1$ and $R^2$ independently of one another mean
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —OH, —$OCH_3$, —CN and —$CO_2CH_3$;
a 3-12-membered cycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered cycloalkyl moiety is optionally connected through —$C_1$-$C_6$-alkylene-, linear or branched, saturated or unsaturated, unsubstituted; or
a 3-12-membered heterocycloalkyl moiety, saturated or unsaturated, unsubstituted or substituted with one, two, three or four substituents independently of one another selected from the group consisting of —F, —Cl, —Br, —I, —OH, —$OCH_3$, —CN and —$CO_2CH_3$; wherein said 3-12-membered heterocycloalkyl moiety is optionally connected through —$C_1$-$C_6$-alkylene-, linear or branched, saturated or unsaturated, unsubstituted;
or
$R^1$ and $R^2$ together with the nitrogen atom to which they are attached form a ring and mean —$(CH_2)_{3-6}$—; —$(CH_2)_2$—O—$(CH_2)_2$—; or —$(CH_2)_2$—$NR^4$—$(CH_2)_2$—, wherein $R^4$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;
$R^3$ means
—$C_1$-$C_6$-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; and
PG is a protecting group;
or a physiologically acceptable salt thereof.

29. A method of treating pain in a patient in need thereof, said method comprising administering to said patient an effective amount therefor of at least one compound according to claim 1.

30. A method of treating a disorder selected from the group consisting of neurodegenerative disorders, neuroinflammatory disorders, neuropsychiatric disorders, and substance abuse/dependence, said method comprising administering to a patient in need thereof an effective amount therefor of at least one compound according to claim 1.

* * * * *